US010358637B2

(12) United States Patent
Samli et al.

(10) Patent No.: US 10,358,637 B2
(45) Date of Patent: Jul. 23, 2019

(54) CARBOHYDRATE-BINDING PROTEIN

(71) Applicants: UNIVERSITY OF GEORGIA RESEARCH FOUNDATION, INC., Athens, GA (US); GLYCOSENSORS AND DIAGNOSTICS, LLC, Athens, GA (US)

(72) Inventors: Kausar N. Samli, Athens, GA (US); Robert J. Woods, Athens, GA (US); Loretta Yang, San Diego, CA (US)

(73) Assignees: University of Georgia Research Foundation, Inc., Athens, GA (US); Glycosensors and Diagnostics, LLC, Athens, GA (US)

( * ) Notice: Subject to any disclaimer, the term of this patent is extended or adjusted under 35 U.S.C. 154(b) by 4 days.

(21) Appl. No.: 15/304,725

(22) PCT Filed: Apr. 17, 2015

(86) PCT No.: PCT/US2015/026374
§ 371 (c)(1),
(2) Date: Oct. 17, 2016

(87) PCT Pub. No.: WO2015/161201
PCT Pub. Date: Oct. 22, 2015

(65) Prior Publication Data
US 2017/0191049 A1 Jul. 6, 2017

Related U.S. Application Data

(60) Provisional application No. 61/981,335, filed on Apr. 18, 2014.

(51) Int. Cl.
*C12N 9/82* (2006.01)
*C12N 9/80* (2006.01)
*C07K 1/14* (2006.01)
*G01N 33/68* (2006.01)

(52) U.S. Cl.
CPC .................. *C12N 9/80* (2013.01); *C07K 1/14* (2013.01); *C12Y 305/01052* (2013.01); *G01N 33/6803* (2013.01); *G01N 2333/978* (2013.01); *G01N 2400/00* (2013.01); *G01N 2440/38* (2013.01)

(58) Field of Classification Search
CPC ....................................................... C12N 9/82
See application file for complete search history.

(56) References Cited

U.S. PATENT DOCUMENTS

| 6,184,027 B1 | 2/2001 | Laine et al. |
| 6,376,210 B1 | 4/2002 | Yuan |
| 6,972,172 B2 | 12/2005 | Dukler et al. |
| 7,368,108 B2 | 5/2008 | DeFrees et al. |
| 9,926,612 B2 | 3/2018 | Woods et al. |
| 2004/0077105 A1 | 4/2004 | Wu et al. |
| 2004/0229314 A1 | 11/2004 | Glucksmann et al. |
| 2006/0040327 A1 | 2/2006 | Amiss et al. |
| 2006/0141480 A1 | 6/2006 | Ramnarayan et al. |
| 2006/0172339 A1 | 8/2006 | Patton et al. |
| 2009/0272913 A1 | 11/2009 | Naciri et al. |
| 2010/0016171 A1 | 1/2010 | Wong et al. |
| 2012/0040474 A1* | 2/2012 | Woods ............. C12N 9/82 436/501 |
| 2014/0005069 A1 | 1/2014 | Yang et al. |
| 2017/0128554 A1 | 5/2017 | Chen et al. |

FOREIGN PATENT DOCUMENTS

| WO | WO 98/42864 A1 | 10/1998 |
| WO | WO 2010/068817 A1 | 6/2010 |
| WO | WO 2012/118928 A2 | 9/2012 |
| WO | WO 2012/170678 A1 | 12/2012 |
| WO | WO 2015/161201 A1 | 10/2015 |
| WO | WO 2015/161201 A8 | 10/2015 |

OTHER PUBLICATIONS

U.S. Appl. No. 15/916,578, filed Mar. 9, 2018, Woods et al.
"Lectenz" [online]. United States Patent and Trademark Office Trademark Electronic Search System (TESS). Trademark application filed on Dec. 26, 2007, published for opposition on Jul. 7, 2009. Available online [retrieved on Aug. 19, 2011]. Retrieved from the Internet: <tess2.uspto.gov/bin/showfield?f=doc&state=4004:787618. 2.1>; 2 pgs.
National Center for Biotechnology Information, National Library of Medicine, National Institutes of Health, GenBank Locus AF165910, Accession No. AF165910, "Chryseobacterium meningosepticum peptide:N-glycosidase F precursor (png) gene, partial cds," [online]. Bethesda, MD [retrieved on May 9, 2018]. Retrieved from the Internet: <URL:ncbi.nlm.nih.gov/nuccore/AF165910>; 2 pgs.
National Center for Biotechnology Information, National Library of Medicine, National Institutes of Health, GenBank Locus FVBPNG, Accession No. J05449, "F.meningosepticum peptide-N-4-(N-acetyl-beta-D-glucosaminyl) asparagine amidase (PNGase F) mRNA, complete cds," [online]. Bethesda, MD [retrieved on May 9, 2018]. Retrieved from the Internet: <URL:ncbi.nlm.nih.gov/nuccore/J05449>; 2 pgs.
National Center for Biotechnology Information, National Library of Medicine, National Institutes of Health, GenBank Locus PNGF_ELIMR, Accession No. P21163, "RecName: Full=Peptide-N(4)-(N-acetyl-beta-D-glucosaminyl)asparagine amidase F; Short=PNGase F; AltName: Full—Glycopeptide N-glycosidase; AltName: Full=N-glycanase; Flags: Precursor," [online]. Bethesda, MD [retrieved on May 9, 2018]. Retrieved from the Internet: <URL:ncbi.nlm.nih.gov/protein/P21163>; 7 pgs.

(Continued)

Primary Examiner — Karen Cochrane Carlson
(74) Attorney, Agent, or Firm — Mueting, Raasch & Gebhardt, P.A.

(57) ABSTRACT

The carbohydrate processing enzyme PNGase F was catalytically inactivated through mutation. Additional mutations yielded a catalytically inactive carbohydrate-binding protein with lectin-like properties including high affinity and specificity N-linked glycans, O-linked glycans, or both.

17 Claims, 47 Drawing Sheets
Specification includes a Sequence Listing.

(56) References Cited

OTHER PUBLICATIONS

National Center for Biotechnology Information, National Library of Medicine, National Institutes of Health, GenBank Locus Q5LH31_BACFN, Accession No. Q5LH31, "Hypothetical Protein," [online]. Bethesda, MD [retrieved on May 9, 2018]. Retrieved from the Internet: <URL:ncbi.nlm.nih.gov/protein/Q5LH31>; 1 pg.
National Center for Biotechnology Information, National Library of Medicine, National Institutes of Health, GenBank Locus Q9XBM8_FLAME, Accession No. Q9XBM8, "Peptide:N-glycosidase F," [online]. Bethesda, MD [retrieved on May 9, 2018]. Retrieved from the Internet: <URL:ncbi.nlm.nih.gov/protein/Q9XBM8>; 1 pg.
National Center for Biotechnology Information, National Library of Medicine, National Institutes of Health, GenBank Locus NGLY1_HUMAN, Accession No. Q96IV0, "RecName: Full=Peptide-N(4)-(N-acetyl-beta-glucosaminyl)asparagine amidase; Short=PNGase; Short=hPNGase; AltName: Full=N-glycanase 1; AltName: Full=Peptide:N-glycanase," [online]. Bethesda, MD [retrieved on May 9, 2018]. Retrieved from the Internet: <URL:ncbi.nlm.nih.gov/protein/Q96IV0>; 8 pgs.
International Application No. PCT/US15/26374, filed Apr. 17, 2015; International Search Report and Written Opinion dated Aug. 10, 2015; 11 pages.
International Application No. PCT/US15/26374, filed Apr. 17, 2015; International Preliminary Report on Patentability dated Oct. 27, 2016; 8 pages.
Ackerman et al., "Highly avid magnetic bead capture: An efficient selection method for de novo protein engineering utilizing yeast surface display," *Biotechnology Progress*, 2009; 25:774-83.
Adams and Scadden, "The hematopoietic stem cell in its place," *Nat Immunol*, Apr. 2006; 7(4):333-7.
Ahmad et al. "Human linker histones: interplay between phosphorylation and O-beta-GlcNAc to mediate chromatin structural modifications," *Cell Division*, Jul. 12, 2011; 6:15.
Alwael et al. "Pipette-tip selective extraction of glycoproteins with lectin modified gold nano-particles on a polymer monolithic phase," *Analyst*, Jun. 21, 2011; 136(12):2619-28. Epub May 6, 2011.
An et al., "Glycomics and disease markers," *Current Opinion in Chemical Biology*, Dec. 2009; 13(5-6):601-7. Epub Sep. 21, 2009.
Arnaud et al., "Binding sugars: from natural lectins to synthetic receptors and engineered neolectins," *Chem Soc Rev*, Jun. 7, 2013; 42(11):4798-813. Epub Jan. 25, 2013.
Asensio et al., "Carbohydrate—Aromatic Interactions," *Acc Chem Res*, Apr. 16, 2013; 46(4):946-54. Epub Jun. 15, 2012.
Bae et al., "Molecular Basis for the Selectivity and Specificity of Ligand Recognition by the Family 16 Carbohydrate-binding Modules from Thermoanaerobacterium polysaccharolyticum ManA," *Journal of Biological Chemistry*, May 2, 2008. 283(18):12415-12425.
Baker and Sali, "Protein Structure Prediction and Structural Genomics," *Science*, Oct. 5, 2001; 294(5540):93-6.
Barakat & Love, "Molecular Diversity in Engineered Protein Libraries," *Curr Opin Chem Biol*, 2007; 11:335-41.
Belien et al., "Phage display based identification of novel stabilizing mutations in glycosyl hydrolase family 11 *B. subtilis* endoxylanase XynA," *Biochem Biophys Res Commun*, Mar. 28, 2008; 368(1):74-80. Epub Jan. 28, 2008.
Benatuil et al., "An improved yeast transformation method for the generation of very large human antibody libraries," *Protein Eng Des Sel*, Apr. 2010; 23(4):155-9. Epub Feb. 3, 2010.
Benz et al., "Experimental validation of molecular dynamics simulations of lipid bilayers: a new approach," *Biophysical Journal*, Feb. 2005; 88(2):805-17. Epub Nov. 8, 2004.
Berman et al., "The Protein Data Bank," *Nucl Acids Res*, Jan. 1, 2000; 28(1):235-42.
Bertozzi et al., "Chemical glycobiology," Mar. 23, 2001, *Science*, 291(5512):2357-64.
Beveridge et al., "Free energy via molecular simulation: applications to chemical and biomolecular systems," *Annu Rev Biophys Biophys Chem*, 1989; 18:431-92.

Bonsor, "Dissecting protein-protein interactions using directed evolution," *Biochem*, Apr. 5, 2011; 50(13):2394-402. Epub Mar. 1, 2011.
Bornscheuer et al., "Survey of protein engineering strategies," *Curr Protoc Protein Sci*, Nov. 2011; Chapter 26, Unit 26.7.
Brannigan et al., "Protein engineering 20 years on," *Nat Rev Mol Cell Biol*, Dec. 2002; 3(12):964-70.
Brustad et al., "Optimizing non-natural protein function with directed evolution," *Curr Opin Chem Biol*, Apr. 2011; 15(2):201-10. Epub Dec. 23, 2010.
Burda et al., "The dolichol pathway of N-linked glycosylation," *Biochim Biophys Acta*, Jan. 6, 1999; 1426(2):239-57.
Carrascal et al., "Energetic decomposition with the generalized-born and Poisson-Boltzmann solvent models: lessons from association of G-protein components," *J Phys Chem B*, Apr. 22, 2010; 114(15):5096-116.
Case et al., "The Amber biomolecular simulation programs," *J Comput Chem*, Dec. 2005; 26(16):1668-88.
Case et al., AMBER 10 User Manual, 2008 [retrieved on Apr. 20, 2018]. Retrieved from the Internet: <URL: infoscience.epfl.ch/record/121435/files/Amber10i.pdf>; 304 pgs.
Chao et al., "Isolating and engineering human antibodies using yeast surface display," *Nat Protocols*, 2006; 1(2):755-68.
Chen et al., "An engineered high affinity Fbs1 carbohydrate binding protein for selective capture of N-glycans and N-glycopeptides," *Nature Comm*. 8; Article No. 15487 (May 23, 2017) doi:10.1038/ncomms15487, 15 pages.
Chica et al., "Semi-rational approaches to engineering enzyme activity: combining the benefits of directed evolution and rational design," *Curr Opin Biol*, 2005; 16: 378-84.
Chowdhury et al. "Improving Antibody Affinity by Mimicking Somatic Hypermutation in vitro," *Nature Biotechnology*, Jun. 1999; 17:568-72.
Christ et al., "Basic ingredients of free energy calculations: a review," *Journal of Computational Chemistry*, Jun. 2010; 31(8):1569-52.
Cobb et al., "Directed evolution: Past, present, and future," *AIChE Journal*, May 2013; 59(5):1432-40.
Cobucci-Ponzano et al., "Engineering the stability and the activity of a glycoside hydrolase," *Protein Eng Des Sel*, Jan. 2011; 24(1-2):21-6. Epub Oct. 27, 2010.
Cooper, "Optical biosensors in drug discovery," *Nat Rev Drug Discov*, Jul. 2002; 1(7): 515-28.
Cummings, "The repertoire of glycan detellninants in the human glycome," *Mol Biosyst*, Oct. 2009; 5(10):1087-104. Epub Jul. 28, 2009.
Cunningham et al., "Glyco-biosensors: Recent advances and applications for the detection of free and bound carbohydrates," *Analyst*, Oct. 2010; 135(10):2471-80. Epub Aug. 11, 2010.
Cylwik et al., "Congenital disorders of glycosylation. Part II. Defects of protein O-glycosylation," *Acta Biochimica Polonica*, 2013; 60(3):361-8. Epub Sep. 19, 2013.
Dance, "From pond scum to pharmacy shelf," *Nat Med*, Feb. 2010; 16(2):146-9.
Debray et al., "Specificity of twelve lectins towards oligosaccharides and glycopeptides related to N-glycosylproteins," *Eur J Biochem*, Jun. 1981; 117(1):41-55.
DeMarco et al. "Structural glycobiology: a game of snakes and ladders," *Glycobiol*. 2008; 18:426-40.
De Ruiter et al., "Free energy calculations of protein-ligand interactions," *Curr Opin Chem Biol*, Aug. 2011; 15(4):547-52. Epub Jun. 22, 2011.
Del Vecchio et al., "Thermodynamic Stability of Ribonuclease B," *Journal of Thermal Analysis and Calorimetry*, 2000; 61:363-8.
Dreier et al., "Ribosome display: a technology for selecting and evolving proteins from large libraries," *Methods Mol Biol*, 2011; 687:283-306.
Drickamer et al., "Evolving views of protein glycosylation," *Trends Biochem Sci*, Sep. 1998; 23(9):321-4.
Dunbrack Jr., "Rotamer libraries in the 21st century," *Cur Opin Struct Biol*, Aug. 2002; 12(4):431-40.

(56) References Cited

OTHER PUBLICATIONS

Fadda et al., "Molecular simulations of carbohydrates and proteincarbohydrate interactions: motivation, issues and prospects," *Drug Discov Today*, Aug. 2010; 15(15-16):596-609. Epub Jun. 8, 2010.
Fan et al., "Detailed Studies on Substrate Structure Requirements of Glycoamidases A and F," *J Biol Chem*, Oct. 24, 1997; 272(43):27058-64.
Feldmeier et al., "Computational protein design of ligand binding and catalysis," *Curr Opin Chem Biol*, Dec. 2013; 17(6):929-33.
Filitcheva, "PNGases: A diverse family of enzymes related by function rather than catalytic mechanism" Ph D. Thesis, Institute of Mol BioSci, Massey University, Palmerston North, New Zealand, 2010; 340 pages.
Freeze, "Update and perspectives on congenital disorders of glycosylation," *Glycobiology*, Dec. 2001; 11(12):129R-143R.
Fu et al., "A detailed structural characterization of ribonuclease B oligosaccharides by 1H NMR spectroscopy and mass spectrometry," *Carbohydr Res*, Aug. 17, 1994; 261(2):173-86.
Gasteiger E., H.C., Gattiker A., Duvaud S., Wilkins M.R., Appel R.D., Bairoch A. in The Proteomics Protocols Handbook (ed. J.M. Walker) pp. 571-607 (Copyright Humana Press, 2005).
Genheden et al., "A comparison of different initialization protocols to obtain statistically independent molecular dynamics simulations," *J Comput Chem*, Jan. 30, 2011; 32(2):187-95.
Genheden et al., "Will molecular dynamics simulations of proteins ever reach equilibrium?" *Phys Chem Chem Phys*, Jun. 28, 2012; 14(24):8662-77. Epub May 22, 2012.
Gera et al., "Protein selection using yeast surface display," *Methods*, Mar. 15, 2013; 60(1):15-26. Epub Mar. 23, 2012.
Ghazarian et al., "A glycobiology review: carbohydrates, lectins and implications in cancer therapeutics," *Acta Histochem*, May 2011; 113(3):236-47. Epub Mar. 2, 2010.
Giancola et al., "Thermodynamic stability of the two isoforms of bovine seminal ribonuclease," *Biochemistry*, Jul. 11, 2000; 39(27):7964-72.
Goonetilleke et al., "Systematic review of carbohydrate antigen (CA 19-9) as a biochemical marker in the diagnosis of pancreatic cancer," *Eur J Surg Oncol*, Apr. 2007; 33(3):266-70. Epub Nov. 9, 2006.
Graf et al., "Selective alteration of substrate specificity by replacement of aspartic acid-189 with lysine in the binding pocket of trypsin," *Biochemistry*, May 5, 1987; 26(9):2616-23.
Groenhof, "Introduction to QM/MM simulations," *Methods Mol Biol*, 2013; 924:43-66.
Grove, et al., "Creating novel proteins by combining design and selection," *Protein Eng Des Sel*, 2010; 23:449-455.
Guillén et al., "Carbohydrate-binding domains: multiplicity of biological roles," *Appl Microbiol Biotechnol*, Feb. 2010; 85(5):1241-9. Epub Nov. 12, 2009.
Guvench et al., "Comparison of protein force fields for molecular dynamics simulations," *Methods Mol Biol*, 2008; 443:63-88.
Hadden et al., "Calculating binding free energies for protein-carbohydrate complexes," *Methods Mol Biol*. 2015; 1273:431-65.
Hakomori, "Tumor-associated carbohydrate antigens," *Annu Rev Immunol*, 1984; 2:103-26.
Haltiwanger and Lowe, "Role of glycosylation in development," *Annu Rev Biochem*, 2004; 73:491-537.
Hancock et al., "Designer enzymes for glycosphingolipid synthesis by directed evolution," *Nat Chem Biol*, Jul. 2009; 5(7):508-14.
Harata et al., "Crystal structures of Urtica dioica agglutinin and its complex with tri-N-acetylchitotriose," *J Mol Biol*, Mar. 31, 2000; 297(3):673-81.
Hart and Copeland, "Glycomics hits the big time," *Cell*, Nov. 24, 2010; 143(5):672-6.
Haseley et al., "Unravelling carbohydrate interactions with Biosensors using surface plasmon resonance (SPR) detection," *Topics in Chemistry*, 2002; vol. 218:93-114.
Hashimoto et al., "KEGG as a glycome informatics resource," *Glycobiology*, May 2006; 16(5):63R-70R. Epub Jul. 13, 2005.

Heimburg-Molinaro et al., "Preparation and analysis of glycan microarrays," *Curr Protoc Protein Sci*, Apr. 2011; Chapter 12:Unit12.10.
Helenius & Aebi, "Intracellular functions of N-linked glycans," *Science*, Mar. 23, 2001; 291(5512):2364-9.
Hess et al., "GROMACS 4: Algorithms for Highly Efficient, Load-Balanced, and Scalable Molecular Simulation," *J Chem Theory Comput*, Mar. 2008; 4(3):435-47.
Honegger et al., "Glycosidase Functions in Sperm-Egg Coat Interaction in Ascidians: a Reconsideration and a New Approach," *Ascidian News* [online]. Dec. 2004. No. 56.
Hou et al., "Assessing the performance of the MM/PBSA and MM/GBSA methods. 1. The accuracy of binding free energy calculations based on molecular dynamics simulations," *J Chem Inf Model*, Jan. 24, 2011; 51(1):69-82. Epub Nov. 30, 2010.
Huang et al., "Chemoenzymatic synthesis and lectin array characterization of a class of N-glycan clusters," *J Am Chem Soc*, Dec. 16, 2009; 131(49):17963-71.
Hummer & Szabo, "Calculation of free-energy differences from computer simulations of initial and final states," *J Chem Physics*, 1996; 105(5):2004-10.
Hutchison et al., "Mutagenesis at a specific position in a DNA sequence," *J Biol Chem*, Sep. 25, 1978; 253(18):6551-60.
Isom et al., "Charges in the hydrophobic interior of proteins," *Proc Natl Acad Sci USA*, Sep. 14, 2010; 107(37):16096-100. Epub Aug. 26, 2010.
Jakeman et al., "A beta-(1,2)-glycosynthase and an attempted selection method for the directed evolution of glycosynthases," *Biochemistry*, Nov. 29, 2011; 50(47):10359-66. Epub Nov. 3, 2011.
Jakobsson et al., "Endosialidases: Versatile Tools for the Study of Polysialic Acid," *Top Curr Chem*, 2015; 367:29-73.
Jiang et al., "De novo computational design of retro-aldol enzymes," *Science*, Mar. 7, 2008; 319(5868):1387-91.
Joao et al., "Effects of glycosylation on protein conformation and amide proton exchange rates in RNase B," *FEBS Lett*, Aug. 3, 1992; 307(3):343-6.
Jokilammi et al. "Construction of antibody mimics from a noncatalytic enzyme-detection of polysialic acid," *J Immunol Meth*, 2004; 295:149-160.
Jorgensen, "The many roles of computation in drug discovery," *Science*, Mar. 19, 2004; 303(5665):1813-8.
Jorgensen, "Efficient Drug Lead Discovery and Optimization," *Acc Chem Res*, Jun. 16, 2009; 42(6):724-33.
Jung & Cho, "Serial affinity chromatography as a selection tool in glycoproteomics," *Anal Chem*, Aug. 6, 2013; 85(15):7125-32. Epub Jul. 10, 2013.
Karanicolas et al., "A De Novo Protein Binding Pair by Computational Design and Directed Evolution," *Mol Cell*, Apr. 22, 2011; 42(2):250-60. Epub Mar. 31, 2011.
Karaveg et al. "Energetics of Substrate Binding and Catalysis by Class 1 (GLycosylhydrolase Family 47)-Mannosidases Involved in N-Glycan Processing and Endoplasmic Reticulum Quality Control," *J Biol Chem*, 2005; 280(33):29837-48.
Karplus & McCammon, "Molecular dynamics simulations of biomolecules," *Nat Struct Biol*, Sep. 2002; 9(9):646-52.
Karplus and Kuriyan, "Molecular dynamics and protein function," *Proc Natl Acad Sci USA*, May 10, 2005; 102(19):6679-85. Epub May 3, 2005.
Kenrick and Daugherty, "Bacterial display enables efficient and quantitative peptide affinity maturation," *Protein Eng Des Sel*, 2010; 23:9-17.
Kirschner et al., "GLYCAM06: A Generalizable Biomolecular Force Field. Carbohydrates," *J Comput Chem*, Mar. 2008. 29(4):622-655. Available online on Sep. 11, 2007.
Kittl and Withers, "New approaches to enzymatic glycoside synthesis through directed evolution," *Carbohydr Res*, Jul. 2, 2010; 345(10):1272-9. Epub Apr. 9, 2010.
Knauer and Lehle, "The oligosaccharyltransferase complex from yeast," *Biochim Biophys Acta*, Jan. 6, 1999; 1426(2):259-73.
Korecka et al. "Bioaffinity magnetic reactor for peptide digestion followed by analysis using bottom-up shotgun proteomics strategy," *J Sep Sci*, Feb. 2008; 31(3):507-15.

(56) References Cited

OTHER PUBLICATIONS

Kornfeld & Kornfeld, "Assembly of asparagine-linked oligosaccharides," *Annu Rev Biochem*, 1985; 54:631-64.
Kozmon and Tvaroška, "Catalytic Mechanism of Glycosyltransferases: Hybrid Quantum Mechanical/Molecular Mechanical Study of the Inverting N-Acetylglucosaminyltransferase I," *J Am Chem Soc*, Dec. 2006;27 128(51):16921-7.
Krishnamoorthy & Mahal, "Glycomic analysis: an array of technologies," *ACS Chem Biol*, Sep. 18, 2009; 4(9):715-32.
Krogh et al., "Protein analysis using enzymes immobilized to paramagnetic beads," *Anal Biochem*, Oct. 1999; 274(2):153-62.
Kuhn et al., "Crystal-Structure of Peptide-$N^4$-(N-Acetyl-β-D-Glucosaminyl)asparagine Amidase F at 2.2-ÅResolution," *Biochemistry*, Oct. 4, 1994; 33(39):11699-706.
Kuhn et al., "Active Site and Oligosaccharide Recognition Residues of Peptide-N4-(N-acetyl-β-D-glucosaminyl)asparagine Amidase F," *Journal of Biological Chemistry*, 1995; 270:29493-29497 (1995).
Kukuruzinska et al., "Protein glycosylation in yeast," *Annu Rev Biochem*, 1987; 56:915-44.
Kuzmanov et al., "The sweet and sour of serological glycoprotein tumor biomarker quantification," *BMC Med*, Feb. 7, 2013; 11:31.
Leach, *Molecular Modelling: Principles and Applications ($2^{nd}$ Edition)*, Pearson: Harlow, England; Apr. 9, 2001. Cover page, title page and table of contents.
Leatherbarrow et al., "Transition-state stabilization in the mechanism of tyrosyl-tRNA synthetase revealed by protein engineering," *Proc Natl Acad Sci USA*, Dec. 1985; 82(23):7840-4.
Lectenz® Bio, "Lectenz® Platform" [retrieved on Jun. 11, 2018]. Available at least as early as Jun. 11, 2018. Retrieved from the Internet: <URL: lectenz.com/technology-2/lectenz-platform>; 6 pgs.
Lee et al., "An optimized approach for enrichment of glycoproteins from cell culture lysates using native multi-lectin affinity chromatography," *J Sep Sci*, Sep. 2012; 35(18):2445-52.
Lemp et al., "Molecular cloning and heterologous expression of N-glycosidase F from Flavobacterium meningosepticum," *J Biol Chem*, 1990; 265(26):15606-10.
Lerner et al., "Evolution of a Catabolic Pathway in Bacteria," *Science*, Dec. 4, 1964; 146(3649):1313-5.
Li and d'Anjou, "Phaunacological significance of glycosylation in therapeutic proteins," *Curr Opin Biotechnol*, Dec. 2009; 20(6):678-84. Epub Nov. 4, 2009.
Lienemann et al., "Toward understanding of carbohydrate binding and substrate specificity of a glycosyl hydrolase 18 family (GH-18) chitinase from Trichoderma harzianum," *Glycobiology*, Jul. 2009; 19(10):1116-26.
Lim et al., "Defining the regulated secreted proteome of rodent adipocytes upon the induction of insulin resistance," *J Proteome Res*, Mar. 2008; 7(3):1251-63. Published online Feb. 1, 2008.
Liener, *The Lectins: Properties, Functions, and Applications in Biology and Medicine*, Academic Press: Orlando, FL; 1986. Cover page, title page and table of contents.
Lo et al., "Optimizing Protein Expresion and Purification of N-glycan Lectenz®: a High Affinity Carbohydrate-Recognizing Protein," Georgia Bio Innovation Summit. Abstract and Poster Presentation, Atlanta, GA; Nov. 2, 2015. 3 pages.
Loo et al., "Using Secretion to Solve a Solubility Problem: High-Yield Expression in *Escherichia coli* and Purification of the Bacterial Glycoamidase PNGase F," *Protein Expression and Purification*, 2002; 24:90-8.
Lopes et al., "Computational design of protein-ligand binding: modifying the specificity of asparaginyl-tRNA synthetase," *J Comput Chem*, Apr. 30, 2010; 31(6):1273-86.
Lundquist and Toone, "The Cluster Glycoside Effect," *Chem Rev*, Feb. 2002; 102(2):555-78.
Lutz, "Beyond directed evolution—semi-rational protein engineering and design," *Curr Opin Biotechnol*, Dec. 2010; 21(6):734-43. Epub Sep. 24, 2010.
Mackerell, Jr., "Empirical force fields for biological macromolecules: overview and issues," *J Comput Chem*, Oct. 2004; 25(13):1584-604.
Manimala et al., "High-throughput carbohydrate microarray profiling of 27 antibodies demonstrates widespread specificity problems," *Glycobiology*, Aug. 2007; 17(8):17C-23C. Epub May 4, 2007.
Martin, "Computationally Guided Mutagenesis: Construction of a Saturation Mutagenesis Phage-Display Library Based on an Inactive OG1cNAcase Mutant," Abstract, PEGS: The Essential Protein Engineering Summit, Boston, MA, Apr. 30-May 4, 2012; 1 pg.
Martin, "Computationally Guided Directed Evolution of O-GlcNAcase into a Reagent Specific for [beta]-O-GlcNAc" Ph D. Thesis Dissertation Abstract, National University of Ireland—Galway, 2013; 3 pages.
Martin, "Computationally Guided Directed Evolution of O-GlcNAcase into a Reagent Specific for [beta]-O-GlcNAc" Ph D. Thesis Dissertation, National University of Ireland—Galway, Dec. 13, 2013; available online [retrieved on Apr. 19, 2018]. Retrieved from the Internet:<URL: hdl.handle.net/10379/4401>; 156 pages.
McCammon et al., "Dynamics of folded proteins," *Nature*, Jun. 16, 1977; 267(5612):585-90.
McCammon, "Theory of biomolecular recognition," *Curr Opin Structural Biology*, Apr. 1998; 8(2):245-9.
McCartney et al., "Glycoside Hydrolase Carbohydrate-Binding Modules as Molecular Probes for the Analysis of Plant Cell Wall Polymers," *Analytical Biochemistry*, Mar. 2004. 326(1): 49-54.
Mega et al., "Characterization of Carbohydrate-Binding Specificity of Concanavalin A by Competitive Binding of Pyridylamino Sugar Chains," *J Biochem*, Mar. 1992; 111(3):396-400.
Meier & Duus, "Carbohydrate dynamics: Antibody glycans wiggle and jiggle," *Nat Chem Biol*, Mar. 2011; 7(3):131-2.
Miller et al., "Construction and screening of antigen targeted immune yeast surface display antibody libraries," *Curr Protoc Cytom*, Jul. 2008; Chapter 4: Unit4.7.
Mills et al., "An extracellular Darwinian experiment with a self-duplicating nucleic acid molecule," *Proc Natl Acad Sci USA*, Jul. 1967; 58(1):217-24.
Moreira et al., "Computational Alanine Scanning Mutagenesis an Improved Methodological Approach," *J Comp Chem*, 2007; 28:644-54. Epub Dec. 28, 2006.
Morris et al., "Selective binding of RNase B glycofolins by polydopamine-immobilized concanavalin A," *Anal Chem*, Jul. 1, 2009; 81(13):5413-20.
Murrell, "The systems biology of glycosylation," *Chembiochem*, 2004; 5(10):1334-47.
Mussar et al., "Peptide: N-glycosidase F: studies on the glycoprotein aminoglycan amidase from Flavobacterium meningosepticum,"*J Biochem Biophys Methods*, 1989; 20(1):53-68.
Nieba et al., "BIACORE analysis of histidine-tagged proteins using a chelating NTA sensor chip," *Anal Biochem*, Oct. 15, 1997; 252(2):217-28.
Noble et al., "A comparison of protein quantitation assays for biophaanaceutical applications," *Mol Biotechnol*, Oct. 2007; 37(2):99-111.
Norris et al., "Purification and crystallization of the endoglycosidase PNGase F, a peptide:N-glycosidase from Flavobacterium meningosepticum," *J Mol Biol*, Aug. 26, 1994; 241(4):624-6.
Norris et al., "The three-dimensional structure of PNGase F, a glycosylasparaginase from Flavobacterium meningosepticum," *Structure*, Nov. 15, 1994; 2(11):1049-59.
Okimoto et al., "High-performance drug discovery: computational screening by combining docking and molecular dynamics simulations," *PLoS Comput Biol*, Oct. 2009; 5(10):e1000528. Epub Oct. 9, 2009.
Ongay et al., "Glycopeptide enrichment and separation for protein glycosylation analysis," *J Sep Sci*, Sep. 2012; 35(18):2341-72.
Parikh et al., "Affinity and Specificity Characterization of Fbs1 via Surface Plasmon Resonance and Glycan Array Screening," (abstract) 2012 CURO (Center for Undergraduate Research Opportunities) Symposium, University of Georgia, Athens, Georgia, Apr. 2, 2012, Poster #47, Program & Abstracts (cover page, title page, program listing, and abstract #47 at pp. 77-78, 6 pages total) [also available electronically as "2012 Book of Abstracts" from the CURO Symposium Books of Abstracts Archive at http://curo.uga.edu/symposium/ ].

(56) References Cited

OTHER PUBLICATIONS

Parikh et al., Affinity and Specificity Characterization of Fbs1 via Surface Plasmon Resonance, (poster) 2012 CURO (Center for Undergraduate Research Opportunities) Symposium, University of Georgia, Athens, Georgia, Apr. 2, 2012, 1 page.
Patel and Hecht, "Directed evolution of the peroxidase activity of a de novo-designed protein," *Protein Eng Des Sel*, Sep. 2012; 25(9):445-52. Epub Jun. 3, 2012.
Patrick and Firth, "Strategies and computational tools for improving randomized protein libraries," *Biomolecular Engineering* 2005; 22:105-112.
Paul et al., "N-Glycan Lectenz® Affinity Chromatography and Biosensors Applications" Georgia Bio Innovation Summit. Abstract and Poster Presentation, Atlanta, GA; Nov. 2, 2015. 3 pages.
Perona et al., "Structural origins of substrate discrimination in trypsin and chymotrypsin," *Biochemistry*, Feb. 7, 1995; 34(5):1489-99.
Pettersen et al., "UCSF Chimera—a visualization system for exploratory research and analysis," *J Comput Chem*, Oct. 2004; 25(13):1605-12.
Pierdominici-Sottile et al., "Free-energy computations identify the mutations required to confer trans-sialidase activity into Trypanosoma rangeli sialidase," *Proteins*, Mar. 2014; 82(3):424-35. Epub Oct. 17, 2013.
Plummer et al., "Demonstration of peptide:N-glycosidase F activity in endo-beta-Nacetylglucosaminidase F preparations," *J Biol Chem*, 1984; 259(17):10700-4.
Porcel et al., "Use of a panel of tumor markers (carcinoembryonic antigen, cancer antigen 125, carbohydrate antigen 15-3, and cytokeratin 19 fragments) in pleural fluid for the differential diagnosis of benign and malignant effusions," *Chest*, Dec. 2004; 126(6):1757-63.
Prien et al., "A multi-method approach toward de novo glycan characterization: a Man-5 case study," *Glycobiology*, May 2010; 20(5):629-47. Epub Jan. 27, 2010.
Rajpal et al. "A general method for greatly improving the affinity of antibodies by using combinatorial libraries," *PNAS*, Jun. 2005; 102(24):8466-71.
Raman et al., "Glycomics: an integrated systems approach to structure-function relationships of glycans," *Nat. Methods*, 2005; 2(11):817-24.
Rao et al., "Mutations of endo-beta-N-acetylglucosaminidase H active site residueAs sp130 anG glu132: activities and conformations," *Protein Sci*, Nov. 1999; 8(11):2338-46.
Rayon et al., "The protein N-glycosylation in plants," *J Exper Botany*, Sep. 1998; 49(326):1463-72.
"The Research Group of Professor Robert J. Woods," GLYCAM; The University of Georgia I Complex Carbohydrate Research Center: Athens, GA. Available online [retrieved on Aug. 19, 2011]. Retrieved from the Internet: <glycam.ccrc.uga.edu/ccrc/pages/ri.html>; 4 pgs.
Roe and Cheatham, "PTRAJ and CPPTRAJ: Software for Processing and Analysis of Molecular Dynamics Trajectory Data," *J Chem Theory Comput*, Jul. 9, 2013; 9(7):3084-95. Epub Jun. 25, 2013.
Rudd et al., "Separation and analysis of the glycoform populations of ribonuclease B using capillary electrophoresis," *Glycoconj J*, Apr. 1992; 9(2):86-91.
Rye & Withers, "Glycosidase mechanisms," *Curr Opin Chem Biol*, Oct. 2000; 4(5):573-80.
Samli and Joshi, "Differential Glycome Gene Expression Profiling of Human Embryonic Stem Cells and Mesenchymal Stem Cells" 8th Jenner Glycobiology and Medicine Symposium, Royal Society of Medicine, University College Dublin, Oct. 21-23, 2007. 1 page.
Samli et al., "Developing Novel Glycan Binding Agents," Conference Abstract in Glycobiology, 2008; 18(11):953.
Samli et al., "Glycoinformatics: Text Mining Lectin and Glycan Interactions in Bioprocesses," Conference Abstract in *Glycobiology*, 2008; 18(11):975.
Samli et al., "Lectenz®: Carbohydrate-Binding Biomolecules Engineered via Computational Modeling and Directed Evolution," Graduate Students and Postdocs in Science 3rd Annual Scientific Research Day. Abstract and Presentation. The University of Georgia, Athens, GA; May 20, 2011. 32 pages.
Samli et al., "Lectenz (R): Carbohydrate-Binding Biomolecules Engineered via Computational Modeling and Directed Evolution," Conference Paper in *Glycobiology*, Nov. 2011; 21(11):1482.
Samli et al., "Lectenz®: Carbohydrate-Binding Biomolecules Engineered via Computationally Modeling and Direct Evolution," Eighth Annual Protein Engineering Summit. Abstract. Boston, MA; Apr. 30-May 4, 2012. 1 page.
Samli et al., "Engineering a High Affinity Carbohydrate-Recognizing Protein via in silico Modeling and Directed Evolution," (poster), 2012 Georgia Life Sciences, Atlanta, GA, Oct. 3, 2012, 1 page.
Samli et al., "Engineering a High Affinity Carbohydrate-Recognizing Protein via in silico Modeling and Directed Evolution" (abstract) 2012 Georgia Life Sciences Summit, Atlanta, GA, Oct. 3, 2012, Poster #61, Conference Program eBook, at p. 68 (91 pages).
Samli et al., "Engineering Carbohydrate Recognizing Biosensors via Computational Modeling and Directed Evolution" (abstract), The 2012 Joint Meeting of the Society for Glycobiology and American Society for Matrix Biology, San Diego, CA, USA, Nov. 11-14, 2012; Conference Program and Abstracts published in Glycobiology, 22(11 ): 1487-1661 (Nov. 1, 2012) (175 pages); abstract #44 at p. 1533 [also available electronically at https://academic.oup.com/glycob/article-lookup/doi/10.1093/glycob/cws127].
Samli et al., "Engineering Carbohydrate Recognizing Biosensors via Computational Modeling and Directed Evolution," Conference Paper in *Glycobiology*, Nov. 2012; 22(11):1533.
Samli et al., "Targeting Glycans with Lectenz®: Engineered Glycan—Binding Biomolecules," Ninth Annual Protein Engineering Summit. Poster. Boston, MA; Apr. 29-May 3, 2013. 1 page.
Samli, "Lectenz: Carbohydrate-Recognizing Biosensor Engineered via Computationally-Guided Directed Evolution," Ph D. Thesis Dissertation Oral Presentation Slides, The University of Georgia, Athens, Georgia, Apr. 18, 2014; 78 pages.
Samli, "Lectenz: Carbohydrate-Recognizing Biosensor Engineered via Computationally-Guided Directed Evolution," Ph D. Thesis Dissertation, The University of Georgia, Athens, Georgia, 2016; 181 pages.
Saul et al., "Crystal structure of Urtica dioica agglutinin, a superantigen presented by MHC molecules of class I and class II," *Structure*, Jun. 15, 2000; 8(6):593-603.
Schlick et al., "Inhibition binding studies of glycodendrimerlectin interactions using surface plasmon resonance," *Tetrahedron*, Jul. 17, 2010; 66(29):5305-10.
Schneider et al., "NIH Image to ImageJ: 25 years of image analysis," *Nat Methods*, Jul. 2012; 9(7):671-5.
Scouras et al., "The dynameomics rotamer library. Amino acid side chain conformations and dynamics from comprehensive molecular dynamics simulations in water," *Protein Sci*, Feb. 2011; 20(2):341-52.
Shim et al., "Directed evolution of a beta-glycosidase from *Agrobacterium* sp. to enhance its glycosynthase activity toward C3-modified donor sugars," *Protein Eng Des Sel*, Sep. 2012; 25(9):465-72.
Showalter and Brüschweiler, "Validation of Molecular Dynamics Simulations of Biomolecules Using NMR Spin Relaxation as Benchmarks: Application to the AMBER99SB Force Field," *J Chem Theory Comput*, May 2007; 3(3):961-75.
Sievers et al., "Fast, scalable generation of high-quality protein multiple sequence alignments using Clustal Omega," *Mol Syst Biol*, Oct. 11, 2011; 7:539.
Sigal et al., "Thiol-beta-lactamase: replacement of the active-site serine of RTEM beta-lactamase by a cysteine residue," *Proc Natl Acad Sci USA*, Dec. 1982; 79(23):7157-60.
Smith, "Filamentous fusion phage: novel expression vectors that display cloned antigens on the virion surface," *Science*, Jun. 14, 1985; 228(4705):1315-7.
Socha and Tokuriki, "Modulating protein stability—directed evolution strategies for improved protein function," *FEBS J*, Nov. 2013; 280(22):5582-95. Epub Jun. 18, 2013.

(56) References Cited

OTHER PUBLICATIONS

Steinbrecher and Labahn, "Towards accurate free energy calculations in ligand protein-binding studies," *Curr Med Chem*, 2010; 17(8):767-85.
Stoltenburg et al., "SELEX—A (r)evolutionary method to generate high-affinity nucleic acid ligands," *Biomol Eng*, Oct. 2007; 24(4):381-403. Epub Jun. 16, 2007.
Stone et al., "T cell receptor engineering," *Methods Enzymol*, 2012; 503:189-222.
Stortz et al., "Comparison of different force fields for the study of disaccharides," *Carbohydrate Research*, Nov. 2, 2009; 344(16):2217-28. Epub Aug. 22, 2009.
Sun et al., "Identification and Characterization of a Novel Prokaryotic Peptide: N-glycosidase From Elizabethkingia Meningoseptica," *J Biol Chem*, Mar. 20, 2015; 290(12):7452-62.
Takashima and Amano, "Glycosylation and secretion of human α-amylases," *Advances in Biological Chemistry*, Feb. 2012; 2:10-9.
Taniguchi et al., "The Second Golden Age of Glycomics: From Functional Glycomics to Clinical Applications," *J Proteome Res*, Feb. 2009; 8(2):425-6.
Tarentino et al., "Deglycosylation of asparagine-linked glycans by peptide:N-glycosidase F," *Biochemistry*, Aug. 13, 1985; 24(17):4665-71.
Tatusova et al, "BLAST 2 Sequences, a new tool for comparing protein and nucleotide sequences," *FEMS Microbiol Lett*, 1999; 174:247-250.
Taylor and Drickamer, Introduction to glycobiology, Edn. 2nd. (Oxford University Press, Oxford ; New York; 2006). Cover page, title page and table of contents.
Taylor and Drickamer, "Structural insights into what glycan arrays tell us about how glycan-binding proteins interact with their ligands," *Glycobiology*, Nov. 2009; 19(11):1155-62. Epub Jun. 15, 2009.
Taylor-Papadimitriou et al., "MUC1 and cancer," *Biochim Biophys Acta*, Oct. 8, 1999; 1455(2-3):301-13.
Thompson et al., "Heparan sulfate phage display antibodies identify distinct epitopes with complex binding characteristics: insights into protein binding specificities," *J Biological Chem*, Dec. 18, 2009; 284(51):35621-31. Epub Oct. 16, 2009.
Tinberg et al., "Computational design of ligand-binding proteins with high affinity and selectivity," *Nature*, Sep. 12, 2013; 501(7466):212-6. Epub Sep. 4, 2013.
Tobin et al., "Directed evolution: the 'rational' basis for 'irrational' design," *Curr Opin Struct Biol*, Aug. 2000; 10(4):421-7.
Tohidkia et al., "Molecular considerations for development of phage antibody libraries," *J Drug Targeting*, Apr. 2012; 20(3):195-208. Epub Sep. 27, 2011.
"Translational Research: merging computational modeling and protein engineering to design biomolecules," Available online [retrieved on Aug. 19, 2011]. Retrieved from the Internet: <ksamli.myweb.uga.edu/Research.html>; p. 1 of 2.
Tretter et al., "Peptide-N4-(N-acetyl-beta-glucosaminyl)asparagine amidase F cannot release glycans with fucose attached alpha 1-3 to the asparagine-linked N-acetylglucosamine residue," *Eur J Biochem*, Aug. 1, 1991; 199(3):647-52.
Tsui and Case, "Theory and Applications of the Generalized Born Solvation Model in Macromolecular Simulations," *Biopolymers*, 2001. 56:275-291. Available online on Dec. 4, 2001.
UniProt Consortium, "Activities at the Universal Protein Resource (UniProt)," *Nucleic Acids Res*, Jan. 2014; 42(Database Issue):D191-8. Epub Nov. 18, 2013.
Van Gunsteren et al., Computation of Free Energy in Practice: Choice of Approximations and Accuracy Limiting Factors, vol. 2. (ESCOM, Leiden; 1993). Cover page, title page and table of contents.
Venekei et al., "Attempts to convert chymotrypsin to trypsin," *FEBS Lett*, Jan. 29, 1996; 379(2):143-7. Corrected and republished Mar. 25, 1996.
Voigt et al., "Computationally focusing the directed evolution of proteins," *J Cell Biochem Suppl Suppl*, 2001; 37:58-63.
Wang et al., "Poisson-Boltzmann Solvents in Molecular Dynamics Simulations," *Comm Computational Physics*, May 2008; 3(5):1010-1031. Epub Jan. 24, 2008.
Wang et al., "N-Terminal Deletion of Peptide:N-Glycanase Results in Enhanced Deglycosylation Activity," *PLoS One*, Dec. 16, 2009; 4(12):e8335.
Weatherly et al., "A Heuristic method for assigning a false-discovery rate for protein identifications from Mascot database search results," *Mol Cell Proteomics*, Jun. 2005; 4(6):762-72. Epub Feb. 9, 2005.
Weerapana et al., "Asparagine-linked protein glycosylation: from eukaryotic to prokaryotic systems," *Glycobiology*, 2006; 16(6):91R-101R.
White et al., "Genome sequence of the radioresistant bacterium *Deinococcus radiodurans* R1," *Science*, Nov. 19, 1999; 286(5444):1571-7.
Wijma & Janssen, "Computational design gains momentum in enzyme catalysis engineering," *FEBS J*, Jul. 2013; 280(13):2948-60. Epub Jun. 3, 2013.
Wijma et al., "Computationally designed libraries for rapid enzyme stabilization," *Protein Eng Des Sel*, Feb. 2014; 27(2):49-58. Epub Jan. 8, 2014.
Willard and Siderovski, "Covalent immobilization of histidine-tagged proteins for surface plasmon resonance," *Anal Biochem*, Jun. 1, 2006; 353(1):147-9. Epub Feb. 23, 2006.
Winter et al., "Redesigning enzyme structure by site-directed mutagenesis: tyrosyl tRNA synthetase and ATP binding," *Nature*, Oct. 21, 1982; 299(5885):756-8.
Woods, "Glycoprotein Structure /Protein-Carbohydrate Interaction," Grant Abstract, Grant No. 2P41RR005351-16, Subproject 0161 [online] National Center for Research Resources, National Institutes of Health, project dates Apr. 4, 2005 to Jan. 31, 2006 [retrieved on Sep. 25, 2014]. Retrieved from the Internet: <http://projectreporter.nih.gov/pr Prj_ info_ desc dtls.cfm ?aid=7181478&icde=21876699&ddparam=&ddvalue=&ddsub=&cr=85&csb=default&cs=ASC&print=yes>; 1 pg.
Woods, "High-Specificity Affinity Reagents for N-Glycosylation Site Mapping and Glycomics," Grant Abstract, Grant No. GM086991 [online]. National Institute of General Medical Sciences, National Institutes of Health, project dates Sep. 1, 2009 to Aug. 31, 2011 [retrieved on Jan. 15, 2013]. Retrieved from the Internet: <http://projectreporter.nih.gov/pr_Prj_info_desc_dtls.cfm?aid=7671759&icde=14958299&ddparam=&ddvalue=&ddsub=&cr=1 &csb=default&cs=ASC&print=yes>; 2 pgs.
Woods et al., "Molecular Mechanical and Molecular Dynamic Simulations of Glycoproteins and Oligosaccharides. 1. GLYCAM_93 Parameter Development," *J Phys Chem*, Mar. 1995; 99(11):3832-46.
Woods & Tessier, "Computational glycoscience: characterizing the spatial and temporal properties of glycans and glycan-protein complexes," *Curr Opin Struct Biol*, Oct. 2010; 20(5):575-83. Epub Aug. 12, 2010.
Wright, "2.2 A resolution structure analysis of two refined N-acetylneuraminyl-lactose—wheat germ agglutinin isolectin complexes," *J Mol Biol*, Oct. 20, 1990; 215(4):635-51.
Wu et al., "Novel Sialoglycan Lectenz® Reagents," 11th Georgia Glycoscience Symposium. Abstract and Poster Presentation, Athens, GA; Apr. 25, 2017. 2 pages.
Yang et al., "Development of a Glycoprofiling Method Using Multiplex Flow Cytometry," USP Workshop on Glycosylation Analysis for Biopharmaceuticals. Abstract and Poster Presentation, Rockville, MD; Aug. 25-26, 2015.
Yang et al., "A Rapid Method for Monitoring Glycosylation Features during Biomanufacturing," Biomanufacturing Technology Summit Abstract and Poster Presentation, Rockville, MD; Jun. 23, 2016.
Yip et al., "Directed evolution combined with rational design increases activity of GpdQ toward a non-physiological substrate and alters the oligomeric structure of the enzyme," *Protein Eng Des Sel*, Dec. 2011; 24(12):861-72. Epub Oct. 6, 2011.
Yu et al., "Phage display screening against a set of targets to establish peptidebased sugar mimetics and molecular docking to predict binding site," *Bioorg Med Chem*, Jul. 1, 2009; 17(13):4825-32. Epub Apr. 1, 2009.

(56) References Cited

OTHER PUBLICATIONS

Zauner et al., "Protein glycosylation analysis by HILIC-LC-MS of Proteinase K-generated N- and O-glycopeptides," *J Sep Sci*, Mar. 2010; 33(6-7):903-10.

Zhang et al., "UniPep—a database for human N-linked glycosites: a resource for biomarker discovery," *Genome Biol*, 2006; 7(8):R73. Epub Aug. 10, 2006.

Zhang et al., "Modification of histones by sugar beta-N-acetylglucosamine (GlcNAc) occurs on multiple residues, including histone H3 serine 10, and is cell cycle-regulated," *J Biol Chem*, Oct. 28, 2011; 286(43):37483-95. Epub Sep. 6, 2011.

Zhao et al, "Structural and mutational studies on the importance of oligosaccharide binding for the activity of yeast PNGase," *Glycobiology*, Feb. 2009; 19(2):118-25. Epub Oct. 14, 2008.

Zoete et al., "MM-GBSA binding free energy decomposition and T cell receptor engineering," *J Mol Recognit*, Mar.-Apr. 2010; 23(2):142-52.

Declaration concerning the publication date of Samli's PhD Thesis titled, "Lectenz: Carbohydrate-Recognizing Biosensor Engineered via Computationally-Guided Directed Evolution," as evidence that the publication was subject to a two-year publication embargo and filed in corresponding EP Patent Application No. 15 78 0061.6. Signed by Dean Suzanne Barbour, Dean of the Graduate School at the University of Georgia, Jan. 2, 2018; 25 pages.

* cited by examiner

Fig. 4
a)

```
        GCTCCGGCAGATAATACGGTAAATATTAAAACATTCGACAAAGTAAAAAATGCCTTT         57
  1      A  P  A  D  N  T  V  N  I  K  T  F  D  K  V  N  A  F

GGTGACGGATTGTCCCAAAGTGCGGAAGGAACCTTTACATTTCCGGCGATGTAACAGCC        117
 20      G  D  G  L  S  Q  S  A  E  G  T  F  T  F  P  A  D  V  T  A
                                                                   T

GTAAAAACGATTAAGATGTTCATTAAAAATGAATGTCCTAATAAAACTTGTGATGAATGG       177
 40      V  K  T  I  K  M  F  I  K  N  E  C  P  N  K  T  C  D  E  W

GATCGTTATGCCAATGTTTATGTAAAAAATAAAACAACAGGTGAGTGGTACGAAATAGGA       237
 60      D  R  Y  A  N  V  Y  V  K  N  K  T  T  G  E  W  Y  E  I  G

CGCTTTATTACTCCATATTGGGTGGGAACGGAAAAATTACCTCGTGGACTGGAAATTGAT       297
 80      R  F  I  T  P  Y  W  V  G  T  E  K  L  P  R  G  L  E  I  D

GTTACAGATTTCAAATCTTTACTATCCGGAAATACAGAACTTAAAATTTATACGGAGACA       357
100      V  T  D  F  K  S  L  L  S  G  N  T  E  L  K  I  Y  T  E  T

TGGCTGGCCAAAGGAAGAGAATACAGTGTAGATTTCGATATTGTATACGGGACACCGGAT       417
120      W  L  A  K  G  R  E  Y  S  V  D  F  D  I  V  Y  G  T  P  D

TATAAATATTCGGCTGTAGTACCTGTAGTTCAGTATAACAAATCATCTATTGACGGAGTC       477
140      Y  K  Y  S  A  V  V  P  V  V  Q  Y  N  K  S  S  I  D  G  V
                                  I

CCTTATGGTAAAGCACATACATTGGCTTTGAAAAAGAATATCCAGTTACCAACAAACACA       537
160      P  Y  G  K  A  H  T  L  A  L  K  K  N  I  Q  L  P  T  N  T
                                  G

GAAAAAGCTTATCTTAGAACTACTATTTCCGGATGGGGACATGCTAAGCCATATGATGCG       597
180      E  K  A  Y  L  R  T  T  I  S  G  W  G  H  A  K  P  Y  D  A

GGAAGCAGAGGTTGTGCAGAATGGTGCTTCAGAACACACACTATAGCAATAAATAATTCG       657
200      G  S  R  G  C  A  E  W  C  F  R  T  H  T  I  A  I  N  N  S
                                                                   A

AATACTTTCCAGCATCAGCTGGGTGCTTTAGGATGTTCAGCAAACCCTATCAATAATCAG       717
220      N  T  F  Q  H  Q  L  G  A  L  G  C  S  A  N  P  I  N  N  Q

AGTCCGGGAAATTGGACTCCCGACAGAGCCGGTTGGTGCCCGGGAATGGCAGTTCCAACA       777
240      S  P  G  N  T  P  D  R  A  G  W  C  P  G  M  A  V  P  T
                  I  A

CGTATAGATGTACTGAATAATTCTTTAATAGGCAGTACTTTTAGTTATGAATATAAATTC       837
260      R  I  D  V  L  N  N  S  L  I  G  S  T  F  S  Y  E  Y  K  F
                                  T

CAGAACTGGACAAATAACGGAACCAATGGAGATGCTTTTTATGCAATTTCCAGTTTTGTG       897
280      Q  N  W  T  N  N  G  T  N  G  D  A  F  Y  A  I  S  S  F  V
            S

ATTGCAAAAAGTAATACACCTATTAGTGCTCCGGTAGTTACAAACTAA                   945
300      I  A  K  S  N  T  P  I  S  A  P  V  V  T  N  *
```

Fig. 4
c)

```
          10         20         30         40         50
   MLFFLPLLKT NLMQKILLCS LITGAQMIFA QTYEITYQNS FEGKINPNQN
          60         70         80         90        100
   HIISITNSDK TLLFNEKIKN KKADFPFEVN EINRKNNEVS QFAFLNNNEI
         110        120        130        140        150
   VKTSDNTILA KQEFKPTSET GKILGYNVKK AVTSVNSNTI EVWYTNDLKV
         160        170        180        190        200
   KGGPSILGQD LGLVLKTVRN GSSVVEATSV KKIKALDDQS LFNGKNITEK
         210        220        230        240        250
   DALTYKDMIW KSRFITIPVF ENETINFSDA SKSDQVIQRF GNGTIILKKV
         260        270        280        290        300
   KIPEIKQGNT IFVELKQKSN GDAYDRTGDV FIIPQERAIS YYTGLTQGVK
         310        320        330        340        350
   SLPVYQNGNG KSYQGVALTP DYLPFIELMR FFTPFGIGHF NEKIQLKGKN
         360        370        380        390        400
   WHNNTPYRQD ITELRPQLSG KEILIGAFIG NYDKGGHQIS LELSIHPDQQ
         410        420        430        440        450
   KIVNNNFVLP VFNTTNVMEM AGQDYPTMFN SDKGVEVEFI LTKDLKNAQL
         460        470        480        490        500
   RYITTGHGGW GAGDEFVPKE NSIYLDGKLA HAFTPWRTDC GSYRLFNPAS
         510        520        530        540        550
   GNFEDGLSSS DLSRSNWCPG TITNPVYINL GNLNAGKHTI QVKIPQGAPE
         560
   GSSQSFWNVS GVLLGQE
```

Fig. 4
d)

```
              10         20         30         40         50
      MNIRLTSLFV SLFLSVPVWA GGHKNLPAKG DLHIPVFENV NVRFSPDTYP
              60         70         80         90        100
      DNYNEADGTG VYHLVNGRII LKKITLPEYK RNVSVSLKVT LASNGDRWDK
             110        120        130        140        150
      SGSCFVLPKS SAINLLTIAR DGMKFPSVDS LKLEKMVGIV PGKDYLPTVE
             160        170        180        190        200
      LMRFMTPFGI GHYSNNNDSL SSKRRPVYIP KWESNVTWQQ DITDLYPLLE
             210        220        230        240        250
      GEAYVGIYID TWTSEGYLVN ADIDVKESRL ACDVLPKRHV EPLMNTVYYM
             260        270        280        290        300
      GQSYPDIFAR RDVSTDFTVP KGAKNIRLKY IVTGHGGHSG GDEFVQKRNI
             310        320        330        340        350
      ISVDGKEVLN FIPWRDDCAS FRRFNPATGV WLIKRLASYI GEKGYTEKEV
             360        370        380        390        400
      EEPLASSDLS RSNWCPGSDV VPEEAVIGTL APGKHTFTVS IPEAQAVDGN
             410
      KLNHWLVSAY LVWEE
```

Fig. 4
e)

```
         10         20         30         40         50
MRKLLIFSIS AYLMAGIVSC KGVDSATPVT EDRLALNAVN APADNTVNIK
         60         70         80         90        100
TFDKVKNAFG DGLSQSAEGT FTFPADVTTV KTIKMFIKNE CPNKTCDEWD
        110        120        130        140        150
RYANVYVKNK TTGEWYEIGR FITPYWVGTE KLPRGLEIDV TDFKSLLSGN
        160        170        180        190        200
TELKIYTETW LAKGREYSVD FDIVYGTPDY KYSAVVPVIQ YNKSSIDGVP
        210        220        230        240        250
YGKAHTLGLK KNIQLPTNTE KAYLRTTISG WGHAKPYDAG SRGCAEWCFR
        260        270        280        290        300
THTIAINNAN TFQHQLGALG CSANPINNQS PGNWAPDRAG WCPGMAVPTR
        310        320        330        340        350
IDVLNNSLTG STFSYEYKFQ SWTNNGTNGD AFYAISSFVI AKSNTPISAP

VVTN
```

Fig. 4 f)
```
          →
     G  I  P  A  P  A  D  N  T  V  N  I  K  T  F  D  K  V  K  N
   GGAATTCCAGCTCCGGCAGATAATACGGTAAATATTAAAACATTCGACAAAGTAAAAAAT
          10        20        30        40        50        60
     A  F  G  D  G  L  S  Q  S  A  E  G  T  F  T  F  P  A  D  V
   GCCTTTGGTGACGGATTGTCCCAAAGTGCGGAAGGAACCTTTACATTTCCGGCCGATGTA
          70        80        90       100       110       120
     T  A  V  K  T  I  K  M  F  I  K  N  E  C  P  N  K  T  C  D
   ACAGCCGTAAAAACGATTAAGATGTTCATTAAAAATGAATGTCCTAATAAAACTTGTGAT
         130       140       150       160       170       180
     E  W  D  R  Y  A  N  V  Y  V  K  N  K  T  T  G  E  W  Y  E
   GAATGGGATCGTTATGCCAATGTTTATGTAAAAAATAAAACAACAGGTGAGTGGTACGAA
         190       200       210       220       230       240
     I  G  R  F  I  T  P  Y  W  V  G  T  E  K  L  P  R  G  L  E
   ATAGGACGCTTTATTACTCCATATTGGGTGGGAACGGAAAAATTACCTCGTGGACTGGAA
         250       260       270       280       290       300
     I  D  V  T  D  F  K  S  L  L  S  G  N  T  E  L  K  I  Y  T
   ATTGATGTTACAGATTTCAAATCTTTACTATCCGGAAATACAGAACTTAAAATTTATACG
         310       320       330       340       350       360
     E  T  W  L  A  K  G  R  E  Y  S  V  D  F  D  I  V  Y  G  T
   GAGACATGGCTGGCCAAAGGAAGAGAATACAGTGTAGATTTCGATATTGTATACGGGACA
         370       380       390       400       410       420
     P  D  Y  K  Y  S  A  V  V  P  V  V  Q  Y  N  K  S  S  I  D
   CCGGATTATAAATATTCGGCTGTAGTACCTGTAGTTCAGTATAACAAATCATCTATTGAC
         430       440       450       460       470       480
     G  V  P  Y  G  K  A  H  T  L  A  L  K  K  N  I  Q  L  P  T
   GGAGTCCCTTATGGTAAAGCACATACATTGGCTTTGAAAAAGAATATCCAGTTACCAACA
         490       500       510       520       530       540
     N  T  E  K  A  Y  L  R  T  T  I  S  G  W  G  H  A  K  P  Y
   AACACAGAAAAAGCTTATCTTAGAACTACTATTTCCGGATGGGGACATGCTAAGCCATAT
         550       560       570       580       590       600
     D  A  G  S  R  G  C  A  E  W  C  F  R  T  H  T  I  A  I  N
   GATGCGGGAAGCAGAGGTTGTGCAGAATGGTGCTTCAGAACACACACTATAGCAATAAAT
         610       620       630       640       650       660
     N  S  N  T  F  Q  H  Q  L  G  A  L  G  C  S  A  N  P  I  N
   AATTCGAATACTTTCCAGCATCAGCTGGGTGCTTTAGGATGTTCAGCAAACCCTATCAAT
         670       680       690       700       710       720
     N  Q  S  P  G  N  W  T  P  D  R  A  G  W  C  P  G  M  A  V
   AATCAGAGTCCGGGAAATTGGACTCCCGACAGAGCCGGTTGGTGCCCGGGAATGGCAGTT
         730       740       750       760       770       780
     P  T  R  I  D  V  L  N  N  S  L  I  G  S  T  F  S  Y  E  Y
   CCAACACGTATAGATGTACTGAATAATTCTTTAATAGGCAGTACTTTTAGTTATGAATAT
         790       800       810       820       830       840
     K  F  Q  N  W  T  N  N  G  T  N  G  D  A  F  Y  A  I  S  S
   AAATTCCAGAACTGGACAAATAACGGAACCAATGGAGATGCTTTTTATGCAATTTCCAGT
         850       860       870       880       890       900
     F  V  I  A  K  S  N  T  P  I  S  A  P  V  V  T  N  L  D  P
   TTTGTGATTGCAAAAAGTAATACACCTATTAGTGCTCCGGTAGTTACAAACTTGGATCCG
         910       920       930       940       950       960

H  H  H  H  H  H  *
   CATCACCATCACCACCATTGA
         970       980
```

Fig. 4
g)

```
PNGase F F. meningosepticum(pOPH6)    ------------------------------------------------------------
PNGase F F. meningosepticum           ------------------------------------------------------------
PNGase F F. miricola                  ------------------------------------------------------------
PNGase F B. fragilis                  ------------------------------------------------------------
PNGase F-II F. meningoseptica         MLFFLPLLKTNLMQKILLCSLITGAQMIFAQTYEITYQNSFRGKINPNQNHIISITNSDK PNGase F F. meningosepticum(pOPH6)    ------------------------------------------------------------
PNGase F F. meningosepticum           ------------------------------------------------------------
PNGase F F. miricola                  ------------------------------------------------------------
PNGase F B. fragilis                  ------------------------------------------------------------
PNGase F-II F. meningoseptica         TLLFNEKIKNKKALFPPEVNEINRKNNEVSQFAPLNNNEIVKTSDNTILAKQEFKPTSET PNGase F F. meningosepticum(pOPH6)    ------------------------------------------------------------
PNGase F F. meningosepticum           ------------------------------------------------------------
PNGase F F. miricola                  -----------------------------------------------------------N
PNGase F B. fragilis                  ------------------------------------------------------------
PNGase F-II F. meningoseptica         GKILGYNVKKAVTSVNSNTIEVWYINDLKVKGGPSILGQDLGLVLKTVRNGSSVVEATSV PNGase F F. meningosepticum(pOPH6)    ----------------------------------------APADNTVNIKTFDKVKNAFG
PNGase F F. meningosepticum           ----------------------------------------APADNTVNIKTFDKVKNAFG
PNGase F F. miricola                  RKLLIPSISAYLM-AGIVSCKGVDSATPVTEDPLALNAVNAPADNTVNIKTFDKVKNAFG
PNGase F B. fragilis                  ---MNIELTSLPV--------SLFLSVP----VNASQHKNLPAKGDLHIPVFENVRVEFE
PNGase F-II F. meningoseptica         KKIKALDDQSLFNGKNITEKEALTYKDM----INK--------SRFITIPVFENETINFS
                                                                                 .  : * .*(:   *.

PNGase F F. meningosepticum(pOPH6)    DG-------------LSQSAEGTFTFPAD-VTAVK-TIKMFIKNECPNKTCDEWDRYANV
PNGase F F. meningosepticum           DG-------------LSQSAEGTFTFPAD-VTTVK-TIKMFIKNECPNKTCDEWDRYANV
PNGase F F. miricola                  DG-------------LSQSAEGTFTFPAD-VTTVK-TIKMFIKNECPNKTCDEWDRYANV
PNGase F B. fragilis                  PDTYPDNYNEADGTGVYHLVNGRIILKKITLPEYKRNVSVSL-KVTLASNGDRWDKSGSC
PNGase F-II F. meningoseptica         DASKSDQ------VIQRFGNGTIILKKVKIPEIKQGNTIFV-ELKQKSNGDAYDRTSDV
                                                  :   :*   :    *    :*   *   ..  *   : *.  ..

PNGase F F. meningosepticum(pOPH6)    YVKNKT-------------------------------TSENYEIGRFITPYWVSTE
PNGase F F. meningosepticum           YVKNKT-------------------------------TSENYEIGRFITPYWVSTE
PNGase F F. miricola                  YVKNKT-------------------------------TSENYEIGRFITPYWVSTE
PNGase F B. fragilis                  FVLPKSSAINLLTIARDSMKF-PSVDGLKLEKMVGIVPGKDYLPTVELMRFWTPFGISHY
PNGase F-II F. meningoseptica         FIIPQSRAISYYTGLTQSVKSLPVYQNSNGKSYQGVALTPDYLPFIELMRFPTPFGISHP
                                       ::  :                                 *:  **;/**;  ;*
```

Fig. 4
g) continued

```
PNGase F F. meningosepticum(pOPH6)    KL--------------------PRGLEIDVTDFKSLLSGHT-ELKIYTETWLAKGREYSVD
PNGase F F. meningosepticum           EL--------------------PRGLEIDVTDFKSLLGQNT-ELKIYTETWLAPGREYSVD
PNGase F F. miricola                  EL--------------------PRGLEIDVTDFKSLLGQNT-ELKIYTETWLAPGREYSVD
PNGase F B. fragilis                  SMNNDSLSSKERPVYIPKNESNVTNQQDITDLYPLLEGEA-YVGIYIDTWTSEGPLVRAD
PNGase F-II F. meningoseptica         NEKIQ--------LKGKNWHNNTFYRQDITELRPQLGGKEILIGAPIGNYDKGSHQISLE
                                         *;*:    *.*;        ;     *   ;

PNGase F F. meningosepticum(pOPH6)    PEIVYSTPDYKY---SAVVPVVQYN-KSSIDSVPYGKA--HTLALKKNIQLPTN---TEK
PNGase F F. meningosepticum           PEIVYSTPDYKY---SAVVPVIQYN-KSSIDSVPYGKA--HTLGLKKNIQLPTN---TEK
PNGase F F. miricola                  PEIVYSTPDYKY---SAVVPVIQYN-KSSIDSVPYGKA--HTLGLKKNIQLPTN---TEK
PNGase F B. fragilis                  IDVKESPLACDVLPKRNVEPLMN----TVVYMSQSYDDLPAR-PDVSTDPFTVPKGAKNIRL
PNGase F-II F. meningoseptica         LSIHPDQQ--KIVNSNFVLEVPNTTNVMEMAQQDYPTMFNSDKGVEVEFILTKDLKNAQL
                                        .:      *  *;;    *  *      .. ..

PNGase F F. meningosepticum(pOPH6)    AYLKTTISGWSHAKPYDAGSRGCAEWCFRTHTIAINNSNTFQHQLGALGCSANPINNQSP
PNGase F F. meningosepticum           AYLKTTISGWSHAKPYDAGSRGCAEWCFRTHTIAINNANTFQHQLGALGCSANPINNQSP
PNGase F F. miricola                  AYLKTTISGWSHAKPYDAGSRGCAEWCFRTHTIAINNANTFQHQLGALGCSANPINNQSP
PNGase F B. fragilis                  KYIVTGHSGHSGGDEFVQ----------KRNIISVDGKEVLSFIPNRDDCASPRPFNPAT
PNGase F-II F. meningoseptica         RYITTGHGSNGAGDEFVP----------KRNSIFLDQKLAHAFTPNRTDCGSYRLPNFAS
                                       *;  *  .*    .  :           :    .           .:  .  *  *  :

PNGase F F. meningosepticum(pOPH6)    GNW--------------------TPDPAGNCPSMAVPTRIDVLMNSLIGGTFSY
PNGase F F. meningosepticum           GNW--------------------APDPAGNCPSMAVPTRIDVLMNSLTGGTFSY
PNGase F F. miricola                  GNW--------------------APDPAGNCPSMAVPTRIDVLMNSLTGGTFSY
PNGase F B. fragilis                  GVWLIKRLASYIGEKGYTEKEVEEPLASSDLSRSNNCPGSDVVPEEAVIGTLAPGKH-TF
PNGase F-II F. meningoseptica         GNP--------------------EDGLGSSDLSRSNNCPGTITNPVYIRLGNLNAGKH-TI
                                       *  :                     . : ****        .  .    *. :

PNGase F F. meningosepticum(pOPH6)    EYKPQNWTNNGTNGDAFYAISSPVIAKSNTPISAPVVTN
PNGase F F. meningosepticum           EYKPQSWTNNGTNGDAFYAISSPVIAKSNTPISAPVVTN
PNGase F F. miricola                  EYKPQSWTNNGTNGDAFYAISSPVIAKSNTPISAPVVTN
PNGase F B. fragilis                  TVGIPEAQAYIGNKLNHWLVSAYLVWER-----------
PNGase F-II F. meningoseptica         QVKIPQGAP-ESSSQSPWNVSGVLLQGE-----------
                                        .;        .: :*.  ;: .:
```

Fig. 10

```
M13.rev
 aggaaacagctatgac ->
AGGAAACAGCTATGACCATGTTAATGCAGCTGGCACGACAGGTTTCCCGACTGGAAAG
CGGGCAGTGAGCGGAAGGCCCATGAGGCCAGTTAATTAAGAGGTACCGCTAGCGCTC
CGGCAGATAATACGGTAAATATTAAAACATTCGACAAAGTAAAAAATGCCTTTGGTGA
CGGATTGTCCCAAAGTGCGGAAGGAACCTTTACATTTCCGGCCGATGTAACAGCCGTA
AAAACGATTAAGATGTTCATTAAAAATGAATGTCCTAATAAAACTTGTNNKGAATGGG
CTCGTNNKGCCAATGTTTATGTAAAAAATAAAACAACAGGTGAGTGGTACGAAATAGG
ACGCTTTATTACTCCATATTGGGTGGGAACGGAAAAATTACCTCGTGGACTGGAAATT
GATGTTACAGATTTCAAATCTTTACTATCCGGAAATACAGAACTTAAAATTTATACGN
NKACATGGCTGGCCAAAGGAAGAGAATACAGTGTAGATTTCGATATTGTATACGGGAC
ACCGGATTATAAATATTCGGCTGTAGTACCTGTAGTTCAGTATAACAAATCANNKNNK
GACGGAGTCCCTTATGGTAAAGCACATACATTGGCTTTGAAAAAGAATATCCAGTTAC
CAACAAACACAGAAAAGCTTATCTTAGAACTACTATTTCCGGATGGNNKCATGCTAA
GCCATATGATGCGGGAAGCAGAGGTTGTGCANNKTGGTGCTTCAGAACACACACTATA
GCAATAAATAATTCGAATACTTTCCAGCATCAGCTGGGTGCTTTAGGATGTTCAGCAA
ACCCTATCAATAATCAGAGTCCGGGAAATTGGACTCCCGACAGAGCCGGTTGGTGCCC
GGGAATGGCAGTTCCAACACGTATAGATGTACTGAATAATTCTTTAATAGGCAGTACT
TTTAGTTATGAATATAAATTCCAGAACTGGACAAATAACGGAACCAATGGAGATGCTT
TTTATGCAATTTCCAGTTTTGTGATTGCAAAAGTAATACACCTATTAGTGCTCCGGT
AGTTACAAACGGATCCGAGCTCATGGCGCGCCTAGGCCTTGACGGCCTTCCGCCAAT
TCGCCCTATAGTGAGTCGTATTACGTCGCG
CTCACTGGCCGTCGTTTTACA
 <- tgaccggcagcaaaatgt
                M13.fwd
A179C = D60A
N = equimolar A, T, C, or G nucleotide mixture
K = equimolar G or T nucleotide mixture
NheI & BamHI restriction sites
```

Fig. 11

```
M13.rev
 aggaaacagctatgac ->
AGGAAACAGCTATGACCATGTTAATGCAGCTGGCACGACAGGTTTCCCGACTGGAAAG
CGGGCAGTGAGCGGAAGGCCCATGAGGCCAGTTAATTAAGAGGTACCGCTAGCGCTC
CGGCAGATAATACGGTAAATATTAAAACATTCGACAAAGTAAAAAATGCCTTTGGTGA
CGGATTGTCCCAAAGTGCGGAAGGAACCTTTACATTTCCGGCCGATGTAACAGCCGTA
AAAACGATTAAGATGTTCATTAAAAATGAATGTCCTAATAAAACTTGT▓▓▓GAATGG▓
▓▓▓CGTTATGCCAATGTTTATGTAAAAATAAAACAACAGGTGAGTGGTACGAAATAGG
ACGCTTTATTACTCCATATTGGGTGGGAACGGAAAAATTACCTCGTGGACTGGAAATT
GATGTTACAGATTTCAAATCTTTACTATCCGGAAATACAGAACTTAAAATTTATACGG
AGACATGGCTGGCCAAAGGAAGAGAATACAGTGTAGATTTCGATATTGTATACGGGAC
ACCGGATTATAAATATTCGGCTGTAGTACCTGTAGTTCAGTATAACAAATCATCT▓▓▓
GACGGAGTCCCTTATGGTAAAGCACATACATTGGCTTTGAAAAGAATATCCAGTTAC
CAACAAACACAGAAAAGCTTATCTTAGAACTACTATTTCCGGATGG▓▓▓CATGCTAA
GCCATATGATGCGGGAAGCAGAGGTTGTGCA▓▓▓TGGTGCTTCAGAACACACACTATA
GCAATAAATAATTCGAATACTTTCCAGCATCAGCTGGGTGCTTTAGGATGTTCAGCAA
ACCCTATCAATAATCAGAGTCCGGGAAATTGGACTCCCGAC▓▓▓GCCGGTTGGTGCCC
GGGAATGGCAGTTCCAACACGTATAGATGTACTGAATAATTCTTTAATAGGCAGTACT
TTTAGTTATGAATATAAATTCCAGAACTGGACAAATAACGGAACCAATGGAGATGCTT
TTTATGCAATTTCCAGTTTTGTGATTGCAAAAGTAATACACCTATTAGTGCTCCGGT
AGTTACAAACGGATCCGAGCTCATGGCGCGCCTAGGCCTTGACGGCCTTCCGCCAAT
TCGCCCTATAGTGAGTCGTATTACGTCGCG
CTCACTGGCCGTCGTTTTACA
<- tgaccggcagcaaaatgt
              M13.fwd
```

▓ = nucleotide mixture resulting in equimolar distribution of all amino acids
▓ = nucleotide mixture resulting in equimolar distribution of all amino acids except aspartic acid (D)
NheI & *BamHI* restriction sites

Fig. 17

PPNL6For Forward PCR Primer:

5'-GTACGAGCTAAAAGTACAGTG-3'   (SEQ ID NO:14)

PNL6Rev Reverse PCR Primer:

5'-TAGATACCCATACGACGTTC-3'   (SEQ ID NO:15)

ForSeqP2 Forward Sequencing Primer:

5'-TCTGCAGGCTAGTGGTGGTG-3'   (SEQ ID NO:16)

Fig. 18

95 °C 5 min
    95 °C 30 sec
    55 °C 30 sec
    72 °C 45 sec
    Repeat 30x Steps 2 - 4.
    72 °C 5 min
    4 °C hold

Fig. 19

PNGaseF-pOPH6 Forward Primer:

5'-CGCAGGCCGGAATTCCAGCTCCGGCAGATAATACc-3'   (SEQ ID NO:17)
                EcoRI

PNGaseF-pOPH6 Reverse Primer:

5'-TGGTGATGCGGATCCAAGTTTGTAACTACCGGAGCAC-3'  (SEQ ID NO:18)
                BamHI

Fig. 20

T7 Forward Primer:

5'-TAATACGACTCACTATAGGG-3'         (SEQ ID NO:19)

His6 XhoI Reverse Primer:

5'-CTCGAGTCAATGGTGGTGATGGTGATG-3'   (SEQ ID NO:20)
       XhoI   C-Terminal His6x Tag Fig. 31
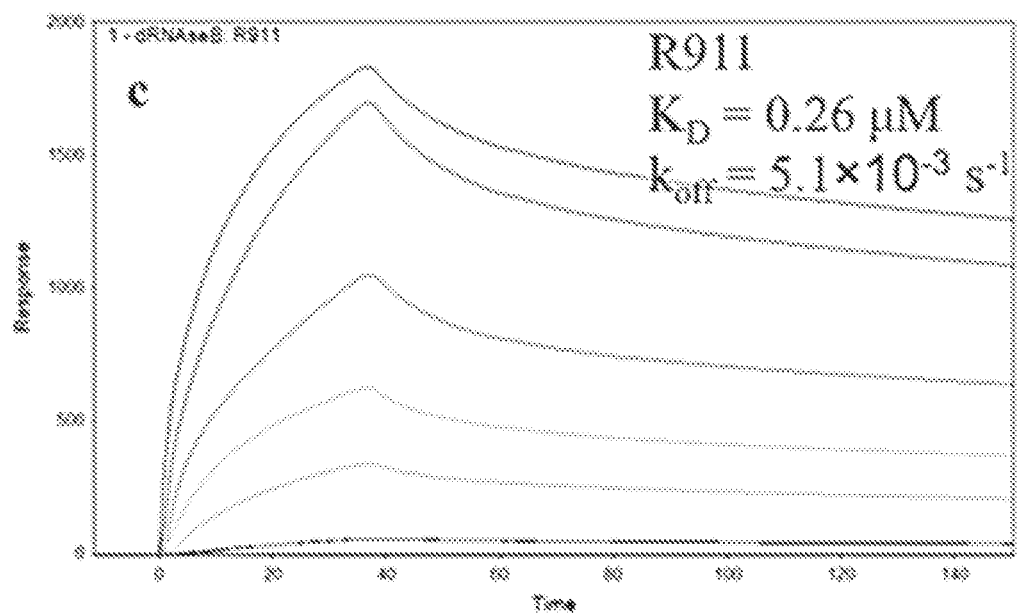
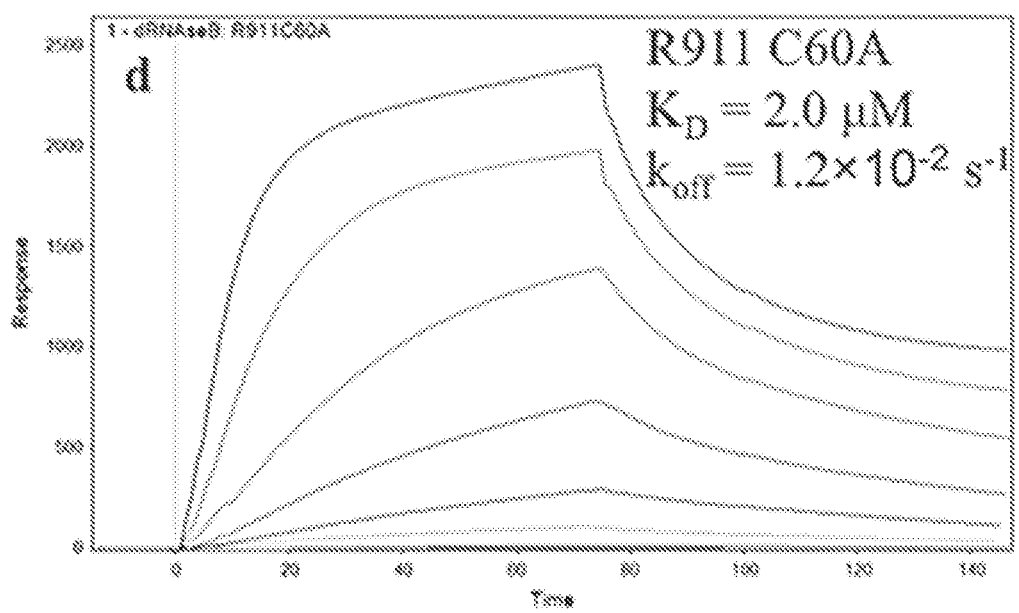

Fig. 44
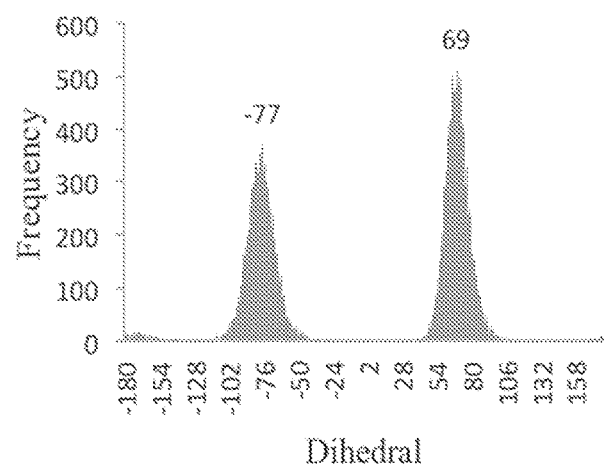
Fig. 45
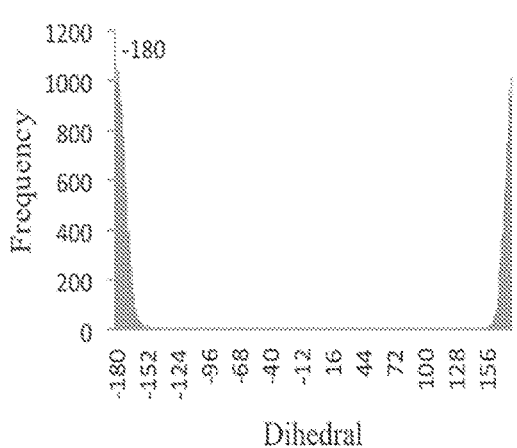
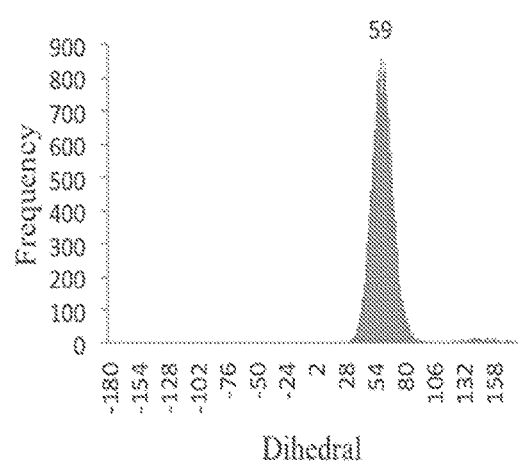

CARBOHYDRATE-BINDING PROTEIN

This application is the § 371 U.S. National Stage of International Application No. PCT/US2015/026374, filed 17 Apr. 2015, which claims the benefit of U.S. Provisional Application Ser. No. 61/981,335, filed Apr. 18, 2014, each of which is incorporated herein by reference in its entirety.

SEQUENCE LISTING

This application contains a Sequence Listing electronically submitted via EFS-Web to the United States Patent and Trademark Office as an ASCII text file entitled "235_02470101_SequenceListing-Corrected_ST25" having a size of 28 kilobytes and created on May 31, 2017. The information contained in the Sequence Listing is incorporated by reference herein.

BACKGROUND

Glycosylation and carbohydrate recognition are integral and essential aspects of eukaryotic biology. The array of glycans present in an organism (the glycome) is a dynamic property depending on many features including cellular localization and temporal state, and may be perturbed in disease states such as cancer, or exploited for adhesion by pathogens. Variations in glycosylation can serve not only as disease biomarkers, but can also impact the pharmacological properties of recombinant therapeutic biologics. Glycan heterogeneity can impact batch-to-batch consistency, immunogenicity, pharmacokinetics, activity, and clearance. Unlike the case of proteins and nucleic acids, the sequencing and structural characterization of glycans is a laborious multi-step process, typically requiring sample enrichment, enzyme digestion, and mass-spectrometric analysis, a process which is not amenable to real-time monitoring. More than two thirds of therapeutic biologics are glycosylated, and batch acceptance requires that the glycosylation patterns fall within set limits.

The exploitation of glycans as biomarkers in diagnostic and therapeutic applications is hindered by difficulties in generating highly specific detection reagents (Kuzmanov et al., *BMC medicine* 11, 31 (2013)), which is not unexpected given the immense diversity of glycan structure (Cummings, *Molecular BioSystems* 5, 1087-1104 (2009)). Glycans are recognized by several classes of proteins, including lectins, antibodies, and enzymes. Lectins typically display low affinities (mM to µM) and broad or context-dependent glycan recognition (Debray et al., *Eur J Biochem* 117, 41-55 (1981); Liener et al., *The Lectins: properties, functions, and applications in biology and medicine* (Academic Press, Orlando; 1986); Bertozzi & Kiessling, *Science* (New York, N.Y.) 291, 2357-2364 (2001)), yet despite these issues, lectin affinity chromatography is the most widely applied technique for the isolation and enrichment of glycans and glycoconjugates. Anti-carbohydrate antibodies may exhibit improved affinity compared to lectins, and may be highly specific for particular glycans, but they can be difficult to generate given that carbohydrates are poor immunogens in general. Glycan-processing enzymes are often very selective with regard to substrate structure, reflecting their essential role in glycan processing. Site directed mutagenesis has been employed to generate inactive mutants, facilitating the characterization of substrate specificity (Rao et al., *Protein Sci* 8, 2338-2346 (1999)).

SUMMARY

The present invention is directed to glycan-specific analytical, diagnostic and therapeutic tools and reagents, their methods of use, and processes for making glycan-specific analytical, diagnostic and therapeutic tools and reagents. An N-glycan processing enzyme, Peptide-$N_4$—(N-acetyl-β-D-glucosaminyl)asparagine amidase (also commonly known as Peptide:N glycanase, or PNGase F) is catalytically inactivated through mutation. Additional mutations yielded a catalytically inactive carbohydrate-binding protein with lectin-like properties including high affinity and specificity for certain glycans. In one embodiment, the catalytically inactive carbohydrate-binding PNGase F protein exhibits affinity and specificity for N-linked glycans; in another embodiment, the catalytically inactive carbohydrate-binding PNGase F protein exhibits affinity and specificity for O-linked glycans, for example O-linked N-acetylglucosamine (O-linked GlcNAc) or O-linked N-acetylgalactosamine (O-linked GalNAc); in yet another embodiment, the catalytically inactive carbohydrate-binding PNGase F protein exhibits affinity and specificity for both N-linked glycans and O-linked glycans. The catalytically inactive carbohydrate-binding PNGase F protein binds a glycan covalently linked to a peptide or protein; optionally the catalytically inactive carbohydrate-binding PNGase F protein also binds the free glycan.

In one aspect, the invention provides a catalytically inactive carbohydrate-binding PNGase F protein having a plurality of amino acid mutations compared to a corresponding wild-type PNGase F protein. Examples of a suitable corresponding wild-type protein include, without limitation, PNGase F from *F. meningosepticum* (SEQ ID NO:1), PNGase F-II from *F. meningosepticum* (SEQ ID NO:3), PNGase F from *Bacteroides fragilis* (SEQ ID NO:4), and PNGase F from *Flavobacterium miricola* (SEQ ID NO:5). The plurality of mutations includes (a) at least one first mutation that reduces or eliminates the catalytic activity of the PNGase F protein; and (b) at least one second mutation that affects binding affinity or binding specificity. The second mutation can include one or both of a mutation that (i) enhances binding affinity to an N-linked glycan; or (ii) adds binding specificity and affinity to an O-linked glycan. The second mutation can add binding specificity and affinity to O-linked GlcNAc, O-linked GalNAc, or both O-linked GlcNAc and O-linked GalNAc. In one embodiment, the catalytically inactive carbohydrate-binding PNGase F protein binds to an N-linked glycan, N-linked glycoconjugate, N-linked glycopeptide, N-linked glycoprotein, or free N-glycan. Additionally or alternatively, the catalytically inactive carbohydrate-binding PNGase F protein binds to an O-linked glycan, O-linked glycoconjugate, O-linked glycopeptide, O-linked glycoprotein, or free O-glycan.

A first (inactivating) mutation can include, for example, a mutation at amino acid position 60, 118, 206 or 248 in *F. meningosepticum* PNGase F (SEQ ID NO:1), or a corresponding position in a homologous PNGase F sequence.

A second mutation (affecting binding affinity and/or binding specificity) can include, for example, a mutation at amino acid position 57, 60, 62, 118, 119, 120, 123, 125, 153, 154, 155, 156, 157, 192, 206 or 248 in *F. meningosepticum* PNGase F (SEQ ID NO: 1), or a corresponding position in a homologous PNGase F sequence. Some mutations can serve as both first and second mutations, in that they can reduce or eliminate catalytic activity as well as affect binding specificity and/or binding affinity.

The catalytically inactive carbohydrate-binding PNGase F protein can include an amino acid substitution at position D57 of SEQ ID NO: 1, or a corresponding position in a homologous PNGase F sequence; examples of suitable substitutions at that position include leucine, alanine, methionine, arginine, lysine, cysteine, or tryptophan.

Alternatively or additionally, the catalytically inactive carbohydrate-binding PNGase F protein can include an amino acid substitution at position D60 of SEQ ID NO:1, or a corresponding position in a homologous PNGase F sequence; examples of suitable substitutions at that position include alanine, cysteine, valine, serine, glycine, or tryptophan.

Alternatively or additionally, the catalytically inactive carbohydrate-binding PNGase F protein can include an amino acid substitution at position Y62 of SEQ ID NO: 1, or a corresponding position in a homologous PNGase F sequence; examples of suitable substitutions at that position include glycine, tryptophan, serine or threonine.

Alternatively or additionally, the catalytically inactive carbohydrate-binding PNGase F protein can include an amino acid substitution at position E118 of SEQ ID NO:1, or a corresponding position in a homologous PNGase F sequence; examples of suitable substitutions at that position include alanine, glutamine, threonine, or cysteine.

Alternatively or additionally, the catalytically inactive carbohydrate-binding PNGase F protein can include an amino acid substitution at position T119 of SEQ ID NO:1, or a corresponding position in a homologous PNGase F sequence; examples of suitable substitutions at that position include alanine, glycine, isoleucine, leucine, or valine.

Alternatively or additionally, the catalytically inactive carbohydrate-binding PNGase F protein can include an amino acid substitution at position W120 of SEQ ID NO:1, or a corresponding position in a homologous PNGase F sequence; examples of suitable substitutions at that position include tyrosine, histidine, glutamine, asparagine, threonine, or serine.

Alternatively or additionally, the catalytically inactive carbohydrate-binding PNGase F protein can include an amino acid substitution at position K123 of SEQ ID NO:1, or a corresponding position in a homologous PNGase F sequence; examples of suitable substitutions at that position include aspartate, glutamate, alanine, glycine, isoleucine, leucine, valine, methionine, phenylalanine, or tryptophan.

Alternatively or additionally, the catalytically inactive carbohydrate-binding PNGase F protein can include an amino acid substitution at position R125 of SEQ ID NO:1, or a corresponding position in a homologous PNGase F sequence; examples of suitable substitutions at that position include tyrosine, alanine, glycine, isoleucine, leucine, valine, methionine, phenylalanine, or tryptophan.

Alternatively or additionally, the catalytically inactive carbohydrate-binding PNGase F protein can include an amino acid substitution at position K153 of SEQ ID NO:1, or a corresponding position in a homologous PNGase F sequence; examples of suitable substitutions at that position include histidine, arginine, glutamine, tryptophan, or tyrosine.

Alternatively or additionally, the catalytically inactive carbohydrate-binding PNGase F protein can include an amino acid substitution at position S154 of SEQ ID NO: 1, or a corresponding position in a homologous PNGase F sequence; examples of suitable substitutions at that position include threonine, asparagine, lysine, glutamine, tryptophan, or tyrosine.

Alternatively or additionally, the catalytically inactive carbohydrate-binding PNGase F protein can include an amino acid substitution at position S155 of SEQ ID NO:1, or a corresponding position in a homologous PNGase F sequence; examples of suitable substitutions at that position include arginine, lysine, aspartate, glutamine, tryptophan, or tyrosine.

Alternatively or additionally, the catalytically inactive carbohydrate-binding PNGase F protein can include an amino acid substitution at position I156 of SEQ ID NO:1, or a corresponding position in a homologous PNGase F sequence; examples of suitable substitutions at that position include leucine, threonine, methionine, glycine, tryptophan, or histidine.

Alternatively or additionally, the catalytically inactive carbohydrate-binding PNGase F protein can include an amino acid substitution at position D157 of SEQ ID NO:1, or a corresponding position in a homologous PNGase F sequence; examples of suitable substitutions at that position include asparagine, glutamate, glutamine, lysine, tryptophan, or tyrosine.

Alternatively or additionally, the catalytically inactive carbohydrate-binding PNGase F protein can include an amino acid substitution at position G192 of SEQ ID NO: 1, or a corresponding position in a homologous PNGase F sequence; examples of suitable substitutions at that position include isoleucine, tryptophan, alanine, histidine, threonine, cysteine, or serine.

Alternatively or additionally, the catalytically inactive carbohydrate-binding PNGase F protein can include an amino acid substitution at position E206 of SEQ ID NO:1, or a corresponding position in a homologous PNGase F sequence; examples of suitable substitutions at that position include serine, tryptophan, histidine, cysteine, or arginine.

Alternatively or additionally, the catalytically inactive carbohydrate-binding PNGase F protein can include an amino acid substitution at position R248 of SEQ ID NO:1, or a corresponding position in a homologous PNGase F sequence; examples of suitable substitutions at that position include tryptophan, serine, proline, valine, aspartate, tyrosine, phenylalanine, or lysine.

In one embodiment, the catalytically inactive carbohydrate-binding PNGase F protein has mutations at positions D57, D60, I156, G192, and E206. Optionally, the catalytically inactive carbohydrate-binding PNGase F protein also includes a mutation at position Y62, E118, S155, R248W, or any combination thereof.

Exemplary catalytically inactive carbohydrate-binding PNGase F proteins of the invention include, but are not limited to, the following PNGase F mutants having a plurality of mutations with respect to a wild-type PNGase F (SEQ ID NO: I1):

(a) D57R, D60A, Y62G, E118A, S155D, I156T, G192C and E206S (b) D57C, D60A, Y62W, E118A, S155Q, I156T, G192T, and E206R (c) D57L, D60C, I156L, G192I, E206S, and R248W (d) D57W, D60C, I156M, G192I, E206W, and R248S (e) D60C, I156L, G192I, E206S, and R248W (f) D57L, D60A, I156L, G192I, E206S, and R248W (g) D57L, I156L, G192I, E206S, and R248W (h) D57L, D60C, E118Q, I156L, G192I, E206S, and R248W (i) D57L, D60C, W120X, I156L, G192I, E206S, and R248W (j) D57L, D60C, W120X, S155X, I156L, G192I, E206S, and R248W (k) D57L, D60C, K153X, I156L, G192I, E206S, and R248W (l) D57L, D60C, S154X, I156L, G192I, E206S, and R248W (m) D57L, D60C, S155X, I156L, G192I, E206S, and R248W (n) D57L, D60C, I156X, G192I, E206S, and R248W (o) D57L, D60C, G192I, E206S, and R248W (p) D57L, D60C, G192I, and R248W (q) D57L, D60C, I156L, D157X, G192I, E206S, and R248W (r) D57L, D60C, I156L, E206S, and R248W (s) D57L, D60C, I156L, G192I, and R248W (t) D57L, D60C, I156L, G192I, and E206S In some embodiments, the catalytically inactive carbohydrate-binding PNGase F protein is expressed by clone D60A, R617, R6113, R911, R9113, or R911C60A.

In another aspect, the invention provides a conjugate that includes, as a first component, a catalytically inactive carbohydrate-binding PNGase F protein, which is covalently linked to a second component. The second component is a proteinaceous component or a nonproteinaceous component. The second component can be a therapeutic agent, such as a drug, or a diagnostic agent, such as a detectable label, or analytical reagent.

In another aspect, the invention provides a fusion protein that includes a catalytically inactive carbohydrate-binding PNGase F protein of the invention. The fusion protein can be conveniently expressed from host cell.

In another aspect, the invention provides an affinity matrix that includes a catalytically inactive carbohydrate-binding PNGase F protein, conjugate or fusion protein. Examples of an affinity matrix include, but are not limited to, a solid support, surface, column, resin, bead, particle and nanoparticle In another aspect, the invention provides a kit that includes a catalytically inactive carbohydrate-binding PNGase F protein, conjugate, fusion protein or affinity matrix, together with instructions for use. Optionally the kit can include buffers, salts, labeling or detection reagents, or other diagnostic or analytical reagents.

In another aspect, the invention provides an isolated polynucleotide encoding a catalytically inactive carbohydrate-binding PNGase F protein, proteinaceous conjugate thereof, or fusion protein as described herein. Also provided is a vector that includes or incorporates the polynucleotide. The vector can be an expression vector or a cloning vector. The invention further provides a host cell that includes said vector. The host cell can be a bacterial cell, a fungal cell (such as yeast) or an animal cell, such as an insect or a mammalian cell. Examples of a suitable host cell include an *Escherichia coli* cell or a yeast cell, such *Saccharomyces cerevisiae*.

In another aspect, the invention provides a method for making a catalytically inactive carbohydrate-binding PNGase F protein. A catalytically inactive carbohydrate-binding PNGase F protein or proteinaceous conjugate thereof, or a fusion protein as described herein, can be expressed, in vitro or in vivo, from an isolated polynucleotide, expression vector, or host cell.

In another aspect, the invention provides a method for detecting an N-linked glycan. The method can include contacting a biological or laboratory sample with a catalytically inactive carbohydrate-binding PNGase F protein, conjugate or fusion protein under conditions to allow binding of PNGase F protein to an N-glycan; and detecting the N-linked glycan. Optionally, the method further includes characterizing the detected N-linked glycan, for example by identifying a constituent saccharide of the glycan, determining saccharide composition of the glycan, determining linkage positions within the glycan, or determining stereochemistry of the glycan.

In another aspect, the invention provides a method for detecting an O-linked glycan. The method can include contacting a biological or laboratory sample with a catalytically inactive carbohydrate-binding PNGase F protein, conjugate or fusion protein under conditions to allow binding of PNGase F protein to an O-linked glycan; and detecting the O-linked glycan.

Optionally, the method further includes characterizing the detected O-linked glycan, for example by identifying a constituent saccharide of the glycan, determining saccharide composition of the glycan, determining linkage positions within the glycan, or determining stereochemistry of the glycan. The O-linked glycan can be, for example, an O-linked GlcNAc or O-linked GalNAc.

In another aspect, the invention provides method for detecting a free N-glycan. The method can include contacting a biological or laboratory sample with a catalytically inactive carbohydrate-binding PNGase F protein, conjugate or fusion protein under conditions to allow binding of PNGase F protein to a free N-glycan; and detecting the free N-glycan.

In another aspect, the invention provides method for detecting a free O-glycan. The method can include contacting a biological or laboratory sample with a catalytically inactive carbohydrate-binding PNGase F protein, conjugate or fusion protein under conditions to allow binding of PNGase F protein to a free O-glycan; and detecting the free O-glycan. The free O-glycan can be, for example, O-GlcNAc or O-GalNAc.

In another aspect, the invention provides a method for enriching, isolating or purifying an N-linked glycan or free N-glycan. The method can include contacting a biological or laboratory sample with a catalytically inactive carbohydrate-binding PNGase F protein, conjugate or fusion protein under conditions to allow binding of PNGase F protein to an N-glycan so as to yield an enriched, isolated or purified N-linked glycan or free N-glycan.

In another aspect, the invention provides a method for enriching, isolating or purifying an O-linked glycan or free O-glycan. The method can include contacting a biological or laboratory sample with a catalytically inactive carbohydrate-binding PNGase F protein, conjugate or fusion protein under conditions to allow binding of PNGase F protein to an O-glycan so as to yield an enriched, isolated or purified O-linked glycan or free O-glycan.

In another aspect, the invention provides a diagnostic or therapeutic composition that includes a catalytically inactive carbohydrate-binding PNGase F protein, conjugate or fusion protein as described herein. The PNGase F protein is optionally detectably labeled. Examples of a suitable detectable label include, without limitation, a radioactive label, a fluorescent label, a phosphorescent label, a colorimetric label, an enzymatic label, an immunological label, a magnetic label, a paramagnetic label, a diamagnetic label and an electromagnetic label.

In another aspect, the invention provides a use of a catalytically inactive carbohydrate-binding PNGase F protein, conjugate or fusion protein as a therapeutic agent, diagnostic agent, or analytical reagent. Also provided is a use of a catalytically inactive carbohydrate-binding PNGase F protein, conjugate or fusion protein for targeted drug delivery. Also provided is a use of a catalytically inactive carbohydrate-binding PNGase F protein, conjugate or fusion protein for detection of the presence or amount of an N-linked glycan or free N-glycan in a biological or laboratory sample. Also provided is a use of a catalytically inactive carbohydrate-binding PNGase F protein, conjugate or fusion protein for detection of the presence or amount of an O-linked glycan or free O-glycan in a biological or laboratory sample. The O-linked glycan can be an O-linked GlcNAc or an O-linked GalNAc; likewise, the free O-glycan can be an O-GlcNAc or an O-GalNAc.

BRIEF DESCRIPTION OF THE DRAWINGS

FIG. 10 shows a sequence (SEQ ID NO:8) and restriction map of non-amplified GenScript Library 1. The sequence of expressed PNGase F clone is underlined and flanked by NheI (BOLD) and BamHI (italicized) restriction sites. A total of eight mutations were engineered into this library construct: D57, D60A, Y62, E118, S155, I156, G192, and E206. The single point A179C nucleotide mutation (indicated by an arrow) was introduced to exhibit the D60A amino acid mutation. This mutation is indicated to enhance affinity interactions and while also either inactivating or significantly diminishing the catalytic activity of the enzyme. The seven site-saturation mutagenesis sites were engineered into this library using NNK codon (highlighted) degeneracy where N represents equimolar A, T, C, or G nucleotide mixture and K represents equimolar G or T nucleotide mixture. M13 forward (SEQ ID NO:9) and reverse (SEQ ID NO:10) primer sequences are indicated (lowercase letters).

FIG. 11 shows a sequence (SEQ ID NO: 11) and restriction map of non-amplified GeneArt Library 2. The sequence of expressed PNGase F clone is underlined and flanked by NheI (BOLD) and BamHI (italicized) restriction sites. A total of six site-saturation mutagenesis sites were engineered into this library construct: D57, D60(-D), I156, G192, E206, and R248. Five of the six site-saturation mutagenesis sites were synthesized with a nucleotide mixture, which results in an equimolar distribution of all amino acids. For the site, D60 (indicated by an arrow), a modified nucleotide mixture resulting in all amino acids except aspartic acid was utilized. M13 forward (SEQ ID NO:12) and reverse (SEQ ID NO:13) primer sequences are indicated (lowercase letters).

FIG. 17 shows yeast colony PCR and sequencing primers.

FIG. 18 shows yeast colony PCR program.

FIG. 19 shows PCR amplification primers for PNGase F clones selected via yeast-display. The 5' bold sequence matches the PNGaseF-pOPH6 sequence and the 3' end matches the PNGase F sequence in the PNGaseF-pPNL6 yeast display plasmid. The lowercase "c" at the 3' end of the PNGaseF-pOPH6 forward primer is a "G" in the PNGaseF-pOPH6 plasmid. The full length PCR product is flanked with EcoRI and BamHI restriction sites used to ligate the digested product into the PNGaseF-pOPH6 empty vector.

FIG. 20 shows PCR amplification primers for PNGaseF-pOPH6 ompA-PNGase F-His6 sequence.

FIG. 44 shows E206S rotamer histogram of Chi1 dihedral angles.

FIG. 45 shows I156L rotamer histograms of Chi1 and Chi2 dihedral angles.

DETAILED DESCRIPTION OF ILLUSTRATIVE EMBODIMENTS

Figure 1:
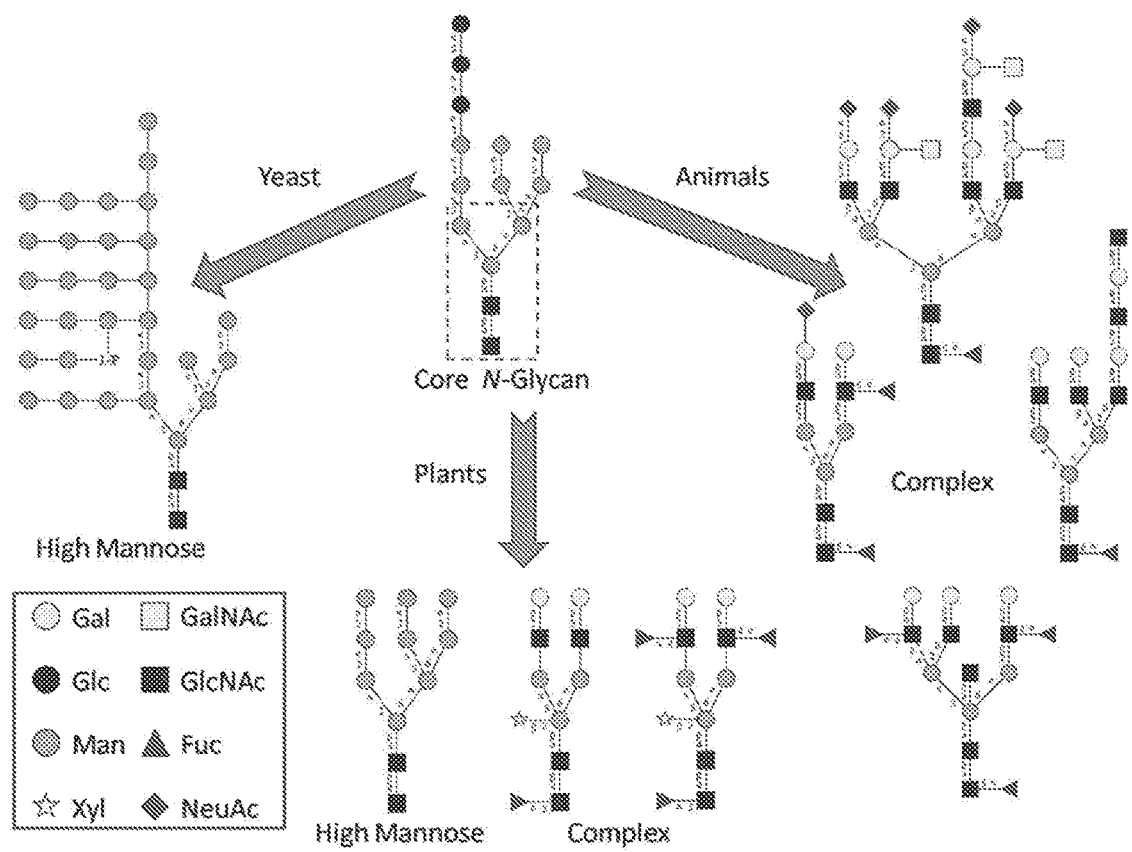
FIG. 1 shows representative examples of N-glycan complexity. The fourteen saccharide N-glycan structure which is attached en bloc to nascent polypeptides prior to modification is show in the center. The highly conserved five-saccharide N-glycan core structure is designated by the dashed box.

The present invention provides a catalytically inactive carbohydrate-binding protein that is derived from the enzyme peptide-$N_4$—(N-acetyl-β-D-glucosaminyl)asparagine amidase (PNGase F) as well as methods for making and using a catalytically inactive carbohydrate-binding PNGase F protein as described herein. A preferred PNGase F enzyme and coding sequence is PNGase F obtained from *Flavobacterium meningosepticum*. The invention is described primarily with respect to PNGase F from *F. meningosepticum*, but it should be understood that other sources of PNGase F can be utilized.

The designation Peptide:N-glycanase (PNGase F) includes a family of enzymes that catalyze a chemical reaction that cleaves an N-linked glycan from asparagine present in a glycopeptide or glycoprotein. More particularly, PNGase F enzymes are a class of N-glycan releasing enzymes that catalyze the cleavage of the amide bond between the asparagine side chain of the polypeptide and the proximal N-acetyl-β-D-glycosamine (GlcNAc) of the N-glycan to yield a (substituted)N-acetyl-β-D-glucosaminylamine and a peptide containing an aspartate residue. The N-linked glycan can be an N4-(acetyl-β-D-glucosaminyl) asparagine residue in which the glucosamine residue may be further glycosylated. The hydrolysis reaction results in the release of the glycan and free ammonia, and conversion of the asparagine to an aspartic acid (see FIG. 3). As used herein, the terms "N-glycan" and "O-glycan" generally refer the free glycan released in the hydrolytic reaction, but in context may also refer to a glycan that is linked to a peptide or other substrate.

The designation "PNGase F" was given to the first known PNGase enzyme isolated from *Flavobacterium meningosepticum*; however, the term "PNGase F" has come to be associated with a family of enzymes that have the glycosidic activity described above. The invention is described primarily using PNGase F from *F. meningosepticum* as the basis for mutation, but the invention encompasses the use of other PNGase F enzymes for that purpose as well.

The catalytically inactive carbohydrate-binding PNGase F protein of the invention contains a plurality of mutations relative to wild-type PNGase F, at least one of which reduces or eliminates catalytic activity of the enzyme. The catalytic activity of PNGase F is reduced or eliminated via site directed mutation ("first" mutation) of at least one residue, preferably at the active site.

Additionally, one or more other amino acid residues are mutated ("second" mutation) so as to affect binding specificity or binding affinity. In one embodiment, a second mutation increases the binding affinity of the catalytically inactive PNGase F for N-linked glycans compared to the binding affinity for N-linked glycans of the corresponding mutant PNGase F having only the first, activity-impairing mutation. In another embodiment, a second mutation alters the binding specificity of the PNGase F so as to add binding specificity and affinity for one or more O-linked glycans (which are non-natural substrates).

The compound to which the catalytically inactive carbohydrate-binding protein binds may be referred to herein as a "ligand" rather than a "substrate" since the enzymatic reaction is substantially curtailed or eliminated.

Thus, in one embodiment, as a result of some or all of the plurality of mutations, the catalytically inactive carbohydrate-binding PNGase F protein binds the natural substrate N-linked glycan with greater affinity than the corresponding wild-type enzyme, or than a corresponding inactive mutant PNGase F that contains only the one or more mutations that reduce or eliminate activity. In another embodiment, as a result of some or all of the plurality of mutations, the catalytically inactive carbohydrate-binding PNGase F protein binds an O-linked glycan, for example an O-linked GlcNAc or an O-linked GalNAc. The O-linked glycan is not a native substrate for PNGase F. In yet another embodiment, as a result of some or all of the plurality of mutations, the catalytically inactive carbohydrate-binding PNGase F protein binds both the natural substrate N-linked glycan and an O-linked glycan, for example an O-linked GlcNAc or an O-linked GalNAc. In embodiments that bind O-linked GlcNAc or O-linked GalNAc, the O-linked GlcNAc can be β-O-linked-GlcNAc or α-O-linked-GlcNAc, and the O-linked GalNAc can be β-O-linked-GalNAc or α-O-linked-GalNAc.

The catalytically inactive carbohydrate-binding PNGase F protein of the invention binds an N-linked glycan, an O-linked glycan, or both. The compound to which the glycan is covalently linked can be, for example, a biomolecule such as a peptide, protein, or lipid to yield a glycopeptide, glycoprotein or glycolipid, respectively; a natural or synthetic polymer or polymeric scaffold; an artificial compound such as a peptoid; an organic linker molecule; a substrate surface, such as a surface of a resin or bead; or generally any organic substrate. In glycopeptides or glycoproteins, N-linked glycans are typically attached to an asparagine residue, and O-linked glycans are typically attached to a serine or threonine residue.

The catalytically inactive carbohydrate-binding PNGase F protein of the invention optionally also binds to the hydrolyzed or released form of the N-linked glycan or O-linked glycan. While the invention is described primarily with respect to binding of glycans that are N-linked or O-linked to another compound, such as peptide asparagine or a peptide serine or threonine, it should be understood that binding of the catalytically inactive carbohydrate-binding PNGase F protein to the corresponding free glycan is also encompassed by the present invention.

The catalytically inactive carbohydrate-binding PNGase F protein of the invention specifically binds to glycosylated compounds or surfaces that contain an N-linked glycan or O-linked glycan (a non-natural substrate), but exhibits a substantially slower rate of cleavage of an N-linked glycan from the compound or surface, compared to the wild-type enzyme. In a preferred embodiment, the catalytically inactive enzyme does not cleave an N-linked glycan from the compound or surface to a significant extent. For example, the cleavage rate can be 50% or less than that observed in a corresponding wild-type enzyme, as described more fully below. In a particularly preferred embodiment, cleavage of the glycosidic bond is not detectable above background levels.

The catalytically inactive carbohydrate-binding PNGase F protein of the invention, which incorporates both first (inactivating) and second (affecting binding specificity and/or binding affinity) mutations, is sometimes referred to herein as a catalytically inactive PNGase F derivative or a catalytically inactive PNGase F mutant, or the shorter designation "PNGase F mutant" and these terms are interchangeable. The corresponding wild-type PNGase F is sometimes referred to herein as the reference compound. Regardless of the terminology employed, however, it should be understood that the catalytically inactive carbohydrate-binding PNGase F of the invention is not just catalytically inactive; additionally, it contains one or more mutations that increase binding affinity toward N-linked glycans and/or add binding specificity and affinity toward O-linked glycans. In other words, the catalytically inactive carbohydrate-binding PNGase F of the invention, which is rendered catalytically inactive by reason of at least one first mutation, for example at position D60 of PNGase F as described in more detail below, contains one or more additional, second mutations that (i) cause enhanced binding affinity toward N-linked glycans, when compared to a corresponding catalytically inactive PNGase F that does not contain the additional (second) mutations, and/or that (ii) add binding specificity and affinity toward O-linked glycans. A catalytically inactive carbohydrate-binding PNGase F that exhibits enhanced binding affinity toward N-linked glycan as in (i) typically has a lower $K_D$ than that of the corresponding PNGase F that carries only a first mutation that reduces or eliminates the catalytic activity. Addition of binding specificity and affinity toward O-linked glycans as in (ii) represents the introduction of a novel specificity as a newly acquired characteristic relative to wild-type PNGase F.

Methods for assessing and comparing binding affinity and specificity, as well as special considerations involved in comparing these two characteristics as between catalytically active (the reference compound) and inactive (the compound of the invention) forms of the enzyme (here, PNGase F) are described herein and in PCT Publication WO 2010/068817, published Jun. 17, 2010, entitled "Glycan-Specific Analytical Tools", and also in US Pat. Pub. 20120040474, published Feb. 16, 2012.

The systematic name for PNGase F is N-linked-glycopeptide-(N-acetyl-β-D-glycosaminyl)-L-asparagine aminohydrolase F; and a recommended name is Peptide-N4-(N-acetyl-β-D-glycosaminyl)asparagine amidase F. Alternative names for, or alternative embodiments of, PNGase F include N-oligosaccharide glycopeptidase, glycopeptide N-glycosidase, glycoamidase, glycopeptidase, N-oligosaccharide glycopeptidase, and N-glycanase (see Table 2). The PNGase F family has a European Commission number for enzymes of # EC 3.5.1.52.

The reference compound PNGase F, which is mutated to form the catalytically inactive carbohydrate-binding protein of the invention, is not limited by source. The PNGase F enzyme (including its nucleic acid coding sequence) that serves as the foundation or platform for the mutations that yield a catalytically inactive carbohydrate-binding PNGase F mutant can be obtained from any convenient organism. PNGase F enzymes are found in bacterial, plant, yeast and animal systems, without limitation.

A preferred PNGase F is a bacterial PNGase F obtained from *Flavobacterium meningosepticum*. *Flavobacterium meningosepticum* is also known as *Chryseobacterium meningosepticum* and *Elizabethkingia meningosepticum*. The invention is described primarily with respect to PNGase F from *F. meningosepticum*. Accordingly, the amino acid positions described herein are specified based on the amino acid sequence of *F. meningosepticum* PNGase F (314 amino acids; SEQ ID NO: 1; FIG. 4A; GenBank Acc. No. J05449; GenBank Acc. No. AF165910; Loo et al., 2002 *Protein Expression & Purification* 24:90-98). FIG. 4A shows two homologous *F. meningosepticum* PNGase F sequences from different strains of *F. meningosepticum*, with variation at eight sites; see also the amino acid sequence deposited for the x-ray crystal structure denoted by Protein Data Bank ID 1PNF. Amino acid SEQ ID NO: 1 is inclusive of these amino acid sequences, as well as other PNGase F amino acid sequences with variation at one or more of positions 39 (A/T), 149 (V/I), 168 (A/G), 219 (S/A), 243 (N/I), 245 (T/A), 269 (I/T), and/or 281 (N/S) as shown in FIG. 4A.

It should nonetheless be understood that other sources of PNGase F can be utilized. In that regard, particularly useful PNGase F enzymes include not only *F. meningosepticum* PNGase F (SEQ ID NO:1), but also PNGase F-II from *F. meningosepticum* (SEQ ID NO:3) (Sun et al., *J. Biol. Chem.*, 2015, 290(12):7452-62), PNGase F obtained from *Bacteroides fragilis* (SEQ ID NO:4), and PNGase F from *Flavobacterium miricola* (SEQ ID NO:5) (Uniprot P21163, also known as *Elizabethkingia miricola* and *Chryseobacterium miricola*). Representative amino acid and nucleic acid sequences can be found in the Swiss Prot, UniProt and GenBank data banks. Representative amino acid sequences include UniProt designations Q9XBM8 (PNGase F from *F.*

*meningosepticum*; SEQ ID NO:1), P21163 (PNGase F from *F. miricola*; SEQ ID NO:5), A0A090KI56-1 (PNGase F-II from *F. meningosepticum*; SEQ ID NO:3) and Q5LH31 (PNGase F from *B. fragilis*; SEQ ID NO:4). Several X-ray crystal structures of PNGase F are available from the Protein Data Bank (PDB) including PDB identifiers 1PNG, 1PNF (with chitobiose ligand), 1PGS, and 3PMS for PNGase F from *Flavobacterium meningosepticum*; PDB identifiers 4R4Z and 4R4X for PNGase F-II from *Flavobacterium meningosepticum*; and PDB identifier 3KS7 for PNGase F from *Bacteroides fragilis*. Amino acid sequences for these PNGase F enzymes are also reported in the PDB deposits.

Other proteins with sequence homology to PNGase F, which can be used as a reference compound for constructing the catalytically inactive carbohydrate-binding PNGase F mutant include PNGase F enzymes identified from the bacteria *Deinococcus radiodurans* (White et al., 1999, Science 286, 1571-1577), and *Plesiocystis pacifica* SIR-1, as well as the eukaryotes *Danio rerio* (zebrafish), *Salmo salar* (Atlantic salmon), and *Ciona intestinalis* (Sea squirt) (Filitcheva, *PNGases: A Diverse Family of Enzymes Related by Function Rather Than Catalytic Mechanism*, Vol. Ph.D., Massey University, Palmerston North, New Zealand, 2010).

Further examples of eukaryotic sources of PNGase F include, but are not limited to, *Mus musculus*, *Homo sapiens* (Uniprot designation Q96IV0), *Caenorhabditis elegans*, *Drosophila melanogaster*, and *Saccharomyces cerevisiae*.

When PNGase F enzymes other than PNGase F from *F. meningosepticum* are utilized, the first (inactivating) and second (affecting binding specificity and/or binding affinity) mutations are made at the corresponding sites in the PNGase F sequence. Corresponding sites can be determined by aligning primary amino acid sequences, or by comparing x-ray crystal structures or using homology modeling, as further described, for example, in PCT Publication WO 2010/068817 and US Pat. Pub. 20120040474. In some embodiments, PNGase enzymes utilized as a basis for mutation according to the present invention have amino acid sequences that are homologous to the amino acid sequence (SEQ ID NO:1) of *F. meningosepticum* PNGase F. Homologous PNGase F enzymes have N-glycanase activity and, within the region or regions involved in substrate binding, their amino acid sequences can share at least 40% identity, 45% identity, 50% identity, 55% identity, 60% identity, 65% identity, 70% identity, 75% identity, 80% identity, 85% identity, 90% identity, 95% identity or 98% identity with the amino acid sequence in the substrate binding region or regions of *F. meningosepticum* PNGase F (SEQ ID NO:1). Overall sequence identity, as applied to the entire amino acid sequence, may be much lower; for example, homologous PNGase F sequences may share only 10% identity, 15% identity, 20% identity, 25% identity, 30% identity, or higher, even though the identity percentage in the binding region or regions is higher. For example, 4R4X PNGase F-II (EC 2.7.7.7) has sequence and structural homology with 3KS7 of about 37%, and the sequence and structural homology with 1PNF PNGase F is about 26%, however the binding sites share remarkable similarity. Percent identity can be determined by aligning the residues of two polypeptides to optimize the number of identical amino acids along the lengths of their sequences; gaps in either or both sequences are permitted in making the alignment in order to optimize the number of identical amino acids, although the amino acids in each sequence must nonetheless remain in their proper order. For example, polypeptides may be compared using the Blastp program of the BLAST 2 search algorithm, as described by Tatusova et al. (FEMS Microbiol. Lett., 174; 247-250, 1999) and available on the world wide web at ncbi.nlm.nih.gov/BLAST/. More recently, the Clustal Omega program has been developed for sequence alignment (Sievers et al., *Molecular System Biology*, 7:539, 2011) and is available on the world wide web at http://www.ebi.ac.uk/Tools/msa/clustalo/. In the comparison of two amino acid sequences using the BLAST search algorithm, structural similarity may be referred to by percent "identity" or may be referred to by percent "similarity." "Identity" refers to the presence of identical amino acids and "similarity" refers to the presence of not only identical amino acids but also the presence of conservative substitutions.

A PNGase F useful in the present invention, including wild-type PNGase F as well as PNGase F mutants having first and/or second mutation as described herein, is conveniently expressed in and optionally isolated from a recombinant expression system as described in more detail herein, including prokaryotic and eukaryotic expression systems such as bacterial, protist, fungal (e.g., yeast, such as *Saccharomyces cerevisiae* or *Pichia* spp.) insect and mammalian systems, which are well-known to the art.

Inactivating Mutation

At least one amino acid in wild-type PNGase F is mutated so as to render the mutant PNGase F catalytically inactive. The one or more mutations that reduce or eliminate catalytic activity are referred to herein as a "first" (inactivating) mutation. In one embodiment, enzymatic activity is reduced or eliminated by mutating amino acid residue 60 in PNGase F, or the corresponding position in PNGase F obtained from another organism. It should be understood herein that whenever reference to an amino acid position in *F. meningosepticum* PNGase F is made herein, it encompasses the corresponding position in PNGase F enzymes obtained from other organisms. In *F. meningosepticum* PNGase F, the wild-type residue at position 60 is an aspartate (D). This residue can be mutated to any other amino acid, provided the mutation reduces or eliminates catalytic activity. Examples of amino acids that can be utilized at position 60 include, without limitation, alanine, arginine, asparagine, cysteine, glutamine, glutamic acid, glycine, histidine, isoleucine, leucine, lysine, methionine, phenylalanine, proline, serine, threonine, tryptophan, tyrosine, or valine, as well as any other amino acid, such as selenocysteine, that reduces or eliminates catalytic activity. Preferred mutations at position 60 of PNGase F include alanine, asparagine, cysteine, valine, serine or glycine. In one embodiment, the mutation at position 60 is alanine, cysteine or asparagine, i.e., D60A, D60C, or D60N. In another embodiment, the mutation at position 60 is any amino acid that reduces or eliminates catalytic activity other than alanine (A), cysteine (C) or asparagine (N). In another embodiment, D60 can be deleted.

Figure 16:
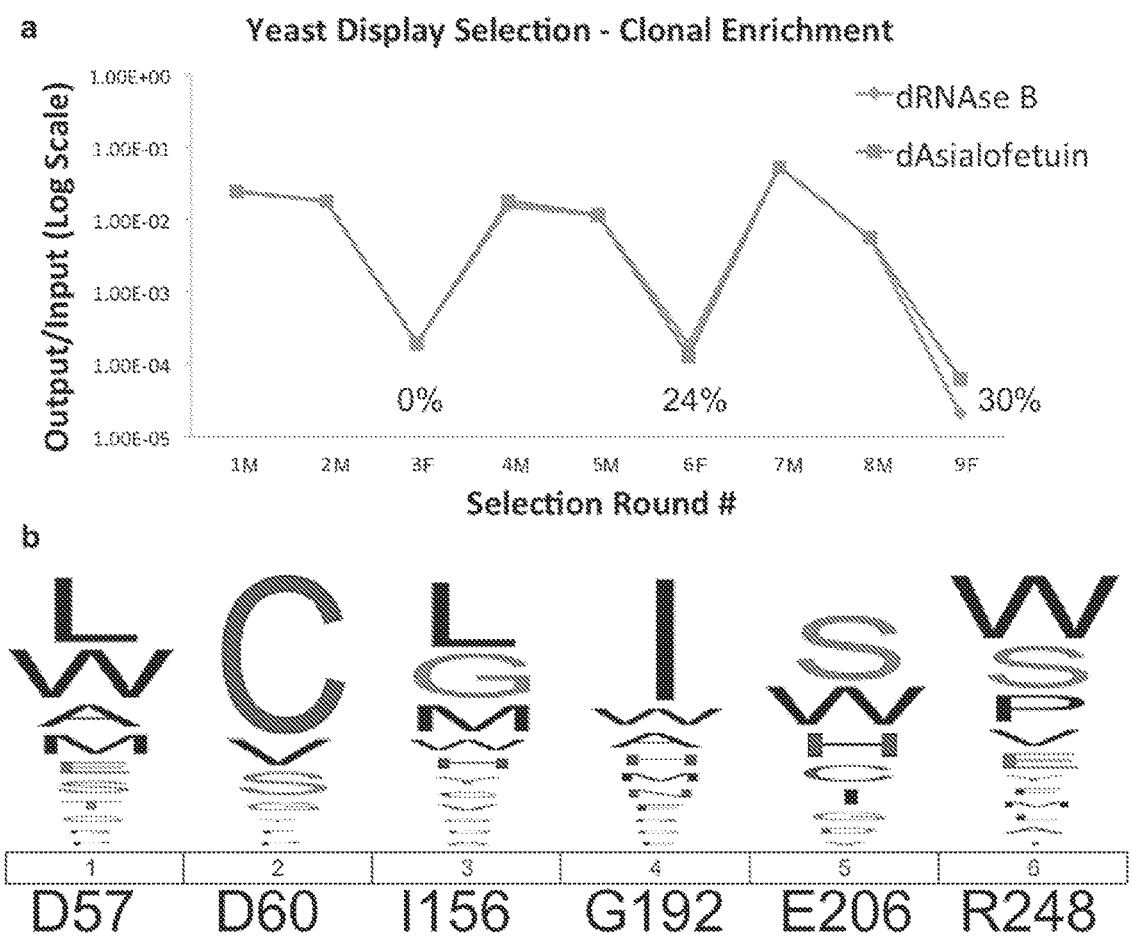
FIG. 16 shows yeast display PNGase F clonal selection and enrichment with GeneArt Library 2. (a) Iterative rounds of yeast display selection, amplification, and percent enrichment of PNGase F clones is shown. An aliquot of each library input sample, negative selection sample, wash sample, and output sample is titered in every round to monitor the progress of the selection and enrichment. Data is displayed as an output/input ratio representing the number of clones recovered from the bead-bound sample after selection relative to the starting number of input clones for that round. MACS based selection was performed on rounds 1M, 2M, 4M, 5M, 7M, and 8M. After every two rounds of MACS, FACS based selection was performed on rounds 3F, 6F, and 9F. Ideally, each round of selection will enrich functionally relevant clones which bind to the target N-glycan structure on either denatured RNase B (dRNase B) or denatured Asialofetuin (dAsialofetuin) leading to convergence after several rounds of selection. Enrichment and convergence are monitored with DNA sequencing of ~50 randomly selected clones after every $3^{rd}$ round of panning via FACS. The enrichment of clone R911 relative to all clones sequenced is shown as a percentage at every $3^{rd}$ round of selection. (b) Amino acid ice logo of enriched clone sequences. The wtPNGase F sequence is shown on the bottom. Preferred amino acids at the six randomized positions are shown as a graphical representation. This data is based on ~150 clone sequences obtained from selection rounds 3F, 6F, and 9F. The top most residue in each position is also the sequence of the selected clone R911.

In another embodiment, enzymatic activity is reduced or eliminated by mutating amino acid residue 206 in PNGase F, or the corresponding position in a PNGase F obtained from another organism. In *F. meningosepticum* PNGase F, the wild-type residue at position 206 is a glutamate (E). This residue can be mutated to any other amino acid, provided the mutation reduces or eliminates catalytic activity. Examples of amino acids that can be utilized at position 206 include, without limitation, alanine, arginine, asparagine, aspartic acid, cysteine, glutamine, glycine, histidine, isoleucine, leucine, lysine, methionine, phenylalanine, proline, serine, threonine, tryptophan, tyrosine, or valine, as well as any other amino acid, such as selenocysteine, that reduces or eliminates catalytic activity. Preferred mutations at position 206 of PNGase F include alanine, serine, arginine, tryptophan, histidine and cysteine (FIG. 16) In one embodiment, the mutation at position 206 is alanine, serine, arginine or tryptophan, i.e., E206A, E206S, E206R or E206W. In another embodiment, the mutation at position 206 is any amino acid that reduces or eliminates catalytic activity other than alanine (A), serine (S), arginine (R) or tryptophan (W). In another embodiment, E206 can be deleted.

In another embodiment, enzymatic activity is reduced or eliminated by mutating amino acid residue 248 in PNGase F, or the corresponding position in PNGase F obtained from another organism. In *F. meningosepticum* PNGase F, the wild-type residue at position 248 is an arginine (R). This residue can be mutated to any other amino acid, provided the mutation reduces or eliminates catalytic activity. Examples of amino acids that can be utilized at position 248 include, without limitation, alanine, asparagine, aspartic acid, cysteine, glutamine, glutamic acid, glycine, histidine, isoleucine, leucine, lysine, methionine, phenylalanine, proline, serine, threonine, tryptophan, tyrosine, or valine, as well as any other amino acid, such as selenocysteine, that reduces or eliminates catalytic activity. Preferred mutations at position 248 of PNGase F include tryptophan, serine, proline, valine, aspartate, tyrosine, phenylalanine, and lysine. In one embodiment, the mutation at position 248 is tryptophan or serine, i.e., R248W or R248S. In another embodiment, the mutation at position 248 is any amino acid that reduces or eliminates catalytic activity other than serine (S) or tryptophan (W). In another embodiment, R248 can be deleted.

In another embodiment, enzymatic activity is reduced or eliminated by mutating amino acid residue 118 in PNGase F, or the corresponding position in PNGase F obtained from another organism. While this mutation does not interfere directly with the catalytic cleavage mechanism as do the other inactivating mutations, it adversely impacts activity by reducing or preventing binding of the natural substrate, N-linked glycan. In *F. meningosepticum* PNGase F, the wild-type residue at position 118 is a glutamate (E). This residue can be mutated to any other amino acid, provided the mutation reduces or eliminates N-linked glycan binding thereby negatively impacting catalytic activity. Examples of amino acids that can be utilized at position 118 include, without limitation, alanine, arginine, asparagine, aspartic acid, cysteine, glutamine, glycine, histidine, isoleucine, leucine, lysine, methionine, phenylalanine, proline, serine, threonine, tryptophan, tyrosine, or valine, as well as any other amino acid, such as selenocysteine, that reduces or eliminates catalytic activity. Preferred mutations at position 118 of PNGase F include alanine or glutamine. In one embodiment, the mutation at position 118 is alanine or glutamine, i.e., E118A or E118Q. In another embodiment, the mutation at position 118 is any amino acid that reduces or eliminates catalytic activity other than alanine (A) or glutamine (Q). In another embodiment, E118 can be deleted.

Any combination of mutations at one or more of D60, E118, E206 or R 248 can be used to render PNGase F catalytically inactive. Moreover, the invention is not limited to mutations at any of these four sites to reduce or eliminate catalytic activity; any mutation that reduces or eliminates catalytic activity can be used.

It should be further noted that mutation at position 118 not only causes inactivation of the enzyme, but by virtue of impacting substrate binding and hence specificity, it adds binding specificity and affinity for O-linked glycans. Thus, a mutation at position 118 can serve as both a first (inactivating) mutation and a second (affecting binding specificity and/or binding affinity) mutation. More generally, mutations at position 60, 206, 248, or any other position that adversely affects activity may additionally have the effect of enhancing affinity for N-linked glycans and/or adding binding specificity and affinity for O-linked glycans. Thus, any first (inactivating) mutation may optionally also serve as a second (affecting binding specificity and/or binding affinity) mutation.

Mutation to Increase Binding Affinity for N-Linked Glycan and/or Alter Ligand Specificity to Include O-Linked Glycan At least one amino acid in wild-type PNGase F is mutated so as to either (i) increase the binding affinity of the catalytically inactive carbohydrate-binding PNGase F for N-linked glycans compared to the binding affinity of the corresponding mutant PNGase F having only the first, activity-impairing mutation, or (ii) alter binding specificity of PNGase F so as to add binding specificity and affinity for one or more O-linked glycans (which are non-natural substrates), or both (i) and (ii). The one or more mutations that increase or alter binding specificity or affinity are referred to herein as a "second" mutation.

Some embodiments of the catalytically inactivated carbohydrate-binding PNGase F mutant exhibit significant binding affinity for both N-linked glycans (natural substrate/ligand) and O-linked glycans (newly acquired). An example is PNGase F mutant R911 (Table 1). These PNGase F mutants can be used to enrich for, select for, or detect a wide variety of compounds such as glycoproteins and glycopeptides that contain N-linked and/or O-linked glycans, as well as free N-glycans and O-glycans.

Other embodiments of the catalytically inactivated carbohydrate-binding PNGase F mutant exhibit enhanced binding affinity for N-linked glycans, compared to wild-type PNGase F or PNGase F having only inactivating mutation (s), while not exhibiting significant binding affinity for O-linked glycans. An example is PNGase F revertant R911 L57D (Table 1). These PNGase F mutants can be used to enrich for, select for, or detect compounds such as glycoproteins and glycopeptides that contain N-linked glycans, as well as free N-glycans.

Other embodiments of the catalytically inactivated carbohydrate-binding PNGase F mutant exhibit significant, newly acquired binding specificity and affinity for O-linked glycans but also show a reduced affinity for N-linked glycans, compared to wild-type PNGase F or PNGase F having only inactivating mutation(s). These PNGase F mutants can be used to enrich for, select for, or detect O-linked glycans, as well as free O-glycans.

Some embodiments of the catalytically inactivated carbohydrate-binding PNGase F mutant that exhibit binding specificity and affinity for O-linked glycans preferentially bind to O-linked GlcNAc; other embodiments of the catalytically inactivated carbohydrate-binding PNGase F mutants that exhibit binding specificity and affinity for O-linked glycans preferentially bind to O-linked GalNAc.

The discovery that some embodiments of the catalytically inactivated carbohydrate-binding PNGase F mutant exhibit binding specificity and affinity for O-linked glycans came as quite a surprise. Initially, in an effort to design catalytically inactive carbohydrate-binding with the potential to recognize a vast number of N-linked glycoconjugates, the N-glycan processing enzyme, peptide-$N_4$—(N-acetyl-β-D-glucosaminyl)asparagine amidase (PNGase F), was selected for conversion into a Lectenz® as described below; general laboratory and computational methods are also described in PCT Publication WO 2010/068817, published Jun. 17, 2010, entitled "Glycan-Specific Analytical Tools", and also in US Pat. Pub. 20120040474, published Feb. 16, 2012. Using computationally-guided library design, followed by directed evolution, a number of potential candidate clones of PNGase F were generated. The mutant protein encoded by clone R911 (Table 1) was unexpectedly found to bind not only N-linked glycans (with higher binding affinity than wild-type PNGase F or the inactivated PNGase F mutant, D60A), but also O-linked glycans. Compounds containing O-linked glycans are not known to serve as substrates for PNGase F. Moreover, as shown in Example 6, below, PNGase F is not enzymatically active against an O-glycosylated substrate, providing strong evidence that any observed O-linked glycan affinity is an acquired property as a result of mutation. To capitalize on its unexpected properties, clone R911 was selected as a basis for further mutation in an effort to discover additional catalytically inactive carbohydrate-binding PNGase F mutants (see Example 6), some of which exhibit higher binding affinity for N-linked glycans, and others of which higher binding affinity for O-linked glycans, such as O-linked GlcNAc and O-linked GalNAc.

Exemplary Mutations for PNGase F

Increased binding affinity for N-linked glycans, or an alteration in ligand specificity to add binding affinity for O-linked glycans, can be achieved by mutation of any one, two, three, four, five, six, seven, eight, nine, ten, eleven, twelve, thirteen, fourteen, fifteen, or all sixteen amino acid residues at positions 57, 60, 62, 118, 119, 120, 123, 125, 153, 154, 155, 156, 157, 192, 206 and 248 of PNGase F, or at corresponding positions in PNGase F obtained from another organism. A preferred catalytically inactive carbohydrate-binding PNGase F protein can include mutations at least three of these positions, at least four of these positions, at least five of these positions, or at least six of these positions. Preferably at least one of residues 60, 118 or 206 is mutated.

Some of the residues at the enumerated positions, for example residues at positions 57, 62, 119, 123, 125, 155, 156, 192 and 248 (see Table 4) are referred to herein as "tepid" residues, and were identified using computer-assisted methods as described in Example 2 and PCT Publication WO 2010/068817, as well as in US Pat. Pub. 20120040474, published Feb. 16, 2012. In brief, important interactions involved in binding were identified computationally, and were separated into residues that are directly involved in specificity (hot residues) and those that are minimally involved in binding, whose mutation may therefore lead to an increase in the affinity (tepid residues). The first group (the "hot" residues) includes residues considered to be essential to defining the specificity of the enzyme. The second group (the "tepid" residues) includes residues proximal to the substrate but not considered to be essential to defining specificity. Residues that are close to the substrate, but not forming strong interactions, are identified herein as candidates for mutations that may increase substrate binding activity and/or alter binding specificity. The results from the analysis were applied to the design of mutagenesis library as described in Example 1, through saturation mutagenesis of the tepid residues, in an attempt to engineer a highly specific high-affinity PNGase F reagent, i.e., a catalytically inactive carbohydrate-binding PNGase F protein of the invention.

Some of the residues at the enumerated positions are present in a "loop" region in PNGase F, centered on I156. Space-filling or other disruptive mutations in the vicinity of I156 are made to skew binding away from N-linked glycans toward smaller O-linked glycans (see Example 4). Additionally or alternatively, an insertion of one, two or three amino acids into the sequence in proximity to amino acids 153-157, for example on either side of position 154, is expected to increase binding specificity and affinity to O-linked glycans.

Suitable mutations include, but are not limited to:

D57: leucine, alanine, methionine, arginine, lysine, cysteine, tryptophan

D60: alanine, cysteine, valine, serine, glycine, tryptophan

Y62: glycine, tryptophan, serine, threonine

E118: alanine, glutamine, threonine, cysteine

T119: alanine, glycine, isoleucine, leucine, valine

W120: tyrosine, histidine, glutamine, asparagine threonine, serine

K123: aspartate, glutamate, alanine, glycine, isoleucine, leucine, valine, methionine, phenylalanine, tryptophan R125: tyrosine, alanine, glycine, isoleucine, leucine, valine, methionine, phenylalanine, tryptophan K153: histidine, arginine, glutamine, tryptophan, tyrosine S154: threonine, asparagine, lysine, glutamine, tryptophan, tyrosine S155: arginine, lysine, aspartate, glutamine, tryptophan, tyrosine I156: leucine, threonine, methionine, glycine, tryptophan, histidine D157: asparagine, glutamate, glutamine, lysine, tryptophan, tyrosine G192: isoleucine, tryptophan, alanine, histidine, threonine, cysteine, serine E206: serine, tryptophan, histidine, cysteine, arginine R248: tryptophan, serine, proline, valine, aspartate, tyrosine, phenylalanine, lysine Examples of individual mutations that can be made to PNGase F are shown Table 1 (the designation "X" refers to any amino acid other than the wild-type amino acid at that position). Table 1 shows exemplary mutants having both a first, inactivating mutation in D60, E118, E206, and/or R248, as well as one or more second mutations. An exemplary mutant is R911, which has 6 mutations relative to wild-type PNGase F (D57L, D60C, I156L, G192I, E206S, R248W). Table 1 also shows revertants based on R911, which revertants contain only four or five mutations relative to wild-type PNGase F. Cells showing wild-type residues are indicated with an asterisk (*).

TABLE 1

| | wtPNGase F | | | | | | | | | | | |
|---|---|---|---|---|---|---|---|---|---|---|---|---|
| | D57 | D60 | Y62 | E118 | W120 | K153 | S154 | S155 | I156 | D157 | G192 | E206 | R248 |
| R617 (Library 1) | R | A | G | A | W* | K* | S* | D | T | D* | C | S | R* |
| R6113 (Library 1) | C | A | W | A | W* | K* | S* | Q | T | D* | T | R | R* |
| R911 (Library 2) | L | C | Y* | E* | W* | K* | S* | S* | L | D* | I | S | W |
| R9113 (Library 2) | W | C | Y* | E* | W* | K* | S* | S* | M | D* | I | W | S |
| R911 L57D | D* | C | Y* | E* | W* | K* | S* | S* | L | D* | I | S | W |
| R911 C60A | L | A | Y* | E* | W* | K* | S* | S* | L | D* | I | S | W |
| R911 C60D | L | D* | Y* | E* | W* | K* | S* | S* | L | D* | I | S | W |
| R911 E118Q | L | C | Y* | Q | W* | K* | S* | S* | L | D* | I | S | W |
| R911 W120X | L | C | Y* | E* | X | K* | S* | S* | L | D* | I | S | W |

TABLE 1-continued

| | wtPNGase F | | | | | | | | | | | | |
|---|---|---|---|---|---|---|---|---|---|---|---|---|---|
| | D57 | D60 | Y62 | E118 | W120 | K153 | S154 | S155 | I156 | D157 | G192 | E206 | R248 |
| R911 | | | Y* | E* | | K* | S* | | | D* | | | |
| W120X/S155X | L | C | | | X | | | X | L | | I | S | W |
| R911 K153X | L | C | Y* | E* | W* | X | S* | S* | L | D* | I | S | W |
| R911 S154X | L | C | Y* | E* | W* | K* | X | S* | L | D* | I | S | W |
| R911 S155X | L | C | Y* | E* | W* | K* | S* | X | L | D* | I | S | W |
| R911 L156X | L | C | Y* | E* | W* | K* | S* | S* | X | D* | I | S | W |
| R911 L156I | L | C | Y* | E* | W* | K* | S* | S* | I* | D* | I | S | W |
| R911 | | | Y* | E* | W* | K* | S* | S* | I* | D* | | | |
| L156I/S206E | L | C | | | | | | | I | | I | E* | W |
| R911 D157X | L | C | Y* | E* | W* | K* | S* | S* | L | X | I | S | W |
| R911 I192G | L | C | Y* | E* | W* | K* | S* | S* | L | D* | G* | S | W |
| R911 S206E | L | C | Y* | E* | W* | K* | S* | S* | L | D* | I | E* | W |
| R911 W248R | L | C | Y* | E* | W* | K* | S* | S* | L | D* | I | S | R* |

Listed below are 20 exemplary PNGase F mutants having amino acid substitutions according to Table 1. These PNGase F mutants have a wild-type PNGase F sequence as in SEQ ID NO:1 at amino acid positions other than those listed below.

Mutant 1: D57R, D60A, Y62G, E118A, S155D, I156T, G192C and E206S

Mutant 2: D57C, D60A, Y62W, E118A, S155Q, I156T, G192T, and E206R

Mutant 3: D57L, D60C, I156L, G192I, E206S, and R248W

Mutant 4: D57W, D60C, I156M, G192I, E206W, and R248S

Mutant 5: D60C, I156L, G192I, E206S, and R248W

Mutant 6: D57L, D60A, I156L, G192I, E206S, and R248W

Mutant 7: D57L, I156L, G192I, E206S, and R248W

Mutant 8: D57L, D60C, E118Q, I156L, G192I, E206S, and R248W

Mutant 9: D57L, D60C, W120X, I156L, G192I, E206S, and R248W

Mutant 10: D57L, D60C, W120X, S155X, I156L, G192I, E206S, and R248W

Mutant 11: D57L, D60C, K153X, I156L, G192I, E206S, and R248W

Mutant 12: D57L, D60C, S154X, I156L, G192I, E206S, and R248W

Mutant 13: D57L, D60C, S155X, I156L, G192I, E206S, and R248W

Mutant 14: D57L, D60C, I156X, G192I, E206S, and R248W

Mutant 15: D57L, D60C, G192I, E206S, and R248W

Mutant 16: D57L, D60C, G192I, and R248W

Mutant 17: D57L, D60C, I156L, D157X, G192I, E206S, and R248W

Mutant 18: D57L, D60C, I156L, E206S, and R248W

Mutant 19: D57L, D60C, I156L, G192I, and R248W

Mutant 20: D57L, D60C, I156L, G192I, and E206S

Also encompassed by the invention are truncated forms of the catalytically inactive carbohydrate-binding PNGase F, which can be truncated at either the N- or the C-terminus, as well as forms having other derivatizations, modifications, insertions or deletions, as long as binding specificity and affinity toward N-linked glycans and/or O-linked glycans are maintained. Truncations can include truncations of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or more amino acids from either or both of the N- or C-terminus.

An enzyme or compound that is "catalytically inactive" as that term is used herein, is one that has reduced catalytic activity, preferably one that has lost at least 50% of its catalytic activity, preferably at least 60% or 70% of its catalytic activity, and has an amino acid composition different from that of the catalytically active enzyme. A catalytically inactive enzyme can be an enzyme that has lost at least 70% of its activity, at least 75% of its activity, at least 80% of its activity, at least 85% of its activity, at least 90% of its activity, or at least 95% of its activity. For example, the cleavage rate can be 50%, 40%, 30%, 25%, 20%, 15%, 10%, or 5% of the cleavage rate observed in a corresponding wild-type enzyme. An enzyme or compound whose activity is "eliminated" is one that has lost at least 90%, or at least 95%, of its catalytic activity, and has an amino acid composition different from that of the catalytically active enzyme. The term "wild-type (WT) enzyme" refers to an enzyme encoded by a gene that has a sequence of a gene as it naturally occurs in an organism, and that has not been altered by human intervention. It is of course understood that a naturally occurring polymorphic form of wild-type enzyme is included within this definition. It is further understood that modifications such as tags or other modifications used in the purification or isolation of a protein that do not otherwise change the natural start or stop codon of a protein fall within the definition of a WT enzyme for purposes of this invention. As used herein, the term "ligand" and "substrate" are used interchangeably, and refer to a molecule to which WT or mutant enzymes can bind.

A catalytically inactive carbohydrate-binding PNGase F protein of the invention, which possesses high binding affinity and high specificity for its substrate, but no longer has significant enzymatic activity toward the substrate, is a Lectenz®. Lectenz® is a registered trademark of Glycosensors and Diagnostics (G&D). "Lectenz®" are proteins that have lectin-like properties and are engineered from carbohydrate-processing enzymes using a combination of forefront computational and experimental methods. Lectenz® may be employed directly in glycomics to aid in sample enrichment and glycosylation site-mapping. See the G&D website at http://glycosensors.com. Lectenz® and their properties, as well as materials and methods for designing, synthesizing, and assaying catalytically inactive carbohydrate-binding proteins, and which may be useful for such purposes in the present invention, are described in WO 2010/068817 and US Pat. Pub. 20120040474, published Feb. 16, 2012, as well as U.S. Provisional Application No. 61/900,746 ("Catalytically Inactive Carbohydrate-Binding Protein Specific for O-Linked N-Acetylglucosamine"). WO 2010/068817, US Pat. Pub. 20120040474, published Feb. 16, 2012, and U.S. Provisional Application No. 61/900,746 are hereby incorporated by reference in their entireties. PCT Publication WO 2010/068817 and U.S. Provisional Application No. 61/900,746 also provide more detailed information concerning meaning of the terms "binding affinity" and "specificity" as used herein.

Conjugates

The invention also includes conjugates of the catalytically inactive carbohydrate-binding PNGase F mutants. A conjugate includes, as a first component, a catalytically inactive carbohydrate-binding PNGase F mutant, which is covalently linked to at least one second component, which may be a proteinaceous component or a nonproteinaceous component. In some embodiments, a conjugate that includes a proteinaceous component can be synthesized as a fusion protein using well-known recombinant DNA methods. In some embodiments, the conjugate includes a proteinaceous or non-proteinaceous component that is chemically or enzymatically conjugated to the catalytically inactive carbohydrate-binding PNGase F mutants.

One example of a conjugate of the invention includes a catalytically inactive carbohydrate-binding PNGase F mutant conjugated to a therapeutic agent, also referred to herein as a drug. This conjugate is analogous to the well-known antibody-drug conjugate (ADC) except that the PNGase F mutant is used in place of the antibody. Drugs that can be conjugated to a catalytically inactive carbohydrate-binding PNGase F mutant include, without limitation, cytotoxins, anti-metabolites, alkylating agents, antibiotics and anti-mitotic agents.

Anti-cancer, anti-inflammatory, pro-inflammatory, and immune-moderating drugs are particularly suitable for conjugation to a catalytically inactive carbohydrate-binding PNGase F protein, since cancerous and precancerous conditions, as well as inflammation and immune conditions, are often associated with changes in protein glycosylation patterns. For example, a therapeutic or diagnostic radioactive agent can be coupled to or incorporated into a catalytically inactive carbohydrate-binding PNGase F mutant to yield a "Lectenz®-drug" conjugate that can be targeted to a cancer glycomarker. In one embodiment, the therapeutic or diagnostic agent can be targeted to mucus linings or membranes, such as in the lungs or gut.

Likewise, anti-viral and anti-bacterial drugs are also particularly suitable for incorporation into a "Lectenz®-drug" conjugate, as targeting viral or bacterial glycosylated biomolecules has great therapeutic potential.

Another example of a conjugate of the invention includes a catalytically inactive carbohydrate-binding PNGase F mutant conjugated to a diagnostic or detection agent. The diagnostic or detection agent can include a detectable label, including but not limited to a radioactive, fluorescent, phosphorescent, colorimetric, enzymatic, immunological, magnetic, paramagnetic, diamagnetic or electromagnetic label. It should be understood that a catalytically inactive carbohydrate-binding PNGase F mutant need not be conjugated to function as a diagnostic or detection agent, as the PNGase F mutant can be detected directly, e.g., via immunoassay.

Another example of a conjugate of the invention includes a catalytically inactive carbohydrate-binding PNGase F mutant conjugated to a marker sequence, for example a peptide such as hexa-histidine or hemagglutinin, to facilitate purification. Included in the invention are, for example, PNGase F fusion proteins that include a catalytically inactive carbohydrate-binding PNGase F mutant covalently linked to glutathione S-transferase (GST), thioredoxin, bovine serum albumin, bovine pancreatic trypsin inhibitor, or fluorescent proteins such as green fluorescent protein (GFP).

Methods of Use

The vast number of potential applications of the catalytically inactive carbohydrate-binding PNGase F protein, because of its lectin-like properties, will be immediately apparent to persons skilled in the art. In general, a catalytically inactive carbohydrate-binding PNGase F mutant, or conjugate thereof, can be used for any of the same purposes for which anti-glycan antibodies are currently used. Thus, the compounds of the invention can be advantageously substituted for anti-glycan antibodies in numerous medical and laboratory methods, including diagnostic, analytical and therapeutic methods. Likewise, a catalytically inactive carbohydrate-binding PNGase F mutant or conjugate thereof, can be used for the same purposes for which lectins are currently used. Thus, the compounds of the invention can be advantageously substituted for lectins in numerous diagnostic and analytical laboratory methods.

Diagnostic and Analytical Methods

A catalytically inactive carbohydrate-binding PNGase F mutant or conjugate thereof can be used to detect N-linked glycans, O-linked glycans, or both, in a biological or synthetic sample. For example, a biological sample, such as a tissue or fluid, can be contacted with the PNGase F mutant or conjugate thereof to detect and/or characterize the level or type of glycosylation and/or glycation in the biological sample. Characterization of the glycan can include identifying a constituent saccharide of the glycan, determining saccharide composition of the glycan, determining linkage positions within the glycan, or determining stereochemistry of the glycan. As another example, a catalytically inactive carbohydrate-binding PNGase F mutant or conjugate thereof can be used for quality control in the synthesis of therapeutic biologics, for example in the synthesis of therapeutic antibodies, to monitor the level or type of glycosylation. See PCT patent publication WO2012/118928, published Sep. 7, 2012. A catalytically inactive carbohydrate-binding PNGase F mutant or conjugate thereof can be utilized as an affinity reagent or as part of an affinity matrix; for example, it can be tethered to a solid support, such as a surface, column, resin, bead, particle or nanoparticle, and used in methods to detect or enrich for O-linked and/or N-linked compounds in or from biological or synthetic samples. Tethered PNGase F mutants can also be used to isolate and/or purify synthetic glycosylated compounds.

Diagnostics can be performed on a biological sample obtained from a subject, but can also be performed in vivo. In in vivo applications, a catalytically inactive carbohydrate-binding PNGase F mutant or conjugate thereof is administered to a subject, and binding of the PNGase F mutant within the subject is detected. Preferably, a conjugate is administered to the subject, wherein the conjugate includes a detectable label so as to facilitate biomedical imaging. Examples of a suitable conjugate include a catalytically inactive carbohydrate-binding PNGase F mutant conjugated to a radiolabel, a paramagnetic label, or a diamagnetic label.

The catalytically inactive carbohydrate-binding PNGase F protein with enhanced binding affinity toward N-linked glycans and/or newly acquired specificity toward O-linked glycans can be used to interrogate biological samples in the search for abnormal glycosylation. Examples of biological samples include, but are not limited to, any biological fluid, tissue, or organ. Examples of the biological fluids include, but are not limited to blood, urine, serum, saliva, cerebraspinal fluid, and semen. In other embodiments, a catalytically inactive PNGase F derivative can be used for a detection of the presence or amount of a target analyte in biological fluids and tissues. Examples of targets are exogenously consumed species, such as plant polysaccharides, carbohydrate-based drugs, and pathogens, whose surfaces are often coated in complex distinct glycans. The catalytically inactive PNGase F derivative also has application in drug discovery and evaluation of biological activity of new glycan-based compounds.

The catalytically inactive carbohydrate-binding PNGase F protein can be used for diagnosing, and/or treating diseases manifested by abnormal glycosylation. It can be used to detect certain tumor antigens comprising glycoproteins, glycolipids, and/or a variety of carbohydrate epitopes. A number of these tumor antigens have been found to be up-regulated in the neoplastic disease state. Examples of tumor antigens that can signal a development and progression of a neoplastic disorder, and that can be detected a catalytically inactive carbohydrate-binding protein include, but are not limited to, carcinoembryonic antigen (CEA), which is a glycoprotein associated with colorectal, gastric, pancreatic, lung, and breast carcinomas, and the developing fetus; carbohydrate antigen 19-9 (CA 19-9), or sialylated Lewis A antigen, which is present in a glycolipid found in patients with pancreatic cancer; and carbohydrate antigen 15-3 (CA15-3), associated with breast cancer.

The presence of the antigen does not necessarily indicate transformation to a cancerous cell; however, its localization in the cell is indicative, as in the case of CEA. For this reason, there is a need for highly selective and high affinity analytical tools. The diagnostic tests currently rely on antibodies that were often generated against the peptide portions of the glycoprotein or sugar portions of glycolipid, however, the exact epitopes are only now being defined. In the examples in which the glycans have been characterized, multiple glycoforms are often present (CEA, for example). Lacking reagents that are able to discriminate between glycoforms, it is currently impossible to determine the extent to which subtle variations in glycosylation correlate with disease state, cancer type, or tissue localization. At present, these questions can be addressed primarily by MS analyses of isolated glycoproteins, which are examined as mixtures of glycoforms. Typically, the only level of glycoform-focusing that is performed is the enrichment in high-mannose containing glycans using lectin (concanavalin A, (Con A)) affinity chromatography. More efficient laboratory analyses and routine clinical diagnostic techniques remain severely limited by the lack of glycoform-specific reagents.

The catalytically inactive carbohydrate-binding PNGase F protein may have utility for quantifying the relative abundances of each glycoform present for any given glycoprotein in a biological sample. As used herein, the term "glycoform" refers to a protein with a specific glycan attached. A glycoprotein can have multiple glycoforms. More specifically, a glycoform is an isoform of a protein that differs only with respect to the number or type of attached glycan; the amino acid sequence is the same for the various glycoforms. Glycoproteins often comprise a number of different glycoforms, with alterations in the attached saccharide or oligosaccharide. Advantageously, a catalytically inactive PNGase F derivative can be used to enrich the biological sample with a particular glycoform. It can likewise be used to identify specific glycosylation sites on the protein surface to which the glycans are attached. It can also be used to separate intact glycopeptides from a proteolytic digest of any glycoprotein. Enriching the sample in the analyte of interest is of great assistance in the further characterization of the glycopeptides fractions. In particular, enrichment facilitates the identification of the peptide sequence and the glycan structure, which can enable the identification within the intact protein of the glycosylation sites and the characterization of the particular glycans present at each glycosylation site.

The catalytically inactive carbohydrate-binding PNGase F protein can be used in monitoring specific glycan modifications of proteins in biological fluids, tissues, organs, or living cells. Recognition is not expected to depend on the identity of the protein, and the catalytically inactive PNGase F derivative is expected to be able to recognize any protein that comprises a given N-linked and/or O-linked glycan, and therefore will be very useful for detection of given glycan modifications.

In yet other embodiments, the catalytically inactive carbohydrate-binding PNGase F protein can be used for in vitro or in vivo staining cells or tissues.

The catalytically inactive carbohydrate-binding PNGase F protein can be employed to monitor N-linked and/or O-linked glycosylation in a mixture, as might arise during the production of recombinant glycoproteins for use in the pharmaceutical or research industries.

In the foregoing embodiments, the catalytically inactive carbohydrate-binding PNGase F protein can be tagged with a stain or a dye and applied to a biological sample comprising cells or tissues or glycoproteins or glycopeptides or oligosaccharides or polysaccharides of interest.

Another aspect of the present invention provides methods of using catalytically inactive carbohydrate-binding PNGase F proteins for analytical applications. The catalytically inactive PNGase F derivative of the present invention can be used as an N-linked or O-linked glycan-specific analytical tool. Glycan-specific analytical tools have potential use as a method of detection in many areas, including environmental, fermentation, food and medical areas and could be used for in vivo or in vitro sensing in humans or animals. For example, the catalytically inactive PNGase F derivative of the present invention can be used as an affinity reagent or as vehicle for tissue staining. As another example, the catalytically inactive PNGase F derivative can be used for enriching a biological sample for N-linked glycans and/or O-linked glycans. In yet other examples, the catalytically inactive PNGase F derivative can be used to determine specific glycosylation sites on glycoproteins.

In certain embodiments, the catalytically inactive carbohydrate-binding PNGase F protein can be used as a reagent for affinity separation, including, for example, affinity chromatography. Affinity chromatography is a method of separating biochemical mixtures, based on a highly specific biological interaction such as that between the binding protein and the glycan. The present invention is not limited to any specific design or chromatographic system. In general, the catalytically inactive PNGase F derivative will be either covalently attached or otherwise immobilized to the solid support, and will constitute a stationary phase. In certain embodiments, the stationary phase that is derivatized with the catalytically inactive PNGase F derivative can be used in column chromatography. In these embodiments, the particles of the solid stationary phase will be used to fill the whole inside volume of the tube (packed column). Alternatively, the solid phase particles will be concentrated on or along the inside tube wall leaving an open, unrestricted path for a biological sample (i.e., the mobile phase) in the middle part of the tube (open tubular column). In other embodiments, the derivatized stationary phase can be used for batch chromatography. In these embodiments, the stationary phase can be added to a vessel and mixed with the biological sample. Although the foregoing example generally focused on affinity chromatography, it is understood that these principals are readily applied to other affinity purification protocols.

Therapeutic Methods

In certain embodiments, the catalytically inactive carbohydrate-binding PNGase F protein of the invention can be used as a therapeutic agent or modified for delivery of an active therapeutic agent. Since the catalytically inactive PNGase F derivative of the present invention has a defined glycan specificity, a delivery of the therapeutic agents can be targeted only to those cells, tissues, or organs that display a biomolecule, such as a glycoprotein or glycolipid with the glycan structure recognized by PNGase F.

The potential therefore exists for the catalytically inactive carbohydrate-binding PNGase F protein to be used as a therapeutic in many applications such as targeted drug delivery. Changes in the levels and locations of N-linked glycans and O-linked glycans have been shown to be associated with many diseases, including cancer. The catalytically inactive PNGase F derivative of the invention has enhanced affinity for one or both of these glycans, relative to the wild-type PNGase F. This invention is thus expected to have direct applications in the field of cancer research, potentially leading to the development of a product for the detection of certain forms of cancer. It is also expected to have utility as a reagent for use in glycomics, wherein it may be used to enrich samples containing N-linked glycan and/or O-linked glycan, for example O-linked GlcNAc and/or O-linked GalNAc, thereby enabling detection and analysis of these important carbohydrates. A catalytically inactive PNGase F derivative can be used as a vehicle for targeted delivery of therapeutic agents.

A catalytically inactive carbohydrate-binding PNGase F mutant, or conjugate thereof, can be administered to a subject to treat or prevent an infection, disease, or disorder. The infection can be, for example, viral, bacterial, parasitic, or fungal. The disease or disorder can result from an exogenous agent, or it can be autologous or autoimmune.

In one embodiment, a catalytically inactive carbohydrate-binding PNGase F mutant is administered to a subject so as to bind to an N-linked glycan, O-linked glycan or both, which glycan is present within the subject, so as to achieve a therapeutic or prophylactic effect. The N-linked glycan or O-linked glycan can be an endogenous biomolecule produced by the subject, or it can be an exogenous biomolecule produced by a pathogen. In one embodiment, the PNGase F mutant binds to an endogenous biomolecule, for example a biomolecule associated with cancer, a precancerous condition, or an immune disorder of the subject. In another embodiment, the PNGase F mutant prevents binding of a pathogen to a host cell; in another embodiment, the PNGase F mutant prevents internalization of a pathogen into a host cell.

In another embodiment, a conjugate of a catalytically inactive carbohydrate-binding PNGase F mutant is administered to a subject, wherein the conjugate includes a therapeutic agent as exemplified above. The therapeutic agent can be an antibiotic agent, for example an agent that targets a microbial pathogen. The therapeutic agent can be an agent that targets an autologous or autoimmune disease, for example an anti-cancer agent, such as a cytotoxin, or an immunoactive agent. Examples of therapeutic agents that can be used for site-specific delivery include, but are not limited to, various chemotherapeutic, antibiotic, and antiviral agents, toxins, radioisotopes, cytokines, etc.

A catalytically inactive carbohydrate-binding PNGase F mutant or conjugate thereof for therapeutic use can be tested for toxicity in suitable animal model systems, for example in rats, mice, monkeys, or rabbits. The usefulness of a PNGase F mutant or conjugate thereof to treat or prevent a viral infection can be assessed by evaluating its ability to inhibit viral replication, inhibit viral transmission or to treat or prevent symptoms associated with viral infection. Likewise the usefulness of a PNGase F mutant or conjugate thereof to treat or prevent a bacterial infection can be assessed by evaluating its ability to inhibit the bacterial replication, or to treat or prevent symptoms associated with bacterial infection. Usefulness in treating cancer can be evaluated by assessing the ability of a PNGase F mutant or conjugate thereof to inhibit the growth or metastasis of cancerous cells, to inhibit angiogenesis, or to cause cell death.

Method of Making

The catalytically inactive carbohydrate-binding PNGase F protein of the invention may be expressed in a host cell using genetic engineering techniques. The term "cell" is meant to include any type of biological cell. The host cell can be a eukaryotic cell or a prokaryotic cell. Preferably, the host cell is a prokaryotic cell such as a bacterial cell; however single cell eukaryotes such as protists or yeasts are also useful as host cells. Preferred host cells are microbial cells, preferably the cells of single-celled microbes such as bacterial cells or yeast cells. Notwithstanding the above preferences for bacterial and/or microbial cells, it should be understood that the PNGase mutant can be expressed without limitation in the cell of an animal, plant, insect, yeast, protozoan, bacterium, or archaebacterium. Examples of microbial cells that can be engineered to express the catalytically inactive PNGase F derivative of the invention, in addition to *E. coli*, include a wide variety of bacteria and yeast including members of the genera *Escherichia, Salmonella, Clostridium, Zymomonas, Pseudomonas, Bacillus, Rhodococcus, Alcaligenes, Klebsiella, Paenibacillus, Lactobacillus, Enterococcus, Arthrobacter, Brevibacterium, Corynebacterium Candida, Hansenula, Pichia* and *Saccharomyces*. Preferred microbial cells include, without limitation, *Escherichia coli, Bacillus subtilis, Bacillus licheniformis, Alcaligenes eutrophus, Rhodococcus erythropolis, Paenibacillus macerans, Pseudomonas putida, Enterococcus faecium, Saccharomyces cerevisiae, Lactobacillus plantarum, Enterococcus gallinarium* and *Enterococcus faecalis*.

A cell that has been genetically engineered to express the catalytically inactive carbohydrate-binding PNGase F protein of the invention may be referred to as a "host" cell, a "recombinant" cell, a "genetically engineered" cell or simply an "engineered" cell. These and similar terms are used interchangeably. A genetically engineered cell contains one or more artificial sequences of nucleotides which have been created through standard molecular cloning techniques to bring together genetic material that is not natively found together. DNA sequences used in the construction of recombinant DNA molecules can originate from any species. For example, plant DNA may be joined to bacterial DNA, or human DNA may be joined with fungal DNA. Alternatively, DNA sequences that do not occur anywhere in nature may be created by chemical synthesis of DNA or by directed mutation of DNA, and incorporated into recombinant molecules. Proteins that result from the expression of recombinant DNA are often termed recombinant proteins. Examples of recombination are described in more detail below and may include inserting foreign polynucleotides (obtained from another species of cell) into a cell, inserting synthetic polynucleotides into a cell, or relocating or rearranging polynucleotides within a cell. Any form of recombination may be considered to be genetic engineering and therefore any recombinant cell may also be considered to be a genetically engineered cell.

As will be appreciated by a person of skill in the art, expression of a protein, such as the catalytically inactive carbohydrate-binding PNGase F protein of the invention, can be achieved through a number of molecular biology techniques. For example, expression can be achieved by introducing into the host cell one or more copies of a polynucleotide encoding the desired protein. The polynucleotide encoding the desired protein may be endogenous or heterologous to the host cell. Preferably, the polynucleotide is introduced into the cell using a vector; however, naked DNA may also be used. The polynucleotide may be circular or linear, single-stranded or double stranded, and can be DNA, RNA, or any modification or combination thereof. The vector can be any molecule that may be used as a vehicle to transfer genetic material into a cell. Examples of vectors include plasmids, viral vectors, cosmids, and artificial chromosomes, without limitation. Examples of molecular biology techniques used to transfer nucleotide sequences into a microorganism include, without limitation, transfection, electroporation, transduction, and transformation. These methods are well known in the art. Insertion of a vector into a target cell is usually called transformation for bacterial cells and transfection for eukaryotic cells, however insertion of a viral vector is often called transduction. The terms transformation, transfection, and transduction, for the purpose of the instant invention, are used interchangeably herein. A polynucleotide which has been transferred into a cell via the use of a vector is often referred to as a transgene.

Preferably, the vector is an expression vector. An "expression vector" or "expression construct" is any vector that is used to introduce a specific polynucleotide into a target cell such that once the expression vector is inside the cell, the protein that is encoded by the polynucleotide is produced by the cellular transcription and translation machinery. Typically an expression vector includes regulatory sequences operably linked to the polynucleotide encoding the desired protein. Regulatory sequences are common knowledge to the person of the skill in the art and may include for example, an origin of replication, a promoter sequence, and/or an enhancer sequence. The polynucleotide encoding the desired protein can exist extrachromosomally or can be integrated into the host cell chromosomal DNA.

Extrachromosomal DNA may be contained in cytoplasmic organelles, such as mitochondria (in most eukaryotes), and in chloroplasts and plastids (in plants). More typically, extrachromosomal DNA is maintained within the vector on which it was introduced into the host cell. In many instances, it may be beneficial to select a high copy number vector in order to maximize the expression of the protein. Optionally, the vector may further contain a selectable marker. Certain selectable markers may be used to confirm that the vector is present within the target cell. Other selectable markers may be used to further confirm that the vector and/or transgene has integrated into the host cell chromosomal DNA. The use of selectable markers is common in the art and the skilled person would understand and appreciate the many uses of selectable markers. Optionally, the vector may further contain a reporter gene. Reporter genes may be used to confirm that the vector is expressing within the target cell, and may be further used to monitor the expression from the vector. The use of reporter genes is common in the art and the skilled person would understand and appreciate the many uses of reporter genes.

A catalytically inactive carbohydrate-binding PNGase F protein of the invention can be isolated and optionally purified from any genetically engineered cell described herein. It can be isolated directly from the cells, or from the culture medium, for example, during an aerobic or anaerobic fermentation process. Isolation and/or purification can be accomplished using known methods.

Also provided by the invention is a kit that includes a catalytically inactive carbohydrate-binding PNGase F mutant, conjugate, fusion protein or affinity matrix, and instructions for use.

The above description of the present invention is not intended to describe each disclosed embodiment or every implementation of the present invention. The examples that follow more particularly exemplify illustrative embodiments. In several places throughout the application, guidance is provided through lists of examples, which examples can be used in various combinations. In each instance, the recited list serves only as a representative group and should not be interpreted as an exclusive list.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

The present invention is illustrated by the following examples. It is to be understood that the particular examples, materials, amounts, and procedures are to be interpreted broadly in accordance with the scope and spirit of the invention as set forth herein.

EXAMPLES

Example 1

Carbohydrate-Recognizing Biosensor Engineered Via Computationally-Guided Directed Evolution With this example, a novel reagent for detecting the core glycopeptide component common to all N-linked glycans has been developed. Through a combination of computationally guided biocombinatorial library design and in vitro directed evolution, the N-glycan processing enzyme, PNGase F from *Flavobacterium meningosepticum*, has been converted to a catalytically inactive protein with enhanced affinity for the substrates of the wild-type enzyme. The engineering of a lectin-like carbohydrate-recognizing biomolecule from a carbohydrate-processing enzyme (a LECTENZ) was initiated in silico to determine optimal carbohydrate-enzyme interactions using molecular dynamics simulations. In silico structure/function analyses were validated by generating focused biocombinatorial libraries for in vitro directed evolution, selection and downstream characterization of LECTENZ candidates. Surface Plasmon Resonance was utilized to determine binding kinetics. Furthermore, enrichment of the N-glycan bearing glycoprotein, Ribonuclease B, and N-glycopeptides was demonstrated via affinity chromatography. Enrichment of N-glycoproteins from MCF7 cell-extract was demonstrated.

Carbohydrate recognition is an integral part of normal biological processes. It is critical for host-pathogen interactions, biological development, and increasingly important for disease-state biomarker detection. Due to the importance of carbohydrate recognition and variation in host glycosylation, glycans are obvious targets for detection, diagnostic, and therapeutic applications. Not only do glycans serve as important disease biomarkers, they also impact the pharmacological properties of therapeutic biologics. For example, glycan heterogeneity can impact the batch-to-batch consistency, immunogenicity, pharmacokinetics, activity, and biological clearance of recombinant glycoproteins. Given that more than two thirds of therapeutic biologics are glycosylated recombinant proteins, new tools for glycosylation analysis during bioprocess monitoring are required.

Reported here is the development of a novel reagent for detecting the core chitobiose component common to all N-linked glycans. Through a combination of computationally guided biocombinatorial library design and in vitro directed evolution, the N-glycan processing enzyme, PNGase F from *Flavobacterium meningosepticum*, has been engineered into a catalytically inactive protein with enhanced affinity for the substrates of the wild-type enzyme. The engineering of a lectin-like carbohydrate-recognizing biomolecule from a carbohydrate-processing enzyme (a Lectenz®) was initiated in silico to determine optimal carbohydrate-enzyme interactions using molecular dynamics simulations. In silico structure/function analyses guided the design of focused biocombinatorial libraries for in vitro directed evolution via yeast-displayed selection of Lectenz® candidates. The selected clone, R911, was observed to have a 10× affinity enhancement ($K_D$=0.26 µM) relative to a non-affinity enhanced control clone (D60A). In addition, enrichment of the N-glycan bearing glycoprotein, Ribonuclease B, and N-glycopeptides was demonstrated via Lectenz® affinity chromatography. Furthermore, successful enrichment of glycoproteins from the cell extract of a human breast cancer cell line, MCF7, demonstrated the utility of R911 Lectenz® as a capture reagent for the enrichment of glycoproteins from complex mixtures. Molecular modeling of R911 provided insights into mutations critical for affinity and specificity, thus rationalizing experimental observations.

The successful creation of the R911 Lectenz® reagent presents not only a unique solution to the challenge of glycopeptide and glycoprotein sample enrichment, but also demonstrates a novel strategy for engineering glycan-targeting reagents for glycans and glycoconjugates of biological relevance.

Significance

Carbohydrate recognition is an integral part of biological processes. It is critical for host-pathogen interactions, biological development, and increasingly important for disease-state biomarker detection.[82] Many tumor antigens are glycoproteins or glycolipids, and a variety of carbohydrate epitopes have been identified that are up-regulated in the disease state.[83] Currently approved carbohydrate tumor markers include[84]: Carcinoembryonic Antigen (CEA), a glycoprotein containing 50-80% carbohydrate associated with colorectal, gastric, pancreatic, lung, and breast carcinomas and the developing fetus[85]; Carbohydrate Antigen 19-9 (CA 19-9), or sialylated Lewis A antigen, which is present in a glycolipid found in patients with pancreatic cancer[85]; and Carbohydrate Antigen 15-3 (CA15-3), the most widely used serum marker for breast cancer, is a glycoprotein fragment derived from mucin protein 1 (MUC1)[86]. Due to the importance of carbohydrate recognition and variation in host glycosylation, glycans are obvious targets for detection, diagnostic, and therapeutic applications.[87-92]

The location of many glycans on the cell surface makes them crucial for cellular interactions and contribution to the control of normal metabolic processes. Glycan structure and abundance are dynamic properties that can be driven by the state of cellular processes, resulting in heterogeneity as biological processes are altered between normal and disease states. Furthermore, unlike DNA and protein synthesis, glycan synthesis is a non-template driven enzymatic process managed by many enzymes in a dynamic manner. The complexity in their synthesis may be attributed to the complex roles of glycans in biological processes; however, alterations in glycosylation machinery and activity can result in systemic effects on glycosylated proteins regardless of their level of abundance.

Glycans also impact the pharmacological properties of recombinant therapeutic biologics. Glycan heterogeneity can impact batch-to-batch consistency, immunogenicity, pharmacokinetics, activity and clearance.[93] Unlike the case of proteins and nucleic acids, the sequencing and structural characterization of glycans is a laborious multi-step process, typically requiring sample enrichment, enzyme digestion, and mass-spectrometric analysis, a process which is not amenable to real-time monitoring. Given that more than two thirds of therapeutic biologics are glycosylated recombinant proteins, new tools for glycosylation analysis during bioprocess monitoring are also required.[94]

Despite the significance of glycans, the discovery and routine laboratory analysis of glycans and glycoconjugates is limited by available isolation and analysis techniques,[82] which is not unexpected given the immense diversity of glycan structure.[95] Thus there is an urgent need for glycan biosensors with defined carbohydrate specificity that can be used to interrogate biological samples to identify abnormal glycosylation states in cancer as well as the production of glycosylated therapeutics biologics.[81]

Glycan Biosynthesis and Diversity

The covalent attachment of glycans to nascent proteins is a non-template driven process and requires approximately 1000 gene products, thus the biosynthesis of oligosaccharides requires a significant investment of cellular resources and defects in the cellular machinery required for glycosylation can be fatal.[91, 96-99] The major types of mammalian protein glycosylation are N- and O-linked glycosylation.

The biosynthesis of N-glycan structures occurs on the endoplasmic reticulum membrane and requires over twenty enzymes in humans prior to its en bloc co-translational attachment to a nascent protein.[100-104] Synthesis begins with a dolichylpyrophosphate carrier and individual monosaccharides are attached sequentially until a fourteen-saccharide N-glycan structure is completed.[102-104] Each different glycosidic linkage requires a unique enzyme. The protein complex, oligosaccharyl transferase, is responsible for the en bloc attachment of the fourteen-saccharide N-glycan structure to an Asn-X-Ser/Thr sequone (where X can be any amino acid, except Pro) on the nascent peptide chain via an N-glycosidic bond to the side chain of the Asn residue.[101, 103] Endoplasmic reticulum chaperones regulate the proper folding of the nascent polypeptide via direct interaction with the N-glycan structure prior to the transfer of the high-mannose containing immature glycoprotein to the Golgi.

The biosynthesis of hybrid and complex glycosylation protein Golgi complex where additional enzymes are responsible for further modification and terminal elaboration of the attached N-glycan structures as glycoproteins migrates through the cis-medial- and trans-Golgi processes. Glycosylated proteins with numerous glycoforms are produced in this manner. The non-template driven enzymatic biosynthesis of glycan structures results in significant glycan diversity.

A core five-saccharide N-glycan structure (from the original fourteen-saccharide structure) is conserved and increasingly terminally modified in higher eukaryotes, thereby yielding highly diverse N-glycosylation (FIG. 1). Yeast express a high mannose form of N-glycosylation.[105] Plants express both high mannose and more complex forms of N-glycosylation.[106] Animals have evolved the most complex N-glycan structures reflected by the highest diversity of terminal modifications.[99]

O-linked glycosylation is the defined by covalent attachment of core saccharide(s) to the hydroxyl group of serine and threonine residues.[107, 108] Two major classes of O-glycans consist of mucins and proteoglycans. Unlike N-glycosylation, which consists of a large core N-glycan structure that is trimmed and terminally modified, mucin-type O-glycans consist of smaller 8 core structures that lead to significant O-glycan diversity. These core structures are similar to the terminal modifications found on N-glycans and are enzymatically attached to proteins only in the Golgi complex.

Mucins consist of long polypeptides with repeating Ser/Thr sequences that serve as attachment sites of core O-glycan structures. The formation of disulfide-linked oligomers can result in the formation of mucins larger than 1 MDa. Unlike mucins, proteoglycans consist of longer repeating oligosaccharide chains (>100 monosaccharide residues) attached to a polypeptide backbone. Often the oligomer consists of repeating amino derived disaccharide hexoses, which are known predominantly as glycosaminoglycans (GAGs). The 3 types of GAGs, which are differentiated according to the repeating disaccharide unit, are: 1) dermatan sulfate/chondroitin sulfate, 2) heparin sulfate/heparin and 3) keratin sulfate. Proteoglycans are a major component of extracellular matrices and connective tissues. In addition to mucins and proteoglycans, other types of O-glycans include α-linked O-fucose, β-linked O-xylose, α-linked O-mannose, β-linked O-GlcNAc, α- or β-linked O-galactose, α- or β-linked O-GalNAc, and α- or β-linked O-glucose glycans.[108]

Figure 2:
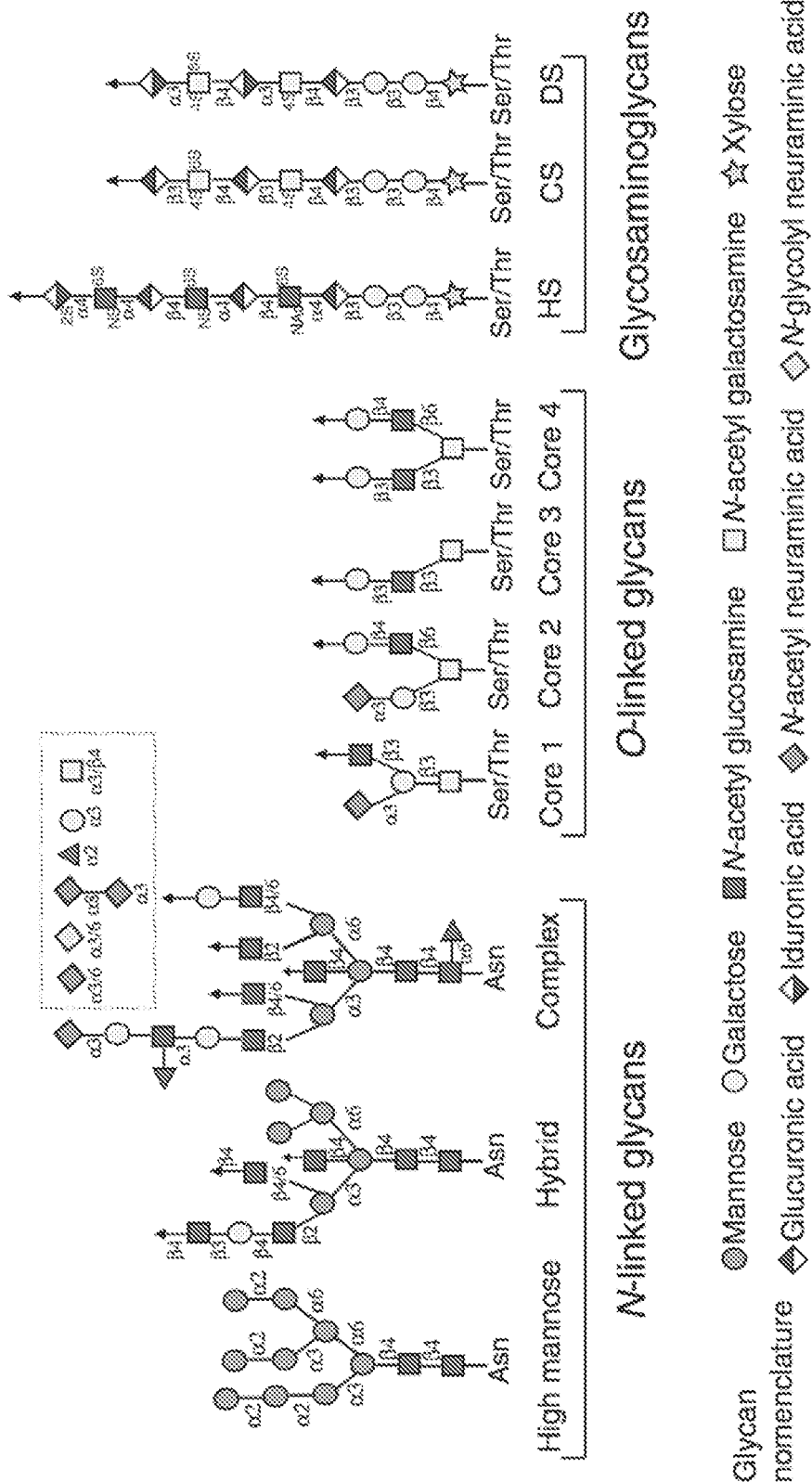
FIG. 2 shows chemical diversity of glycans. Different classes of glycans in the symbol nomenclature developed as a collaborative effort to homogenize glycan representation. Directionality is from nonreducing end at the top to the reducing end at the bottom with the arrows indicating the extension at the nonreducing end. Linkages between monosaccharides contain the anomeric configuration of the monosaccharide (α, alpha and β, beta) and the oxygen atom in the reducing end monosaccharide to which it is linked to. "/" is used to represent either- or case (β3/4 means β3 or β4). In the case of complex N-linked glycans, the common terminal motifs attached to Gal are shown in a dotted box. Abbreviations HS, CS and DS correspond to heparin or heparin sulfate, chondroitin sulfate and dermatan sulfates, respectively. Reprinted by permission from Macmillan Publishers Ltd: Nature Methods, Raman, R., et al., Glycomics: an integrated systems approach to structure-function relationships of glycans. 2, 817-824, copyright 2005.

The non-template driven process of enzymatic biosynthesis of N- and O-glycans provides significant diversity to protein structure and function by post-translational modification via glycosylation. Examples of 0- and N-linked glycan chemical and structural diversity are presented in FIG. 2.[96] Variations in glycan synthesis provide added complexity in the form of variant glycoforms of each protein. Given that proteins frequently have multiple glycosylation sites and each site can have various glycoforms, deciphering the complexity of glycan biosynthesis and the downstream roles of glycoproteins and their glycoforms is an immense challenge.

Glycan Recognition

Glycans are recognized by several classes of proteins, including lectins, antibodies, and enzymes. Lectins, glycan-binding proteins (many of which require metal ions for function), frequently have millimolar to micromolar affinities and increased avidity effects due to multivalent interactions enhances affinity.[80, 109] Although some lectins can discriminate between dissimilar structures, most lectins display remarkably broad specificity, towards similar carbohydrate structures.[110-112] Historically, lectins have been identified from plant or fungal sources, although an increasing number are being identified in animals. Lectin affinity chromatography is the most widely applied glycan, glycopeptide, or glycoprotein isolation technique. However, for whole glycoproteome studies, a limitation of this approach is that it biases glycan detection to a subset of glycoproteins based on the selection of lectin column(s).[80]

It is important to note that the capacity for glycans to be branched, and to display differences among linkage configurations, results in their recognition being highly influenced by both the composition and 3D structure of the glycan.[113] In addition, when the structural similarity of monosaccharides is taken into account, it is common for biologically-unrelated glycans cross react with the same lectin or antibody in a concentration-dependent manner. Thus if enough glycan or protein is present, a weaker, but nevertheless specific, interaction may be detected and potentially misinterpreted.[82, 114, 115] For example, Wheat Germ agglutinin and *Urtica dioica* agglutinin (UDA) are known to recognize both terminal N-acetylglucosamine (GlcNAc) and neuraminic acid (Neu5Ac) in the same binding site, by virtue of the fact that these monosaccharides may be oriented in such a way that they present a common 3D binding motif.[116, 117] In addition, UDA recognizes both chitotriose (GlcNAcβ1-4GlcNAcβ1-4GlcNAc) associated with fungal cell surfaces, and the mannose (Man)-containing trisaccharide Manβ1-4GlcNAcβ1-4GlcNAc common to N-linked glycans.[118, 119] Because such cross-reactivities are inseparable, they present the core challenge in generating or applying reagents for the characterization of glycan composition. The choice of reagent used for sample enrichment or isolation can therefore bias the outcome of glycomic analyses toward a subset of glycoconjugates based on the binding properties of the lectin or antibody.[80]

Antibodies recognize glycan structures with greater affinity and specificity than lectins; however, they are difficult to generate given that carbohydrates are poor immunogens in general. Thus only a limited selection of anti-carbohydrate antibodies is available and many display cross-reactivity to similar glycan structures.[82, 114]

In contrast to lectins or antibodies, glycan-processing enzymes are often exquisitely selective with regard to substrate structure, reflecting their essential role in glycan processing. Glycosyl hydrolases generally recognize both of the monosaccharide residues comprising the glycosidic linkage, and are often specific for position and configuration of the linkage. For example, the enzymes Endo-β-N-acetylglucosaminidase H (Endo H) and chitinase, from various sources, are all members of family 18 of the glycohydrolases and share similar tertiary structures. Despite these similarities, Endo H is exclusively active on the GlcNAcβ1-4GlcNAc linkage when present in the N-glycan core sequence Manβ1-4GlcNAcβ1-4GlcNAc sequence; it does not hydrolyze the same linkage in chitin.[120] This specificity contrasts with that seen for the lectin UDA. Additionally, many carbohydrate-processing enzymes have non-catalytic carbohydrate-binding modules, which serve to enhance the specificity of enzyme-substrate interactions.[121] Site-directed mutagenesis is often employed to generate inactive mutants, facilitating the characterization of substrate specificity.[120]

An interesting opportunity therefore exists to employ inactive mutants of carbohydrate-processing enzymes as reagents for detecting substrate. Such lectin-like enzyme-derived (Lectenz®) reagents would in principle have the advantage of retaining the inherent specificity of the wild-type enzyme. Indeed examples exist where a single point mutation in an enzyme can lead to a reagent capable of being used in an affinity column to capture specific glycans (polysialic acid) or peptides (anhydrotrypsin).[122, 123] However, as enzymes have evolved for turnover, simple inactive point mutants do not generally have affinities high enough to be practical reagents.

PNGase F

Figure 3:
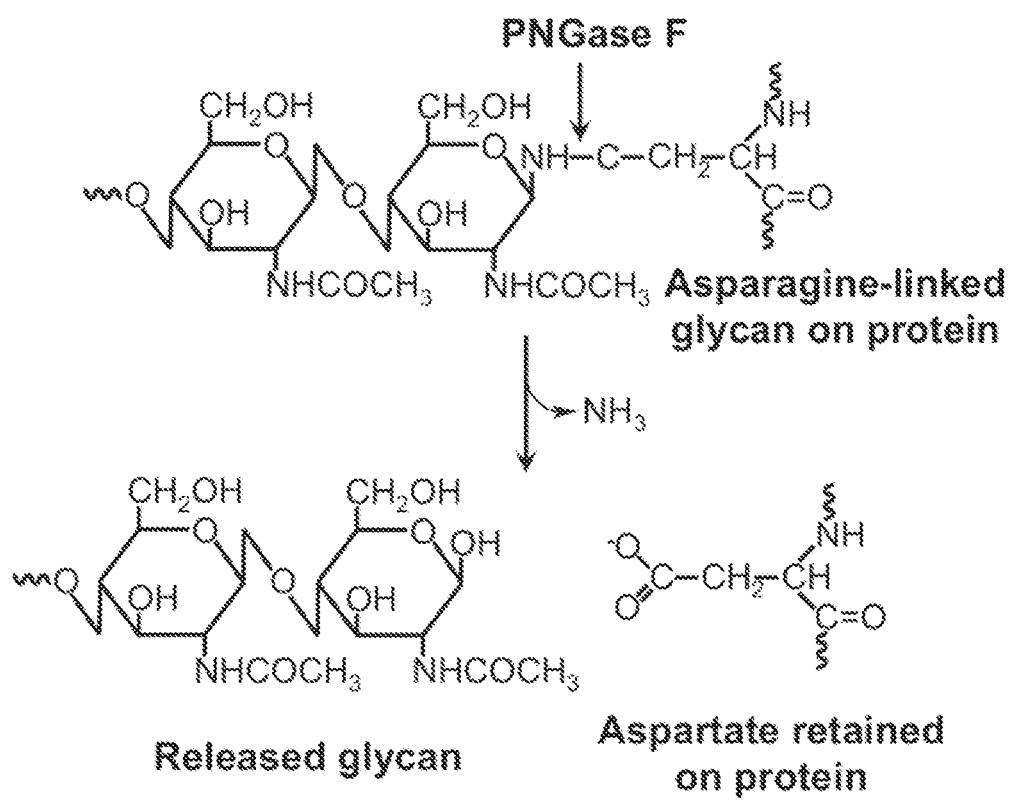
FIG. 3 shows the PNGase F deglycosylation reaction. PNGase F catalyzes the release of N-linked glycans from the polypeptide backbone by cleaving the N-glycosidic bond (amide bond) between the asparagine side chain and the proximal GlcNAc. In addition to the released of free ammonia, the asparagine on the polypeptide protein backbone is converted to an aspartic acid.

Peptide:N-glycanase (PNGase) enzymes (Table 2) are a class of N-glycan releasing enzymes that catalyze the cleavage of the amide bond between the asparagine side chain of the polypeptide and the proximal N-acetyl-β-D-glycosamine (GlcNAc) of the N-glycan. The hydrolysis reaction results in the release of the glycan and free ammonia, and conversion of the asparagine to an aspartic acid (FIG. 3).

TABLE 2

Peptide:N-glycanase nomenclature.

| | |
|---|---|
| Systematic name | N-linked-glycopeptide-(N-acetyl-β-D-glycosaminyl)-L-asparagine aminohydrolase |
| Recommended name | Peptide-N⁴-(N-acetyl-β-D-glycosaminyl)asparagine amidase |
| Synonyms | PNGase, N-oligosaccharide glycopeptidase, Glycopeptidase, Glycoamidase, N-Glycanase |
| Enzyme Commission # | EC 3.5.1.52 |

Discovery of PNGase F

The N-glycan processing enzyme, Peptide-N$^4$—(N-acetyl-β-D-glucosaminyl)asparagine amidase (PNGase F) was identified from the gram negative soil bacterium *Flavobacterium meningosepticum* (formerly known as *Chryseobacterium meningosepticum* and *Elizabethkingia meningosepticum*) by Plummer et al. in 1984.[124] PNGase enzymes have been identified from various species across plants, animals, and fungi; however, PNGase F stands in contrast to these other PNGase enzymes as it was the only confirmed bacterial PNGase enzyme for 30 years since its initial discovery. Recently, a novel PNGase F-II was identified from the same organism, *F. meningosepticum*, with altered N-glycanase activity.

Early studies of PNGase F indicated that the enzyme could catalyze the release of all N-glycans.[124] However, this was due to enzyme preparations containing a mixture of PNGase F and Endo-β-N-acetylglucosaminidase F (Endo F) from *F. meningosepticum*.[125] Endo F cleaves the glycosidic bond of the chitobiose moiety whereas PNGase F cleaves the amide bond at the glycosylaminyl junction.[126] These results confirmed that PNGase F was in fact a peptide:N-glycosidase and not an endoglycosidase, resulting in its reclassification. Additional experiments using fetuin glycopeptides and erythropoietin from Chinese hamster ovary cells indicated that the activity of the enzyme was markedly improved on denatured glycoproteins that had been pre-treated with detergents, requiring significantly less enzyme for deglycosylation.[125] However, optimal reaction conditions including buffer composition weren't established until later studies that demonstrated decreased PNGase F activity in the presence of some detergents and metal ions. These studies also confirmed optimal enzymatic activity at pH 8.0 and buffer compositions were optimized to use Tris buffer with no sodium chloride.[126, 127]

Cloning and heterologous expression of PNGase F in *E. coli*, in 1989, allowed high purity preparations for continued study and led to its rapid adoption for total N-glycoprotein deglycosylation.[128] However, Tretter, et al. demonstrated in 1991 that in contrast to PNGase A, core α1,3 fucosylation of the asparagine-linked GlcNAc conferred resistance of a glycopeptide or glycoprotein to PNGase F.[129] Shortly after in 1994, two three-dimensional x-ray crystal structures of PNGase F (PDB IDs 1PNG & 1PGS) were obtained (sans ligand), leading to significant interest in identifying the active site and the hypothesis that the reason α1,3 fucosylation confers resistance is likely due to the C3 position of the asparagine-linked GlcNAc being buried into the hydrophobic groove of the binding cleft.[130-132] This hypothesis was confirmed when x-ray crystallography data was obtained for a co-crystalized PNGase F: chitobiose complex.

The X-Ray Crystal Structure of PNGase F

Figure 4:
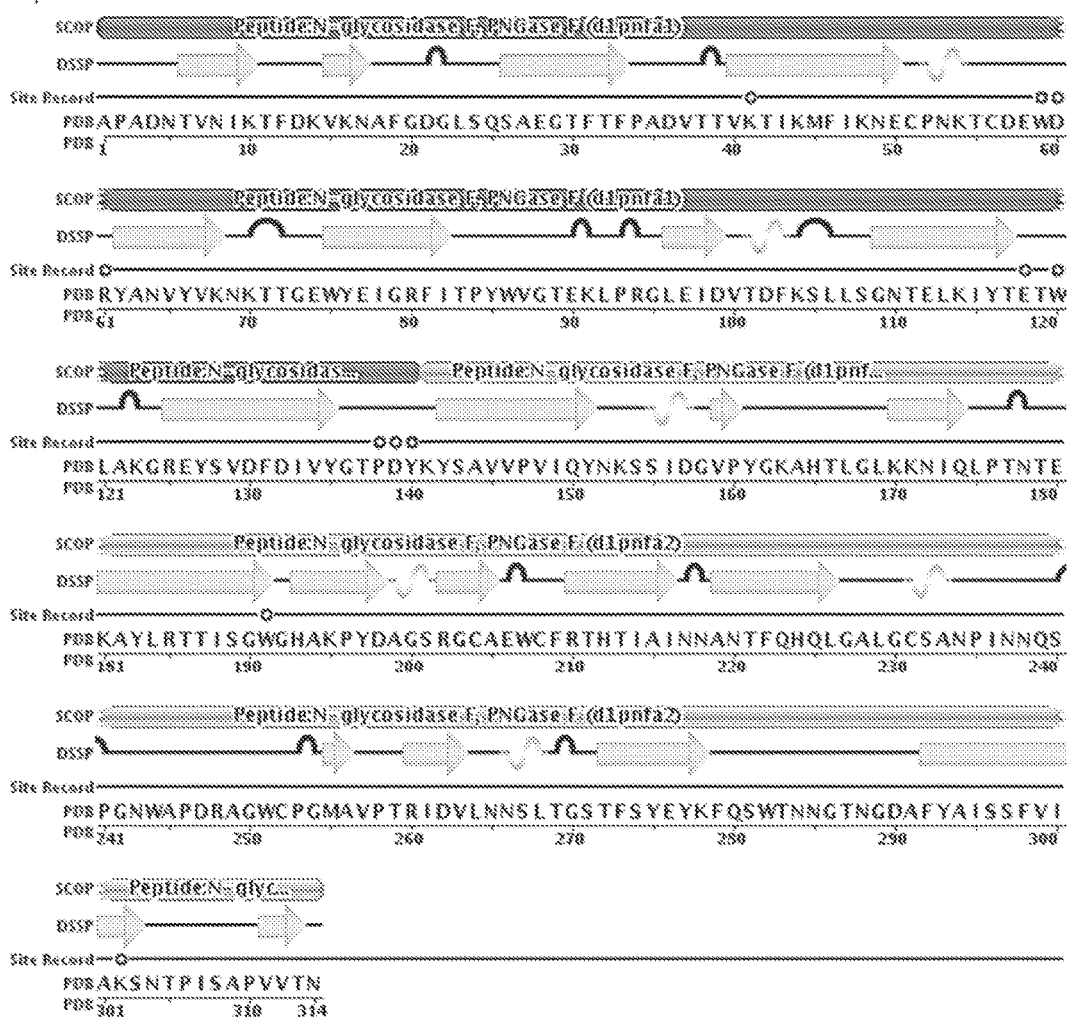
FIG. 4 shows PNGase F sequences. a) The cDNA sequence of the coding region of the PNGase F gene (SEQ ID NO:2) from the CDC3552 isolate of *Flavobacterium meningosepticum* (also known as *Elizabethkingia meningoseptium*) with the deduced amino acid sequence (SEQ ID NO:1). Amino acid numbers are shown on the left, nucleotide numbers on the right (as published in Loo et al., 2002 *Protein Expression & Purification* 24:90-98). b) The 314 amino acid sequence (SEQ ID NO:1) is depicted and annotated. The two domains are labeled d1pnfa1 & d1pnfa2. Residue 431 corresponds with the reducing GlcNAc and 432 with the 2$^{nd}$ GlcNAc of the chitobiose ligand. Three disulphide bonds are located at 51-56, 204-208, and 231-252. Image from the RCSB PDB (rcsb.org) of PDB ID 1PNF (Kuhn et al., 1995 *Journal of Biological Chemistry* 270, 29493-29497). c) The amino acid sequence of PNGase F-II from *F. meningosepticum* (also known as *E. meningosepticum*) (SEQ ID NO:3). d) The amino acid sequence of PNGase F from *Bacteroides fragilis* (SEQ ID NO:4). e) The amino acid sequence of PNGase F from *F. miricola* (also known as *E. miricola*) (SEQ ID NO:5). f) A pOPH6 coding sequence (SEQ ID NO:7) and the expressed PNGase F including a N-terminal secretion tag and a C-terminal hexa-His tag (SEQ ID NO:6). The arrow indicates the start of the PNGase F sequence and the asterisk indicates the stop codon. g) Protein sequence alignment of the pOPH6 coding sequence (amino acids 4-317 of SEQ ID NO:6), PNGase F from *F. meningosepticum* (SEQ ID NO:1; PDB identifier 1PNF), PNGase F from *F. miricola* (SEQ ID NO:5), PNGase F from *B. fragilis* (SEQ ID NO:4; PDB identifier 3KS7), and PNGase F-II from *F. meningosepticum* (SEQ ID NO:3; PDB identifier 4R4X).

The first structure of PNGase F co-crystalized with the chitobiose ligand, N,N'-diacetylchitobiose, (PBD ID 1PNF) was published in 1995 by Kuhn, et al. at 2.0 Å resolution.[133] The annotated sequence of the crystallized PNGase F enzyme is presented in FIG. 4. Consistent with the uncomplexed structures (PDB IDs 1 PNG & 1PGS), there were no significant changes to the conformation of the complexed PNGase F:chitobiose structure, indicating that the conformation is unaffected by binding of the chitobiose ligand. The folded protein consists of two domains, which are comprised of residues 1-137 and 143-314 respectively. Both domains have eight-stranded antiparallel β-sandwiches that lie adjacent to each other such that the interface runs the full length of the β-sheets with extensive hydrogen bonding contacts. Three possible binding sites had been postulated based on three grooves in the uncomplexed structures.[132] The first groove, a bowl shape, on one face of the molecule, contained residues similar to the active site of L-asparaginases.[132] A shallow S-shaped cleft on the opposite face containing a number of acidic residues and threonine residues was postulated as a second possible binding site.[132] A deep cleft at the interface between the two domains at one end of the molecule was postulated as a third binding site. This cleft, containing several acidic residues and serines, possessed the unique attribute of having five tryptophan residues.[132]

The 1PNF structural model confirms the deep cleft at the interface of the two domains as the binding cleft for the chitobiose ligand. The orientation of the α-chitobiose ligand in the binding cleft shows the N-acetyl group of the reducing GlcNAc extended into a deep hydrophobic pocket (data not shown). Five water molecules are positioned between the protein and chitobiose interface. The N-acetyl a group of the second GlcNAc is facing the solvent accessible side of the binding cleft. The C3 position of the reducing GlcNAc is facing into the binding cleft, confirming that there would be no space for the glycan to fit into this groove if it is 1,3 fucosylated. Unlike the C3 position, the C6 position is pointed outwards towards the solvent exposed side of the cleft, indicating that α1,6 fucosylation at this position does not sterically hinder access to the binding cleft.

An extensive network of hydrogen bond interactions is also evidence between the protein and ligand, many of which are facilitated through 5 water molecules positioned in the interface between the protein and the ligand (Wat$^{75}$, Wat$^{146}$, Wat$^{346}$, Wat$^{348}$, Wat$^{349}$). Three of these water molecules (Wat$^{75}$, Wat$^{146}$, Wat$^{346}$) are also present in nearly identical positions in the uncomplexed structures.[130, 132] A total of 10 residues (D60, R61, Y85, E118, W120, S155, G190, W191, E206, R248) are involved in the network of hydrogen bonds with water molecules and the ligand. A schematic diagram showing the intermolecular hydrogen bonding contacts as originally published by Kuhn, et al. is reproduced in FIG. 5.[133] A three-dimensional representation of this schematic network of hydrogen bonding contacts is presented in FIG. 6.

Active Site Residues of PNGase F

Point mutagenesis studies of active site residues in PNGase F have identified D60 as the primary catalytic residue and E206 as likely contributing to stabilization of reaction state intermediates.[133] Based on the position of the chitobiose ligand, D60 and E206 would span both sides of the amine bond that the enzyme would cleave. However, structures of PNGase F complexed with a glycopeptide have not been deposited, thus a mechanism has yet to be confirmed. Mutagenesis studies of E118, which is at the opposite end of the ligand interacting with O6 of the 2$^{nd}$ GlcNAc, indicates that E118 is critical for substrate recognition, a prerequisite for catalytic activity likely mediated by D60 and E206. A model for the reaction mechanism has been proposed facilitated by D60A, E206, and R248, with D60 as the primary catalytic residue.[132, 134] In this model, R248 is postulated to form a hydrogen bond with the carbonyl oxygen of the N-glycosidic bond, thus making the Asn-carbonyl carbon more susceptible to nucleophilic attack by a hydroxide ion. This nucleophilic attack would be facilitated by Wat$^{346}$ (Wat$^{422}$ in PDB ID 1PGS), which is present in both complexed and uncomplexed structures, and is located proximal to D60, E206, and R248. A hydroxide ion could be formed by transfer of a proton from Wat$^{346}$ to D60. The Asn-carbonyl carbon would undergo nucleophilic attack from the hydroxide ion, forming the transition state intermediate. D60 would donate its proton to the nitrogen of the amine bond, completing the cleavage of the amide bond. This proposed model would require the pK$_a$ of D60 being raised from 4.5 to ~8.0, the pH optimum of the reaction. Such a shift in the local environment of the active site could be made feasible by a hydrophobic environment caused by nearby aromatic residues (Y85, W251, W207, and W191) surrounding E206 and D60.

The Significance of PNGase F

Since the discovery of PNGase F 30 years ago, it has become a standard tool for releasing N-linked glycans prior to characterization. PNGase F has the broadest specificity for N-glycans bearing glycoproteins, as it recognizes both the chitobiose core as well as the asparagine-linked peptide motif common to N-glycan peptide and protein conjugates. Substrate specificity studies have confirmed that the minimum glycan motif required for catalytic activity is the chitobiose core.[135] In addition, the minimal peptide motif recognized is the Asn-X-Ser/Thr glycosylation motif common to all N-linked glycans.[135] Interestingly, optimal enzyme activity was observed with the chitobiose-linked pentapeptide, Tyr-Ile-Asn-Ala-Ser (SEQ ID NO:21), indicating that the enzyme recognizes residues both upstream and downstream of the glycan-linked asparagine.[135]

Given the broad specificity of PNGase F for the N-glycopeptide core common to all N-glycan bearing glycoproteins, this enzyme would be an ideal candidate for engineering into an N-glycopeptide recognizing reagent. There is currently no single detection reagent that can recognize and enrich N-glycopeptides. Such a reagent would be of significant interest to the glycoscience community and engineering it is the focus of this example.

Overview

Recent advances in both theoretical and experimental approaches present unique opportunities to advance the field of glycomics. Specifically, employing computational chemistry and structural biology tools with high throughput directed evolution strategies makes feasible the rational in silico design of novel protein libraries focused towards identifying clones with desired functionality.[8-15] Computational docking and molecular dynamics have become indispensible tools for investigating the highly complex and flexible nature of protein-glycan interactions.[9, 70] Furthermore, determining binding free energies to evaluate thermodynamic contributions that drive the binding interactions is a powerful computational technique that provides insight into protein-ligand interactions broken down per amino acid that cannot be determined any other way.[8, 10, 12] These computational tools serve to advance understanding of biomolecular interactions and guide the development of biomolecules with novel functionality. Coupling in silico structural analysis, molecular dynamics (MD) and binding free energy decomposition strategies with in vitro directed evolution will enable knowledge-based protein engineering that will not only advance both disciplines but also spur the development of novel biomolecules relevant to the field of glycomics.[3, 31, 40]

Given the advances in in silico and in vitro protein engineering methodologies and the need for novel glycan detecting reagents, this example describes a novel lectin-like glycan-recognizing biomolecule engineered from a glycan-processing enzyme, which are called Lectenz®. (Lectenz® is a federally registered trademark of Glycosensors & Diagnostics, LLC.) Since glycan-processing enzymes have exquisite specificity for their glycan substrates, they serve as an ideal starting point to generate a catalytically inactive variant for affinity enhancement. Specifically, the *Flavobacterium meningosepticum* N-glycan processing enzyme, PNGase F, is engineered into a catalytically-inactive, affinity-enhanced variant for detecting the core glycopeptide component common to all N-linked glycans.

Figure 7:
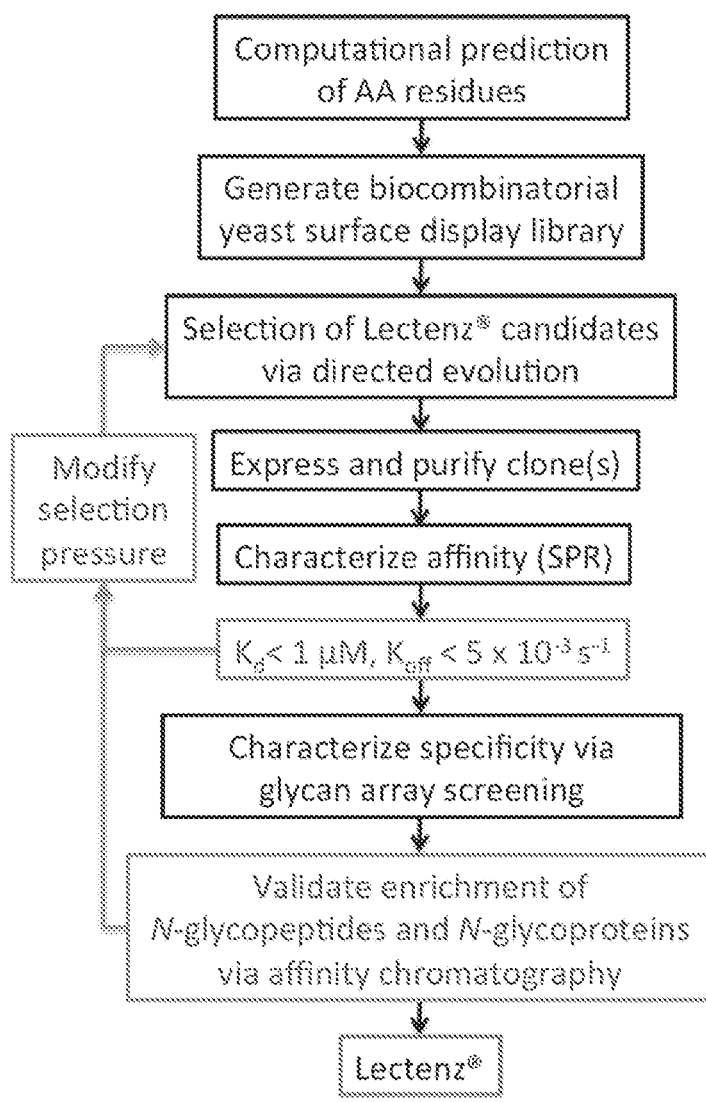
FIG. 7 shows a schematic representation of the Lectenz® design strategy. Shown is the integrative strategy utilizing computational methods, knowledge-based library design, selection, and downstream characterization and validation. Light gray boxes indicate checkpoints where if a selected candidate fails to meet the desired threshold, the selection process can be repeated with modified selection conditions. Once a selected candidate satisfies the specificity and affinity characterization requirements, it is coupled to an affinity matrix to validate affinity chromatography based enrichment of N-glycopeptides and N-glycoproteins.

A schematic of the Lectenz® design strategy is presented in FIG. 7. The wild-type PNGase F enzyme, has previously been co-crystallized (PDB ID: 1PNF) with the N,N'-diacetylchitobiose disaccharide in the active site at 2.0 Å resolution.[133] This structural model is used to conduct molecular dynamics simulations and binding free energy decomposition analysis to identify critical and tepid amino acid residues proximal to the chitobiose ligand. Critical residues are not selected for saturation mutagenesis, whereas tepid residues with weak ligand-binding interaction energies are selected for saturation mutagenesis via directed evolution. Directed evolution is performed using a yeast display system to select for mutagenized PNGase F clones with affinity for the target N-glycan bearing glycoprotein, Ribonuclease B (RNase B). The selected Lectenz®, R911, is characterized via surface plasmon resonance for kinetic analysis, glycan array screening for specificity determination, and employed in Lectenz® affinity chromatography for N-glycopeptide and N-glycoprotein sample enrichment.

The successful creation of a lectin-like reagent from a carbohydrate processing enzyme (a Lectenz®) presents not only a unique solution to the challenge of N-glycopeptide and N-glycoprotein sample enrichment, but also demonstrates a novel strategy for engineering glycan-targeting reagents for glycans and glycoconjugates of biological relevance.

REFERENCES

1. Wijma, H. J. et al. Computationally designed libraries for rapid enzyme stabilization. Protein Eng Des Sel 27, 49-58 (2014).
2. Wijma, H. J. & Janssen, D. B. Computational design gains momentum in enzyme catalysis engineering. Febs J 280, 2948-2960 (2013).
3. Feldmeier, K. & Höcker, B. Computational protein design of ligand binding and catalysis. Current Opinion in Chemical Biology 17, 929-933 (2013).
4. Tinberg, C. E. et al. Computational design of ligand-binding proteins with high affinity and selectivity. Nature 501, 212-216 (2013).
5. Jiang, L. et al. De novo computational design of retro-aldol enzymes. Science 319, 1387-1391 (2008).
6. Patrick, W. M. & Firth, A. E. Strategies and computational tools for improving randomized protein libraries. Biomolecular Engineering 22, 105-112 (2005).
7. Chica, R. A., Doucet, N. & Pelletier, J. N. Semi-rational approaches to engineering enzyme activity: combining the benefits of directed evolution and rational design. Current Opinion in Biotechnology 16, 378-384 (2005).
8. Hou, T., Wang, J., Li, Y. & Wang, W. Assessing the performance of the MM/PBSA and MM/GBSA methods. 1. The accuracy of binding free energy calculations based on molecular dynamics simulations. Journal of chemical information and modeling 51, 69-82 (2011).
9. Woods, R. J. & Tessier, M. B. Computational glycoscience: characterizing the spatial and temporal properties of glycans and glycan-protein complexes. Current Opinion in Structural Biology 20, 575-583 (2010).
10. Steinbrecher, T. & Labahn, A. Towards accurate free energy calculations in ligand protein-binding studies. Curr Med Chem 17, 767-785 (2010).
11. D. A. Case, T. A. D., T. E. Cheatham, III, C. L. Simmerling, J. Wang, R. E. Duke, R. Luo, R. C. Walker, W. Zhang, K. M. Merz, B. Roberts, B. Wang, S. Hayik, A. Roitberg, G. Seabra, I. Kolossvai, K. F. Wong, F. Paesani, J. Vanicek, J. Liu, X. Wu, S. R. Brozell, T. Steinbrecher, H. Gohlke, Q. Cai, X. Ye, J. Wang, M.-J. Hsieh, G. Cui, D. R. Roe, D. H. Mathews, M. G. Seetin, C. Sagui, V. Babin, T. Luchko, S. Gusarov, A. Kovalenko, and P. A. Kollman (University of California, San Francisco, 2010).
12. Carrascal, N. & Green, D. F. Energetic decomposition with the generalized-born and Poisson-Boltzmann solvent models: lessons from association of G-protein components. The journal of physical chemistry. B 114, 5096-5116 (2010).
13. Hess, B., Kutzner, C., van der Spoel, D. & Lindahl, E. GROMACS 4: Algorithms for Highly Efficient, Load-Balanced, and Scalable Molecular Simulation. Journal of Chemical Theory and Computation 4, 435-447 (2008).
14. Okimoto, N. et al. High-performance drug discovery: computational screening by combining docking and molecular dynamics simulations. PLoS Comput Biol 5, e1000528 (2009).
15. Berman, H. M. et al. The Protein Data Bank. Nucl. Acids Res. 28, 235-242 (2000).
16. Karanicolas, J. et al. A De Novo Protein Binding Pair By Computational Design and Directed Evolution. Mol Cell 42, 250-260 (2011).
17. Lutz, S. Beyond directed evolution-semi-rational protein engineering and design. Current Opinion in Biotechnology 21, 734-743 (2010).
18. Grove, T. Z., Hands, M. & Regan, L. Creating novel proteins by combining design and selection. Protein Eng Des Sel 23, 449-455 (2010).
19. Brannigan, J. A. & Wilkinson, A. J. Protein engineering 20 years on. Nature Reviews. Molecular Cell Biology 3, 964-970 (2002).
20. Winter, G., Fersht, A. R., Wilkinson, A. J., Zoller, M. & Smith, M. Redesigning enzyme structure by site-directed mutagenesis: tyrosyl tRNA synthetase and ATP binding. Nature 299, 756-758 (1982).
21. Sigal, I. S., Harwood, B. G. & Arentzen, R. Thiol-beta-lactamase: replacement of the active-site serine of RTEM beta-lactamase by a cysteine residue. Proc Natl Acad Sci USA 79, 7157-7160 (1982).
22. Hutchison, C. A., 3rd et al. Mutagenesis at a specific position in a DNA sequence. J Biol Chem 253, 6551-6560 (1978).
23. Leatherbarrow, R. J., Fersht, A. R. & Winter, G. Transition-state stabilization in the mechanism of tyrosyl-tRNA synthetase revealed by protein engineering. Proc Natl Acad Sci USA 82, 7840-7844 (1985).
24. Graf, L. et al. Selective alteration of substrate specificity by replacement of aspartic acid-189 with lysine in the binding pocket of trypsin. Biochemistry 26, 2616-2623 (1987).
25. Perona, J. J., Hedstrom, L., Rutter, W. J. & Fletterick, R. J. Structural origins of substrate discrimination in trypsin and chymotrypsin. Biochemistry 34, 1489-1499 (1995).
26. Venekei, I., Szilagyi, L., Graf, L. & Rutter, W. J. Attempts to convert chymotrypsin to trypsin. FEBS Lett 379, 143-147 (1996).
27. Lerner, S. A., Wu, T. T. & Lin, E. C. Evolution of a Catabolic Pathway in Bacteria. Science 146, 1313-1315 (1964).
28. Mills, D. R., Peterson, R. L. & Spiegelman, S. An extracellular Darwinian experiment with a self-duplicating nucleic acid molecule. Proc Natl Acad Sci USA 58, 217-224 (1967).

29. Smith, G. P. Filamentous fusion phage: novel expression vectors that display cloned antigens on the virion surface. Science 228, 1315-1317 (1985).
30. Tobin, M. B., Gustafsson, C. & Huisman, G. W. Directed evolution: the 'rational' basis for 'irrational' design. Curr Opin Struct Biol 10, 421-427 (2000).
31. Bonsor, D. A. & Sundberg, E. J. Dissecting protein-protein interactions using directed evolution. Biochemistry 50, 2394-2402 (2011).
32. Cobb, R. E., Chao, R. & Zhao, H. Directed evolution: Past, present, and future. AIChE Journal 59, 1432-1440 (2013).
33. Socha, R. D. & Tokuriki, N. Modulating protein stability-directed evolution strategies for improved protein function. Febs J 280, 5582-5595 (2013).
34. Stone, J. D., Chervin, A. S., Aggen, D. H. & Kranz, D. M. T cell receptor engineering. Methods Enzymol 503, 189-222 (2012).
35. Shim, J. H., Chen, H. M., Rich, J. R., Goddard-Borger, E. D. & Withers, S. G. Directed evolution of a beta-glycosidase from Agrobacterium sp. to enhance its glycosynthase activity toward C3-modified donor sugars. Protein Eng Des Sel 25, 465-472 (2012).
36. Patel, S. C. & Hecht, M. H. Directed evolution of the peroxidase activity of a de novo-designed protein. Protein Eng Des Sel 25, 445-452 (2012).
37. Yip, S. H. et al. Directed evolution combined with rational design increases activity of GpdQ toward a non-physiological substrate and alters the oligomeric structure of the enzyme. Protein Eng Des Sel (2011).
38. Jakeman, D. L. & Sadeghi-Khomami, A. A beta-(1,2)-glycosynthase and an attempted selection method for the directed evolution of glycosynthases. Biochemistry 50, 10359-10366 (2011).
39. Cobucci-Ponzano, B., Perugino, G., Rossi, M. & Moracci, M. Engineering the stability and the activity of a glycoside hydrolase. Protein Eng Des Sel 24, 21-26 (2011).
40. Brustad, E. M. & Arnold, F. H. Optimizing non-natural protein function with directed evolution. Current Opinion in Chemical Biology 15, 201-210 (2011).
41. Lopes, A., Schmidt Am Busch, M. & Simonson, T. Computational design of protein-ligand binding: modifying the specificity of asparaginyl-tRNA synthetase. Journal of computational chemistry 31, 1273-1286 (2010).
42. Kittl, R. & Withers, S. G. New approaches to enzymatic glycoside synthesis through directed evolution. Carbohydrate Research 345, 1272-1279 (2010).
43. Yu, L. et al. Phage display screening against a set of targets to establish peptide-based sugar mimetics and molecular docking to predict binding site. Bioorganic & Medicinal Chemistry 17, 4825-4832 (2009).
44. Thompson, S. M. et al. Heparan sulfate phage display antibodies identify distinct epitopes with complex binding characteristics: insights into protein binding specificities. The Journal of biological chemistry 284, 35621-35631 (2009).
45. Hancock, S. M., Rich, J. R., Caines, M. E., Strynadka, N.C. & Withers, S. G. Designer enzymes for glycosphingolipid synthesis by directed evolution. Nature chemical biology 5, 508-514 (2009).
46. Belien, T., Verjans, P., Courtin, C. M. & Delcour, J. A. Phage display based identification of novel stabilizing mutations in glycosyl hydrolase family 11 B. subtilis endoxylanase XynA. Biochemical and Biophysical Research Communications 368, 74-80 (2008).
47. Chao, G. et al. Isolating and engineering human antibodies using yeast surface display. Nat. Protocols 1, 755-768 (2006).
48. Gera, N., Hussain, M. & Rao, B. M. Protein selection using yeast surface display. Methods 60, 15-26 (2013).
49. Tohidkia, M. R., Barar, J., Asadi, F. & Omidi, Y. Molecular considerations for development of phage antibody libraries. Journal of drug targeting 20, 195-208 (2012).
50. Kenrick, S. A. & Daugherty, P. S. Bacterial display enables efficient and quantitative peptide affinity maturation. Protein Eng Des Sel 23, 9-17 (2010).
51. Dreier, B. & Pluckthun, A. Ribosome display: a technology for selecting and evolving proteins from large libraries. Methods in molecular biology 687, 283-306 (2011).
52. Stoltenburg, R., Reinemann, C. & Strehlitz, B. SELEX-A (r)evolutionary method to generate high-affinity nucleic acid ligands. Biomolecular Engineering 24, 381-403 (2007).
53. Bornscheuer, U. & Kazlauskas, R. J. Survey of protein engineering strategies. Curr Protoc Protein Sci Chapter 26, Unit 26 27 (2011).
54. Leach, A. R. Molecular modelling: principles and applications, Edn. 2nd. (Prentice Hall, Harlow, England; New York; 2001).
55. Groenhof, G. Introduction to QM/MM simulations. Methods Mol Biol 924, 43-66 (2013).
56. Karplus, M. & McCammon, J. A. Molecular dynamics simulations of biomolecules. Nat Struct Biol 9, 646-652 (2002).
57. Karplus, M. & Kuriyan, J. Molecular dynamics and protein function. Proc Natl Acad Sci USA 102, 6679-6685 (2005).
58. Baker, D. & Sali, A. Protein Structure Prediction and Structural Genomics. Science 294, 93-96 (2001).
59. Mackerell, A. D., Jr. Empirical force fields for biological macromolecules: overview and issues. J Comput Chem 25, 1584-1604 (2004).
60. Stortz, C. A., Johnson, G. P., French, A. D. & Csonka, G. I. Comparison of different force fields for the study of disaccharides. Carbohydrate Research 344, 2217-2228 (2009).
61. Fadda, E. & Woods, R. J. Molecular simulations of carbohydrates and protein-carbohydrate interactions: motivation, issues and prospects. Drug Discovery Today 15, 596-609 (2010).
62. Genheden, S. & Ryde, U. A comparison of different initialization protocols to obtain statistically independent molecular dynamics simulations. J Comput Chem 32, 187-195 (2011).
63. Kirschner, K. N. et al. GLYCAM06: a generalizable biomolecular force field. Carbohydrates. J Comput Chem 29, 622-655 (2008).
64. Guvench, O. & MacKerell, A. D., Jr. Comparison of protein force fields for molecular dynamics simulations. Methods Mol Biol 443, 63-88 (2008).
65. Benz, R. W., Castro-Roman, F., Tobias, D. J. & White, S. H. Experimental validation of molecular dynamics simulations of lipid bilayers: a new approach. Biophysical journal 88, 805-817 (2005).
66. Showalter, S. A. & Brlschweiler, R. Validation of Molecular Dynamics Simulations of Biomolecules Using NMR Spin Relaxation as Benchmarks: Application to the AMBER99SB Force Field. Journal of Chemical Theory and Computation 3, 961-975 (2007).

67. McCammon, J. A., Gelin, B. R. & Karplus, M. Dynamics of folded proteins. Nature 267, 585-590 (1977).
68. de Ruiter, A. & Oostenbrink, C. Free energy calculations of protein-ligand interactions. Current Opinion in Chemical Biology 15, 547-552 (2011).
69. Christ, C. D., Mark, A. E. & van Gunsteren, W. F. Basic ingredients of free energy calculations: A review. Journal of Computational Chemistry, NA-NA (2009).
70. DeMarco, M. L. & Woods, R. J. Structural glycobiology: a game of snakes and ladders. Glycobiology 18, 426-440 (2008).
71. Wang, J., Tan, C., Tan, Y.-H., Lu, Q. & Luo, R. Poisson-Boltzmann Solvents in Molecular Dynamics Simulations. Communications in computational physics 3, 22 (2008).
72. Jorgensen, W. L. Efficient Drug Lead Discovery and Optimization. Accounts of Chemical Research 42, 724-733 (2009).
73. Jorgensen, W. L. The many roles of computation in drug discovery. Science 303, 1813-1818 (2004).
74. McCammon, J. A. Theory of biomolecular recognition. Current Opinion in Structural Biology 8, 245-249 (1998).
75. Hummer, G. & Szabo, A. Calculation of free-energy differences from computer simulations of initial and final states. Journal of Chemical Physics 105, 2004 (1996).
76. van Gunsteren, W. F. et al. Computation of Free Energy in Practice: Choice of Approximations and Accuracy Limiting Factors, Vol. 2. (ESCOM, Leiden; 1993).
77. Beveridge, D. L. & DiCapua, F. M. Free energy via molecular simulation: applications to chemical and biomolecular systems. Annu Rev Biophys Biophys Chem 18, 431-492 (1989).
78. Zoete, V., Irving, M. B. & Michielin, O. MM-GBSA binding free energy decomposition and T cell receptor engineering. Journal of molecular recognition: JMR 23, 142-152 (2010).
79. Pierdominici-Sottile, G., Palma, J. & Roitberg, A. E. Free-energy computations identify the mutations required to confer trans-sialidase activity into Trypanosoma rangeli sialidase. Proteins 82, 424-435 (2014).
80. Krishnamoorthy, L. & Mahal, L. K. Glycomic analysis: an array of technologies. ACS chemical biology 4, 715-732 (2009).
81. Arnaud, J., Audfray, A. & Imberty, A. Binding sugars: from natural lectins to synthetic receptors and engineered neolectins. Chem Soc Rev 42, 4798-4813 (2013).
82. Kuzmanov, U., Kosanam, H. & Diamandis, E. P. The sweet and sour of serological glycoprotein tumor biomarker quantification. BMC medicine 11, 31 (2013).
83. Hakomori, S. Tumor-associated carbohydrate antigens. Annu Rev Immunol 2, 103-126 (1984).
84. Porcel, J. M. et al. Use of a panel of tumor markers (carcinoembryonic antigen, cancer antigen 125, carbohydrate antigen 15-3, and cytokeratin 19 fragments) in pleural fluid for the differential diagnosis of benign and malignant effusions. Chest 126, 1757-1763 (2004).
85. Goonetilleke, K. S. & Siriwardena, A. K. Systematic review of carbohydrate antigen (CA 19-9) as a biochemical marker in the diagnosis of pancreatic cancer. Eur J Surg Oncol 33, 266-270 (2007).
86. Taylor-Papadimitriou, J., Burchell, J., Miles, D. W. & Dalziel, M. MUC1 and cancer. Biochim Biophys Acta 1455, 301-313 (1999).
87. Ghazarian, H., Idoni, B. & Oppenheimer, S. B. A glycobiology review: carbohydrates, lectins and implications in cancer therapeutics. Acta histochemica 113, 236-247 (2011).
88. Hart, G. W. & Copeland, R. J. Glycomics hits the big time. Cell 143, 672-676 (2010).
89. Taniguchi, N., Hancock, W., Lubman, D. M. & Rudd, P. M. The Second Golden Age of Glycomics: From Functional Glycomics to Clinical Applications. Journal of Proteome Research 8, 425-426 (2009).
90. An, H. J., Kronewitter, S. R., de Leoz, M. L. & Lebrilla, C. B. Glycomics and disease markers. Current Opinion in Chemical Biology 13, 601-607 (2009).
91. Freeze, H. H. Update and perspectives on congenital disorders of glycosylation. Glycobiology 11, 129R-143R (2001).
92. Haltiwanger, R. S. & Lowe, J. B. Role of glycosylation in development. Annu Rev Biochem 73, 491-537 (2004).
93. Li, H. & d'Anjou, M. Pharmacological significance of glycosylation in therapeutic proteins. Current Opinion in Biotechnology 20, 678-684 (2009).
94. Dance, A. From pond scum to pharmacy shelf. Nat Med 16, 146-149 (2010).
95. Cummings, R. D. The repertoire of glycan determinants in the human glycome. Molecular BioSystems 5, 1087-1104 (2009).
96. Raman, R., Raguram, S., Venkataraman, G., Paulson, J. C. & Sasisekharan, R. Glycomics: an integrated systems approach to structure-function relationships of glycans. Nat Methods 2, 817-824 (2005).
97. Murrell, M. P., Yarema, K. J. & Levchenko, A. The systems biology of glycosylation. Chembiochem 5, 1334-1347 (2004).
98. Helenius, A. & Aebi, M. Intracellular functions of N-linked glycans. Science 291, 2364-2369 (2001).
99. Drickamer, K. & Taylor, M. E. Evolving views of protein glycosylation. Trends in Biochemical Sciences 23, 321-324 (1998).
100. Kornfeld, R. & Kornfeld, S. Assembly of asparagine-linked oligosaccharides. Annu Rev Biochem 54, 631-664 (1985).
101. Knauer, R. & Lehle, L. The oligosaccharyltransferase complex from yeast. Biochim Biophys Acta 1426, 259-273 (1999).
102. Burda, P. & Aebi, M. The dolichol pathway of N-linked glycosylation. Biochim Biophys Acta 1426, 239-257 (1999).
103. Hashimoto, K. et al. KEGG as a glycome informatics resource. Glycobiology 16, 63R-70R (2006).
104. Weerapana, E. & Imperiali, B. Asparagine-linked protein glycosylation: from eukaryotic to prokaryotic systems. Glycobiology 16, 91R-101 (2006).
105. Kukuruzinska, M. A., Bergh, M. L. & Jackson, B. J. Protein glycosylation in yeast. Annu Rev Biochem 56, 915-944 (1987).
106. Rayon, C., Lerouge, P. & Faye, L. The protein N-glycosylation in plants. J. Exp. Bot. 49, 1463-1472 (1998).
107. Taylor, M. E. & Drickamer, K. Introduction to glycobiology, Edn. 2nd. (Oxford University Press, Oxford; New York; 2006).
108. Cylwik, B., Lipartowska, K., Chrostek, L. & Gruszewska, E. Congenital disorders of glycosylation. Part II. Defects of protein O-glycosylation. Acta Biochimica Polonica 60, 361-368 (2013).
109. Lundquist, J. J. & Toone, E. J. The Cluster Glycoside Effect. Chemical Reviews 102, 555-578 (2002).
110. Debray, H., Decout, D., Strecker, G., Spik, G. & Montreuil, J. Specificity of twelve lectins towards oligosaccharides and glycopeptides related to N-glycosyl-proteins. Eur J Biochem 117, 41-55 (1981).

111. Liener, I. E., Sharon, N. & Goldstein, I. J. The Lectins: properties, functions, and applications in biology and medicine. (Academic Press, Orlando; 1986).
112. Bertozzi, C. R. & Kiessling, L. L. Chemical glycobiology. Science (New York, N.Y.) 291, 2357-2364 (2001).
113. Meier, S. & Duus, J. Carbohydrate dynamics: Antibody glycans wiggle and jiggle. Nature chemical biology 7, 131-132 (2011).
114. Cunningham, S., Gerlach, J. Q., Kane, M. & Joshi, L. Glyco-biosensors: Recent advances and applications for the detection of free and bound carbohydrates. Analyst 135, 2471-2480 (2010).
115. Manimala, J. C., Roach, T. A., Li, Z. & Gildersleeve, J. C. High-throughput carbohydrate microarray profiling of 27 antibodies demonstrates widespread specificity problems. Glycobiology 17, 17C-23C (2007).
116. Wright, C. S. 2.2 A resolution structure analysis of two refined N-acetylneuraminyl-lactose-wheat germ agglutinin isolectin complexes. J Mol Biol 215, 635-651 (1990).
117. Saul, F. A. et al. Crystal structure of *Urtica dioica* agglutinin, a superantigen presented by MHC molecules of class I and class II. Structure 8, 593-603 (2000).
118. Harata, K. & Muraki, M. Crystal structures of *Urtica dioica* agglutinin and its complex with tri-N-acetylchitotriose. J Mol Biol 297, 673-681 (2000).
119. Huang, W., Wang, D., Yamada, M. & Wang, L. X. Chemoenzymatic synthesis and lectin array characterization of a class of N-glycan clusters. J Am Chem Soc 131, 17963-17971 (2009).
120. Rao, V., Cui, T., Guan, C. & Van Roey, P. Mutations of endo-beta-N-acetylglucosaminidase H active site residueAs sp130 anG glu 132: activities and conformations. Protein Sci 8, 2338-2346 (1999).
121. Guillén, D., Sanchez, S. & Rodríguez-Sanoja, R. Carbohydrate-binding domains: multiplicity of biological roles. Applied Microbiology & Biotechnology 85, 1241-1249 (2010).
122. Jakobsson, E., Schwarzer, D., Jokilammi, A. & Finne, J. Endosialidases: Versatile Tools for the Study of Polysialic Acid. Topics in current chemistry (2012).
123. Korecka, L. et al. Bioaffinity magnetic reactor for peptide digestion followed by analysis using bottom-up shotgun proteomics strategy. J Sep Sci 31, 507-515 (2008).
124. Plummer, T. H., Elder, J. H., Alexander, S., Phelan, A. W. & Tarentino, A. L. Demonstration of peptide:N-glycosidase F activity in endo-beta-N-acetylglucosaminidase F preparations. Journal of Biological Chemistry 259, 10700-10704 (1984).
125. Tarentino, A. L., Gomez, C. M. & Plummer, T. H., Jr. Deglycosylation of asparagine-linked glycans by peptide:N-glycosidase F. Biochemistry 24, 4665-4671 (1985).
126. Mussar, K. J., Murray, G. J., Martin, B. M. & Viswanatha, T. Peptide: N-glycosidase F: studies on the glycoprotein aminoglycan amidase from *Flavobacterium meningosepticum*. Journal of biochemical and biophysical methods 20, 53-68 (1989).
127. Haselbeck, A. & Hosel, W. Studies on the effect of the incubation conditions, various detergents and protein concentra-tion on the enzymatic activity of N-glycosidase F (Glycopeptidase F) and endoglycosidase F. Topics in Biochemistry 8, 1-4 (1988).
128. Lemp, D., Haselbeck, A. & Klebl, F. Molecular cloning and heterologous expression of N-glycosidase F from *Flavobacterium meningosepticum*. J Biol Chem 265, 15606-15610 (1990).
129. Tretter, V., Altmann, F. & MÄRz, L. Peptide-N4-(N-acetyl-β-glucosaminyl)asparagine amidase F cannot release glycans with fucose attached a1→3 to the asparagine-linked N-acetylglucosamine residue. European Journal of Biochemistry 199, 647-652 (1991).
130. Norris, G. E., Stillman, T. J., Anderson, B. F. & Baker, E. N. The three-dimensional structure of PNGase F, a glycosylasparaginase from *Flavobacterium meningosepticum*. Structure 2, 1049-1059 (1994).
131. Norris, G. E., Flaus, A. J., Moore, C. H. & Baker, E. N. Purification and crystallization of the endoglycosidase PNGase F, a peptide:N-glycosidase from *Flavobacterium meningosepticum*. J Mol Biol 241, 624-626 (1994).
132. Kuhn, P., Tarentino, A. L., Plummer, T. H., Jr. & Van Rocy, P. Crystal structure of peptide-N4-(N-acetyl-beta-D-glucosaminyl)asparagine amidase F at 2.2-A resolution. Biochemistry 33, 11699-11706 (1994).
133. Kuhn, P. et al. Active Site and Oligosaccharide Recognition Residues of Peptide-N4-(N-acetyl-β-D-glucosaminyl)asparagine Amidase F. Journal of Biological Chemistry 270, 29493-29497 (1995).
134. Filitcheva, J. PNGases: A Diverse Family of Enzymes Related by Function Rather Than Catalytic Mechanism, Vol. Ph.D. (Massey University, Palmerston North; 2010).
135. Fan, J. Q. Detailed Studies on Substrate Structure Requirements of Glycoamidases A and F. Journal of Biological Chemistry 272, 27058-27064 (1997).

Example 2

Computationally-Guided Design of Biocombinatorial Libraries

Computationally Guided Library Design

Figure 8:
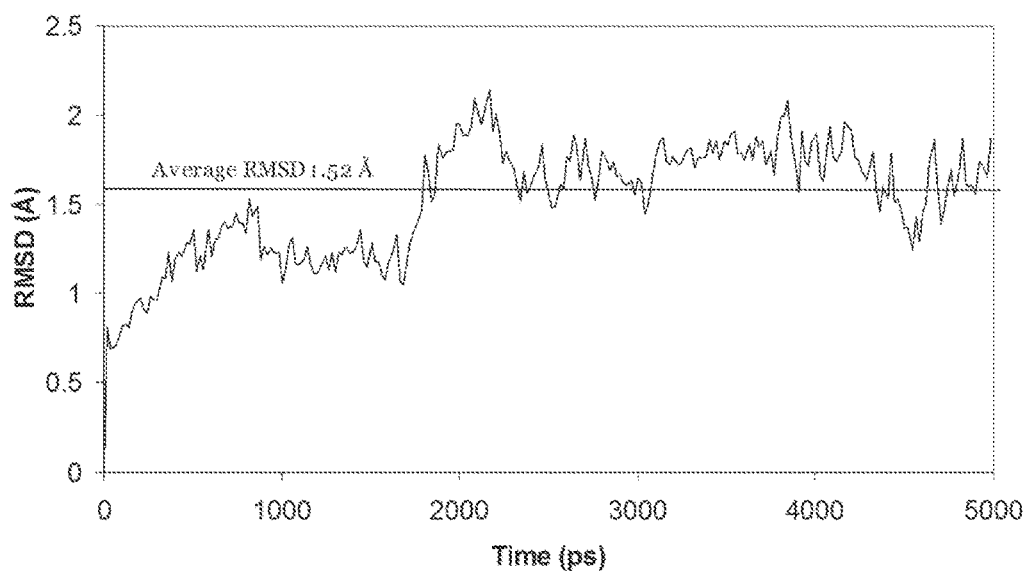
FIG. 8 shows RMSD in the Cα positions in the PNGase F—chitobiose complex. MD simulation data generated by Woods, et al.
Figure 9:
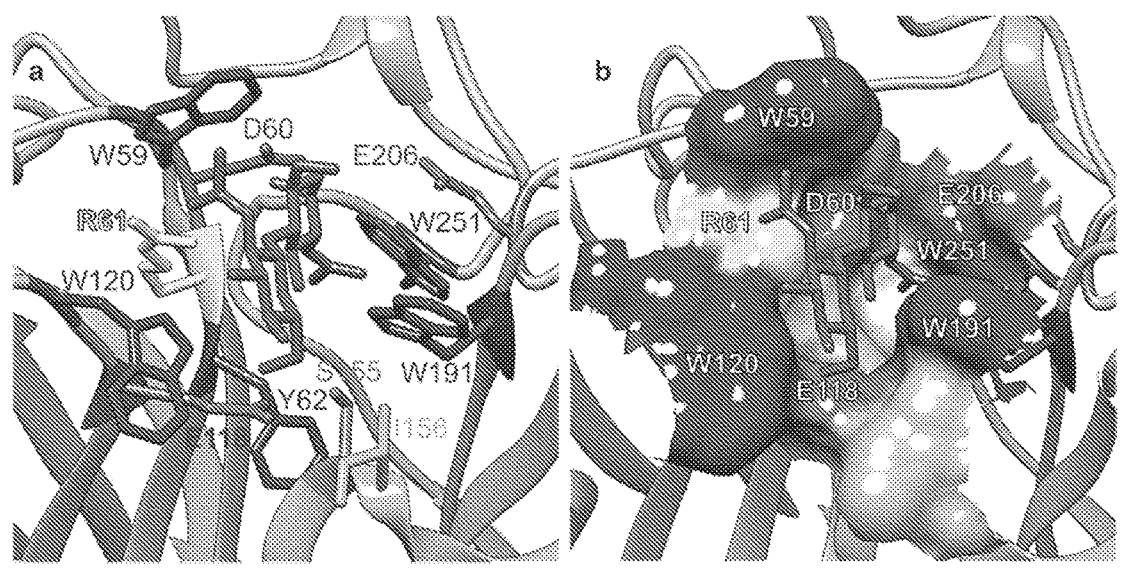
FIG. 9 shows a PNGase F binding pocket. a) Residues within 4.5 Å of the disaccharide chitobiose ligand in the binding site of PNGase F. b) The solvent accessible surface with critical residues for binding are labeled. PDB ID 1PNF. Molecular graphics made with UCSF Chimera package.

The wild-type *Flavobacterium meningosepticum* N-glycan processing enzyme, wtPNGase F, has previously been co-crystallized (PDB ID: 1PNF) with a chitobiose disaccharide in the active site at a 2.0 Å resolution.[1] Using this 1PNF x-ray crystal structural model a 5 ns fully solvated MD simulation of the PNGase F—N,N'-diacetylchitobiose (GlcNAcβ1-4GlcNAc) complex in water at room temperature and pressure employing the AMBER-GLYCAM protein-carbohydrate force field was preformed.[2-4] The root mean squared difference (RMSD) in the positions of the Ca atoms, relative to the experimental structure, was determined as a function of the simulation time and the relative low 1.5 Å average RMSD (FIG. 8) indicated that the simulation reproduced the experimental structure. Additionally, the complex maintained experimentally observed hydrogen bond interactions between the disaccharide ligand and the protein (Table 3). Given that the simulation of the complex appeared to be stable and consistent with experimental structural data, the interaction energies were then computed. Data from the heating and pre-equilibration period (1 ns) were not included in the subsequent analysis. Using the MM-GBSA protocol as implemented in AMBER, per-residue molecular mechanical (MM) contributions to the binding energy were computed for each of the 314 amino acids in PNGase F over the period of 2-5 ns; the generalized Born (GB) continuum solvent model was employed to estimate desolvation energies.[5] Additionally, MD data were employed in computational alanine scanning. FIG. 9 depicts residues within 4.5 Å of the ligand.

TABLE 3

Experimental and theoretical hydrogen bond lengths observed between chitobiose and PNGase F. Data generated by Woods, et al.

| Hydrogen bonds | 1PNF X-ray Data (Å) | Average from MD Simulation (Å) |
| --- | --- | --- |
| D60-Oδ-GlcNAc316 O1 | 3.02 | 2.76 ± 0.1 |
| D60-O-GlcNAc316 NAc | 2.97 | 2.84 ± 0.1 |
| R61-NH-GlcNAc317 OAc | 2.84 | 2.91 ± 0.1 |
| R61-NH-GlcNAc316-O4 | 2.92 | 2.90 ± 0.1 |
| R61-NH2-GlcNAc317 OAc | 3.03 | 2.90 ± 0.1 |
| W120-Nε-GlcNAc317-O6 | 2.93 | 2.98 ± 0.1 |
| W191-Nε-GlcNAc316-O3 | 2.96 | 3.06 ± 0.1 |

& E118) that were indicated to make slightly unfavorable interactions with the substrate. These three residues have each been associated with the catalytic function of PNGase F, which may explain their role in destabilizing the substrate.[1] Based on point mutant studies, D60 has been identified as the primary catalytic residue, whereas E206 and E118 are proposed to help stabilize high-energy reaction intermediates.[1] Consistent with experimental observations of hydrogen bonds and aromatic stacking in the complex, the energy decomposition analysis confirmed that R61, W120, W58, W191, and W251 are critical to ligand binding.[1]

TABLE 4

Approximate residue contributions (kcal/mol) to the binding free energy for wtPNGase F bound to substrate, chitobiose. Residues listed are within 4.5 Å of the ligand or contributed at least 0.5 kcal/mol to either the total molecular mechanical (van der Waals and electrostatics) interaction energy ($\Delta E_{MM}$) or the total binding free energy ($\Delta G_{BINDING}$). Residues required for catalytic activity are indicated in bold.[1] Library columns indicate residues selected for optimization for knowledge-based library design: A = alanine, X = all 20 amino acids, X(–D) = 19 amino acids (excluding aspartic acid). MM-GBSA data generated by Woods, et at.

| Critical Contact Zone Residues | $\Delta E_{VDW}$ | $\Delta E_{ELE}$ | $\Delta E_{MM}$ | $\Delta G_{GB+SA}$ | $\Delta G_{BINDING}$ | Library 1 | Library 2 |
| --- | --- | --- | --- | --- | --- | --- | --- |
| R61 | −1.5 | −15.1 | −16.7 | 12.3 | −4.4 | | |
| W120 | −3.1 | −2.3 | −5.4 | 1.9 | −3.5 | | |
| W59 | −3.1 | −0.2 | −3.3 | 0.3 | −3.0 | | |
| W191 | −1.3 | −1.6 | −2.9 | 1.3 | −1.6 | | |
| W251 | −0.7 | −0.3 | −1.0 | 0.1 | −0.9 | | |
| E118 | −0.5 | −0.1 | −0.5 | 0.6 | 0.1 | X | |
| D60 (nucleophile) | −0.9 | −3.9 | −4.8 | 5.2 | 0.4 | A | X(–D) |
| E206 | −0.3 | 2.1 | 1.8 | −1.1 | 0.7 | X | X |

| Proximal residues making only weak contributions | $\Delta E_{VDW}$ | $\Delta E_{ELE}$ | $\Delta E_{MM}$ | $\Delta G_{GB+SA}$ | $\Delta G_{BINDING}$ | Library 1 | Library 2 |
| --- | --- | --- | --- | --- | --- | --- | --- |
| Y62 | −0.6 | −0.1 | −0.6 | 0.0 | −0.6 | X | |
| D57 | −0.1 | 3.0 | 2.9 | −3.5 | −0.6 | X | X |
| I156 | −0.2 | 0.1 | −0.2 | −0.1 | −0.3 | X | X |
| S155 | −0.3 | 0.2 | −0.1 | −0.1 | −0.1 | X | |
| R248 | −0.1 | −1.2 | −1.4 | 1.2 | −0.1 | | X |
| G192 | 0.0 | 0.1 | 0.0 | 0.0 | 0.0 | X | X |
| T119 | −0.2 | −0.6 | −0.7 | 0.8 | 0.1 | | |
| K123 | 0.0 | −0.5 | −0.5 | 0.6 | 0.1 | | |
| R125 | 0.0 | −0.4 | −0.4 | 0.6 | 0.1 | | |
| Sub-total Interaction Energy $\Delta G_{BINDING}$ | −12.9 | −20.8 | −33.7 | 20.1 | −13.6 | | |

The estimated interaction energies for residues proximal to the ligand (within 4.5 Å) in addition to any other residues that contributed at least 0.5 kcal/mol to either the total molecular mechanical (sum of van der Waals, $\Delta E_{VDW}$, and electrostatic, $\Delta E_{ELE}$) interaction energy ($\Delta E_{MM}$) or the binding free energy are listed in Table 4. The per residue binding free energy ($\Delta G_{BINDING}$) was computed as the sum of the molecular mechanical interaction energy ($\Delta E_{MM}$) and the desolvation energy ($\Delta G_{GB+SA}$) of that residue. The per-residue energy analysis enabled the residues proximal to the binding site (FIG. 9) to be categorized into critical and tepid based on per residue binding free energy.

Critical residues made significantly stabilizing interactions, with the exception of the three residues (D60, E206, Equally important, nine additional residues, proximal to the ligand, were identified that were not making significant energetic contributions to binding. These nine weakly contributing, or tepid, residues represent the best opportunity for affinity enhancement by utilizing site-saturation mutagenesis libraries for directed evolution. Additionally, relative to wild-type PNGase F, the computational replacement of D60 or E206 with alanine (D60A, E206A) indicated that these mutants should have favorable interaction energies (Table 5). In particular, the D60A interaction energy indicates markedly improved substrate affinity relative to wild-type (wt) PNGase F, thus the D60A mutant was selected for expression and further experimental analysis.

TABLE 5

Computational alanine scanning of PNGase F bound to chitobiose. Interaction energies (kcal/mol) for favorable mutants are identified relative to wtPNGase F. Data generated by Woods, et al.

| Contact Zone Residues | $\Delta\Delta E_{MM}$ | $\Delta\Delta G_{GB+SA}$ | $\Delta\Delta G_{BINDING}$ |
|---|---|---|---|
| D60A | 1.8 | −4.0 | −2.2 |
| E206A | −1.9 | 1.2 | −0.7 |

Yeast Display Library Construction

Two yeast surface displayed biocombinatorial libraries were designed, which incorporated several computationally predicted residues for optimization as indicated in Table 4. Library 1 (GenScript, Piscataway, N.J.) was synthesized using NNK codon degeneracy and it incorporated a fixed D60A mutation in all the clones. NNK codon degeneracy reduces the probably of introducing a random stop codon while also minimizing codon bias relative to NNN codon degeneracy.[6] The sequence and sites of mutations for GenScript Library 1 are shown in FIG. 10. Library 2 (GeneArt AG, Regensburg, Germany) was synthesized using cassette mutagenesis which results in an equimolar distribution of all amino acids and it incorporated a randomized D60 position using 19 amino acids (i.e.: excluding D). The sequence and sites of mutations for GeneArt Library 2 are shown in FIG. 11.

Figure 12:
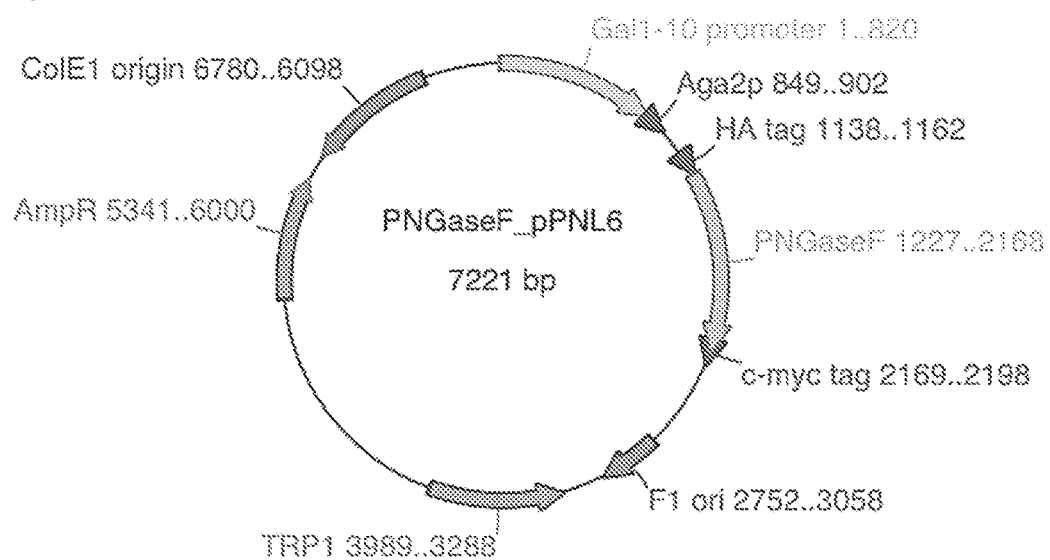
FIG. 12 shows a PNGase F modified pPNL6 yeast display library plasmid map.
Figure 13:
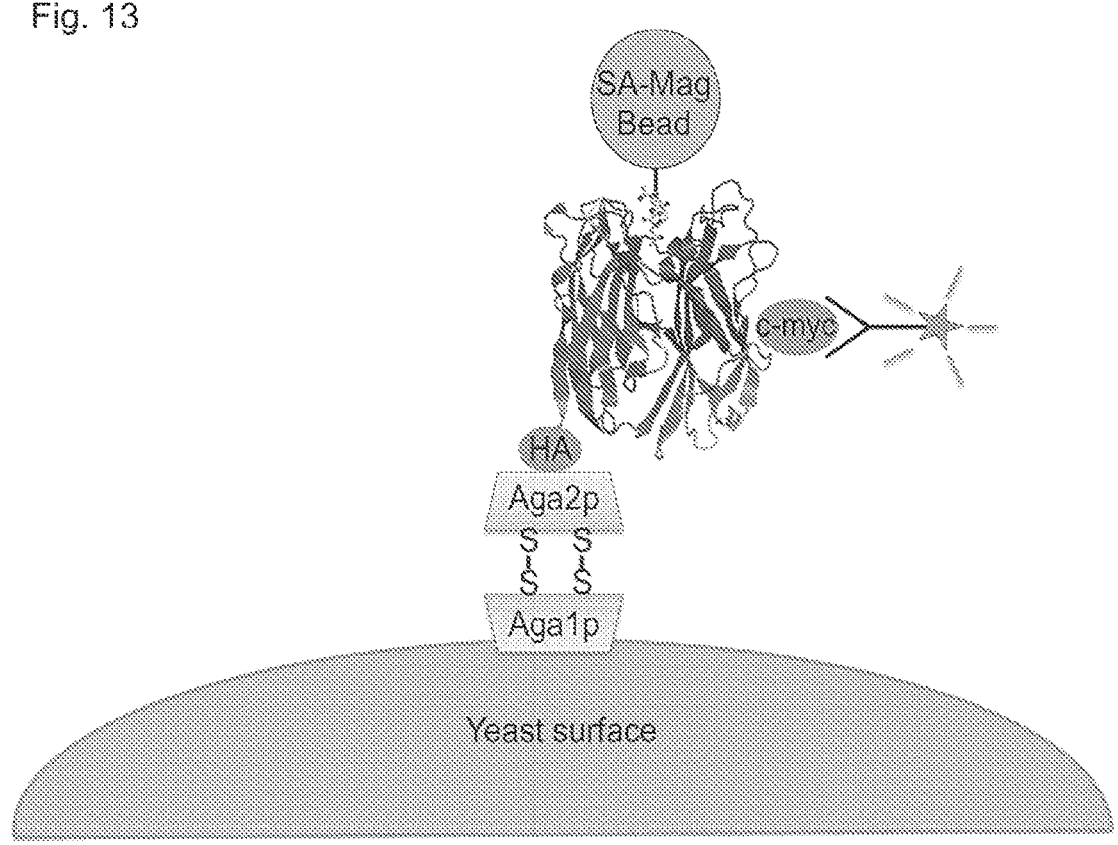
FIG. 13 shows a yeast cell-surface display. Representation of Aga2p-PNGase F fusion protein displayed via Aga1p on the yeast cell surface. Selected PNGase F clone(s) interact with the N-glycan target. The N-glycan target is biotinylated and bound to streptavidin coated magnetic beads. The original pPNL6 construct includes a HA tag between the Aga2p protein and the fused protein, PNGase F in this case. A C-terminal c-myc tag is included and is detected with an anti-c-myc fluorescent antibody by flow cytometry to confirm expression of the full length Aga2p-PNGase F fusion protein on the yeast cell surface prior to each round of selection. Approximately, 50,000 copies of Aga-2p protein are normally displayed on the yeast cell surface.

Synthetic degenerate oligonucleotides were constructed with the objective being to include the defined amino acid subsets at the defined position (FIGS. 10 and 11). PCR products were obtained using these oligonucleotide and full-length fragments were gel purified. The full-length products of both libraries were cloned into the pPNL6 vector using the NheI and BamHI restriction sites. The Pacific Northwest National Laboratory provided an aliquot of a yeast cell-surface displayed nonimmune library of human antibody scFv fragments (pPNL6).[7] This library was modified to replace the scFv fragment with the PNGase F enzyme (PNGaseF-pPNL6) as depicted in FIG. 12 (Dr. Loretta Yang). EBY100 yeast cells were transformed with the PNGase F-pPNL6 libraries for surface display (FIG. 13).[8] Titration and random sequencing of clones was carried out to assess the quality of the library, the efficiency of transformation, and the percent sequence space covered. A summary of sequence coverage estimates for both libraries is presented in Table 6. Library 1 was designed with seven sites for site-saturation mutagenesis. The theoretical diversity of the number of unique clones is $1.28 \times 10^9$. However, based on the sequence identity and the total number of transformants the estimated synthesized diversity is only $2.40 \times 10^6$ clones. This represents sequence coverage of approximately 0.18% indicating inefficiency both in construction and transformation of Library 1. Library 2 was designed with six sites for site-saturation mutagenesis, representing a theoretical diversity of $6.08 \times 10^7$ unique clones. The estimated synthesized diversity of Library 2 was determined to be $1.36 \times 10^7$ clones. Library 2 has sequence coverage of approximately 22.3%, and based on the number of clones represents a 5.7-fold higher synthesized diversity than Library 1.

TABLE 6

Comparison of theoretical and estimated synthesized library diversity and coverage of sequence space.

| | Amino Acid Randomization | Theoretical Diversity | Synthesized Diversity | % coverage |
|---|---|---|---|---|
| Library 1 | 7 ($20^7$) | $1.28 \times 10^9$ | $\sim 2.40 \times 10^6$ | $\sim 0.18\%$ |
| Library 2 | 6 ($20^5 \times 19^1$) | $6.08 \times 10^7$ | $\sim 1.36 \times 10^7$ | $\sim 22.3\%$ |

Directed Evolution of PNGase F Clones Via Yeast Surface Display

The constructed yeast-displayed PNGase F libraries were utilized for selecting clones with enhanced affinity for target N-glycans. Yeast libraries were grown overnight in selective growth media in a shaking incubator at 30° C. for approximately 24 hours. The expression and display of the Aga2p-PNGase F fusion protein on the yeast cell surface is under a Gal1-10 promoter (FIGS. 12 & 13), thus the yeast libraries were induced overnight in galactose containing media in a shaking incubator at 20° C. Induction efficiency was determined via flow cytometry using a primary anti-c-myc antibody to detect the C-terminal c-myc tag on the fully expressed Aga-2p-PNGase F fusion protein (data not shown). An induced yeast display library with at least 60% induced clones was used for selection of high affinity clones against N-glycan targets.

Figure 14:
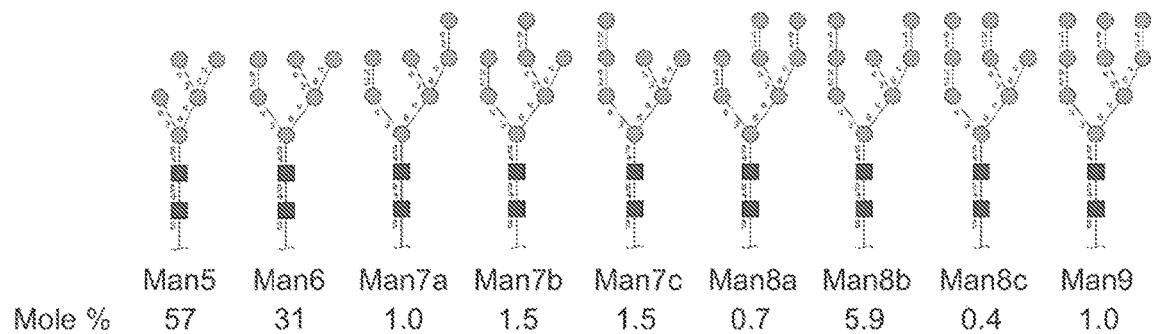
FIG. 14 shows ribonuclease B glycoforms. RNase B has a single N-glycosylation site at N34, which can consist of nine glycoforms of $Man_{5-9}GlcNAc_2$. The mole percentage of these glycoforms is listed below each of the nine glycan structures.

Two N-glycan targets were employed in the selection strategy to enrich clones that will retain the broad specificity of wtPNGase F enzyme for N-glycan structures. The primary N-glycan target was bovine pancreatic Ribonuclease B (RNase B), which contains a single N-glycosylation site at asparagine 34 (N34) and has nine high mannose glycoforms (FIG. 14).[9-11] The reported average molecular weight of RNase B is 15,095 Da derived from the relative abundance of each of the glycosylated species.[12] RNase B and its non-glycosylated form RNase A, with a reported molecular weight of 13,680 Da, are well-characterized enzymes and frequently used as standards for validating carbohydrate analysis techniques.[11-16] Interestingly, based on comparison of NMR spectra of RNase A and RNase B, the N-glycosylation of RNase B has no discernable impact on its structure.[17] However, RNase B exhibits greater stability than RNase A, consistent with observations that glycosylation reduces the denaturing tendency promoted by the preferential hydration of the groups buried in the core of the protein.[14, 15] A secondary N-glycan target was Asialofetuin which is created by enzymatically desialylating fetuin with a neuraminidase, and contains less than 0.5% N-acetylneuraminic acid. Fetuin, isolated from fetal calf serum, is a 48.4 kDa glycoprotein with three N-glycosylation sites and five O-glycosylation sites and has relatively more complex N-glycan structures in comparison to the high mannose structures found on RNase B.[18] The percent weight composition of fetuin is 74% polypeptide, 8.3% hexose, 5.5% hexosamines, and 8.7% sialic acid. Both N-glycan target glycoproteins were denatured to make the N-glycans fully accessible to the yeast surface displayed PNGase F clones. Furthermore, the denatured glycoproteins were biotinylated in order to present them on Dynabeads® Biotin Binder, streptavidin coated 2.8 μm magnetic beads for selection and for detection with fluorescently labeled streptavidin for FACS.

The selection strategy incorporated two rounds of Magnetic-Activated Cell Sorting (MACS) using streptavidin coated 2.8 μm magnetic beads (Dynabeads® Biotin Binder) (FIG. 15) followed by a third round of Fluorescence-Activated Cell Sorting (FACS) using denatured RNase B and Asialofetuin as target N-glycans.[19, 20] The library underwent negative selection against uncoated magnetic beads at the start of first round of selection to remove any bead-binding clones from the library prior to positive selection against N-glycan targets of interest.

The set of 2× MACS and 1× FACS rounds of selection were repeated for a total of nine rounds (FIG. 16a). The target N-glycan bearing RNase B was exclusively used for all nine rounds of selection with Library 1. However, both N-glycan bearing RNase B and Asialofetuin glycoproteins were concurrently used as targets for Library 2 during parallel rounds of selection. A portion of the amplified library output from round three with RNase B was concurrently selected against Asialofetiun during rounds 4-6. The outputs from both target RNase B and Asialofetuin selections were pooled after round six. As before, a portion of this combined output pool was again concurrently selected against both target RNase B and Asialofetuin during rounds 7-9 in parallel. At the end of the round nine, both RNase B and Asialofetiun selection output pools were recombined once again.

During nine rounds of iterative selection and amplification (approximately 50 clones were sequenced at the end of every $3^{rd}$ round) enrichment of clones was observed. The clone with the highest level of enrichment, designated R911, had the following mutations relative to wtPNGase F: D57L, D60C, I156L, G192I, E206S, and R248W. A graphical representation of the prevalence of amino acids at the six computationally selected mutagenesis sites can be viewed in FIG. 16b.

a relatively small glycine residue has been replaced with a bulky hydrophobic isoleucine side chain. An increase in the hydrophobicity of the binding pocket may enhance protein-carbohydrate interactions; however, the presence of a bulky side chain could also partially block access to the binding pocket. To investigate the utility of the selected R6 and R9 clones as Lectenz® affinity reagents and characterize their properties, the selected PNGase F clones were cloned into a bacterial expression vector for expression and purification in an E. coli.

Methods

Molecular Dynamics and Per-Residue Binding Free Energy Decomposition

A 5 ns fully solvated MD simulation of the PNGase F—N,N'-diacetylchitobiose (GlcNAcβ1-4GlcNAc) complex was performed in water at room temperature and pressure employing the AMBER-GLYCAM protein-carbohydrate force field. The per-residue contributions to the binding energy was computed for each of the 313 amino acids in PNGase F, employing the generalized Born (GB) continuum solvent model as implemented in AMBER.[5] In a typical MM-GB/PB calculation, the free energy is computed for the protein ($\Delta G_{PROTEIN}$), ligand ($\Delta G_{LIGAND}$), and complex ($\Delta G_{COMPLEX}$) for each structural "snapshot" extracted from the MD trajectories. From the 5 ns trajectory, the first 1 ns was discarded and 2000 snapshots were selected (at 2 ps intervals) from the remaining 4 ns for molecular mechanical (MM) binding energy analysis. The binding free energy ($\Delta G_{BINDING}$) is then computed by subtraction. As shown in Equation 1, averaging over the entire trajectory results in the

TABLE 7

Sequences of enriched clones from Library 1 and Library 2 selections. Listed are identities of the preferred amino acids at the residues selected for site-saturation mutagenesis. For comparison, the wtPNGase F sequence is included. Clones R617 and R6113 were selected from Library 1 solely against the target N-glycan bearing RNase B glycoprotein. Clones R911 and R9113 were selected from Library 3 against both target N-glycan bearing RNase B and Asialofetuin glycoproteins. The asterisks represent sites that were not selected for site-saturation mutagenesis.

|  | wtPNGase F | | | | | | | | |
| --- | --- | --- | --- | --- | --- | --- | --- | --- | --- |
|  | D57 | D60 | Y62 | E118 | S155 | I156 | G192 | E206 | R248 |
| R617 (Library 1) | R | A* | G | A | D | T | C | S | R* |
| R6113 (Library 1) | C | A* | W | A | Q | T | T | R | R* |
| R911 (Library 2) | L | C | Y* | E* | S* | L | I | S | W |
| R9113 (Library 2) | W | C | Y* | E* | S* | M | I | W | S |

Sequence identity of the top two enriched clones selected from both Library 1 and Library 2 are summarized in Table 7. The selection of tryptophan in multiple sites is significant because aromatic side chains are known to interact with the hydrophobic face of monosaccharides.[21] The D60 position in Library 2, which was subjected to site-saturation mutagenesis to 19 amino acids (except D), showed the same D60A mutation in both R9 clones. This may indicate that a cysteine in this position is highly favored for binding interactions. However, the presence of cysteine in all four enriched clones is potentially also a cause for concern as the addition of a single cysteine could potentially disrupt the three pre-existing disulfide bonds at 51-56, 204-208, and 231-252 in PNGase F. Other interesting observations include the preference for E118A and I156T mutations in both the R6 clones from Library 1. Similarly, both the R9 clones from Library 2 show a preference for D60C and G192I mutations. The G192I mutation is significant because final average interaction energies ($<\Delta G_{BINDING}>$), where the averaging is over the MD snapshots.

$$<\Delta G_{BINDING}> = <\Delta G_{COMPLEX}> - <\Delta G_{PROTEIN}> - <\Delta G_{LIGAND}> \quad \text{Equation 1}$$

The free energies of the components are computed by separating the energies into three categories (Equation 2), namely molecular mechanical ($\Delta E_{MM}$: electrostatic and van der Waals), entropic ($\Delta S_{MM}$), and solvation ($\Delta G_{SOLVATION}$).

$$<\Delta G> = <\Delta E_{MM}> - T<\Delta S_{MM}> + <\Delta G_{SOLVATION}> \quad \text{Equation 2}$$

Computational Alanine Scanning and Electrostatic Scanning

Following the single trajectory mutation protocol proposed in the Kollman group and implemented in AMBER, the set of snapshots for the wild type complex was employed for each mutant calculation of the energy terms in Equations 1 and 2.[9] The mutant side chain is truncated, replacing Cγ with a hydrogen atom, and setting the Cβ-H bond length and direction to those of the residue in the wild type Cβ-Cγ. The underlying approximations of the single trajectory mutation protocol are that the mutant and the wild type undergo similar conformational changes from the unbound to the bound state, and that local side chain reorganizations are small perturbations relative to the alanine mutation itself.[9] One can run separate trajectories on the wild type and mutant species, however this introduces substantial noise (due to lack of cancellation of internal energy components) and is computationally demanding. Separate simulations would be justified in the case of mutations to larger or charged residues.

In order to probe for the effect of an ionized residue at a particular position, alanine scanning was modified to employ an alanine with a theoretical net positive (Ala+) or negative (Ala−) charge. All atoms in the alanine carried the standard partial charges, while the total charge on the residue was set to +1 or −1 by adjusting the charge on the Cβ atom.

Synthesis of Yeast-Displayed PNGase F Clones Library

The GenScript library was synthesized (GenScript, Piscataway, N.J.) using NNK codon degeneracy and incorporates mutagenesis sites as indicated under Library 1 in Table 4. The GeneArt library was synthesized (Life Technologies, Carlsbad, Calif.) with a nucleotide mixture which results a equimolar distribution of all amino acids and it incorporates a randomized D60 position using 19 amino acids (i.e.: excluding D) as indicated under Library 2 in Table 4). The synthesized libraries were cloned into the pPNL6 vector (FIG. 12).

Yeast Display Library Transformation into EBY100

The cloned libraries in the PNGaseF-pPNL6 vector were transformed into EBY100 yeast cells for surface display (FIG. 13 and Table 6) per the recommended protocol.[8]

Induction of Yeast Display Library

The yeast library was induced as per the recommended protocol in the Yeast Display scFv Antibody Library User's Manual (Rev: MF031112) (sysbio.org/dataresources/index.stm) provided by Pacific Northwest National Laboratory (Richland, Wash.). The EBY100 transformed yeast libraries are induced in galactose containing media to express the surface displayed the Aga2p-PNGase F clones (FIG. 13)_Induction efficiency is determined by flow cytometry to ensure at least 60% of the yeast cells are expressing the C-terminal c-myc tag (data not shown).

Directed Evolution of PNGase F Clones Library Via Yeast Surface Display

The N-glycan bearing glycoproteins, RNase B (Sigma R7884) and Asialofetuin (Sigma A4781), were used as selection targets.[9, 18] Both glycoproteins were denatured to ensure maximum exposure of the N-glycan and glycopeptide region to the yeast surface displayed PNGase F clones.

Figure 15:
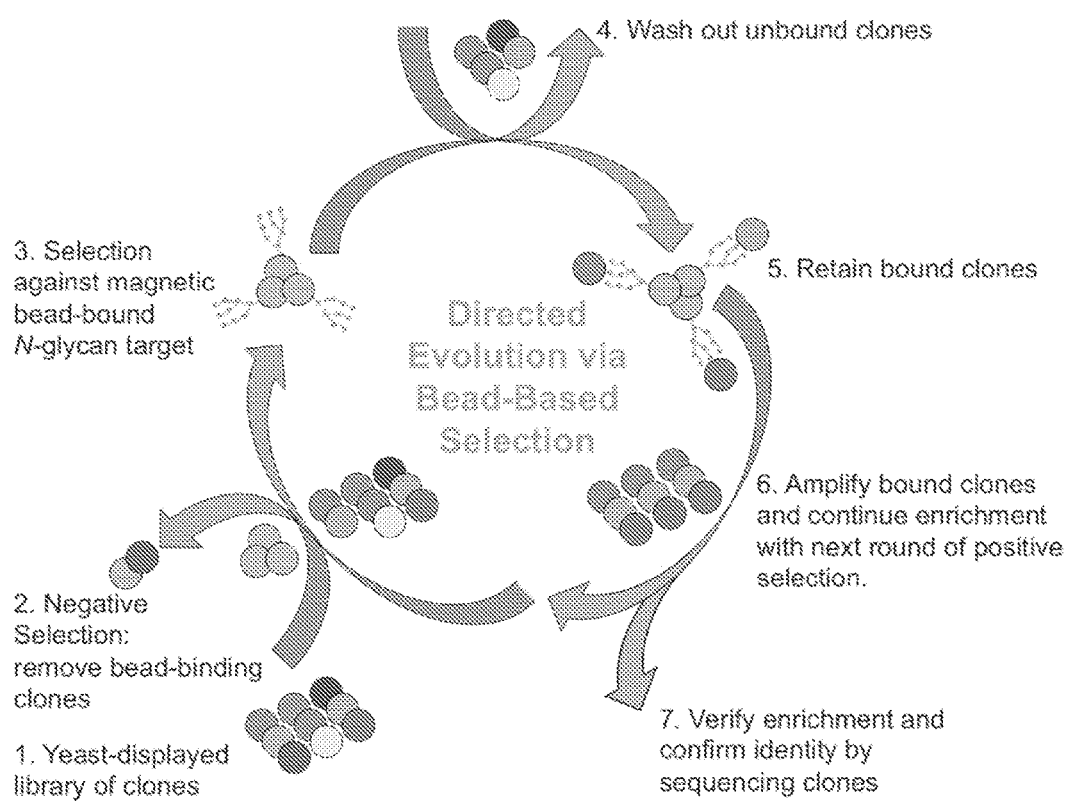
FIG. 15 shows Magnetic-Activated Cell Sorting (MACS) of yeast cells. Yeast-displayed PNGase F library selection against N-glycan target bound to magnetic beads. Steps 1-2: The PNGase F library is subjected to a negative selection against biotin-streptavidin magnetic beads (no dRNase B) at the start of the first round of selection to remove any biotin-streptavidin-magnetic bead-binding clones. Step 3: Biotinylated denatured RNase B is pre-incubated with streptavidin coated magnetic beads (2.8 um diameter) prior to initiating positive selection. Step 4: Unbound yeast clones are washed away. Step 5: Bound yeast clones are retained. Step 6: Bound clones are amplified for the next round of selection. Step 7: Clones are sequenced to monitor enrichment and convergence after each round of FACS (not shown). The converged clone(s) are selected as Lectenz® candidate(s) for downstream characterization.

The selection strategy incorporates two rounds of magnetic activated cell sorting (MACS; FIG. 15) followed by a third round of fluorescence activated cell sorting (FACS) using a mixture of denatured RNase B and denatured Asialofetuin as target N-glycans.[19, 20] The set of 2× MACS and 1× FACS rounds of selection were repeated for a total of nine rounds as described in FIG. 16a.

Yeast Colony PCR for Sequencing

Approximately, 50 colonies from every third round of selection were picked and mixed in 20 µL of 0.1% SDS in molecular biology grade water (Thermo Scientific SH30538.02) and heated for 5 minutes at 95° C., then stored on ice. 2 µL of lysed yeast cell mixture was used to provide template DNA for amplification through polymerase chain reaction (PCR). A PCR master mix was prepared using Taq DNA Polymerase (Life Technologies 10966-034) and dNTP mix (Life Technologies 18427-013) with a final volume of 50 µL per reaction, as per the manufacturers recommended protocol. Forward and reverse primers (FIG. 17) were mixed into the PCR master mix at a final concentration of 0.2 µM. PCR was performed with a Mastercycler EP (Eppendorf) with a thermocycle programmed as shown in FIG. 18. PCR product (1163 base pair length) was verified using a 0.7% Agarose gel and imaged using a Multiimage Light Cabinet (Alpha Innotech, Inc.) and submitted for sequencing to MWG Operon using a forward sequencing primer (FIG. 17).

REFERENCES

1. Kuhn, P. et al. Active Site and Oligosaccharide Recognition Residues of Peptide-N4-(N-acetyl-β-D-glucosaminyl)asparagine Amidase F. Journal of Biological Chemistry 270, 29493-29497 (1995).
2. Woods, R. J., Dwek, R. A., Edge, C. J. & Fraser-Reid, B. Molecular Mechanical and Molecular Dynamic Simulations of Glycoproteins and Oligosaccharides. 1. GLYCAM_93 Parameter Development. The Journal of Physical Chemistry 99, 3832-3846 (1995).
3. Case, D. A. et al. The Amber biomolecular simulation programs. J Comput Chem 26, 1668-1688 (2005).
4. Kirschner, K. N. et al. GLYCAM06: a generalizable biomolecular force field. Carbohydrates. J Comput Chem 29, 622-655 (2008).
5. Tsui, V. & Case, D. A. Theory and applications of the generalized Born solvation model in macromolecular simulations. Biopolymers 56, 275-291 (2001).
6. Patrick, W. M. & Firth, A. E. Strategies and computational tools for improving randomized protein libraries. Biomolecular Engineering 22, 105-112 (2005).
7. Miller, K. D., Pefaur, N. B. & Baird, C. L. Construction and screening of antigen targeted immune yeast surface display antibody libraries. Curr Protoc Cytom Chapter 4, Unit 4 7 (2008).
8. Benatuil, L., Perez, J. M., Belk, J. & Hsieh, C. M. An improved yeast transformation method for the generation of very large human antibody libraries. Protein Eng Des Sel 23, 155-159 (2010).
9. Morris, T. A., Peterson, A. W. & Tarlov, M. J. Selective binding of RNase B glycoforms by polydopamine-immobilized concanavalin A. Analytical chemistry 81, 5413-5420 (2009).
10. Mega, T., Oku, H. & Hase, S. Characterization of Carbohydrate-Binding Specificity of Concanavalin A by Competitive Binding of Pyridylamino Sugar Chains. J Biochemistry 111, 396-340 (1992).
11. Fu, D., Chen, L. & O'Neill, R. A. A detailed structural characterization of ribonuclease B oligosaccharides by 1H NMR spectroscopy and mass spectrometry. Carbohydr Res 261, 173-186 (1994).
12. Noble, J. E., Knight, A. E., Reason, A. J., Di Matola, A. & Bailey, M. J. A comparison of protein quantitation assays for biopharmaceutical applications. Mol Biotechnol 37, 99-111 (2007).
13. Prien, J. M., Prater, B. D. & Cockrill, S. L. A multimethod approach toward de novo glycan characterization: a Man-5 case study. Glycobiology 20, 629-647 (2010).
14. Giancola, C. et al. Thermodynamic stability of the two isoforms of bovine seminal ribonuclease. Biochemistry 39, 7964-7972 (2000).
15. Del Vecchio, P., Catanzano, F., de Paola, B. & Barone, G. Thermodynamic Stability of Ribonuclease B. Journal of Thermal Analysis and Calorimetry 61, 363-368 (2000).

16. Rudd, P. M., Scragg, I. G., Coghill, E. & Dwek, R. A. Separation and analysis of the glycoform populations of ribonuclease B using capillary electrophoresis. Glycoconj J 9, 86-91 (1992).
17. Joao, H. C., Scragg, I. G. & Dwek, R. A. Effects of glycosylation on protein conformation and amide proton exchange rates in RNase B. FEBS Lett 307, 343-346 (1992).
18. Zauner, G., Koeleman, C. A., Decider, A. M. & Wuhrer, M. Protein glycosylation analysis by HILIC-LC-MS of Proteinase K-generated N- and O-glycopeptides. J Sep Sci 33, 903-910 (2010).
19. Chao, G. et al. Isolating and engineering human antibodies using yeast surface display. Nat. Protocols 1, 755-768 (2006).
20. Ackerman, M. et al. Highly avid magnetic bead capture: An efficient selection method for de novo protein engineering utilizing yeast surface display. Biotechnology Progress 25, 774-783 (2009).
21. Asensio, J. L., Arda, A., Caflada, F. J. & Jiménez-Barbero, J. Carbohydrate-Aromatic Interactions. Accounts of Chemical Research 46, 946-954 (2012).

Example 3

Experimental Characterization of Lectenz® Candidates

The four Lectenz® candidates (R617, R6113, R911, and R9113) selected from the computationally-guided yeast-display library selections were expressed in an *E. coli* expression system and purified via Immobilized Metal Affinity Chromatography (IMAC) followed by Size Exclusion Chromatography (SEC) to obtain pure protein. The purified proteins were used to investigate their utility as N-glycopeptide affinity reagents using Surface Plasmon Resonance (SPR), glycan array screening, and affinity chromatography.

Cloning of PNGase F Clones into a Bacterial Expression Vector

The high yield and soluble expression of *Flavobacterium meningosepticum* PNGase F in *E. coli* using the pOPH6 bacterial expression vector was reported by Loo et al.[1] The pOPH6 vector incorporates a N-terminal OmpA periplasmic secretion tag to direct PNGase F to the periplasm. The construct also includes a C-terminal histidine tag for IMAC purification of expressed PNGase F. Using this vector, a D60A point mutant was constructed by site-directed mutagenesis (Dr. Loretta Yang).

In addition, the yeast-display selected PNGase F clones (R617, R6113, R911, and R9113) were also cloned into the pOPH6 vector using oligonucleotide primers (FIG. 19). The primers were designed to PCR amplify PNGase F clone sequences from PNGase F-pPNL6 vectors, and introduce flanking EcoRI and BamHI restriction sites into the full length PCR product. The PCR products were double-digested with EcoRI and BamHI restriction enzymes and ligated into previously double-digested pOPH6 empty vector. DNA sequencing confirmed successfully cloning of R617, R6113, R911, and R9113 into pOPH6 vectors. However, expressed protein could not be detected via Western Blot using a mouse anti-His6× HRP conjugated antibody. Thus, a new expression vector, pOPH6 II, was designed.

Figure 21:
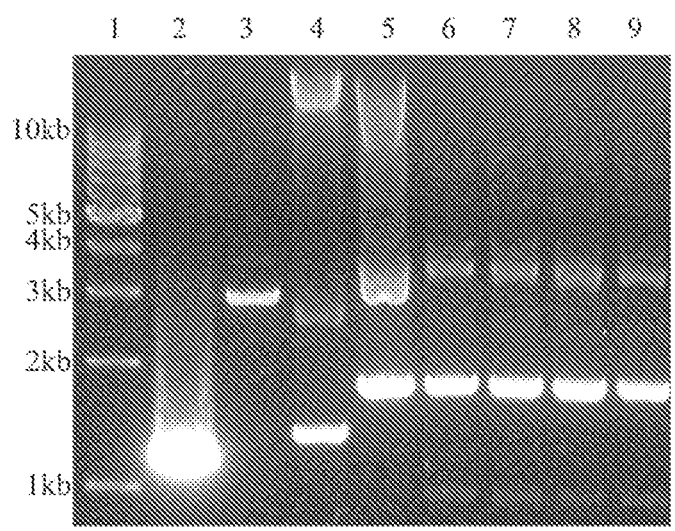
FIG. 21 shows a DNA gel of pOPH6 II and PNGase F cloning. Lane 1=1 kb DNA step ladder. Lane 2=pBluescript II KS(–) 2921 bp. Lane 3=pBluescript II KS(–) XbaI and XhoI double digest 2858 bp. Lane 4=Failed insertion/ligation with incorrect sequence. Lane 5-9=Ligated PNGaseF-pOPH6 II vector 3923 bp with correct PNGaseF-pOPH6 II sequences (both supercoiled and uncoiled migration bands are visible).
Figure 22:
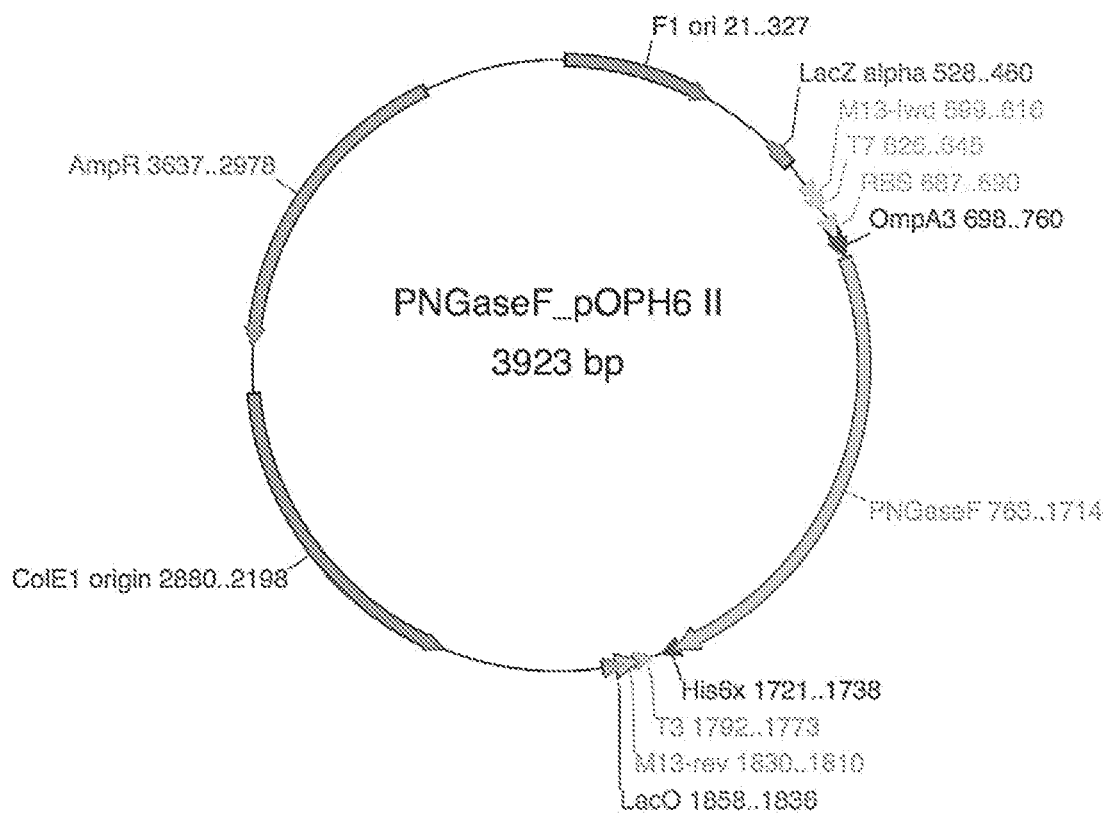
FIG. 22 shows a PNGase F-pOPH6 II vector map. The *E. coli* expression vector, pOPH6 II, was based on the pBluescript II KS(–) vector and has the OmpA-PNGase F-His6× sequence from pOPH6 for expression. The PNGase F-pOPH6 II expression plasmid is used for the D60A single point mutant as well as the four PNGase F clones selected from the yeast-display library selections: R617, R6113, R911, and R9113.

The pOPH6 II bacterial expression vector was based on the pBluescript II KS(−) vector. Custom oligonucleotide primers were designed to PCR amplify the ompA-PNGase F-His6× sequences from the pOPH6 vector (FIG. 20). To ensure the entire sequence of interest was included a T7 forward primer was used which includes the XbaI restriction site upstream of the OmpA sequence. In addition, the reverse primer was designed to introduce a XhoI restriction site immediate downstream of the stop codon. These restriction sites were used to double digest the PCR product and clone the gene into Xba I and XhoI double-digested pBluescript II KS(−) vector (FIG. 21). The ligated plasmid containing the OmpA-PNGase F-His6 expression sequence clone was identified as PNGaseF-pOPH6 II and a vector map is provided in FIG. 22. Five pOPH6 II plasmids were constructed, each containing one of the five PNGase F clones of interest: D60A, R617, R6113, R911, and R9113. Unlike the original pOPH6 vector, expression and purification was successfully achieved using the pOPH6 II vector.

Expression and Purification of PNGase F Clones

Expression of yeast-display selected PNGase F clones using the original pOPH6 vector was unsuccessful using previously published protocols.[1,2] However, expression and purification was successfully achieved with the PNGase F-pOPH6 II vector using a protocol developed by Filitcheva et al.[2] This protocol was adapted to optimize expression and purification of PNGase F clones.

All five PNGase F-pOPH6 II (D60A, R617, R6113, R911, and R9113) plasmids were transformed into *E. coli* BL21-Gold(DE3) competent cells for expression. Expression of the protein of interest is under the control of the isopropyl-1-thio-β-D-galactopyranoside (IPTG) inducible T7 promoter. In summary, starter 50 mL LB cultures containing 100 µg/mL carbenicillin were inoculated with a single transformed colony selected from a LB-carbenicillin agar plate and grown overnight in a shaking incubator at 37° C. The culture was expanded to 37° C. pre-warmed 1 L LB with carbenicillin. The temperature was dropped to 22° C. between $OD_{600}$ 0.4-0.5 and the culture was induced with IPTG and incubation continued for approximately 22 hours. The culture was harvested by collecting the cell pellet and subjecting it to mechanical cell lysis via a French Press. The cell lysate was centrifuged to separate insoluble cell debris from the supernatant containing the periplasmic fraction. This periplasmic fraction was loaded onto an IMAC column and the PNGase F clone eluted over an imidazole gradient. The fractions of the elution peak were pooled and concentrated using a 10 kDa cutoff Vivaspin concentrator and run through size exclusion chromatography for enhanced purity. The PNGase F clone elution peak fractions were pooled, concentrated, and protein yield determined by UV 280 absorbance ($A_{280}$).

Figure 23:
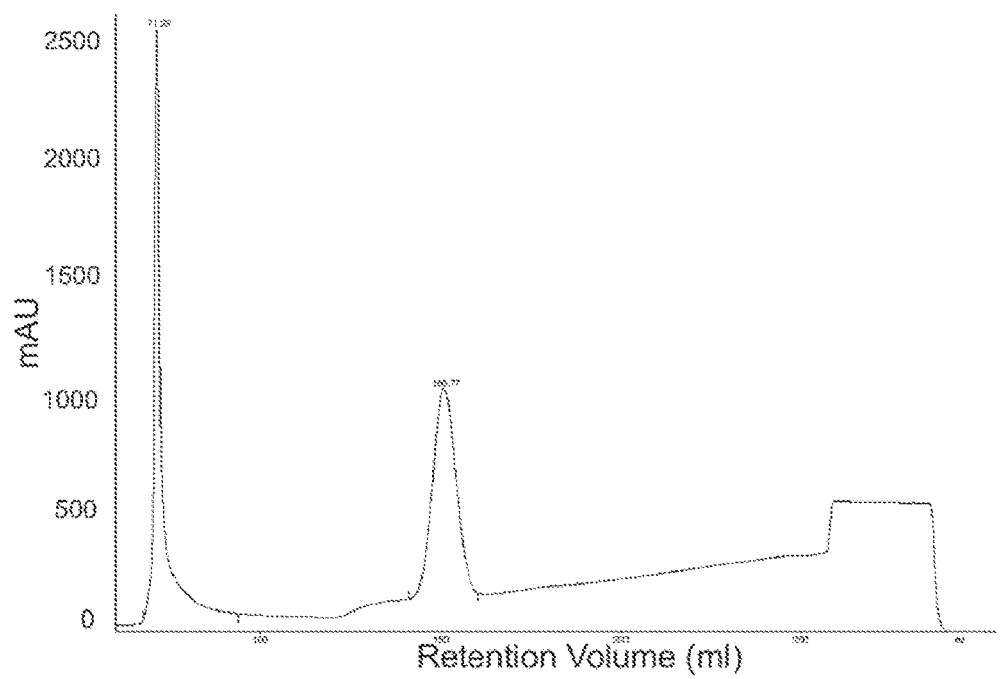
FIG. 23 shows gradient elution profile of D60A. The first sharp peak is a 50 mM imidazole wash (8.3% B). The second peak corresponds with elution of D60A with an absorbance maximum at ~110 mM imidazole (20.5% B).
Figure 24:
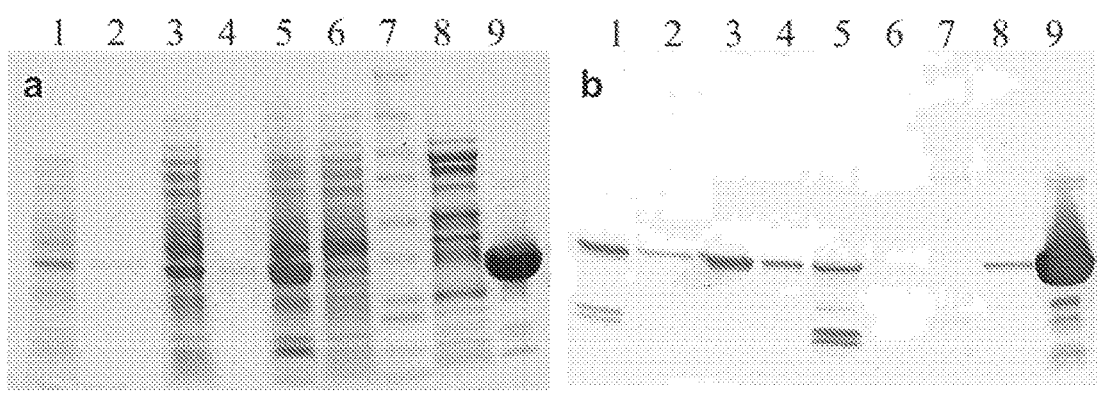
FIG. 24 shows SDS-PAGE and Western Blot of IMAC purified D60A clone, a) Coomassie stained denaturing SDS-PAGE of D60A expression and IMAC purification samples. b) Western Blot of duplicate gel of D60A expression and IMAC purification samples. 1:5000 dilution of mouse anti-His6 HRP antibody used and developed with DAB substrate. A 36 kDa band corresponding with expressed D60A is visible across lanes 1-3, 5, and 8-9. Lane 1=culture. Lane 2=culture supernatant. Lane 3=soluble periplasmic fraction. Lane 4=positive control PNGase F (300 ng). Lane 5=insoluble cell lysate. Lane 6=loading flow through. Lane 7=Protein markers: 250 kDa, 150 kDa, 100 kDa, 75 kDa (visible on blot), 50 kDa, 37 kDa (green), 25 kDa, 20 kDa (visible on blot), 15 kDa, 10 kDa (green). Lane 8=50 mM imidazole wash. Lane 9=Pooled elution peak fractions from imidazole gradient (24 µg).
Figure 25:
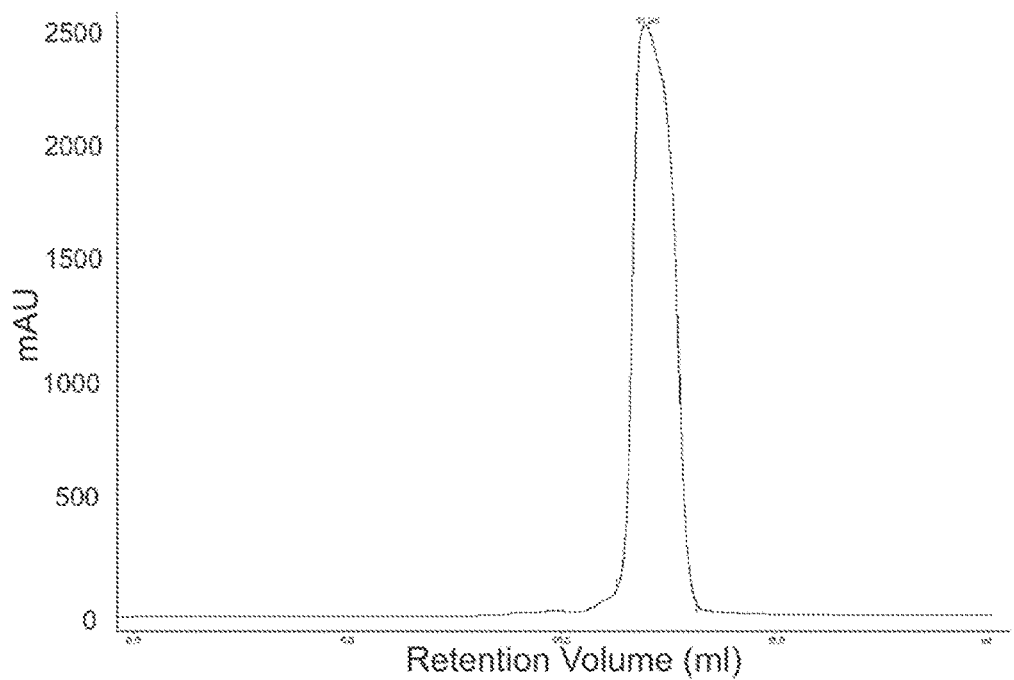
FIG. 25 shows a D60A SEC chromatogram on a Superdex 75 10/300 GL column. IMAC elution fractions were run through SEC to obtain high purity D60A protein. Both wtPNGase F and D60A eluted at 12 ml retention volume.
Figure 26:
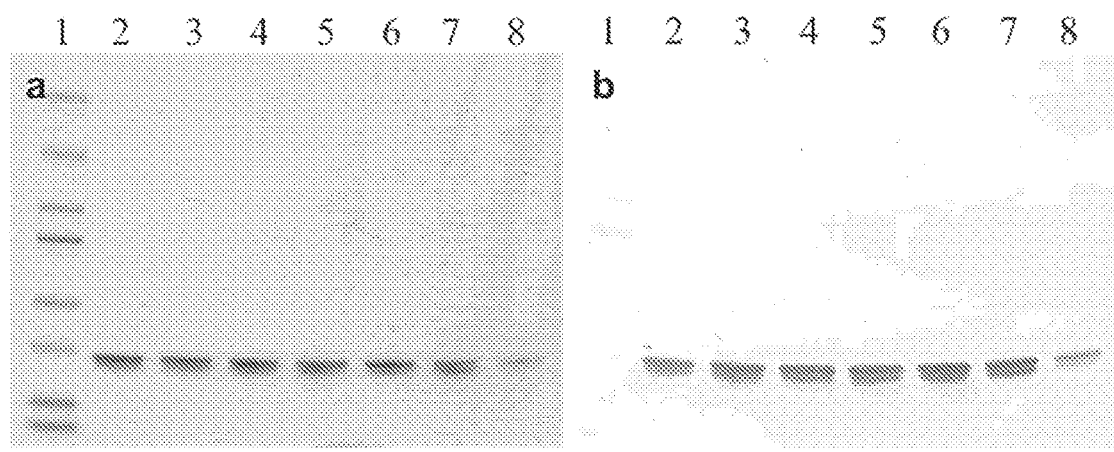
FIG. 26 shows SDS-PAGE and Western Blot of SEC purified D60A clone. a) Coomassie stained denaturing SDS-PAGE of D60A SEC elution peak fractions. b) Western Blot of duplicate gel of D60A SEC elution peak fractions. 1:5000 dilution of mouse anti-His6 HRP antibody used and developed with DAB substrate. A 36 kDa band corresponding with expressed D60A is visible across lanes 2-7. Lane 1=Protein markers (not visible in Western Blot): 250 kDa, 150 kDa, 100 kDa, 75 kDa, 50 kDa, 37 kDa (green), 25 kDa, 20 kDa. Lanes 2-7=D60A elution fractions (1 µg each). Lane 8=Positive control PNGase F (500 ng). The gel bands were purposefully allowed to migrate longer than normal in order to visualize doublet bands around 36 kDa corresponding with OmpA-D60A and D60A without the N-terminal OmpA secretion tag.

The IMAC and SEC chromatogram elution profiles of expressed wtPNGase F and the D60A clone were similar. FIG. 23 shows the IMAC elution chromatogram of D60A. Expression and IMAC purification samples were analyzed by denaturing SDS-PAGE and Western Blot and gel and blot images are shown in FIG. 24. Similarly, FIGS. 25 and 26 show the corresponding SEC elution chromatogram of D60A, and SDS-PAGE and Western Blot images are shown in FIG. 26. SDS-PAGE gel comparison of the soluble periplasmic fraction sample (FIG. 24*a* Lane 3) with the insoluble cell lysate (FIG. 24*a* Lane 5) indicates a significantly larger 36 kDa protein band consistent with D60A migration is present in the insoluble cell lysate. However, only a small portion of this protein band was detected on the Western Bot (FIG. 24*b* Lanes 5). Taken together these data suggest that a majority of the expressed D60A protein was in the soluble periplasmic fraction (FIG. 24 Lane 3) and a minimal amount was in the insoluble cell lysate (FIG. 24*b* Lane 5) by Western Blot and that the significantly larger 36 kDa band observed in the coomassie stained gel of the insoluble cell lysate was not D60A (FIG. 24a Lane 5). Analysis of the loading flow through sample indicates that the his-tagged D60A protein was specifically being retained on the IMAC column as no D60A protein was detected in the Western Blot (FIG. 24 Lane 6). A significant amount of non-specific proteins were visible in the SDS-PAGE gel (FIG. 24 Lane 6) of the same loading flow through sample. The 50 mM imidazole wash step removed the majority of non-specific proteins with minimal loss of D60A protein as seen in FIG. 24 Lane 8. Thus, the IMAC eluted D60A pooled sample shows minimal contamination with non-specific proteins in FIG. 24 Lane 9, even when the gel and duplicate blot were overloaded with 24 µg of total protein. SEC purification of D60A improves the purity even further as neither non-specific protein elution peaks (FIG. 25) nor protein bands were detected by SDS-PAGE and Western Blot analysis (FIG. 26) of the individual eluted fractions. Wild-type PNGase F and D60A clones were both successfully expressed and purified with a yield of ~3.0 mg high purity protein from a 1 L expression culture each. The identities of purified PNGase F and D60A were confirmed by MALDI. Additionally, sequence identity of D60A was also confirmed by LC-MS/MS.

Figure 27:
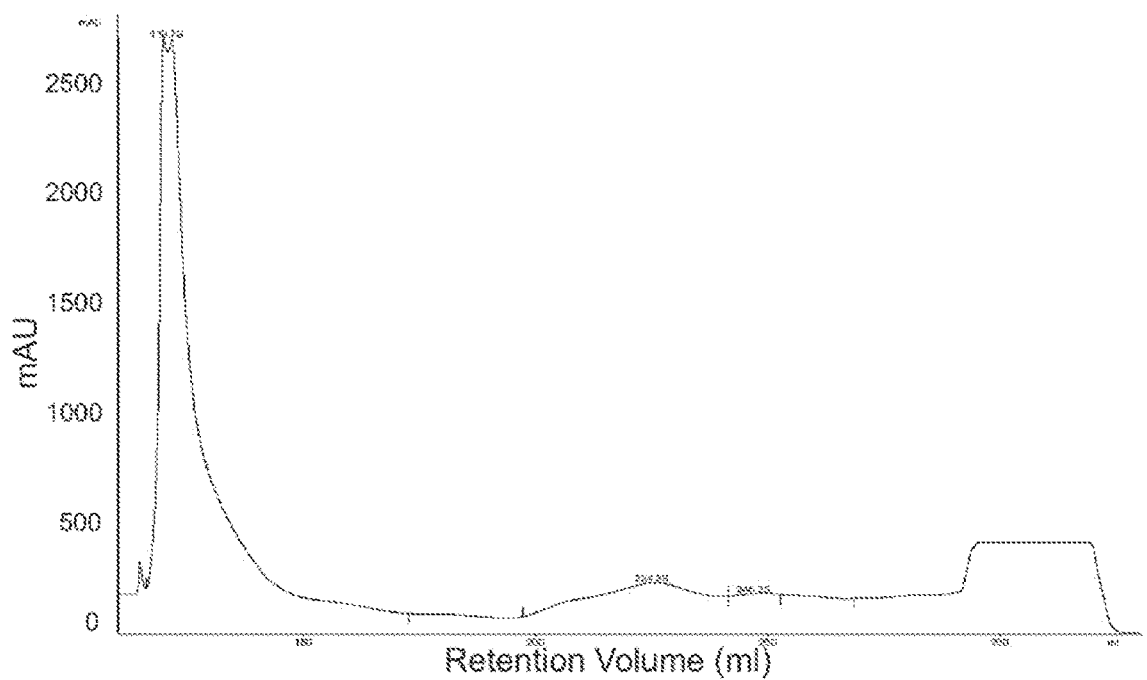
FIG. 27 shows a R911 IMAC elution chromatogram. Gradient elution profile of R911. The first sharp peak is a 50 mM imidazole wash (8.3% B). The shallow broad peaks correspond with elution of R911 and between 14.5% B-31% B.
Figure 28:
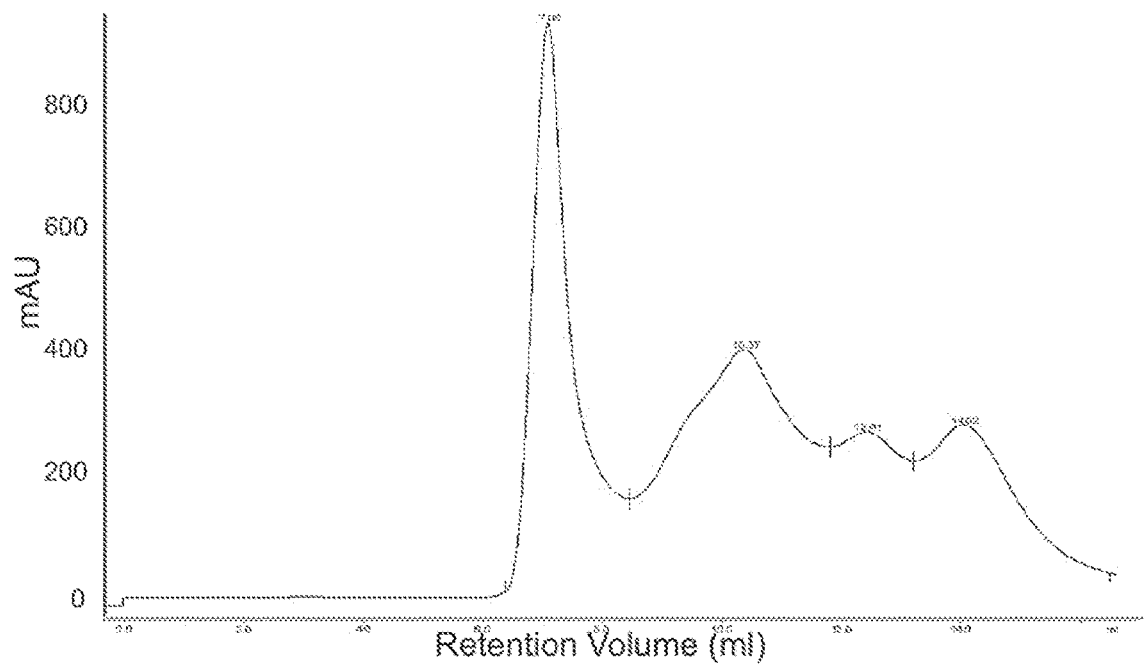
FIG. 28 shows a R911 SEC chromatogram on a Superose 12 10/300 GL column. IMAC elution fractions were run through SEC. The fourth peak with a peak maximum at 14.02 mL retention volume is consistent with D60A elution on this same column.
Figure 29:
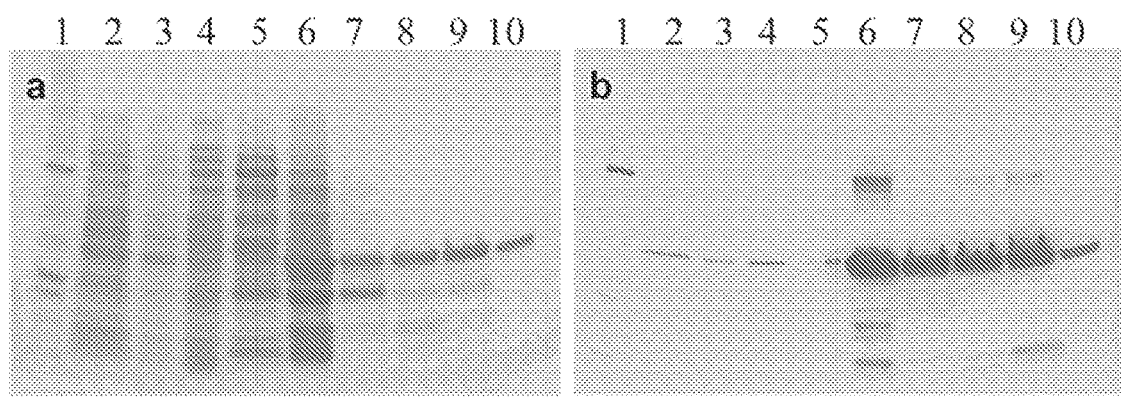
FIG. 29 shows SDS-PAGE and Western Blot of IMAC and SEC purified R911. a) Coomassie stained denaturing SDS-PAGE of R911 IMAC and SEC elution fractions. b) Western Blot of duplicate gel of R911 IMAC and SEC elution fractions. 1:5000 dilution of mouse anti-His6 HRP antibody used and developed with DAB substrate. A 36 kDa band corresponding with expressed R911 is visible across lanes 2-9. Lane 1=Protein markers: 250 kDa, 150 kDa, 100 kDa, 75 kDa, 50 kDa, 37 kDa, 25 kDa, 20 kDa, 15 kDa, 10 kDa. Lane 2=culture. Lane 3=insoluble cell lysate. Lane 4=soluble periplasmic fraction. Lane 5=50 mM imidazole wash. Lane 6=pooled IMAC elution fractions #42-63. Lane 7=SEC fraction #15 corresponding to second SEC elution peak in FIG. 28 with 10.37 mL retention volume. Lane 8=SEC fraction #23 corresponding to third SEC elution peak in FIG. 28 with 12.41 mL retention volume. Lane 9=SEC pooled fractions #29-37 corresponding to fourth SEC elution peak in FIG. 28 with 14.02 mL retention volume. Lane 10=Positive control D60A (1 µg).

The IMAC and SEC chromatogram elution profiles of R911 differed significantly from those of wtPNGase F and D60A as shown in FIGS. 27 and 28. However, denaturing SDS-PAGE and Western Blot analysis of R911 expression and purification samples indicate similar results as that of PNGase F and D60A, suggesting that the difference in elution profiles of the R911 may be due to changes in structure of the native R911 relative to native PNGase F and D60A which cannot be distinguished by comparing denaturing gels. A significant difference in the IMAC elution profile of R911 was the elution of broad peak between 14.5% B and 31% B gradient (FIG. 27) compared to the relatively sharp D60A IMAC elution peak at 20.5% B (FIG. 23). Similarly, the R911 SEC elution profile shows four distinct elution peaks (FIG. 28) of which the three latter elution peaks correspond to relatively pure R911 elution samples by denaturing SDS-PAGE and Western Blot analysis (FIG. 29 Lanes 7, 8, and 9). Given these data, and that size exclusion chromatography separates proteins based on size and shape, it was likely that R911 structural isomers (likely a mixture of folded and misfolded R911) were present which cannot be distinguished by denaturing gel analysis. Furthermore, of these three R911 elution peaks, only the third elution peak, with a peak maximum at 14.02 mL retention volume, was consistent with D60A elution (peak maximum also at ~14 mL) on the same Superose 12 10/300 GL column. This indicates that the third R911 elution peak at 14.02 mL retention volume was the correctly folded R911 isomer. The total R911 protein yield from a 2 L LB culture is ~2.0 mg, corresponding to ~1.31 mg (65%) from SEC elution peak 1, ~0.3 mg (15%) from SEC elution peak 2, and ~0.4 mg (20%) from SEC elution peak 3. With only 20% of the total R911 correctly folded, the effective yield was only ~0.4 mg. Circular dichroism or NMR experiments could help to identify the general structural difference between these hypothesized three folded and misfolded R911 isomers.

Several attempts were made to express and purify R617, R113, and R9113 clones; however, the IMAC elution profile always had a similarly board but even shallower elution profile relative to R911 with insufficient quantity of protein for detection by Western Blot. Wild-type PNGase F has three disulfide bonds required for proper folding, and since all four yeast-display selected clones introduced a cysteine residue at one of the site for mutagenesis (Table 6), it would not be surprising if the addition of an extra cysteine was contributing to the suspected misfolded R911 and the inability to purify his-tagged R617, R6113, and R9113 for study. Thus point mutants R617 C57D, R6113 C192G, R911 C60A, and R9113 C60A were constructed where R617 and R6113 cysteine residues were reverted back to wild-type and R911 and R9113 cysteine residues were mutated to alanine instead of wild-type aspartate given that D60 is required for catalytic activity. Table 8 lists the physical and chemical properties of PNGase F clones of interest.

TABLE 8

Physical and chemical properties of PNGase F clones. ExPASy ProtParam calculated properties based on amino acid sequence are reported.[3] Molecular weight, isoelectric point, and extinction coefficients (ε) values are listed.

| PNGase F Clones (326 Amino Acids) | Molecular Weight | Isoelectric Point | $\varepsilon$ ($M^{-1}$ $cm^{-1}$) | $\varepsilon$ ($L$ $g^{-1}$ $cm^{-1}$) | $\varepsilon$ $^{1\%}$ |
|---|---|---|---|---|---|
| wtPNGase F | 36251.6 | 7.75 | 73715 | 2.0334 | 20.334 |
| D60A | 36207.6 | 8.14 | 73715 | 2.0359 | 20.359 |
| R617 | 36104.5 | 8.70 | 72225 | 2.0004 | 20.004 |
| R617 C192G | 36058.4 | 8.74 | 72225 | 2.0030 | 20.030 |
| R6113 | 36260.7 | 8.82 | 77725 | 2.1435 | 21.435 |
| R6113 C57D | 36272.7 | 8.74 | 77725 | 2.1428 | 21.428 |
| R911 | 36281.8 | 8.36 | 79215 | 2.1833 | 21.833 |
| R911 C60A | 36249.7 | 8.40 | 79215 | 2.1853 | 21.853 |
| R9113 | 36372.9 | 8.36 | 84715 | 2.3291 | 23.291 |
| R9113 C60A | 36340.8 | 8.40 | 84715 | 2.3311 | 23.311 |

The successful expression of cysteine point mutants was confirmed by Western Blot analysis of IMAC purified R617 C57D, R6113 C192G, R911 C60A, and R9113 C60A (data not shown). However, only sufficient amount of R911 C60A could be produced for experimental requirements, thus only R911 and R911 C60A were investigated further. The cysteine point mutants confirmed that the presence of an extra cysteine is contributing only in part to the altered elution profiles and the proposed structural isomers of R911. Interestingly, the elution profile of R911 C60A (data not shown) was consistent with that of R911 (FIGS. 27, 28, 29), indicating that other five mutated residues must also contribute to the altered IMAC and SEC elution profile of R911.

Activity and Kinetic Studies

In order to convert the wtPNGase F enzyme into a high affinity Lectenz® reagent, catalytic activity needed to be abolished while simultaneously enhancing affinity. The PNGase F D60A single point mutant was of particular interest for three reasons: 1) residue D60 is required for catalytic activity based on D60N point mutant studies that demonstrated this mutation made the enzyme catalytically inactive[4], 2) computational alanine scanning data (Table 5) predicted favorable interaction energy for substrate affinity, and 3) given that the D60A single point mutant was not affinity enhanced via directed evolution, it was appropriate to use D60A as a catalytically inactive, non-affinity enhanced control for comparison to the affinity enhanced R911 clone.

TABLE 9

Bovine pancreatic RNase properties. RNase A and RNase B was obtained from Sigma. The reported purities of RNase A and RNase B are 90% and 80% respectively as determine by SDS-PAGE. RNase B is the glycosylated variant of RNase A. The glycosylation site at N34 is reported to have nine glycoforms, thus the reported mass is an average derived from the relative abundance of each of the glycosylated species[a].[5] Molecular weight, isoelectric point, and extinction coefficients ($\epsilon$) values are listed.

| RNase (124 Amino Acids) | Molecular Weight (Da) | Isoelectric Point | $\epsilon$ ($M^{-1}$ $cm^{-1}$) | $\epsilon$ (L $g^{-1}$ $cm^{-1}$) | $\epsilon$ $^{1\%}$ |
|---|---|---|---|---|---|
| RNase A | 13,700 | 9.6 | 8,640 | 0.71 | 7.1 |
| RNase B | 15,095[a] | — | 8,213 | 0.80 | 8.0 |

The enzymatic activity of clones D60A and R911 were both investigated. Properties of the glycosylated substrate, RNase B, and the non-glycosylated version, RNase A, are presented in Table 9. A gel shift assay was used to determine N-deglycosylation catalytic activity of the clones on denatured RNase B relative to the wtPNGase F enzyme (Table 10). The D60A single point mutant has significantly decreased catalytic activity (~13% relative to wtPNGase F) while the R911 clone displayed no detectable catalytic activity in samples from overnight reactions. The deglycosylation of RNase B was further confirmed by matrix-assisted laser desorption/ionization (MALDI) mass spectrometry (MS) using an AB SCIEX 5800 TOF-TOF. The deglycosylated RNase B product's mass was confirmed to be consistent with RNase A, with the difference being that N34 becomes D34 due to deamination by PNGase F during the N-glycan cleavage reaction.[6]

TABLE 10

Deglycosylation activity of PNGase F clones. A gel shift assay was used to determine deglycosylation activity of PNGase F clones relative to wtPNGase F. 50 ng of wtPNGase F, D60A, and R911 each was incubated with 50 µg of denatured RNase B in 50 mM EPPS, pH 8.0 in a 50 µL reaction volume at 37° C. overnight. Samples were analysed on a SDS-PAGE gel and altered migration of deglycosylated RNase B product relative to RNase B was observed. The scanned gel image was analyzed by ImageJ software to quantitate deglycosylated product relative to RNase B substrate.[7] Deglycosylated product confirmed by MALDI TOF-TOF mass spectrometry.

|  | wtPNGase F | D60A | R911 |
|---|---|---|---|
| Deglycosylation Activity on RNase B | 100% | 13.4% | Not detected |

Biomolecular interaction kinetic experiments were conducted on a Biacore 3000 instrument via surface plasmon resonance (SPR). SPR is a phenomenon that occurs when plane-polarized incident light stimulates oscillations of electrons, or the propagation of electromagnetic waves (plasmons), parallel to a metal (conductive)/dielectric interface. Plasmon waves propagate at the interface of the metal and liquid (or air) mediums extending out about 300 nm, and changes at the interface due to the adsorption of molecules to the surface results in changes in wave propagation causing a shift in the angle of the reflected incident light under conditions of total internal reflection. Total internal reflection is achieved by placing a glass prism placed directly against a gold surface, where plasmons are excited. Due to the high sensitivity of SPR to shifts in mass, it has been adapted for biomolecular interaction measurement.[8] By using a carboxy-modified dextran gold surface, a target ligand of interest can be covalently immobilized onto a dextran-derivatized gold surface using amine coupling.

The evaluation of lectin-carbohydrate interactions by SPR is a well-established technique for kinetic analysis.[9, 10] CM-5 carboxy methyl dextran sensor chips are utilized for amine-coupling of ligands of interest. However, this approach results in a randomized orientation of the ligand and may not be suitable where ligand orientation is particularly critical for interaction with an analyte of interest or the effect of ligand orientation is of specific interest. Ligand orientation can be achieved by using a Ni-NTA derivatized dextran surface to capture histidine-tagged proteins.[11] This approach has a significant drawback that the capture molecule will leech off the surface since they are not covalently linked. Recently, covalent immobilization of histidine-tagged proteins to overcome leeching has been demonstrated.[12] Using microfluids, an analyte of interest is flowed through a flow cell containing the immobilized ligand where interactions between the biomolecules (immobilized ligand and analyte) can occur. Simultaneously, on the opposite side of the sensor surface the degree of change in the angle of the reflected light is proportional to the change in mass.

Figure 30:
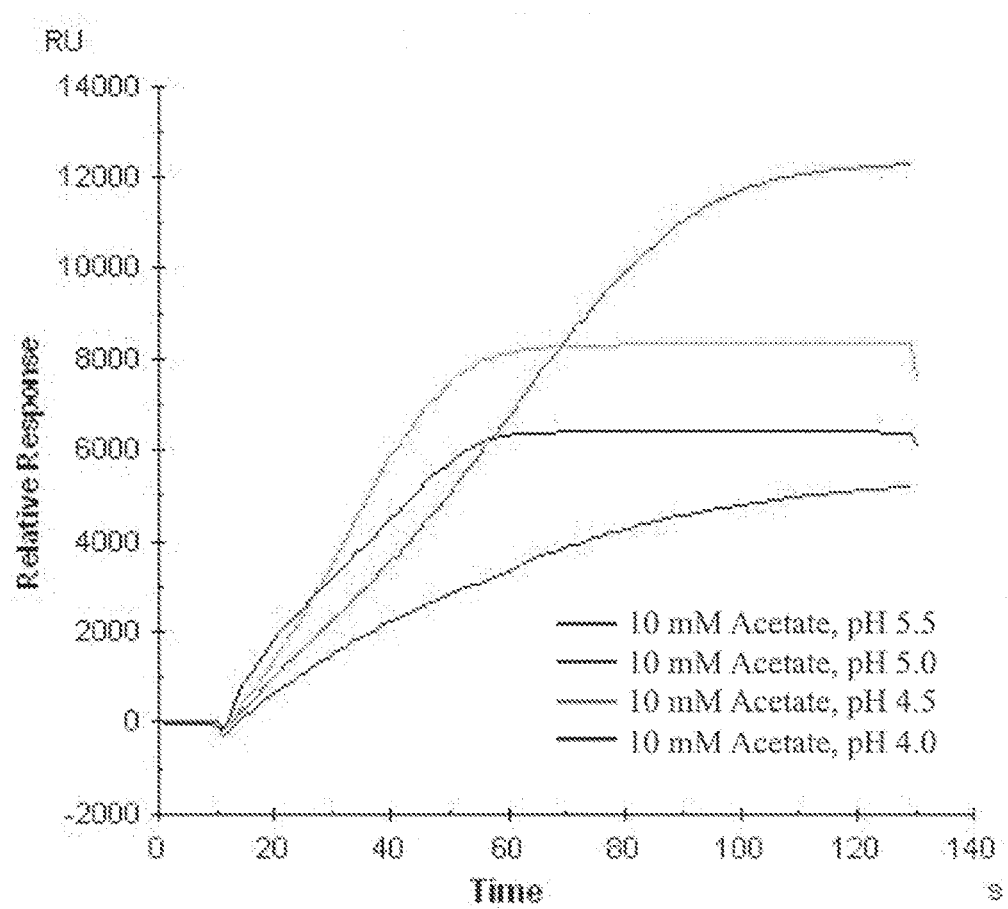
FIG. 30 shows RNase B pH scouting. A 10 mM acetate pH 5.5 coupling buffer yielded the most efficient coupling of RNase ligands to the carboxy methyl dextran CM-5 sensor surface chip.

Denatured RNase B and denatured RNase A, which has the same peptide sequence as RNase B but lacks N-glycosylation, were covalently coupled to CM-5 chips using amine-coupling chemistry. Prior to immobilizing the RNase ligands to the carboxy methyl dextran surface on the CM-5 sensor chip a pH scouting experiment indicated an optimal pH of 5.5 for efficient coupling (FIG. 30). A high-density surface was prepared with sufficient ligand coupling to yield a theoretical $R_{MAX}$ of ~3000 RU. To assess the impact of the D60C mutation in R911 relative to wtPNGase F, the R911 C60A mutant was also evaluated. Steady-state binding kinetics using a bimolecular interaction model was determined using a Biacore 3000 instrument.

Figure 31:
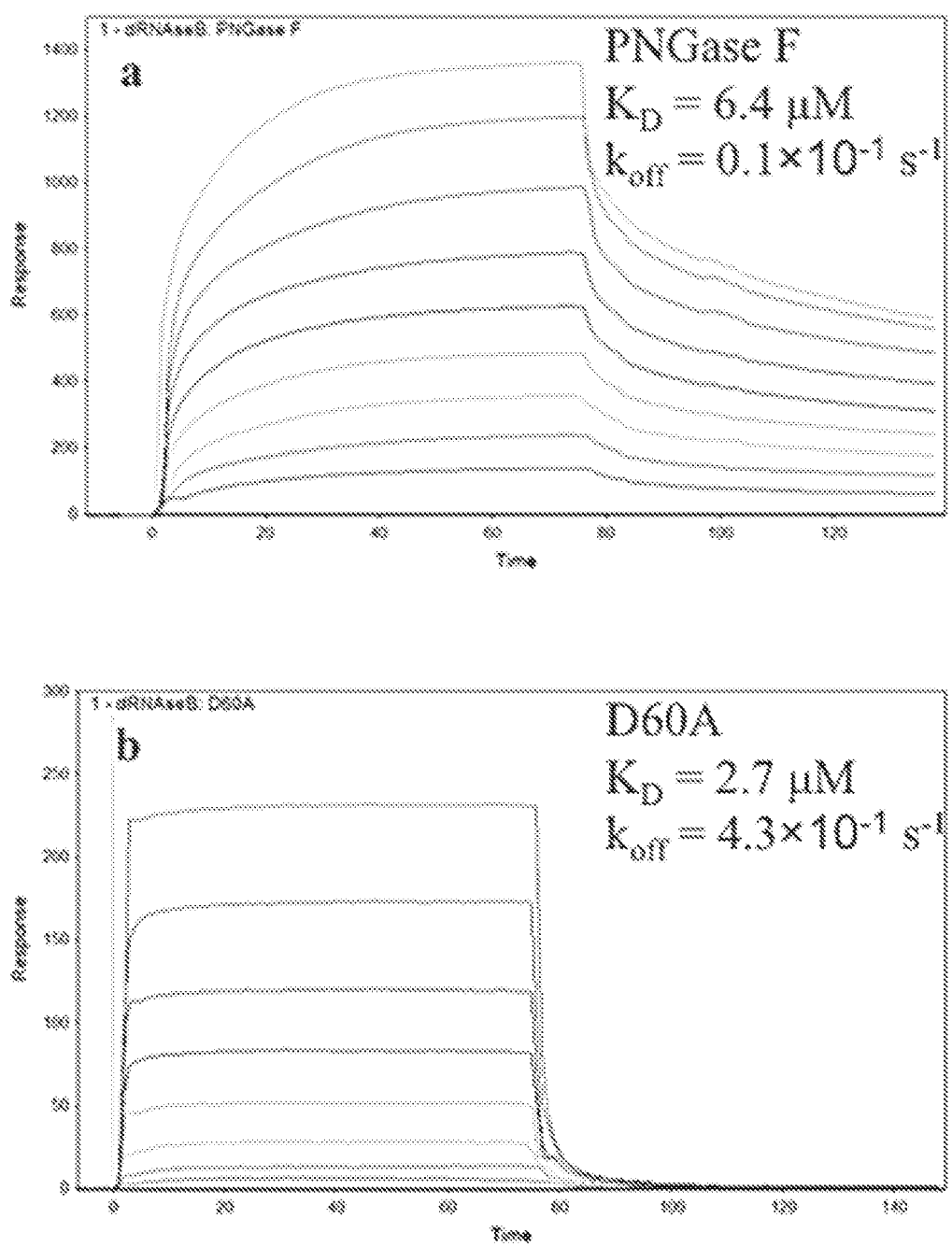
FIG. 31 shows SPR sensograms of wtPNGase F, D60A, R911, and R911 C60A. A high-density surface was prepared by immobilizing denatured RNase B to yield a maximum response ($R_{MAX}$) of ~3200 RU. a) wtPNGase F: 250 nM-64 µM serial dilutions, b) D60A: serial dilutions 72 nM-20 µM, c) R911: 78 nM-5 µM serial dilutions, and d) R911 C60A: 78 nM-10 µM serial dilutions. The data obtained were analyzed by Scrubber 2.0c.

The use of SPR to measure binding kinetics between RNase B and yeast PNGase enzyme and a mutant enzyme has been demonstrated.[13] Using a similar strategy, denatured RNase B was immobilized on a CM-5 sensor chip and serially-diluted concentrations of wtPNGase F, D60A, R911, and R911 C60A were passed over the sensor surface, while binding kinetics were measured. A summary of the kinetic results is presented in Table 11 and sensograms are shown in FIG. 31. The wtPNGase F has a $K_D$ of 6.4 µM and an off-rate ($k_{off}$) of $0.1 \times 10^{-1}$ $s^{-1}$. Relative to the D60A control clone ($K_D$=2.7 µM), the selected R911 clone has 10× enhanced affinity ($K_D$=0.26 µM). Furthermore, the selected R911 clone has an 84× decreased off-rate ($k_{off}$=$5.1 \times 10^{-3}$ $s^{-1}$) relative to the D60A control clone ($k_{off}$=$4.3 \times 10^{-1}$ $s^{-1}$). The R911 C60A variant clone exhibited only 1.3× enhanced affinity ($K_D$=2.0 µM) and 35× decreased off-rate ($k_{off}$=$1.2 \times 10^{-2}$ $s^{-1}$) relative to the D60A control clone. Denatured Ribonuclease A (dRNase A) was also utilized as a negative control ligand as it is a non-glycosylated version of RNase B; however, unsurprisingly specific kinetic measurements could not be measured given that RNase A lacks the N-glycan moiety recognized by PNGase F. Specifically, a high-density surface with immobilized dRNase A was prepared to yield a theoretical maximum response ($R_{MAX}$) of ~1800 RU; however, measured responses with wtPNGase F, D60A, R911, and R911 C60A exceeded $R_{MAX}$, indicating that interactions were non-specific.

TABLE 11

Surface plasmon resonance kinetic data for PNGase F clones.
Dissociation ($K_D$) and off-rate constants ($k_{off}$) for the interaction between
denatured glycoprotein RNase B (dRNase B) with PNGase F mutagenized
clones as determined by surface plasmon resonance. Kinetic data s as
determined with dRNase B as immobilized ligand on CM5 sensor chip
and PNGase F clone analytes. Experimental ΔG binding interaction
energy ($\Delta G_{BIND\text{-}EXP}$) was calculated from the $K_D$.

| PNGase F Clones | $\Delta G_{BIND\text{-}EXP}$ (kcal/mol) | $K_D$ (M) | Relative Affinity Enhancement | $k_{off}$ (s$^{-1}$) | Relative Off-Rate Enhancement |
|---|---|---|---|---|---|
| wtPNGase F | −7.103 | 6.4 × 10$^{-6}$ | — | 0.1 × 10$^{-1}$ | — |
| D60A | −7.609 | 2.7 × 10$^{-6}$ | 1x | 4.3 × 10$^{-1}$ | 1x |
| R911 | −8.990 | 2.6 × 10$^{-7}$ | 10x | 5.1 × 10$^{-3}$ | 84x |
| R911 C60A | −7.768 | 2.0 × 10$^{-6}$ | 1.3x | 1.2 × 10$^{-2}$ | 35x |

The activity assay and kinetic data indicate that the selected R911 clone is catalytically inactive and has significantly enhanced affinity relative to the non-affinity enhanced PNGase F D60A control clone. In addition, the enhanced off-rate of R911 is significant because a slow off-rate is a key criteria for a useful affinity reagent to enrich target glycans, unlike enzymes, which generally have rapid turn-over to release product. The kinetic analysis of R911 C60A clone provides additional insight into the importance of the cysteine residue at position 60. Both the affinity and the off-rate are negatively impacted by the C60A mutation. This indicates two critical pieces of information: I) the D60C mutation in R911 is critical for high affinity and 2) that improved affinity also directly impacts the slower off-rate of R911. Based on these results, R911 satisfies the kinetic criteria for a Lectenz® candidate. A computational modeling-based analysis of the energetic contributions of R911 mutations relative to wtPNGase F is discussed in Example 4.

Lectenz® Affinity Chromatography

Lectin affinity chromatography is the most widely applied technique for the isolation and enrichment of glycans and glycoconjugates.[14] Despite the inherent limitations of current carbohydrate-detection reagents like antibodies and lectins, numerous affinity-based glycan and glycoconjugate enrichment formats have been developed signifying the critical need for this application. Common enrichment techniques include lectins conjugated to agarose/sepharose packed in centrifugal devices, spin or low-pressure LC columns, and HPLC-compatible matrices that enable high-pressure/high flow rate lectin chromatography, and lectin-modified gold nanoparticles embedded in pipette-tips.[14, 15] Recently, serial lectin affinity chromatography has been employed to enrich glycoproteins of interest from complex samples like sera and cancer cell lysates.[16, 17] However, the choice of reagent used for sample enrichment or isolation can therefore bias the outcome of glycomic analyses toward a subset of glycoconjugates based on the binding properties of the lectin or antibody.[18]

The application of the R911 Lectenz® candidate for enrichment of glycoconjugates in an affinity chromatography format was investigated. Using HiTrap N-hydroxysuccinamide (NHS)-activated HP columns, purified PNGase F D60A and R911 clones were covalently linked to the column matrix to evaluate affinity chromatography based enrichment of N-glycopeptides and N-glycoproteins. The coupling efficiencies of the clones to the NHS-activated columns consistently ranged between 80%-87% for all NHS-activated column-coupling reactions. The binding buffer consisted of 10 mM HEPES, 10 mM NaCl, pH 7.4 whereas the elution buffer consisted of 10 mM HEPES, 150 mM NaCl, pH 7.4, and a constant flow rate of 0.4 mL/min throughout all chromatography runs.

Enrichment of RNase B Versus RNase A

Figure 32:
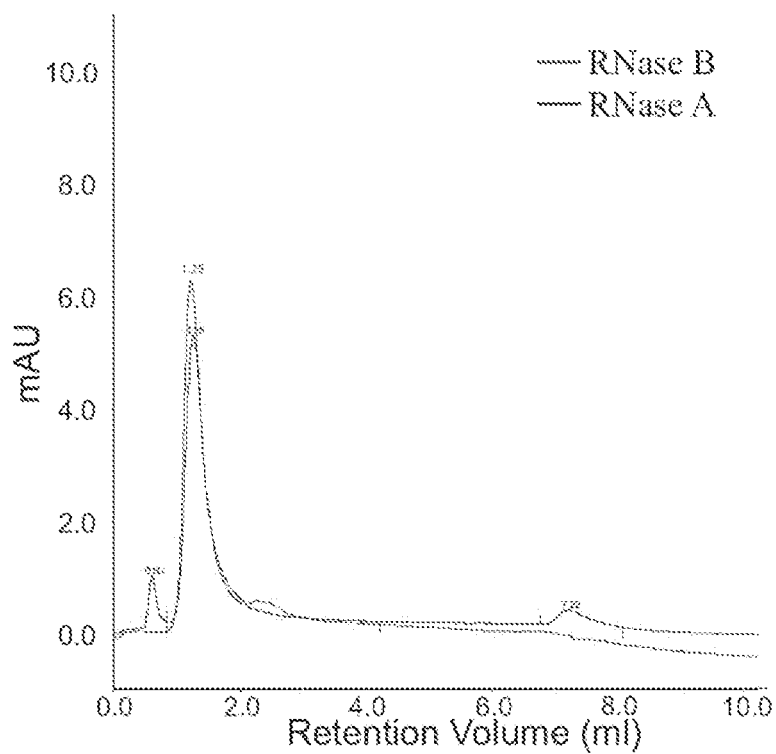
FIG. 32 shows D60A affinity chromatography with RNase A and RNase B.

The control D60A affinity chromatography results indicate no enrichment of N-glycosylated RNase B relative to RNase A (FIG. 32). The flow through peaks at 1.25 mL retention volume indicate that both RNase B and RNase A flowed through the column during initial loading (0-5 mL retention volume) and were not retained due to interactions with D60A. No elution peak was observed for RNase B when running elution buffer (5-10 mL retention volume). A small elution peak is visible for RNase A at 7.22 mL retention volume. This may be attributed to impurities in the RNase A sample as it is 90% pure and likely contains some RNase B as a contaminant. In addition, wtPNGase F is known to recognize both the chitobiose core as well as the peptide glycosylation sequone (Asn-X(-Pro)-Ser/Thr) on the peptide backbone, thus, it is possible that the Asn-Leu-Thr glycosylation sequone on RNAse A is being weakly recognized by the D60A single point mutant. Nonetheless, the relative quantity of the small elution peak observed from the RNase A is minimal.

Figure 33:
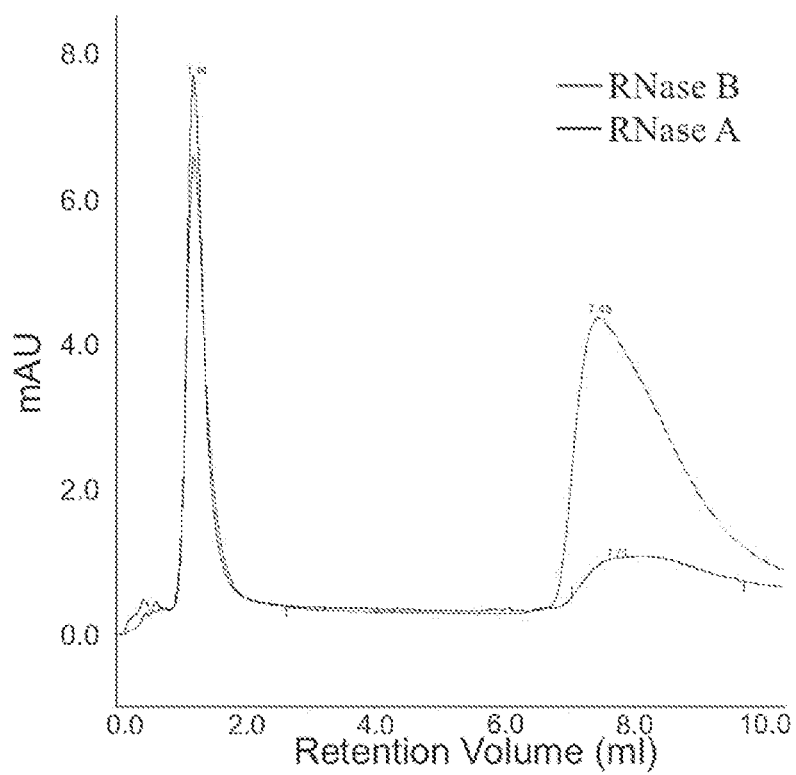
FIG. 33 shows R911 Lectenz® affinity chromatography of RNase A vs RNase B.
Figure 34:
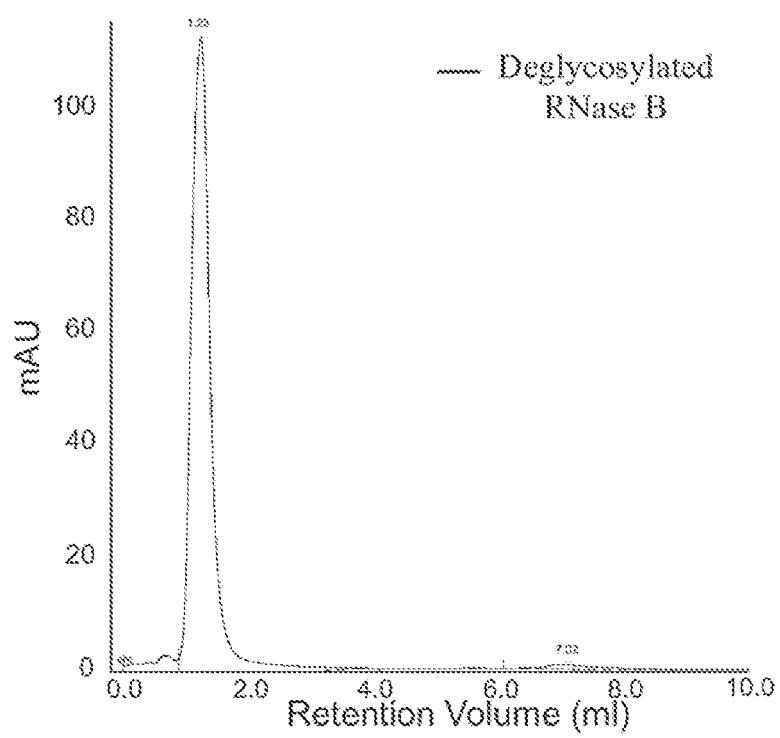
FIG. 34 shows R911 Lectenz® affinity chromatography of deglycosylated RNase B.

Unlike D60A, R911 affinity chromatography loading and elution profiles indicate enrichment of N-glycosylated RNase B compared to RNase A (FIG. 33). To confirm specific R911:RNase B glycan interactions, RNase B was deglycosylated with PNGase F. The deglycosylated RNase B was run through the R911 affinity column (FIG. 34). The chromatogram shows that degyclosylated RNase B was not retained by R911 and flowed through the column. Taken together, these results confirm specific interaction between R911 and RNase B glycans.

Affinity Chromatography of RNase A and RNase B Tryptic Digests

Figure 35:
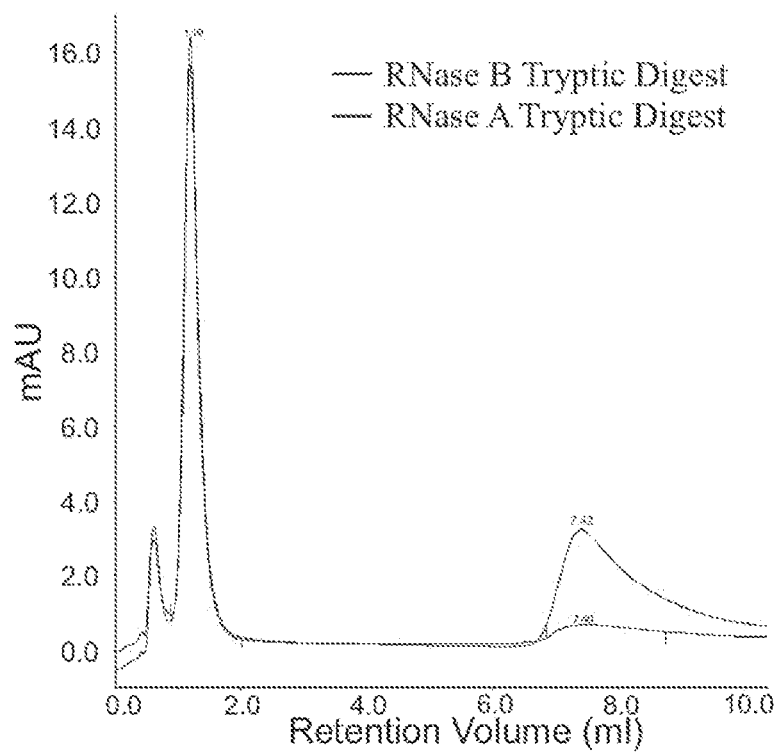
FIG. 35 shows R911 Lectenz® affinity chromatography of tryptic digests of RNase A and RNase B.

To investigate the separation of peptides from N-glycopeptides using R911, RNase A and RNase B were digested with trypsin. The tryptic digests were loaded on to the R911 column. RNase A tryptic digest peptides flowed through the column, where as part of the RNase B tryptic digest sample was retained on the column and eluted with elution buffer (FIG. 35). The flow through and elution samples were analysed by LC-MS/MS which confirmed that some N-glycopeptides were enriched.

Competitive Elution of RNase B with Free Chitobiose

Figure 36:
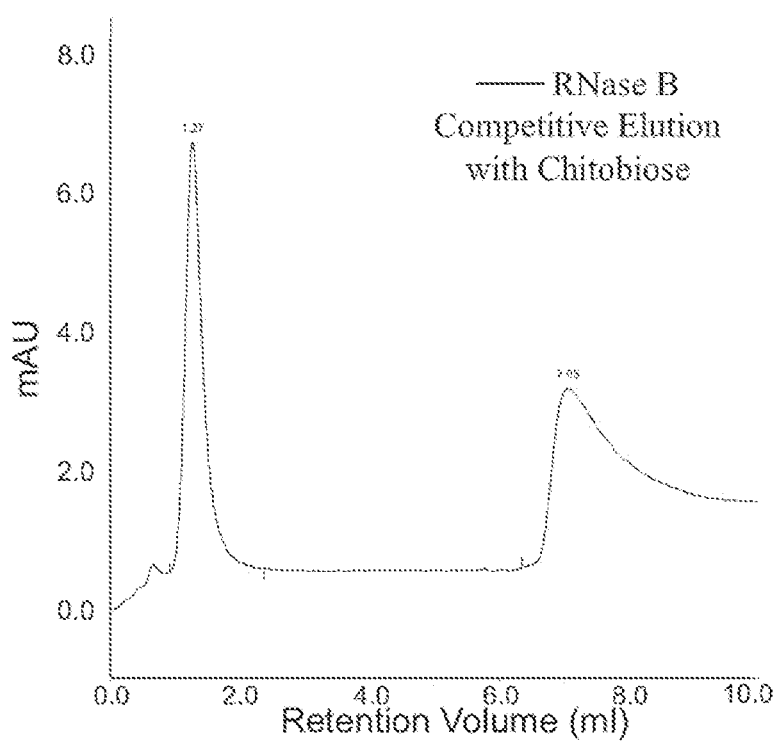
FIG. 36 shows R911 Lectenz® affinity chromatography of RNase B using free chitobiose for competitive elution.

Competitive elution with chitobiose of R911 bound RNase B was performed to further confirm specific interaction of R911 with the chitobiose core of N-glycan structure. RNAse B was first loaded onto the R911 affinity matrix and then competitively eluted with free chitobiose in the binding buffer, instead of the standard elution buffer (FIG. 36). LC-MS/MS analysis of the eluted sample confirmed that RNase B was competitively eluted with chitobiose.

Figure 37:
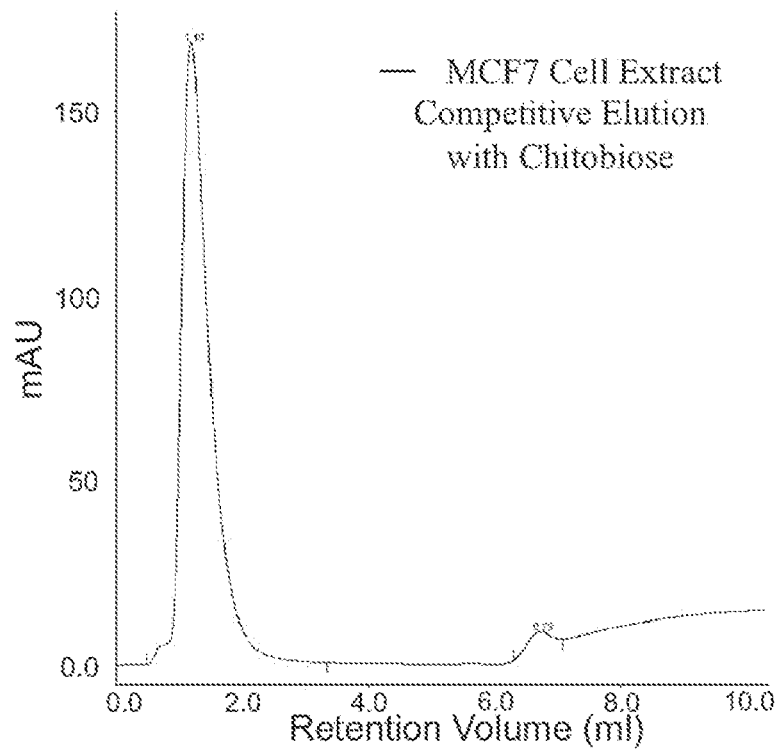
FIG. 37 shows R911 Lectenz® affinity chromatography of MCF7 cell extract using free chitobiose for competitive elution.

Enrichment of N-Glycoproteins from MCF7 Whole Cell Extract Using Competitive Elution with Chitobiose The application of the R911 as an N-glycoprotein affinity enrichment reagent was demonstrated using MCF7 whole cell extract. Cell extract (100 μg) was loaded onto a R911 affinity column and then competitively eluted with free chitobiose in the binding buffer, instead of the standard elution buffer (FIG. 37). A majority of cell extract proteins flowed through the column corresponding with the observed peak at 1.19 mL retention volume and approximately 6.6 μg of protein was retained on the column and competitively eluted with free chitobiose corresponding with the peak at 6.63 mL retention volume.

The stock MCF7 cell extract sample and the competitively eluted sample were analyzed by LC-MS/MS and proteins were identified with UniProt and UniPep databases.[19, 20] R911 Lectenz® Affinity Chromatography (LAC) results were compared with a reported Multi-Lectin Affinity Chromatography (MLAC) experiment also conducted with MCF7 cell extract using Jac, ConA and WGA lectins and are summarized in Table 12.[17] MLAC with MCF7 cell extract resulted in the elution of 88 proteins of which 84% are glycoproteins. R911 Lectenz® affinity chromatography resulted in the elution of 73 proteins of which 71.2% are glycoproteins. The glycoproteins eluted by R911 LAC are predominantly different than the glycoproteins eluted by MLAC. Furthermore, 1 glycoproteins identified by MLAC were present in the MCF7 cell extract, but not enriched by R911 LAC. These differences are not surprising given the different specificities of the capture reagents employed for enrichment.

A summary of glycoprotein enrichment by R911 LAC is provided in Table 13. Relative to the MCF7 cell extract stock sample, the R911 LAC eluted glycoprotein sample represents a 3.4× glycoprotein enrichment. Furthermore, the eluted glycoproteins consist of 42.5% (31)N-glycoproteins and 28.8% (21)O-glycoproteins, representing a 2.0× fold N-glycoprotein enrichment and 5.2× O-glycoprotein enrichment.

The enrichment of O-glycoproteins by R911 LAC was unexpected given that R911 is derived from the N-glycan processing enzyme PNGase F and substrate specificity of the enzyme for the N-glycopeptide and chitobiose core is well established.[4, 21-24] Insight into the enrichment of O-glycoproteins is provided from the observation that 76% (16) of the eluted O-glycoproteins are O-GlcNAcylated, indicating that the common structural motif being recognized of R9 11 is likely the reducing GlcNAc of both N-glycoproteins and O-GlcNAcylated glycoproteins.[25, 26] Thus, enrichment of both N-glycoproteins and O-GlcNAcylated glycoproteins can be achieved by the R911 Lectenz® making it a unique capture reagent which can recognize a common core motif in both N-glycoproteins and O-GlcNAcylated glycoproteins. The enriched N-glycoproteins and O-glycoproteins are listed in Tables 14 and 15 respectively.

TABLE 12

Comparison of MLAC and R911 Lectenz ® affinity chromatography with MCF7 cell extract.

| Chromatography | Multi-Lectin Affinity Chromatography[17] | Lectenz ® Affinity Chromatography |
|---|---|---|
| Capture reagent(s) | Jac, Con A, WGA Lectins | R911 Lectenz ® |
| Capture reagent (mg) | 3.4 mg total lectin | 0.22 mg R911 Lectenz ® |
| MCF7 cell extract (mg) | 0.7 mg | 0.1 mg |
| Capture conditions | O/N incubation at 4° C. | 0.4 mL/min flow-rate at 4° C. |
| Eluted glycoproteins | 86.5% | 71.2% |
| Differences | 11 glycoproteins detected in common that were eluted by MLAC, but not by Lectenz ® | Majority of eluted glycoproteins are different than MLAC |

TABLE 13

R911 Lectenz ® affinity chromatography enrichment of MCF7 cell extract glycoproteins.

| | Stock MCF7 Cell Extract Sample | R911 Lectenz ® Eluted MCF7 Sample | Enrichment |
|---|---|---|---|
| Total glycoprotein % | 26.9% | 71.2% | 3.4x |
| N-glycoprotein % | 21.2% | 42.5% | 2.0x |
| O-glycoprotein % | 5.5% | 28.8% (76% are O-GlcNAcylated) | 5.2x |

TABLE 14

Eluted MCF7 N-glycoproteins identified by LC-MS/MS.

| Accession | Gene Symbol | Cellular Location | N-Glycoprotein | Mass (kDa) |
|---|---|---|---|---|
| 8WZ42-2 | TITIN | Golgi, cytoplasm, nucleus | Isoform 2 of Titin | 3803.48 |
| P21333-2 | FLNA | trans-Golgi, cytoplasm, cytoskeleton | Isoform 2 of Filamin-A | 279.83 |
| P19835-2 | CEL | Secreted | Isoform Short of Bile salt-activated lipas | 71.77 |
| P02768 | ALBU | Secreted | Serum Albumin Precursor | 69.30 |
| P29401 | TKT | extracellular vesicular exosome, nucleus, peroxisome, cytosol | Transketolase | 67.82 |
| P04264 | KRT1 | extracellular space | Keratin, type II cytoskeletal 1 | 65.98 |
| P35908 | KRT2A | Golgi, extracellular space | Keratin, type II cytoskeletal 2 epiderma | 65.38 |
| P33527 | Z29074 | extracellular space | Keratin 9, cytoskeletal, (Cytokeratin 9) | 62.07 |
| P48669 | K2CF | extracellular vesicular exosome | Keratin, Type II Cytoskeletal 6F (Cytokeratin 6F) (CK 6F) (K6F Keratin) | 60.01 |
| P13645 | KICJ | extracellular vesicular exosome, cytoplasm | Keratin, Type I Cytoskeletel 10 (Cytokeratin 10) (K10) (CK 10) | 59.46 |

TABLE 14-continued

Eluted MCF7 N-glycoproteins identified by LC-MS/MS.

| Accession | Gene Symbol | Cellular Location | N-Glycoprotein | Mass (kDa) |
|---|---|---|---|---|
| P04745 | AMY1A | Secreted | Alpha-amylase 1 | 57.71 |
| P19013 | K2C4 | cytoskeleton | Keratin, Type II Cytoskeletal 4 (Cytokeratin 4) (K4) (CK4) | 57.21 |
| P01008 | SERPINC1 | Secreted, extracellular space | Antithrombin-III | 52.55 |
| P08729 | K2C7 | Golgi apparatus, cytoplasm, cytoskeleton | Keratin, Type II Cytoskeletal 7 (Cytokeratin 7) (K7) (CK 7) | 51.29 |
| P16233 | PNLIP | Secreted | Pancreatic triacylglycerol lipase | 51.11 |
| P15086 | CBPB1 | Secreted | Carboxypeptidase B | 47.32 |
| P15085 | CBPA1 | Secreted | Carboxypeptidase A1 | 47.09 |
| O60664 | PLIN3 | Golgi, endosome membrane | Perilipin-3 | 47.03 |
| P48052 | CBPA2 | Secreted | Carboxypeptidase A2 | 46.98 |
| P28799-2 | GRN | Secreted | Isoform 2 of Granulins | 46.94 |
| Q9H8S1 | Q9H8S1 | Secreted | cDNA FLJ13286 fis, clone OVARC1001154, highly similar to homo sapiens clone 24720 Epithelin 1 and 2 mRNA | 44.08 |
| P55259-2 | GP2 | Secreted | Isoform Beta of Pancreatic secretory granule membrane major glycoprotein GP2 | 43.35 |
| P09467 | FBP1 | extracellular vecisular exosome, cytosol | Fructose-1,6-bisphosphatase 1 | 36.80 |
| Q9NP79 | VTA1 | cytoplasm, endosome membrane | Vacuolar protein sorting-associated protein VTA1 homolog | 33.84 |
| Q01105 | SET | ER, cytoplasm, nucleus | Protein SET | 33.45 |
| P09493-3 | TPM1 | extracellular vesicular exosome, cytoplasm, cytoskeleton | Isoform 3 of Tropomyosin alpha-1 chain | 32.84 |
| P06753 | TPM3 | extracellular vesicular exosome, cytoplasm, cytoskeleton | Tropomyosin alpha-3 chain | 32.78 |
| P09093 | CEL3A | Secreted | Chymotrypsin-like elastase family member 3A | 29.45 |
| P17538 | CTRB1 | Secreted | Chymotrypsinogen B | 27.83 |
| F5H753 | TPM1 | cytoplasm, cytoskeleton | Tropomyosin alpha-1 chain | 27.51 |
| P62158 | CALM1 | exosome vesicles, plasma membrane, cytoplasm, cytoskeleton | Calmodulin | 16.81 |

TABLE 15

Eluted MCF7 O-glycoproteins identified by LC-MS/MS. Sixteen of the twenty-one O-glycoproteins are confirmed to be O-GlcNAcylated*.[25, 26]

| Accession | Gene Symbol | Cellular Location | O-Glycoprotein | Mass (kDa) |
|---|---|---|---|---|
| O60271-7 | JIP4 | membrane, cytosol, extracellular space | Isoform 7 of C-Jun-amino-terminal kinase-interacting protein 4 | 54.35 |
| A34720 | KRT8 | cytoplasm, nucleus, | *Cytokeratin 8 (version 2)-human (P05787) | 53.70 |
| P45379-10 | TNNT2 | cytosol | *Isoform 10 of Troponin T, cardiac muscle | 35.56 |
| P35030-2 | TRY3 | Secreted | Isoform B of Trypsin-3 | 28.12 |
| P10412 | HIST1H1E | nucleus, chromosome | *Histone H1.4 | 21.83 |
| P55145 | MANF | Secreted | Mesencephalic astrocyte-derived neurotrophic factor | 20.67 |
| P05451 | REG1A | Secreted, extracellular space | *Lithostathine-1-alpha | 18.70 |
| A6ND86 | CELA2A | Secreted | Chymotrypsin-like elastase family member 2A (P08217) | 15.55 |
| Q5TEC6 | Q5TEC6 | nucleus, chromosome | *Histone H3 | 15.40 |
| P68431 | H31 | nucleus, chromosome | *Histone H3.1 | 15.38 |
| Q71DI3 | H32 | nucleus, chromosome | *Histone H3.2 | 15.36 |

TABLE 15-continued

Eluted MCF7 O-glycoproteins identified by LC-MS/MS. Sixteen of the twenty-one
O-glycoproteins are confirmed to be O-GlcNAcylated*.[25, 26]

| Accession | Gene Symbol | Cellular Location | O-Glycoprotein | Mass (kDa) |
|---|---|---|---|---|
| P84243 | H33 | nucleus, chromosome, extracellular vesiclular exosome | *Histone H3.3 | 15.30 |
| Q6NXT2 | H3C | nucleus, chromosome | *Histone H3.3C | 15.19 |
| P16104 | H2AX | nucleus, chromosome | *Histone H2A.x | 15.12 |
| Q0VAF6 | SYCN | secretory granule membrane, transport vesicle membrane | Syncollin | 14.38 |
| P04908 | H2A1B | nucleus, chromosome | *Histone H2A type 1-B/E | 14.11 |
| Q16777 | H2A2C | nucleus, chromosome | *Histone H2A type 2-C | 13.96 |
| P06899 | H2B1J | nucleus, chromosome | *Histone H2B type 1-J | 13.88 |
| O60814 | H2B1K | nucleus, chromosome | *Histone H2B type 1-K | 13.86 |
| P0C0S5 | H2AZ | nucleus, chromosome | *Histone H2A.Z | 13.53 |
| P62805 | H4 | nucleus, chromosome | *Histone H4 | 11.34 |

Glycan Array Screening

The glycan array, developed by the Consortium for Functional Glycomics (CFG), consists of 610 unique mammalian glycans (version 5.1) and has proven to be an invaluable tool in determining the specificity of glycan-binding proteins.[27, 28] A library of natural and synthetic glycans are modified with an amino linker containing a spacer. The glycans are covalently linked to NHS-activated glass surface via the amino-modified spacer linker. Each glycan is printed in replicates of six on the array. The surface immobilized glycans predominantly do not include the peptide glycosylation sequone (Asn-X(-Pro)-Ser/Thr); two exceptions being linkers Sp22 (peptide NST) and Sp24 (peptide KVANKT) (SEQ ID NO:22). The lack of peptide sequone is a deviation from the normal biological context of glycan interactions. For many carbohydrate-recognizing proteins, which recognize terminal glycan structures, this is not a significant issue (e.g.: terminal sialic acid recognizing lectins). However, this is a significant issue for those carbohydrate-processing enzymes which recognize glycan structures in the context of the protein on which the glycan is displayed or being transferred to as in the case of various transerferases. Given that the wtPNGase F enzyme is known to recognize the glycopeptide consisting of the sequone and the asparagine-linked chitobiose core the lack of the peptide sequone on the immobilized glycan is a limitation.

PNGase F D60A and R911 clones were submitted to the CFG's Protein-Glycan Interaction Core (formerly Core H) for glycan array screening. The purified proteins were labeled with DyLight 488 and dye:protein labeling ratios were determined to be 2.1:1 for D60A and 8.2:1 for R911. The labeled proteins were incubated on the arrays at a final concentration of 200 μg/mL in buffer consisting of 10 mM HEPES, 10 mM NaCl, pH 7.4 containing 0.1% BSA. After incubation, the array was washed in the same buffer without 0.1% BSA. The dried arrays were scanned on a microarray scanner and signal intensities for individual glycan features/spots were quantitated.

Figure 38:
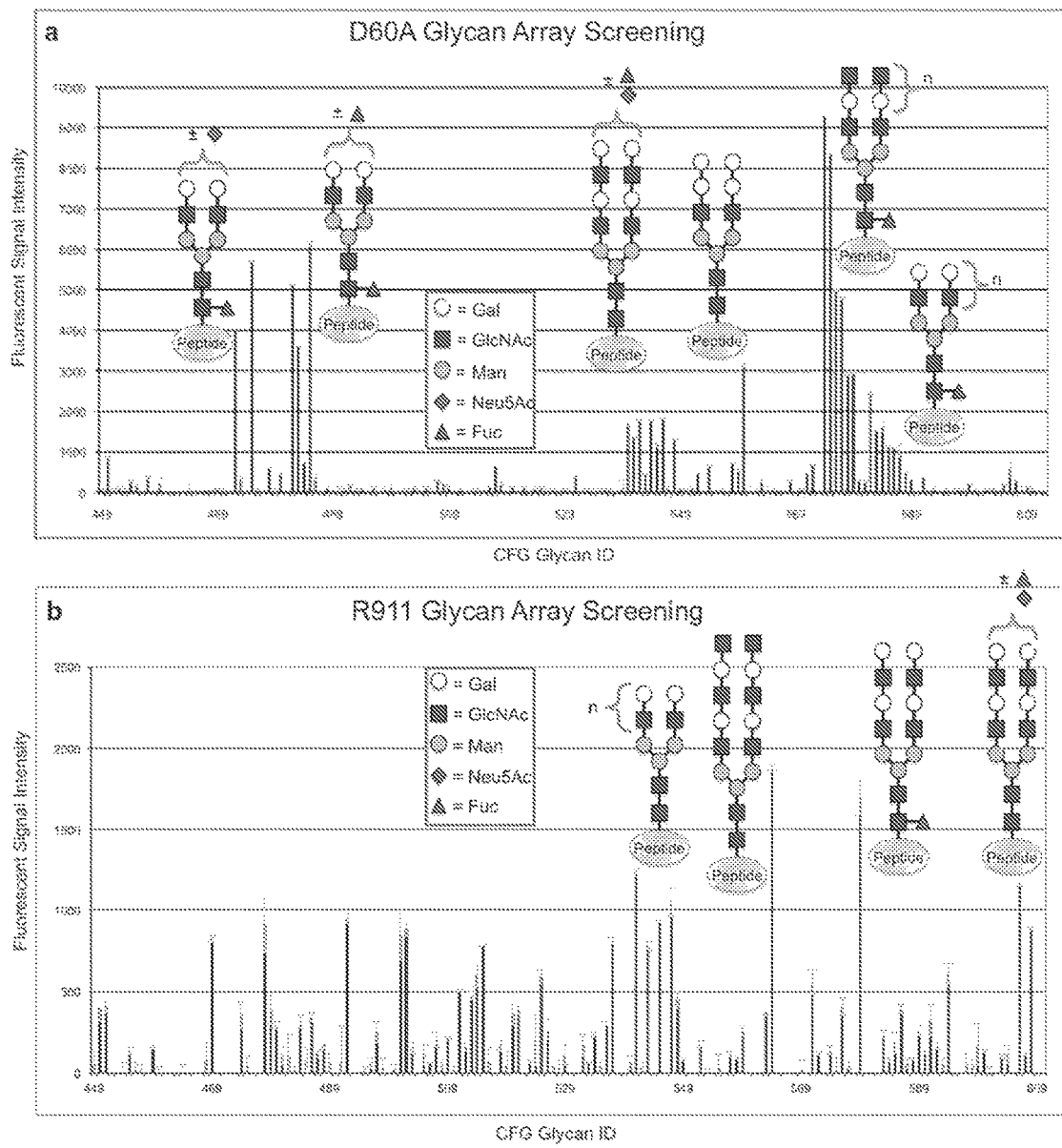
FIG. 38 shows glycan array screening of D60A and R911 clones.

FIG. 38 shows a side-by-side comparison of glycan array screening results for D60A and R911 clones. In summary, high signal intensity, indicating binding interactions with surface-immobilized N-glycans (with and without α1,6 core fucosylation), consistent with the reported specificity of the wtPNGase F enzyme was observed for labeled D60A. Furthermore, a lack of signal intensity for D60A interactions with α1,3 core fucosylated glycans was also observed. This is consistent with wtPNGase F's inability to release glycans with α1,3 linked fucose to the asparagine linked N-acetylglucosamine, whereas an α1,6 core fucosylated N-glycans can be released.

In the case of the labeled R911 clone, a noticeably reduced, but above background, signal intensity for similar surface-immobilized N-glycan structures was observed for labeled R911. The lower signal to noise ratio for the R911 data set may be due the possibility that the specificity of the R911 clone has been altered due to the selected mutations. However, this is inconsistent with both SPR affinity data and R911 Lectenz® affinity chromatography results. Thus, the more likely cause for the low signal to noise ratio and the seemingly diminished specificity relative to D60A is the high dye:R911 protein labeling ratio of 8.2:1. A high dye-labeling ratio can damage the binding site due to the higher probability that a dye molecule will react with an available amine group in the binding pocket. The ideal labeling ration is 2:1, as was the case with D60A. To obtain more robust glycan array-based specificity results the R911 glycan array screening will need to be repeated with a lower dye to protein labeling ratio. Unfortunately, due to the limited availability of purified R911 as a result of low expression yield, and the need to characterize R911 using multiple techniques, a repeat experiment could not be immediately performed.

Methods

Expression of PNGase F Clones

PNGase F-pOPH6 II (D60A, R617, R6113, R911, and R9113) plasmids were transformed into E. coli BL21-Gold (DE3) competent cells obtained from Agilent Technologies (230132) for expression. For each clone, a single colony picked from a Luria Bertani (LB) agar plate (100 μg/ml Carbenicillin) was cultured in 50 mL LB media containing 100 μg/ml Carbenicillin in a shaker (250-300 RPM) over night at 37° C. The following day the culture was expanded into 37° C. pre-warmed 1 L LB media with 100 μg/ml Carbenicillin. Between $OD_{600}$ of 0.4-0.5 the temperature was dropped from 37° C. to 22° C. and induced with 1 mM IPTG and the culture was induced overnight (~20 hours). The cell pellet was harvested at 4500×g (30 minutes) using Avanti JA10 rotor at 4° C. The R911 culture yielded approximately an 8 g cell pellet from a 1 L LB culture. The cell pellet was resuspended in ice cold 20 mL IMAC binding buffer (0.1M EPPS, 0.5M NaCl, 0.01M Imidazole, pH 8.50). An EDTA-free protease inhibitor tablet from Roche (05892791001) was dissolved into 1 mL binding buffer or molecular grade water and mixed into the resuspended cell pellet. Cells were subjected to mechanical lysis three times using a French press at 6,000 psi. The cell lysate was centrifuged at 30,000×g (45 minutes) in an Avanti JA17 rotor at 4° C. to separate insoluble cell debris from the supernatant containing the periplasmic fraction. The supernatant was collected and filtered using a 0.8 μm filter for every 5 mL of supernatant.

Immobilized Metal Affinity Chromatography of PNGase F Clones

The filtered periplasmic fraction was loaded onto an IMAC column and the PNGase F clone eluted over an imidazole gradient using an AKTA Purifier UPC 10. IMAC Binding buffer (A) consisted of 0.1M EPPS, 0.5M NaCl, 0.01M Imidazole, pH 8.50 and the IMAC Elution buffer (B) consisted of 0.1M EPPS, 0.5M NaCl, 0.5M Imidazole, pH 8.50. A GE Healthcare HisTrap HP column (17-5247-01) was washed, charged with $Ni^{2+}$, and equilibrated using the manufacturers recommended protocol. A programmed method (Unicorn 5.1) was used for all purification runs. In summary, the nickel-charged HisTrap column was equilibrated in 5 CV binding buffer at 3.5 mL/min flow rate. The periplasmic fraction (~20 ml) was loaded into the column at a flow rate of 2 mL/min using a P-960 sample pump. The loaded column was washed with 9 CV of binding buffer (100% A) at a 2 mL/min flow rate. Non-specifically bound proteins were eluted with a 10 CV step elution of 8.3% B (equivalent to 50 mM Imidazole) at a 2 mL/min flow rate. A 43% B gradient elution over 18 CV at a flow rate of 2 mL/min was used to elute the Ni-bound histidine-tagged PNGase F clone and 2.5 mL fractions of eluted protein were collected. The column was wash with 100% B step elution for 8 CV at a flow rate of 2 mL/min followed by re-equilibration with 100% A over 5 CV at a flow rate of 3.5 mL/min. Using a Vivaspin 20 (10 kDa cutoff) concentrator, the eluted protein containing fractions were pooled and concentrated down to ~250 μL final volume for additional purification via SEC.

Size Exclusion Chromatography of PNGase F Clones

Approximately, 250 μL of the concentrated IMAC sample was loaded into a 500 μL injection loop for SEC purification using either a SuperDex 75 10/300 GL or a Superose 12 10/300 GL column. The Superose 12 column provided enhanced purification of R911 relative to the SuperDex 75 column. As before, an automated method (Unicorn 5.1) was used for the purification run on the AKTA Purifier UPC 10. The column was equilibrated with 1.5 CV running buffer (50 mM EPPS, pH 8.00) at a flow rate of 0.4 mL/min. The sample was injected into the column by flushing the 0.5 mL loop with 2.5 mL running buffer and then the flow rate dropped to 0.2 mL/min. Fraction collection (0.5 mL) was initiated at 6.75 mL retention volume. The fractions corresponding to the elution peak were pooled and concentrated using a 10 kDa cutoff Vivaspin 20 concentrator and protein yield determined by UV 280 absorbance ($A_{280}$). Typical yield after SEC purification of the D60A control clone was ~3.0 mg from a 0.5 L LB culture. In comparison, typical yield for R911 and R911 C60A clones was ~0.3 mg from a 2 L LB culture.

SDS-PAGE & Coomassie Staining

Bio-Rad 4-20% TGX gels (456-1093 and 456-1094) and recommended buffers were used for SDS-PAGE of protein samples. All samples were denatured using the manufacturers recommended Laemmli sample buffer recipe at 6× stock concentration containing β-Mercaptoethanol and incubated at 95° C. for 5 minutes prior to loading on the gel. The gel was run for 35 minutes at 200 V (150 mA max). Gels were Coomassie stained using Life Technologies' SimplyBlue SafeStain (LC6060) per the recommended rapid microwave staining and destaining procedure.

Western Blot

The following buffers, reagents, and solutions were used for Western Blot with modified manufacturer protocols:
1. 10× Transfer buffer (1 L): 250 mM Tris (30.28 g/L), 1.92 M Glycine (144.1 g/L), 0.05% SDS (5 g/L), pH adjusted to 8.3 by HCl.
2. 10× TBS (I L): 1.4 M NaCl (81.82 g/L), 250 mM Tris base (30.28 g/L), pH adjusted to 7.4 by HCl.
3. 10× BLOTTO (100 mL): 10% Non-fat dry milk (10 g) from Bio-Rad (170-6404XTU), 90% NANOpure water (90 mL).
4. 1× Blocking buffer (500 mL): 0.5 mL (500 μL) Tween 20, 50 mL 10× BLOTTO, 50 mL 10× TBS, 400 mL NANOpure water.
5. 5% Blocking buffer (100 mL for two membranes): 5% non-fat dry milk (4 g), 96 mL of 1× Blocking buffer.
6. 1× TBS (100 mL): 10 mL 10× TBS, 90 mL NANOpure water,
7. 1× Transfer buffer with methanol (1 L) pH 8.3: 100 mL of 10× Transfer buffer, 150 mL of methanol, 750 mL of NANOpure water.
8. PVDF Hybond-P membrane from GE Healthcare (RPN303F).
9. Horseradish peroxidase (HRP) conjugated mouse anti-histidine antibody from Alpha Diagnostic (HISP 2-HRP).
10. Thermo Scientific Pierce Metal Enhanced DAB substrate solution (34065).

Protein transfer using TGX gels and PVDF membrane was conducted at 100 V (350 mA max) for 30 minutes with the transfer apparatus kept on ice. A magnetic stir bar was used to circulate the transfer buffer during the transfer process. Post-transfer, the membrane was washed 3× with 20 mL NANOpure water and then blocked in 20 mL 5% blocking buffer for 45 minutes on a shaking platform following by incubation with the anti-histidine HRP conjugated antibody (1:5000) in 10 mL of 1× blocking buffer overnight at 4° C. on a shaker. The following day, the membrane was washed with 20 mL 1× blocking buffer for 5 minutes each followed by 3× washes with 20 mL of 1× TBS also for 5 minutes each on a shaker. The membrane was rinsed with 20 mL NANOpure water before addition of the DAB substrate for development. Depending on the amount of protein loaded on the gel and transferred to the membrane, the membrane was allowed to develop between 1-10 minutes. The membrane was rinsed one final time with 20 mL NANOpure water and then dried before scanning using a standard desktop scanner.

Deglycosylation Activity of PNGase F Clones

A gel shift assay was used to determine deglycosylation activity of PNGase F clones relative to wtPNGase F. 50 ng of wtPNGase F, D60A, and R911 each was incubated with 50 μg of denatured RNase B in 50 mM EPPS, pH 8.0 in a 50 μL reaction volume at 37° C. overnight. Samples were analysed on a SDS-PAGE gel and altered migration of deglycosylated RNase B product relative to RNase B was observed. The scanned gel image was analyzed by ImageJ software to quantitate deglycosylated product relative to RNase B substrate (Supplementary Table 4).[7] Deglycosylated product confirmed by MALDI TOF-TOF mass spectrometry.

Protein Denaturation 5 mg, 0.113 µmol asialofetuin (44,189 g/mol), purchased from Sigma (A4781-50MG) was dissolved in 1 mil 0.1 M Tris-HCl (pH 8.0) containing 6 M guanidine HCl (95.53 g/mol) (573 mg in 1 mL) and reduced by the addition of 28 mg, 182 µmol DTT (154.25 g/mol) for 1 h at 55° C., followed by addition of 128 mg, 692 µmol iodoacetamide (184.96 g/mol) for 30 minutes at room temperature. 0.5 mL of the mixture was desalted with Thermo Scientific Pierce D-Salt Polyacrylamide Desalting Columns, collecting 0.5 mL fractions after the void volume of 1.75 mL.

MALDI Mass Spectrometry

Mass spectrometry was performed using an ABI 5800 MALDI TOF-TOF High Resolutions Mass Spectrometer. Sinapinic Acid matrix was prepared by re-suspending ~10 mg Sinapinic Acid in 1 ml volume of 30% acetonitrile (ACN) and 0.3% TFA. Matrix to protein sample was mixed at a ratio of 30:1 resulting in 4 pmols of total protein. The sample spotted (1 µL) a MALDI plate and air dried prior to loading the plate in to the ABI 5800.

LC-MS/MS D60A Sequence Identification

The protein sample was prepared by adding 8 µL of 40 mM $NH_4HCO_3$ to 10 µL of D60A sample (10 µg) for a total volume of 18 µL. The sample was reduced with 2 µL of 1 M DTT for one hour at 56° C. and carboxyamidomethylated with 20 µL of 55 mM iodoacetamide in the dark for 45 minutes. Trypsin (20 µg) was reconstituted with 80 µL of 40 mM $NH_4HCO_3$ and 10 µL (2.5 µg) was added to the sample to digest proteins overnight at 37° C. After digestion, the peptides were acidified with 5 µL of 1% trifluoroacetic acid (TFA). Desalting was performed with a C18 spin column, and the sample was dried down in a vacuum centrifuge. The peptides were re-suspended with 19 µL of mobile phase A (0.1% formic acid in water) and 1 µL of mobile phase B (80% acetonitrile and 0.1% formic acid in water). The samples were loaded onto a nanospray tapered capillary column/emitter self-packed with C18 reverse-phase resin via a nitrogen pressure bomb for 10 minutes at 1000 psi for each run. Each run consisted of a 160 minute gradient of increasing mobile phase B at a flow rate of approximately 200 nL per minute. For the initial protein identification run a LC-MS/MS analysis was performed on a Finnigan LTQ-XL equipped with a nanoelectrospray ion source. An instrument method was used to collect a full MS spectra and generate MS/MS spectra for the 8 most intense peaks using collision-induced dissociation (38% normalized collision energy) with dynamic exclusion set for 30 second intervals. The resulting data was searched against an *E. coli* database with D60A sequence, as well as a target only database, using a Sequest Algorithm. Sequest parameters were altered to search for modifications allowing for oxidation of methionine and alkylation of cysteine. Peptide mass tolerance was set at 1000 ppm and fragment ion tolerance was set at 1 Dalton. Results were filtered at a false discovery rate (FDR) of 1%.

Surface Plasmon Resonance

The ligands, denatured RNase B, native RNase B, and denatured RNase A, which has the same peptide sequence as RNase B but lacks N-glycosylation, were covalently coupled to CM-5 chips using amine-coupling chemistry. Optimal coupling conditions were determined by pH scouting of acetate buffers as per Biacore's recommended protocol (FIG. 31). A high-density surface area was prepared with sufficient ligand coupling to achieve a calculated $R_{MAX}$ of 3000 RU. For ligand immobilization, the coupling buffer consisting of 10 mM Acetate buffer, pH 5.5 was used. The PNGase F clones used as analytes were D60A, R911, and R911 C60A in a serial dilution concentration range starting from 10 µM down to 72.5 nM. The running buffer consisted of 10 mM HEPES, 10 mM NaCl, pH 7.4. Steady-state binding kinetics using a bimolecular interaction model were determined using Scrubber 2.0c (Table 10 and FIG. 32).

Glycan Array Screening

The D60A and R911 clones were submitted to the Consortium for Functional Glycomics' Protein-Glycan Interaction Core (formerly Core H) for glycan array screening.[29] Purified D60A was labeled with DyLight 488 and dye:protein labeling ratio was determined to be 2.1:1. Purified R911 was similarly labeled and the dye:protein labeling ratio was determined to be 8.2:1. The clones were incubated on the arrays at a final concentration of 200 µg/mL in buffer consisting of 10 mM HEPES, 10 mM NaCl, pH 7.4 containing 0.1% BSA. After a 1 hour incubation, the array was washed in the same buffer without 0.1% BSA four times. Slides are dried under a stream on nitrogen and processed using the standard glycan array data acquisition and analysis protocol. After slides have been dried following the last wash, they are placed in the PerkinElmer ScanArray scanner and data is obtained for each wavelength used for detection (DyLight 488). The PMT setting used is 70% and the laser power used is 90%. After saving, the images are opened in Imagene software and a grid is used to align the spots on the slide using the biotin control spots. Once aligned, the amount of binding to each spot is quantified. The data is analyzed using Microsoft Excel, where the highest and lowest spot of the 6 replicates is removed, and the average of the 4 remaining spots is displayed graphically and in a table along with appropriate statistics.

Lectenz® Affinity Chromatography

Using 1 mL HiTrap NHS-activated HP columns manufactured by GE Healthcare (17-0716-01) purified PNGase F D60A and R911 clones were covalently linked to the column matrix to evaluate affinity chromatography based enrichment of N-glycopeptides and N-glycoproteins. Using the manufacturers recommended protocol, coupling efficiencies of PNGase F clones to the NHS-activated columns consistently ranged between 80%-87% for all NHS-activated column-coupling reactions. The standard binding buffer consisted of 10 mM HEPES, 10 mM NaCl, pH 7.4 where as the standard elution buffer consisted of 10 mM HEPES, 150 mM NaCl, pH 7.4. For competitive elution experiments, the elution buffer consisted of 10 mM HEPES, 10 mM NaCl, 235.6 µM (100 µg/mL) chitobiose, pH 7.4. Chitobiose was obtained from Sigma (D1523-10). The regeneration buffer consisted of 10 mM HEPES, 500 mM NaCl, pH 7.4. An AKTA Purifier UPC 10 (GE Healthcare) was used for all chromatography experiments configured with a 100 µL sample injection loop, 1 mL HiTrap NHS-activated columns, $UV_{280}$ detection. For all chromatography runs, the flow rate of 0.4 mL/min was constant. The column was equilibrated with 10 mL or 10 column volumes (CV) of binding buffer, followed by 100 µL injection of sample. The sample was allowed to flow through the column using binding buffer over 5 CV to wash out unbound sample. The bound sample was eluted with elution buffer over 5 CV. During binding and elution 0.5 mL fractions were collected. The column was regenerated with 5 CV regeneration buffer and re-equilibrated in 5 CV binding buffer.

MCF7 Cell Extract Preparation

Human breast cancer MCF7 cells were cultured in DMEM media supplemented with 10% fetal bovine serum. Cells were passaged and harvested using trypsin-free cell release. Approximately, $2.3 \times 10^7$ cells were harvested and washed 3× with 10 mL of phosphate buffered saline at 4° C.

by centrifugation at 1000×g for 5 minutes. The cell pellet was resuspended in 1.5 mL of filter sterilized cell lysis buffer (10 mM Tris-HCl, pH 7.5, 150 mM NaCl, 1% v/v Nonidet P-40) with EDTA-free protease inhibitor cocktail (Roche Diagnostics, Mannheim, Germany) and incubated on ice for 30 minutes.[17] The cells were ultra-sonicated (Misonix Ultrasonic Liquid Processor Model S-4000) at intervals of 15 seconds for a total of 2 minutes, with a 15 second pause between treatments (30% amplitude). The lysed cells were centrifuged at 17,000×g for 1 hour in an Eppendorf 5430R at 4° C. The supernatant containing the MCF7 cell extract was stored at −80° C. in 50 µL aliquots. Protein concentration of the MCF7 cell extract was determined to be 10.67 mg/mL using a Thermo Scientific Pierce BCA protein assay kit (23277). An aliquoted MCF7 cell extract stock was thawed on ice and diluted to 1 mg/mL using 10 mM HEPES, 10 mM NaCl, at pH 7.4. Using a 100 µL sample loop, 100 µg of 1 mg/mL MCF7 cell extract was injected into the R911 Lectenz® affinity column for glycoprotein enrichment.

LC-MS/MS Protein Identification of R911 Lectenz® Affinity Chromatography Eluted Samples MCF7 cell extract and proteins eluted from the R911 Lectenz® affinity column were reduced, alkylated and digested with sequence grade trypsin (Promega) using a standard in-solution digest protocol.[30] The samples were acidified with 1% trifluroacetic acid and desalting was performed using C18 spin columns (Silica C18, The Nest Group, Inc.). Peptides were dried down and resuspended with 39 µL of buffer A (0.1% formic acid) and 1 µL of buffer B (80% Acetonitrile and 0.1% formic acid). The samples were spun through a 0.2 µm filter (Nanosep, Pall Corp) before being loaded into an autosampler tube and racked into an Ultimate 3000 LC System (Thermo Scientific—Dionex).

LC-MS/MS analysis was performed on an Orbitrap Fusion Tribrid (Thermo Scientific) utilizing a nanospray ionization source. For each sample, 10 µL was injected and separated via a 180-minute gradient of increasing buffer B at a flow rate of approximately 200 nL per minute. An instrument method was used to collect full mass spectrum every three seconds and continuously trap and fragment the most intense ions with 38% collision-induced dissociation (CID) and record the resulting MS/MS spectra. Dynamic exclusion was utilized to exclude precursor ions from selection process for 60 seconds following a second selection within a 10 second window.

All MS/MS spectra were searched against a UniProt human database utilizing the SEAQUEST algorithm (Proteome Discoverer 1.4, Thermo Scientific). The SEAQUEST parameters were set to allow for tryptic peptides with a maximum of two internal missed cleavages. Mass tolerances were set to 20 ppm for precursor ions and 0.5 Da for fragment ions. Dynamic mass increases were allowed to account for oxidation of methionine and alkylation of cysteine residues. The spectra were also searched against a random database generated by reversing the human database to determine the false-discovery rate (FDR) of identification. ProteoIQ utilized all SEAQUEST search result files and databases to filter peptide matches and attain accurate protein identifications.[31] Peptides passing a 20% FDR were considered for protein identification and only proteins surviving a 2% FDR were reported.

Identification of MCF7 Cell Extract Glycoproteins Using UniPep and UniProt Databases UniProt verified protein identification lists generated from LC-MS/MS analysis of the stock MCF7 sample and the R911 Lectenz® affinity chromatography eluted MCF7 sample were processed through the UniPep database to identify proteins with experimentally confirmed N-glycopeptides.[20] In addition, potential glycoproteins with N-linked glycosites were also identified via UniPep based on the presence of the N-glycosylation sequone (Asn-X-Ser/Thr). A final list of N- and O-glycoproteins included only those proteins that were confirmed as glycoproteins by UniPep, UniProt, and literature reports.[19, 20, 25, 26, 32] In addition, proteins that were predicted to have an N-glycosylation site were only included in the final list if UniProt subcellular localization descriptions were consistent with those expected for glycosylated proteins (Golgi, secreted, vesicular exosome, extracellular space, and histones).

REFERENCES

1. Loo, T., Patchett, M. L., Norris, G. E. & Lott, J. S. Using Secretion to Solve a Solubility Problem: High-Yield Expression in *Escherichia coli* and Purification of the Bacterial Glycoamidase PNGase F. Protein Expression and Purification 24, 90-98 (2002).
2. Filitcheva, J. PNGases: A Diverse Family of Enzymes Related by Function Rather Than Catalytic Mechanism, Vol. Ph.D. (Massey University, Palmerston North; 2010).
3. Gasteiger E., H. C., Gattiker A., Duvaud S., Wilkins M. R., Appel R. D., Bairoch A. in The Proteomics Protocols Handbook (ed. J. M. Walker) 571-607 (Copyright Humana Press, 2005).
4. Kuhn, P. et al. Active Site and Oligosaccharide Recognition Residues of Peptide-N4-(N-acetyl-β-D-glucosaminyl)asparagine Amidase F. Journal of Biological Chemistry 270, 29493-29497 (1995).
5. Noble, J. E., Knight, A. E., Reason, A. J., Di Matola, A. & Bailey, M. J. A comparison of protein quantitation assays for biopharmaceutical applications. Mol Biotechnol 37, 99-111 (2007).
6. Kuhn, P., Tarentino, A. L., Plummer, T. H., Jr. & Van Roey, P. Crystal structure of peptide-N4-(N-acetyl-beta-D-glucosaminyl)asparagine amidase F at 2.2-A resolution. Biochemistry 33, 11699-11706 (1994).
7. Schneider, C. A., Rasband, W. S. & Eliceiri, K. W. NIH Image to ImageJ: 25 years of image analysis. Nat Meth 9, 671-675 (2012).
8. Cooper, M. A. Optical biosensors in drug discovery. Nat Rev Drug Discov 1, 515-528 (2002).
9. Schlick, K. H. & Cloninger, M. J. Inhibition binding studies of glycodendrimer-lectin interactions using surface plasmon resonance. Tetrahedron 66, 5305-5310 (2010).
10. Haseley, S. R., Kamerling, J. P. & Vliegenthart, J. F. G. Unravelling carbohydrate interactions with Biosensors using surface plasmon resonance (SPR) detection. Host-Guest Chemistry 218, 93-114 (2002).
11. Nieba, L. et al. BIACORE analysis of histidine-tagged proteins using a chelating NTA sensor chip. Analytical Biochemistry 252, 217-228 (1997).
12. Willard, F. S. & Siderovski, D. P. Covalent immobilization of histidine-tagged proteins for surface plasmon resonance. Analytical Biochemistry 353, 147-149 (2006).
13. Wang, S. et al. N-Terminal Deletion of Peptide:N-Glycanase Results in Enhanced Deglycosylation Activity. PLoS ONE 4, e8335 (2009).
14. Ongay, S., Boichenko, A., Govorukhina, N. & Bischoff, R. Glycopeptide enrichment and separation for protein glycosylation analysis. J Sep Sci 35, 2341-2372 (2012).

15. Alwael, H. et al. Pipette-tip selective extraction of glycoproteins with lectin modified gold nano-particles on a polymer monolithic phase. Analyst 136, 2619-2628 (2011).
16. Jung, K. & Cho, W. Serial affinity chromatography as a selection tool in glycoproteomics. Anal Chem 85, 7125-7132 (2013).
17. Lee, L. Y. et al. An optimized approach for enrichment of glycoproteins from cell culture lysates using native multi-lectin affinity chromatography. J Sep Sci 35, 2445-2452 (2012).
18. Krishnamoorthy, L. & Mahal, L. K. Glycomic analysis: an array of technologies. ACS chemical biology 4, 715-732 (2009).
19. Consortium, T. U. Activities at the Universal Protein Resource (UniProt). Nucleic Acids Research 42, D191-D198 (2014).
20. Zhang, H. et al. UniPep—a database for human N-linked glycosites: a resource for biomarker discovery. Genome biology 7, R73 (2006).
21. Fan, J. Q. Detailed Studies on Substrate Structure Requirements of Glycoamidases A and F. Journal of Biological Chemistry 272, 27058-27064 (1997).
22. Tretter, V., Altmann, F. & MÄRz, L. Peptide-N4-(N-acetyl-β-glucosaminyl)asparagine amidase F cannot release glycans with fucose attached α1→3 to the asparagine-linked N-acetylglucosamine residue. European Journal of Biochemistry 199, 647-652 (1991).
23. Mussar, K. J., Murray, G. J., Martin, B. M. & Viswanatha, T. Peptide: N-glycosidase F: studies on the glycoprotein aminoglycan amidase from *Flavobacterium meningosepticum*. Journal of biochemical and biophysical methods 20, 53-68 (1989).
24. Tarentino, A. L., Gomez, C. M. & Plummer, T. H., Jr. Deglycosylation of asparagine-linked glycans by peptide: N-glycosidase F. Biochemistry 24, 4665-4671 (1985).
25. Zhang, S., Roche, K., Nasheuer, H. P. & Lowndes, N. F. Modification of histones by sugar beta-N-acetylglucosamine (GlcNAc) occurs on multiple residues, including histone H3 serine 10, and is cell cycle-regulated. J Biol Chem 286, 37483-37495 (2011).
26. Ahmad, W. et al. Human linker histones: interplay between phosphorylation and O-beta-GlcNAc to mediate chromatin structural modifications. Cell division 6, 15 (2011).
27. Taylor, M. E. & Drickamer, K. Structural insights into what glycan arrays tell us about how glycan-binding proteins interact with their ligands. Glycobiology 19, 1155-1162 (2009).
28. Adams, G. B. & Scadden, D. T. The hematopoietic stem cell in its place. Nat Immunol 7, 333-337 (2006).
29. Heimburg-Molinaro, J., Song, X., Smith, D. F. & Cummings, R. D. Preparation and analysis of glycan microarrays. Curr Protoc Protein Sci Chapter 12, Unit 12 10 (2011).
30. Lim, J. M. et al. Defining the regulated secreted proteome of rodent adipocytes upon the induction of insulin resistance. J Proteome Res 7, 1251-1263 (2008).
31. Weatherly, D. B. et al. A Heuristic method for assigning a false-discovery rate for protein identifications from Mascot database search results. Mol Cell Proteomics 4, 762-772 (2005).
32. Takashima, S. Glycosylation and secretion of human α-amylases. Advances in Biological Chemistry 02, 10-19 (2012).

Example 4

Molecular Dynamics Simulations of PNGase F Clones

Conformational analysis of PNGase F clones D60A, R911, and R911 C60A relative to the wtPNGase F enzyme was investigated via MD Simulations, from which per-residue interaction energies were computed. The x-ray crystallography-based structural model of the wtPNGase F enzyme with the N,N'-diacetylchitobiose disaccharide in the active site at 2.0 Å resolution, has previously been reported (PDB ID: 1PNF).[1] The 1PNF model was used to construct mutagenized models of D60A, R911, and R911 C60A clones. In addition, the co-crystalized N,N'-diacetylchitobiose disaccharide ligand in the binding pocket of wtPNGase F served as a guide to position modified N-glycan structures into the binding pocket of the constructed models of PNGase F clones.

Structural Models of D60A, R911, and R911 C60A

Rotamer Selection for Building Models

The wtPNGase F model, 1PNF, was used as a template to build models of PNGase clones D60A, R911, and R911 C60A. Two rotamer libraries were used to select side chain rotamers for R911 mutations. The x-ray crystallography-based, backbone dependent, Dunbrack library was used to select rotamers and build models R911 Dun and R911 C60A Dun.[2] In addition, the MD-based, backbone independent, Dynameomics library was also used to select rotamers and build models R911 Dyn and R911 C60A Dyn.[3] The highest probability rotamers with the least amount of steric clashes were selected. Dunbrack rotamers evaluated and selected for building R911 Dun and R911 C60A Dun models are listed in Table 16. Similarly, Dynameomics rotamers for R911 Dyn and R911 C60A Dyn are listed in Table 17. Rotamers for D57L, D60C, I156L, G192I, and R248W mutations are shown in the context of the neighboring residues. The rotamers for E206S are not shown as no clashes were predicted. MD simulations and free energy decomposition were computed to evaluate which rotamers best approximated experimental interaction energies. The rotamer models with the best approximations are used for all subsequent computational studies.

TABLE 16

Dunbrack library rotamer selection. Selected rotamers are indicated by asterisks (*). Rotamers with the highest probability and lowest number of steric clashes were selected for R911 Dun and R911 C60A Dun models (shaded).

| R911 Rotamer | Rotamer Probability (%) | Average Angles Chi1 | Chi2 | Clashes # | Selected Dunbrack Rotamer Clash Description and Orientation |
|---|---|---|---|---|---|
| 1. D57L | 64.4334 | −173 | 61.4 | 4 | |
| 2. D57L | 28.6281 | −64.6 | 175.9 | 7 | |

TABLE 16-continued

Dunbrack library rotamer selection. Selected rotamers are indicated by asterisks (*).
Rotamers with the highest probability and lowest number of steric clashes were selected for R911 Dun and R911 C60A Dun models (shaded).

| R911 Rotamer | Rotamer Probability (%) | Average Angles Chi1 | Chi2 | Clashes # | Selected Dunbrack Rotamer Clash Description and Orientation |
|---|---|---|---|---|---|
| 3. D57L* | 4.2279 | −165.4 | 171.3 | 1 | Clash w/T119; similar orientation as D57 |
| 1. D60C | 74.2327 | 179.8 | 1 | | |
| 2. D60C | 25.3616 | −62.4 | 3 | | |
| 3. D60C* | 0.4057 | 63.4 | 0 | | similar orientation as D60 |
| 1. I156L | 93.2665 | −63.1 | 175.6 | 5 | |
| 2. I156L* | 4.0482 | −87.2 | 49.8 | 0 | |
| 1. G192I | 39.1625 | 62.1 | 170.9 | 21 | |
| 2. G192I | 34.202 | −65.1 | 169.6 | 17 | |
| 3. G192I | 10.5124 | −169.1 | 167.9 | 17 | |
| 4. G192I | 8.6498 | −59.8 | −60 | 16 | |
| 5. G192I* | 4.5635 | −166.8 | 66.7 | 14 | Clash with C204, D290, W191, H193 |
| 1. E206S | 41.8529 | −65.9 | 0 | | |
| 2. E206S | 31.6039 | 65.4 | 0 | | |
| 3. E206S* | 26.5433 | 179.2 | 0 | | same orientation as E206 |
| 1. R248W | 40.4783 | −63.5 | 100.4 | 9 | Clash with E206, W207 |
| 2. R248W | 29.7865 | −70.3 | 0.4 | 22 | |
| 3. R248W* | 10.8433 | −59.8 | −87.2 | 7 | Clash with P253 |

TABLE 17

Dynameomics library rotamer selection. Selected rotamers are indicated by asterisks (*).
Rotamers with the highest probability and lowest number of steric clashes were selected for R911 Dyn and R911 C60A Dyn models.

| R911 Rotamer | Rotamer Probability (%) | Average Angles Chi1 | Chi2 | Steric Clashes # | Selected Dynameomic Rotamer Clash Description and Orientation |
|---|---|---|---|---|---|
| 1. D57L | 65.1945 | 292 | 168.5 | 9 | |
| 2. D57L* | 24.054 | 183 | 66.6 | 4 | Clashes: R61, L121; same orientation as D57 |
| 3. D57L | 4.5273 | 275.1 | 79.8 | 9 | |
| 1. D60C | 56.2557 | 298.5 | | 3 | |
| 2. D60C | 28.6878 | 183.7 | | 3 | |
| 3. D60C* | 15.0565 | 54.8 | | 0 | same orientation as D60 |
| 1. I156L* | 65.1945 | 292 | 168.5 | 4 | Clashes: F292, GlcNAc |
| 2. I156L | 24.054 | 183 | 66.6 | 7 | |
| 3. I156L | 4.5273 | 275.1 | 79.8 | 1 | |
| 1. G192I | 42.5492 | 53.3 | 167.1 | 19 | |
| 2. G192I | 28.2902 | 300.9 | 176.6 | 18 | |
| 3. G192I | 22.6888 | 301.9 | 299 | 15 | |
| 4. G192I | 3.7004 | 187.2 | 165.7 | 16 | |
| 5. G192I* | 1.4194 | 184.1 | 68.3 | 13 | Clashes: C204, D290, A291, W191 |
| 1. E206S* | 73.0609 | 310.9 | | 0 | |
| 2. E206S | 24.8453 | 40.7 | | 0 | |
| 3. E206S | 2.0938 | 189.4 | | 2 | Clashes: W248 |
| 1. R248W* | 28.2145 | 294.7 | 98.5 | 7 | Clashes: W207 |
| 2. R248W | 16.4889 | 291.4 | 348.1 | 20 | |
| 3. R248W | 13.8124 | 181.8 | 259.2 | 24 | |

MD Simulations for Validating Rotamers

MD simulations (100 ns) of the wtPNGase F, D60A, and all 4 rotamer models were performed with the N,N'-diacetylchitobiose disaccharide (GlcNAcβ1-4GlcNAc-αOH). The root mean squared difference (RMSD) in the positions of Cα atoms, relative to the wtPNGase F experimental structure (1PNF), was determined as a function of the simulation time. The average RMSD for each of the 6 models over the course of the 100 ns simulation were low, stable, and ranged between 1.2 Å and 1.3 Å, indicating structural equilibration. A list of 6 structural models used for rotamer analysis and the average RMSD value for each MD simulation is listed in Table 18.

TABLE 18

Structural models of wtPNGase F and clones for rotamer selection. 100 ns MD simulations were run for each model. The 1PNF x-ray structure with the co-crystalized α-chitobiose ligand represents wtPNGase F. The remaining 5 models were constructed from the 1PNF reference structure. The average RMSD value for each simulation is listed.

| Structural Model | Ligand | Average RMSD (Å) |
|---|---|---|
| 1PNF | GlcNAcβ1-4GlcNAc-αOH | 1.2404 |
| D60A | GlcNAcβ1-4GlcNAc-αOH | 1.2369 |
| R911 Dun | GlcNAcβ1-4GlcNAc-αOH | 1.2908 |
| R911 C60A Dun | GlcNAcβ1-4GlcNAc-αOH | 1.3090 |

TABLE 18-continued

Structural models of wtPNGase F and clones for rotamer selection. 100 ns MD simulations were run for each model. The 1PNF x-ray structure with the co-crystalized α-chitobiose ligand represents wtPNGase F. The remaining 5 models were constructed from the 1PNF reference structure. The average RMSD value for each simulation is listed.

| Structural Model | Ligand | Average RMSD (Å) |
|---|---|---|
| R911 Dyn | GlcNAcβ1-4GlcNAc-αOH | 1.3377 |
| R911 C60A Dyn | GlcNAcβ1-4GlcNAc-αOH | 1.3061 |

Figure 39:
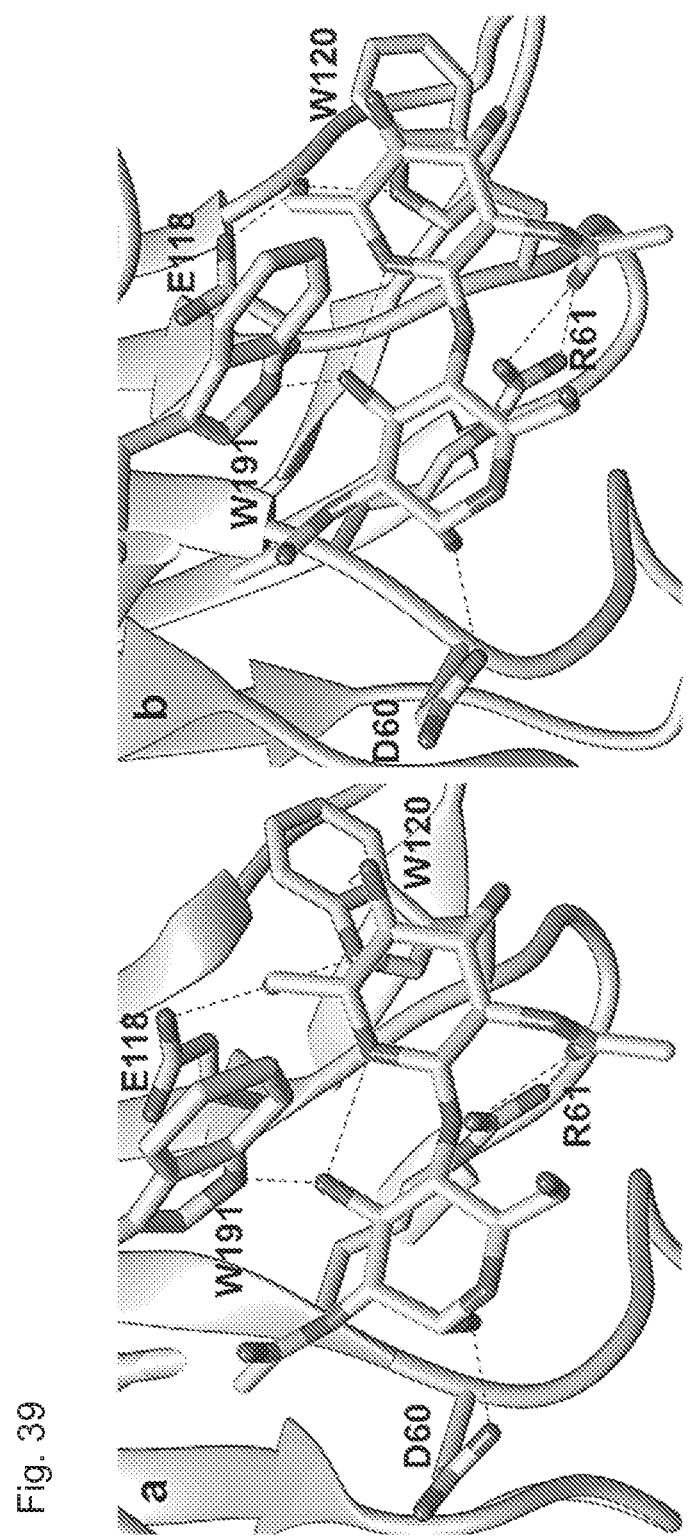
FIG. 39 shows experimental and theoretical hydrogen bonds. Seven hydrogen bonds between wtPNGase F residues D60, R61, E118, W120 and W191 and the chitobiose ligand (outlined) are depicted by the dashed lines. a) Hydrogen bonds reported in the experimental 1PNF x-ray crystallography data. b) Theoretical hydrogen bonds computed from 1PNF MD simulation data.

In addition to confirming the stability of the simulations, reproducibility of experimentally observed hydrogen bond lengths in 1PNF X-ray data was confirmed. The therorectical hydrogen bonds lengths between protein and the N,N'-diacetylchitobiose disaccharide (GlcNAcβ1-4GlcNAc-αOH) ligand in the 1PNF (wtPNGase F) MD simulation are compared to the experimentally determined hydrogen bond lengths in Table 19 and depicted in FIG. 39. The MD simulation of the 1PNF model accurately reproduced experimental hydrogen bond lengths. Since the other models are derived from 1PNF and consistent RMSD values across all models indicated structural stability, it was assumed that the remainder of the models were structurally valid as there was no experimental hydrogen bond length data for the R911 and R911 C60A clones.

TABLE 19

Experimental and theoretical hydrogen bond lengths observed between chitobiose and PNGase F. *The 316 O1 atom of the anomeric hydroxyl in the 1PNF x-ray crystal model is renumbered to 315 O1 in the 1PNF MD simulation.

| Hydrogen bonds | 1PNF X-ray Data (Å)[1] | Average from 1PNF MD Simulation (Å) |
|---|---|---|
| D60-Oδ-GlcNAc316 O1* | 2.64 | 2.64 ± 0.11 |
| D60-O-GlcNAc316 NAc | 2.86 | 3.03 ± 0.17 |
| R61-NH-GlcNAc317 OAc | 2.84 | 2.85 ± 0.14 |
| R61-NH-GlcNAc316-O4 | 2.81 | 2.97 ± 0.16 |
| R61-NH2-GlcNAc317 OAc | 2.99 | 3.11 ± 0.21 |
| E118-Oε-GlcNAc317-O6 | 2.57 | 2.75 ± 0.18 |
| W120-Nε-GlcNAc317-O6 | 2.90 | 3.10 ± 0.19 |
| W191-Nε-GlcNAc316-O3 | 2.80 | 3.00 ± 0.15 |

Energy Convergence and MM-GBSA of Rotamer Models

Figure 40:
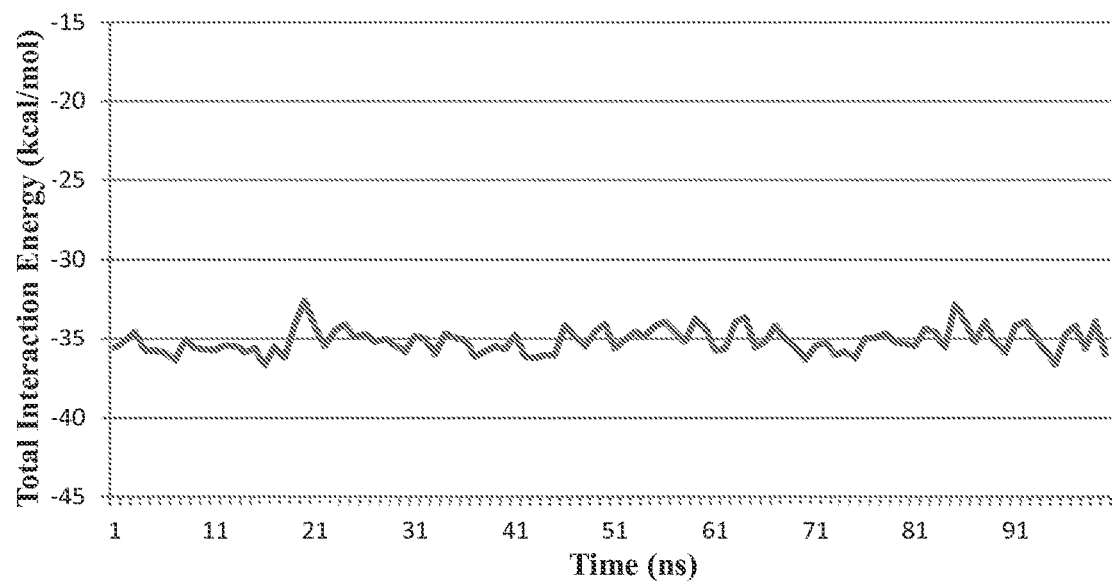
FIG. 40 shows interaction energy stability during 100 ns 1PNF MD simulation.
Figure 41:
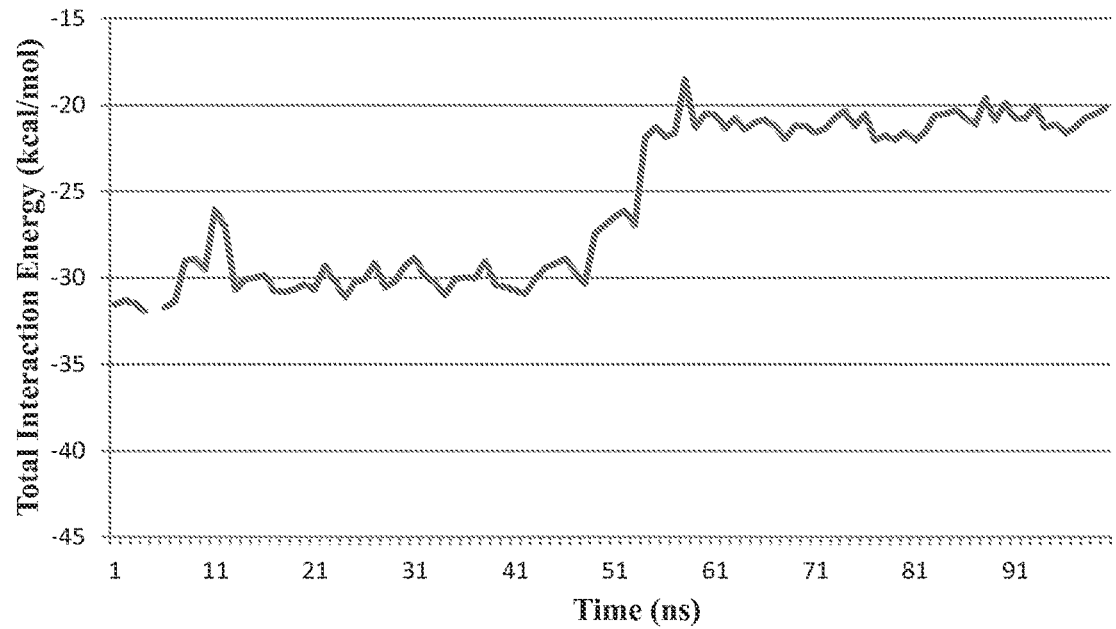
FIG. 41 shows interaction energy stability during 100 ns R911 Dun MD simulation. Interaction energy does not stabilize until after 55 ns into the simulation. Energy data at 5 ns could not be obtained due to loss of data caused by hardware failure of computing node.
Figure 42:
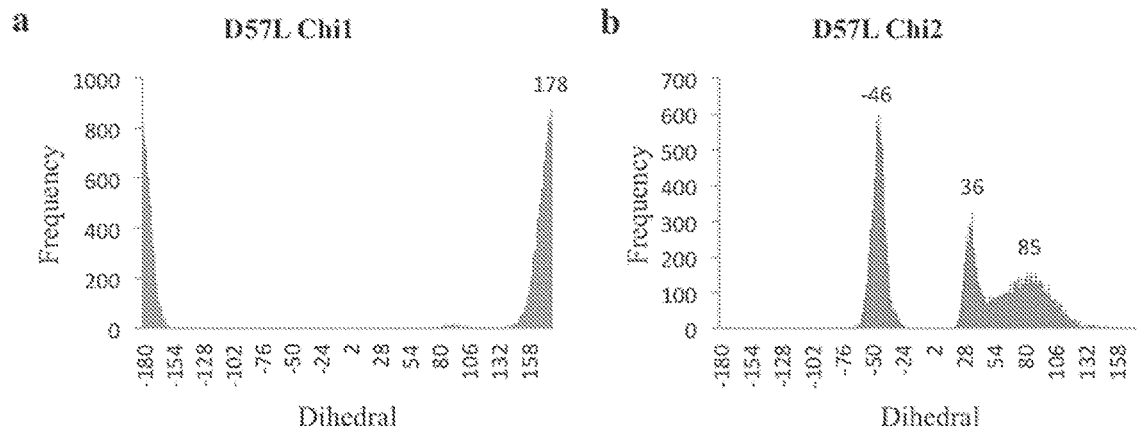
FIG. 42 shows D57L rotamer histograms of Chi1 and Chi2 dihedral angles.
Figure 43:
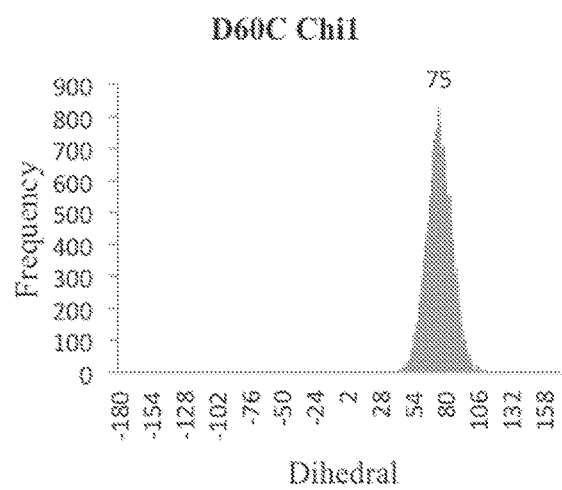
FIG. 43 shows D60C rotamer histogram of Chi1 dihedral angle.
Figure 46:
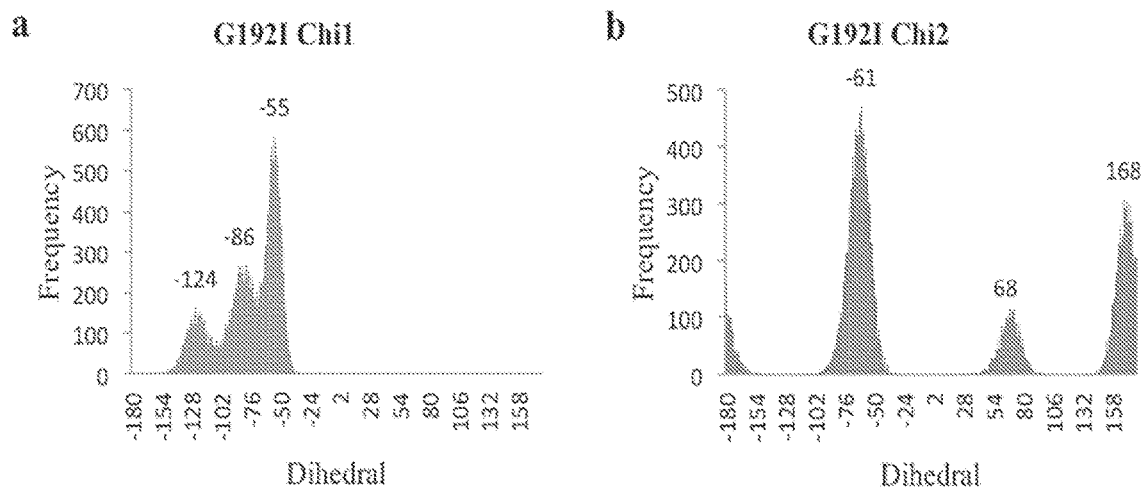
FIG. 46 shows G192I rotamer histograms of Chi1 and Chi2 dihedral angles.
Figure 47:
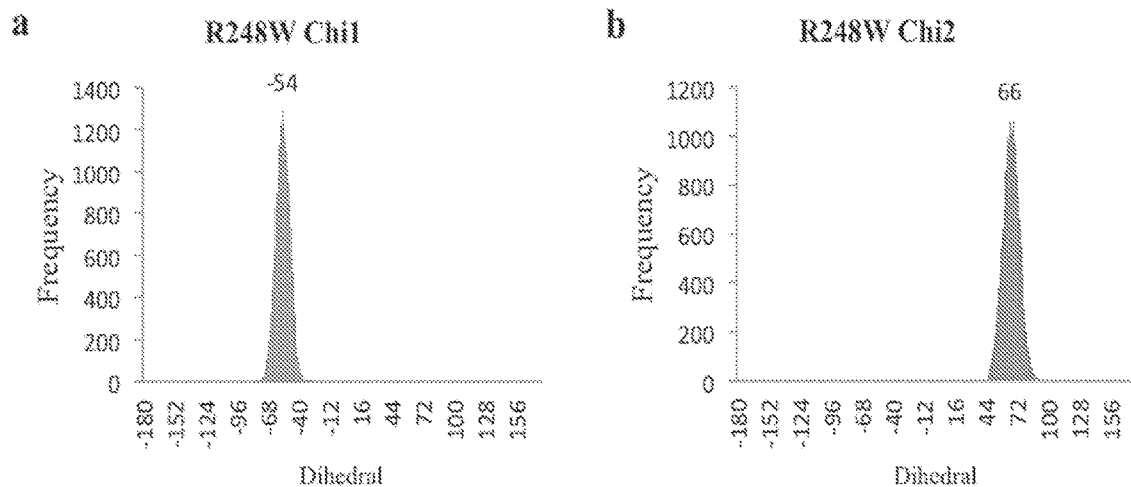
FIG. 47 shows R248W rotamer histograms of Chi1 and Chi2 dihedral angles.

After confirming that the MD simulation of the complex was stable and consistent with experimental structural data, interaction energy was computed at a 1 ns interval over the duration of the 100 ns MD trajectory. FIG. 40 shows stable interaction energy over trajectory time indicating energy convergence for the 1PNF MD simulation during the 100 ns MD simulation. In comparison, FIG. 41 shows lack of energy convergence during the first 54 ns of the R911 Dun MD simulation. Unlike the R911 Dun MD simulation, the R911 Dyn simulation had stable interaction energy throughout the 100 ns simulation. Analysis of the R911 Dun conformations before and after the 10 kcal/mol interaction energy transition at 54 ns indicated that the conformations during the latter half of the simulation is similar to the R911 Dyn MD simulation. This is specifically observed in the orientation of the R911 D57L mutation that destabilizes R61 hydrogen bonds with the N-acetyl group of the second GlcNAc. The R911 Dynameomics model adopts this conformation during energy minimization & equilibration and remains stable in this conformation throughout the 100 ns production run. However the R911 Dunbrack model only adopts the altered R61 orientation in the latter half of the simulation. This would indicate that the Dunbrack model is taking longer to adopt the altered R61 orientation relative to the R9 11 dynameomics model. Thus, the selection of the latter half of the R911 Dun MD simulation for molecular mechanics generalized Born surface area (MM-GBSA) analysis is rationalized in part by the altered conformation of the R61 which is consistent in both R911 Dunbrack and R911 Dynameomics trajectories. This also demonstrates the importance of longer simulation runs employed in this study to accommodate the sampling requirements to reach energy convergence. Energy convergence analysis of the other MD simulations with the chitobiose (GlcNAcβ1-4GlcNAc-αOH) ligand indicated all simulations had reached structural convergence after the first 60 ns. Therefore, MD production data from the converged portion of the trajectory (last 40 ns) was subjected to MM-GBSA energy analysis.

The binding energy was decomposed into contributions from direct electrostatic interactions, polar and non-polar desolvation and van der Waals contacts, employing the MM-GBSA method.[4] The MM-GBSA procedure yielded total interaction energy of −35.1 kcal/mol for wtPNGase F (1PNF). This values overestimates the experimental binding free energy of −7.1 kcal/mol for wtPNGase F (Table 10), which is a typical characteristic of MM-GBSA calculations that omit entropic penalties associated with ligand binding.[4] Entropic effects, arising from changes in conformational flexibility can be estimated, but may require very long MD simulations in order to achieve convergence.[5] However, it may be anticipated that entropic effects arising from reduction in the flexibility of protein side chains will be most significant for those residues that interact strongly with the ligand, and least significant for the tepid or cold residues. For these reasons, the entropic contributions were not computed. Furthermore, conserved water molecules are not included in these MM-GBSA energy estimations and the lack of conserved waters may yield inaccurate estimated energies for E206S, D60C, and R248W, sites that are known to interact with conserved water molecules in the wild-type PNGase F complex experimental X-ray data.[1] In addition, due to approximations made in estimating the decomposed per residue contributions, computed binding energies may have relatively high error, thus making quantitative assessment impermissible. Therefore, qualitative analysis of MM-GBSA data is appropriate.[6]

Since 1PNF represents the structure of the wtPNGase F enzyme, the D60A single point mutant, which was used as a non-affinity optimized experimental control, was similarly used as a control structural model for comparison against the R911 and R911 C60A Dunbrack and Dynameomics rotamer models. The estimated per residue $\Delta G_{BINDING}$ (kcal/mol) energies of the mutagenized residues from these 6 MD simulations with the chitobiose (GlcNAcβ1-4GlcNAc-αOH) ligand are presented in Table 20.

TABLE 20

Estimated MM-GBSA interaction action energies of rotamer models. Sub-total $\Delta G_{BINDING}$ (kcal/mol) of mutagenized residues were compared across 1PNF (wtPNGase F), D60A, and all 4 rotamer models complexed with the chitobiose (GlcNAcβ1-4GlcNAc-αOH) ligand. Sub-total $\Delta\Delta G_{BINDING}$ (kcal/mol) energies relative to the D60A control clone indicated that the Dynameomics rotamer models of R911 and R911 C60A best approximated experimental binding free energy ($\Delta\Delta G_{BIND\text{-}EXP}$) trends (bold), unlike the Dunbrack models (italic).

| Residue | 1PNF wtPNGase F | D60A | R911 Dun | R911 C60A Dun | R911 Dyn | R911 C60A Dyn |
|---|---|---|---|---|---|---|
| D57/-/L | −0.3 ± 0.7 | −0.3 ± 0.7 | −0.1 ± 0.0 | −0.1 ± 0.0 | −0.1 ± 0.0 | 0.0 ± 0.0 |
| D60/A/C/A | −1.8 ± 1.7 | −2.1 ± 1.2 | −1.5 ± 0.5 | −0.8 ± 1.1 | −4.5 ± 0.5 | −0.1 ± 0.2 |
| I156/-/L | −1.1 ± 0.2 | −1.0 ± 0.3 | −0.2 ± 0.1 | −0.9 ± 0.2 | −0.1 ± 0.0 | −0.1 ± 0.1 |
| G192/-/I | 0.0 ± 0.1 | 0.0 ± 0.1 | −0.9 ± 0.3 | −0.9 ± 0.3 | −0.8 ± 0.2 | −2.9 ± 0.5 |
| E206/-/S | 0.7 ± 0.9 | 0.7 ± 0.9 | −0.1 ± 0.3 | −0.1 ± 0.3 | −0.1 ± 0.0 | −1.1 ± 0.9 |
| R248/-/W | −0.1 ± 0.5 | −0.1 ± 0.5 | −0.1 ± 0.1 | 0.2 ± 0.1 | −0.6 ± 0.1 | −0.5 ± 0.2 |
| Sub-total | −2.7 ± 1.0 | −2.8 ± 0.8 | −2.9 ± 0.3 | −2.6 ± 0.5 | −6.1 ± 0.2 | −4.6 ± 0.5 |
| $\Delta G_{BINDING}$ Sub-total | −0.0 ± 1.2 | — | −0.2 ± 0.8 | 0.2 ± 0.9 | −3.4 ± 0.8 | −1.9 ± 0.9 |
| $\Delta\Delta G_{BINDING}$ | | | | | | |
| $\Delta\Delta G_{BIND\text{-}EXP}$ | 0.5 | — | −1.9 | −0.7 | −1.9 | −0.7 |

The total $\Delta G_{BINDING}$ for 1PNF (−2.7 kcal/mol) and D60A (−2.8 kcal/mol) are similar, and indicate that the D60A mutation is slightly energetically favourable, consistent with previous analysis (Table 4). The experimental $\Delta\Delta G_{BIND\text{-}EXP}$ of 1PNF relative to the D60A model confirms that the D60A mutation is energetically favourable by −0.5 kcal/mol. Comparison of the Dunbrack rotamer models, R911 Dun and R911 C60A Dun, relative to D60A indicates that estimated $\Delta\Delta G_{BINDING}$ interaction energies are not significantly different than 1PNF. The results from the Dunbrack models are inconsistent with experimental data. However, comparison of the Dynameomics rotamer models, R911 Dyn and R911 C60A Dyn, relative to D60A confirms interaction energy trends consistent with experimental data. Specifically, the R911 C60A mutation relative to R911 has relatively unfavorable interaction energy, but not worse than 1PNF. This data also supports the importance of the D60C mutation in R911 for affinity enhancement relative to 1PNF and D60A. Based on the reproducibility of the experimental interaction energies, romater conformations of the mutagenized residues were determined from the MD simulation. Furthermore, the Dynameomic rotamer models, R911 Dyn and R911 C60A Dyn, were selected for MD simulations using additional glycan and glycotripeptide ligands.

Rotamer Conformations from R911 Dyn MD Simulation

Figure 48:
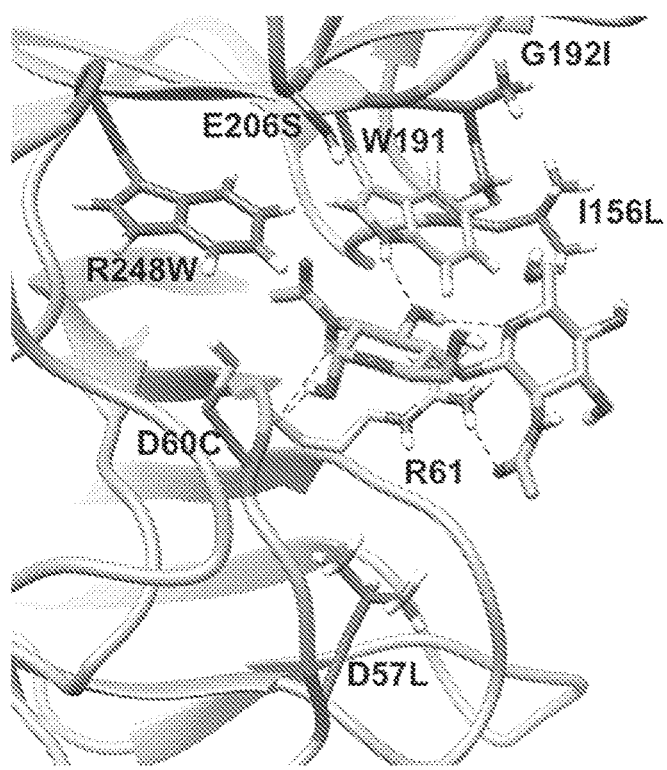
FIG. 48 shows R911 Dyn MD simulation hydrogen bonds and preferred rotamers. Five theoretical hydrogen bonds between R911 residues D60C, R61 and W191 and the chitobiose ligand (outlined) are depicted by dashed lines. Rotamers of R911 mutations (orange) are depicted in the most frequent orientation extracted from the simulation trajectory at 73 ns.

Rotamer dihedral angles of mutagenized residues from the R911 Dyn MD simulation were extracted from the energetically converged portion of the trajectory (last 40 ns). Dihedral angle frequency histograms were plotted to identify preferred dihedral angles of all 6 mutagenized residues (FIGS. 42-47). The preferred rotamer conformations were identified and are listed in Table 21. Four rotamers had multiple preferred conformations (D57L Chi2, E206S Chi1, G192I Chi1, and G192I Chi2). Therefore, the most preferred combination of rotamers were identified based on frequency of occurrence in extracted frames from the last 40 ns of the converged trajectory (Table 22). It was assumed that the most frequent set of rotamer combinations represents the most favored orientation for ligand interaction. A snapshot from the trajectory depicting the most favored set of rotamer conformations from the R911 Dyn MD simulation are shown in FIG. 48.

TABLE 21

Rotamer conformations from R911 Dyn MD simulation. Preferred rotamer dihedral angels are listed for all 6 mutagenized residues (*). The selected Dynameomics rotamer (Dyn) representing the initial conformation at the start of the MD simulation are include for comparison.

| R911 Residue | Rotamer Source | Conformation | | Probablity (%) | Average Angles | | Clashes |
|---|---|---|---|---|---|---|---|
| | | Chi1 | Chi2 | | Chi1 | Chi2 | |
| D57L | Dyn | t | g+ | 24.05 | 183.0 | 66.6 | 4 |
| D57L* | MD | t | g− | 41.80 | 178.0 | −46.0 | |
| D57L | MD | t | g+ | 22.59 | 178.0 | 36.0 | |
| D57L | MD | t | g+ | 35.60 | 178.0 | 85.0 | |
| D60C | Dyn | g+ | | 15.05 | 54.8 | | 0 |
| D60C* | MD | g+ | | 99.00 | 75.0 | | |
| I156L | Dyn | g− | t | 65.19 | 292.0 | 168.5 | 4 |
| I156L* | MD | t | g+ | 99.00 | −180.0 | 59.0 | |
| G192I | Dyn | t | g+ | 1.41 | 184.1 | 68.3 | 13 |
| G192I* | MD | g− | g− | 84.06 | −55.0 | −61.0 | |
| G192I | MD | g− | g− | 15.94 | −86.0 | −61.0 | |
| E206S | Dyn | g− | | 73.06 | 310.9 | | 0 |
| E206S | MD | g+ | | 54.65 | 69.0 | | |
| E206S* | MD | g− | | 45.35 | −77.0 | | |
| R248W | Dyn | g− | g− | 28.21 | 294.7 | 98.5 | 7 |
| R248W* | MD | g− | g− | 99.00 | −54.0 | 66.0 | |

TABLE 22

Frequency of preferred rotamer combinations in R911 Dyn MD simulation. The frequency of preferred set of rotamer dihedral angles is listed. The most frequent set of rotamer conformations is indicated in bold type and depicted in FIG. 48.

| Frequency | D57L Chi2 | G192I Chi1 | G192I Chi2 | E206S Chi1 | Probability % |
|---|---|---|---|---|---|
| 1570 | −46 | −55 | −61 | −77 | 22.52 |
| 1477 | 85 | −55 | −61 | 69 | 21.19 |
| 949 | −46 | −55 | −61 | 69 | 13.61 |
| 868 | 36 | −55 | −61 | 69 | 12.45 |
| 565 | 85 | −55 | −61 | 77 | 8.11 |
| 431 | 36 | −55 | −61 | −77 | 6.18 |
| 303 | −46 | −86 | −61 | −77 | 4.35 |
| 287 | 85 | −86 | −61 | 69 | 4.12 |
| 153 | 85 | −86 | −61 | 77 | 2.19 |
| 139 | 36 | −86 | −61 | −77 | 1.99 |
| 137 | 36 | −86 | −61 | 69 | 1.97 |
| 92 | −46 | −86 | −61 | 69 | 1.32 |

MD Simulations and Binding Free Energy Decomposition (MM-GBSA) of PNGase F Clones with N-Glycan and N-Glycotripeptide Ligands Using the previously validated R911 and R911 C60A Dynameomics structural models as well as 1PNF and D60A models, 100 ns MD simulations were conducted with modified ligands. One set of four simulations was conducted with the β-chitobiose ligand (GlcNAcβ1-4GlcNAc-βOH) given that the attachment of the oligosaccharide moiety to $N_\delta$ of the asparagine is in the β-configuration. The 1PNF structure of the wtPNGase F enzyme co-crystalized with α-chitobiose ligand, even though in solution an equilibrium state containing a mixture of both α- and β-anomeric configurations of the $O_1$ hydroxyl group on the reducing end exists.[1] A second set of four simulations was conducted with the asparagine-linked glycotripeptide motif, GlcNAcβ1-4Glc-NAc-β-Asn-X[-P]-Thr, recognized by wtPNGase F. Substrate requirement studies with PNGase F have confirmed that this is the essential motif required for optimal catalytic activity.[7] As RNase B was used as the N-glycan bearing glycoprotein target for experimental studies, the RNase B peptide sequence was used for the essential glycotripeptide ligand (GlcNAcβ1-4GlcNAc-β-Asn-Leu-Thr). In addition, residue E206 of the 1PNF and D60A models was modified to reflect the protonated state of the carboxyl group (GLH206). Optimal catalytic activity for the wtPNFase F is reported around pH 8.0-8.5, thus protonation of glutamate ($pK_a$ ~4.1) would normally be unlikely. However, point mutant studies of the neighboring hydrophobic tryptophan residues 207 and 251 indicate that a hydrophobic environment is critical for catalytic activity, and that this hydrophobic environment would raise the $pK_a$ of E206, potentially to ~8.5.[8,9]

Analysis of PNGase F Clones Complexed with the Fi-Chitobiose Ligand

Stable simulation trajectories of all models were confirmed by RMSD analysis, followed by energy convergence analysis to confirm stable interaction energies. As with the prior rotamer model studies, data from the converged portion of the trajectories was subjected to MM-GBSA energy analysis. Table 23 summarizes the models of the PNGase F clones complexed with the β-chitobiose ligand used for MD simulations, the calculated average RMSD, and the estimated relative binding energies.

Estimated total theoretical binding free energy (Total $\Delta G_{BINDING}$) of all clones overestimate the experimental binding free energy ($\Delta\Delta G_{BIND-EXP}$) due to the omission of entropic penalties as previously discussed.[4,5] Relative $\Delta\Delta G_{BINDING}$ interaction energies of the 6 mutagenized residues for the 3-chitobiose ligand simulations reproduced the experimental observed interaction energy trends. The wtPNGase F enzyme has marginally less favorable total interaction energy (0.1 kcal/mol) relative to D60A whereas both R911 (−1.8 kcal/mol) and R911 C60A (−0.5 kcal/mol) have favorable interaction energies relative to D60A, with R911 being more favorable than R911 C60A.

TABLE 23

Structural models of wtPNGase F and clones used for MD simulations and MM-GBSA. Structural models with the β-chitobiose ligand in the binding pocket were constructed to conduct 100 ns MD simulations. Simulation stability was confirmed by analyzing RMSD over simulation time and the average RMSD values are listed. Estimated total theoretical binding energy for all 314 amino acids (Total $\Delta G_{BINDING}$) of each clone are listed (kcal/mol). Estimated theoretical binding interaction energy (Sub-total $\Delta\Delta G_{BINDING}$) comprised only of the 6 mutagenized residues of all clones relative to D60A are listed (kcal/mol). For comparison, experimental binding free energy ($\Delta\Delta G_{BIND-EXP}$) of all clones relative to D60A are also listed (kcal/mol).

| Structural Model | Ligand | RMSD (Å) | Total $\Delta G_{BINDING}$ | Sub-total $\Delta\Delta G_{BINDING}$ | $\Delta\Delta G_{BIND-EXP}$ |
|---|---|---|---|---|---|
| 1PNF | GlcNAcβ1-4GlcNAc-βOH | 1.2440 | −39.1 | 0.1 ± 1.3 | 0.5 |
| D60A | GlcNAcβ1-4GlcNAc-βOH | 1.2674 | −31.5 | — | — |
| R911 Dyn | GlcNAcβ1-4GlcNAc-βOH | 1.2944 | −17.9 | −1.8 ± 1.1 | −1.9 |
| R911 C60A Dyn | GlcNAcβ1-4GlcNAc-βOH | 1.2890 | −18.3 | −0.5 ± 1.0 | −0.7 |

MM-GBSA energy analysis and per-residue contributions were computed to determine over the converged portion of the β-chitobiose ligand trajectories (last 40 ns) were used for $\Delta\Delta G_{BINDING}$ relative to D60A. Decomposed energy contributions consist of the total molecular mechanical interaction energy ($\Delta E_{MM}$), comprised of the sum of van der Waals ($\Delta E_{VDW}$) and electrostatics ($\Delta E_{ELE}$) components. The total binding free energy ($\Delta G_{BINDING}$) is comprised of the generalized Born approximation of polar and non-polar solvation components ($\Delta G_{GB+SA}$) and $\Delta E_{MM}$. The interaction energies (of the 6 residues mutagenized in wtPNGase F) for all 4 models (1PNF, D60A, R911 Dyn, R911 C60A Dyn) complexed with β-chitobiose are summarized in Tables 24-27.

TABLE 24

MM-GBSA of 1PNF complexed with β-chitobiose. Estimated per residue contributions to the binding free energy (kcal/mol) for wtPNGase F complexed with β-chitobiose are shown. The interaction energy consists of only the 6 residues selected for mutagenesis via directed evolution for the R911 clones. Residues required for catalytic activity are indicated in bold.

| Key Contact Zone Residues | $\Delta E_{VDW}$ | $\Delta E_{ELE}$ | $\Delta E_{MM}$ | $\Delta G_{GB+SA}$ | $\Delta G_{BINDING}$ |
|---|---|---|---|---|---|
| D57 | −0.1 | 1.9 | 1.8 | −2.2 | −0.4 ± 0.5 |
| D60 (nucleophile) | −0.8 | −14.7 | −15.6 | 13.5 | −2.1 ± 1.4 |
| I156 | −0.9 | 0.2 | −0.7 | −0.4 | −1.1 ± 0.2 |
| G192 | −0.1 | −0.2 | −0.3 | 0.2 | 0.0 ± 0.1 |
| E206 | −0.6 | 5.3 | 4.7 | −3.7 | 1.0 ± 0.9 |
| R248 | −0.1 | −0.7 | −0.8 | 0.7 | −0.1 ± 0.4 |
| Sub-total Interaction Energy $\Delta G_{BINDING}$ | −2.7 | −8.2 | −10.9 | 8.2 | −2.7 ± 0.8 |

TABLE 25

MM-GBSA of D60A complexed with β-chitobiose. Estimated per residue contributions to the binding free energy (kcal/mol) for D60A complexed with β-chitobiose are shown. The interaction energy consists of only the 6 residues selected for mutagenesis via directed evolution for the R911 clones.

| Key Contact Zone Residues | $\Delta E_{VDW}$ | $\Delta E_{ELE}$ | $\Delta E_{MM}$ | $\Delta G_{GB+SA}$ | $\Delta G_{BINDING}$ |
|---|---|---|---|---|---|
| D57 | −0.1 | 2.3 | 2.2 | −2.5 | −0.3 ± 0.5 |
| D60A | −1.0 | −2.5 | −3.5 | 1.7 | −1.8 ± 0.4 |
| I156 | −0.9 | 0.2 | −0.7 | −0.4 | −1.1 ± 0.2 |
| G192 | −0.1 | 0.0 | −0.1 | 0.1 | 0.0 ± 0.1 |
| E206 | −0.6 | 2.6 | 1.9 | −1.2 | 0.7 ± 2.0 |
| R248 | −0.1 | −1.9 | −2.1 | 1.9 | −0.2 ± 0.5 |
| Sub-total Interaction Energy $\Delta G_{BINDING}$ | −3.0 | 0.7 | −2.3 | −0.2 | −2.7 ± 1.0 |

TABLE 26

MM-GBSA of R911 Dyn complexed with β-chitobiose. Estimated per residue contributions to the binding free energy (kcal/mol) for R911 complexed with β-chitobiose are shown. The interaction energy consists of only the 6 residues selected for mutagenesis via directed evolution for the R911 clones.

| Key Contact Zone Residues | $\Delta E_{VDW}$ | $\Delta E_{ELE}$ | $\Delta E_{MM}$ | $\Delta G_{GB+SA}$ | $\Delta G_{BINDING}$ |
|---|---|---|---|---|---|
| D57L | −0.1 | −0.1 | −0.1 | 0.1 | −0.1 ± 0.1 |
| D60C | −0.2 | 0.2 | 0.0 | −0.2 | −0.2 ± 0.2 |
| I156L | −0.3 | 0.2 | −0.1 | −0.2 | −0.3 ± 0.2 |
| G192I | −1.8 | −2.3 | −4.1 | 1.0 | −3.1 ± 0.6 |
| E206S | −0.5 | −0.9 | −1.4 | 1.0 | −0.4 ± 0.4 |
| R248W | −0.4 | −0.1 | −0.6 | 0.2 | −0.4 ± 0.2 |
| Sub-total Interaction Energy $\Delta G_{BINDING}$ | −3.4 | −2.9 | −6.3 | 1.8 | −4.5 ± 0.4 |

TABLE 27

MM-GBSA of R911 C60A Dyn complexed with β-chitobiose. Estimated per residue contributions to the binding free energy (kcal/mol) for R911 C60A complexed with β-chitobiose are shown. The interaction energy consists of only the 6 residues selected for mutagenesis via directed evolution for the R911 clones.

| Key Contact Zone Residues | $\Delta E_{VDW}$ | $\Delta E_{ELE}$ | $\Delta E_{MM}$ | $\Delta G_{GB+SA}$ | $\Delta G_{BINDING}$ |
|---|---|---|---|---|---|
| D57L | −0.1 | −0.1 | −0.2 | 0.1 | −0.1 ± 0.0 |
| D60A | −1.0 | −2.5 | −3.4 | 1.9 | −1.6 ± 0.2 |
| I156L | −0.1 | 0.0 | −0.1 | 0.0 | −0.1 ± 0.0 |
| G192I | −0.9 | −0.2 | −1.1 | 0.1 | −1.0 ± 0.3 |
| E206S | −0.2 | −0.6 | −0.7 | 0.6 | −0.1 ± 0.0 |
| R248W | −0.6 | 0.3 | −0.3 | 0.0 | −0.3 ± 0.1 |
| Sub-total Interaction Energy $\Delta G_{BINDING}$ | −2.9 | −3.0 | −5.9 | 2.7 | −3.2 ± 0.2 |

Analysis of the decomposed energy indicates that both G192 and E206 in wtPNGase F and the D60A clone have unfavorable $\Delta G_{BINDING}$ interaction energy, consistent with the 5 ns MD simulation energy decomposition results used to identify tepid and hot residues for library design (Table 3). The yeast-display selected mutations G192I and E206S contribute favorably towards the estimated interaction energy of R911 and R911 C60A. In addition, the D57L, I156L, and R248W mutations are also estimated to have slightly favorable interaction energies.

TABLE 28

Estimated MM-GBSA theoretical interaction action energies of models complexed with β-chitobiose. Sub-total $\Delta G_{BINDING}$ (kcal/mol) of mutagenized residues were compared across 1PNF (wtPNGase F), D60A, R911 Dyn, and R911 C60A Dyn. Sub-total $\Delta\Delta G_{BINDING}$ (kcal/mol) energies relative to the D60A control clone are indicated. For comparison, experimentally determined binding interaction energy ($\Delta\Delta G_{BIND-EXP}$) of clones is also listed relative to D60A.

| Residue | 1PNF (GLH206) | D60A (GLH206) | R911 Dyn | R911 C60A Dyn |
|---|---|---|---|---|
| D57/—/L | −0.4 ± 0.5 | −0.3 ± 0.5 | −0.1 ± 0.1 | −0.1 ± 0.0 |
| D60/A/C/A | −2.1 ± 1.4 | −1.8 ± 0.4 | −0.2 ± 0.2 | −1.6 ± 0.2 |
| I156/—/L | −1.1 ± 0.2 | −1.1 ± 0.2 | −0.3 ± 0.2 | −0.1 ± 0.0 |
| G192/—/I | 0.0 ± 0.1 | 0.0 ± 0.1 | −3.1 ± 0.6 | −1.0 ± 0.3 |
| E206/—/S | 1.0 ± 0.9 | 0.7 ± 2.0 | −0.4 ± 0.4 | −0.1 ± 0.0 |
| R248/—/W | −0.1 ± 0.4 | −0.2 ± 0.5 | −0.4 ± 0.2 | −0.3 ± 0.1 |
| Sub-total $\Delta G_{BINDING}$ | −2.7 ± 0.8 | −2.7 ± 1.0 | −4.5 ± 0.4 | −3.2 ± 0.2 |
| Sub-total $\Delta\Delta G_{BINDING}$ | 0.1 ± 1.3 | — | −1.8 ± 1.1 | −0.5 ± 1.0 |
| $\Delta\Delta G_{BIND-EXP}$ | 0.5 | — | −1.9 | −0.7 |

A comparison of the theoretical $\Delta G_{BINDING}$ interaction energy of all clones with the β-chitobiose ligand is provided in Table 28. Experimental binding energies of the clones relative to D60A ($\Delta\Delta G_{BIND-EXP}$) is also included. Of particular importance is D60, the residue required for catalytic activity. Both D60 and D60A make significant favorable interactions, whereas D60C, is estimated to have a significantly less favorable contribution of 0.2 kcal/mol. This theoretical data is contrary to experimental data on R911 and the R911 C60A clones, which indicates that the D60C mutation makes a −1.2 kcal/mol greater contribution ($\Delta\Delta G_{BIND-EXP}$) towards the overall R911 binding energy relative to R911 C60A (Table 10). This discrepancy is likely due to the experimental data being generated using denatured RNase B as the N-glycan bearing target ligand, not β-chitobiose as in the MD simulation. This is significant as reports of point mutant studies using D60N, D60E, and D60C, all indicate that D60 is required for catalytic activity.[1, 8] These reports are consistent with the significantly decreased catalytic activity observed for the D60A point mutant (Table 10). The critical role of D60 is also supported by 1PNF crystal structure data indicating D60 directly interacts with the anomeric hydroxyl of the reducing GlcNAc of the bound chitobiose ligand.[1] In the case of a glycopeptide, the anomeric hydroxyl would be replaced with the glycosidic bond that the enzyme hydrolyzes. Furthermore, substrate specificity requirement studies with wtPNGase F enzyme demonstrate that the enzyme recognizes both the asparagine-linked carbohydrate moiety as well as the peptide portion consisting of the N-X-T glycosylation sequone.[7] Therefore, MD simulations with the β-chitobiose ligand can neither sufficiently simulate experimental interactions D60 has at the site of the glycosidic linkage of N-glycans, nor interactions of the wtPNGase enzyme with the peptide sequone common to N-linked glycans.

Analysis of PNGase F Clones Complexed with a Glycotripeptide Ligand

Figure 50:
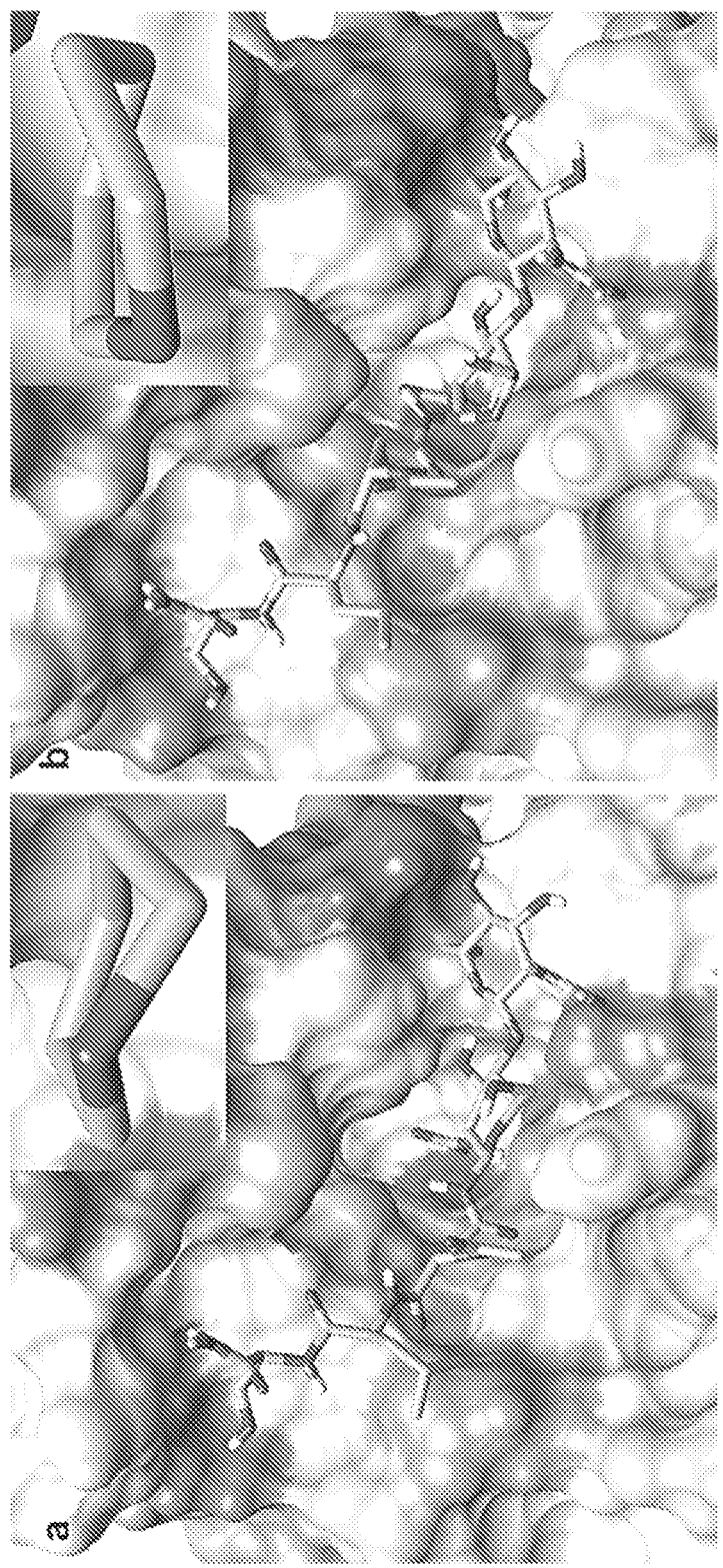
FIG. 50 shows chair and skew-boat ring conformations of reducing GlcNAc in wtPNGase F complexed with glycotripeptide. Surface hydrophobicity depicted of wtPNGase F with glycotripeptide within the binding pocket. a) $^4C_1$ chair conformation of reducing GlcNAc observed during first ~70 ns of MD simulation (60 ns snapshot). Inset shows the $^4C_1$ conformation with ring atoms only. b) Skew-boat conformation during the last 26 ns of the simulation (86 ns snapshot). Inset shows the skew-boat conformation with ring atoms only.
Figure 51:
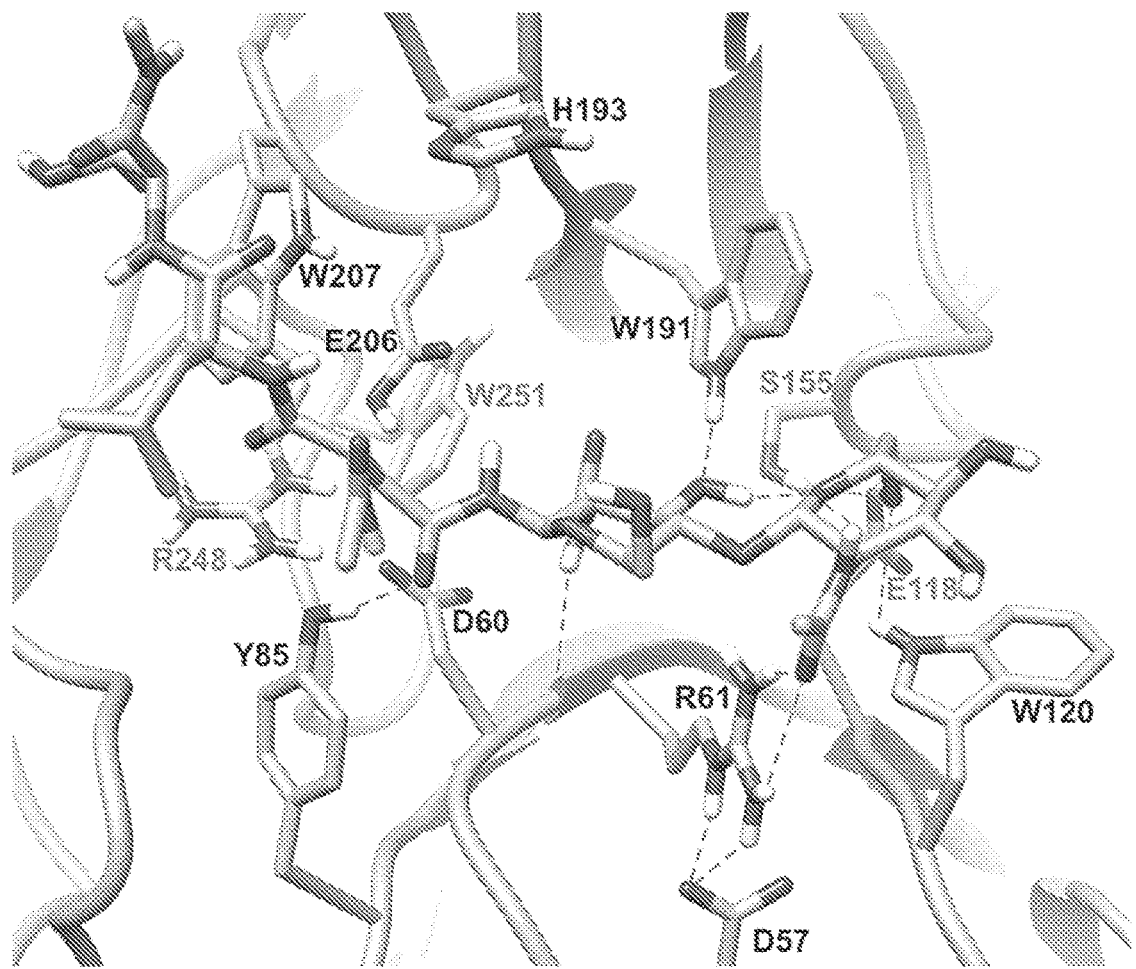
FIG. 51 shows 1PNF (GLH206) and glycotripeptide MD simulation hydrogen bonds at 60 ns time point. Hydrogen bonds are depicted as dashed lines. The glycotripeptide ligand is outlined in green. Amino acid residues critical for catalytic activity (D60 and E206), substrate recognition, and stabilizing interactions are depicted. The simulated hydrogen bonds D60-O -GlcNAc316 NAc and Y85-OH-N316-Oδ (chitobiose-linked asparagine) are depicted towards the center. The reducing GlcNAc is in a $^4C_1$ conformation.
Figure 52:
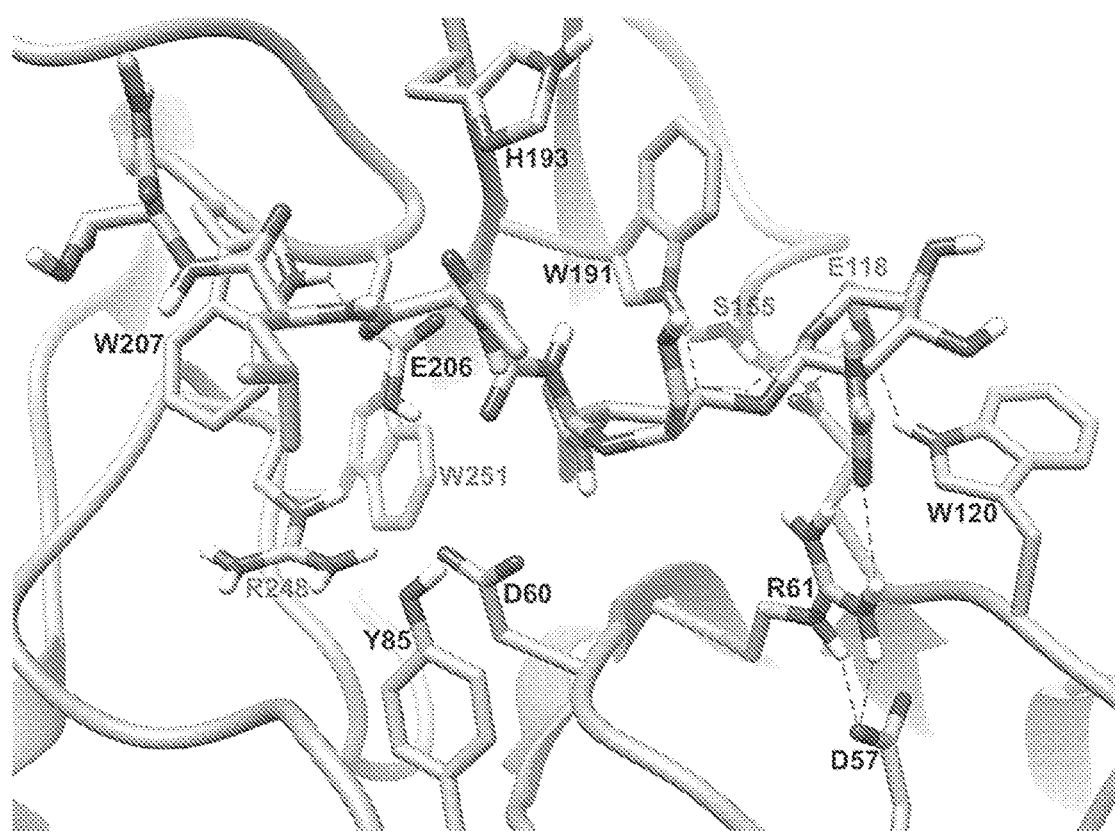
FIG. 52 shows 1PNF (GLH206) and glycotripeptide MD simulation hydrogen bonds at 84 ns time point. Hydrogen bonds are depicted as dashed lines. The glycotripeptide ligand is outlined. Amino acid residues critical for catalytic activity (D60 and E206), substrate recognition, and stabilizing interactions are depicted. The simulated W207-Nε-N316-O (chitobiose-linked asparagine) is depicted towards the top left. The reducing GlcNAc is in a skew-boat conformation.

MD simulations with the clones complexed with the common N-linked glycotripeptide (GlcNAcβ1-4GlcNAc-β-Asn-Leu-Thr) were conducted to more accurately model binding interactions and estimate interaction energies. In order to neutralize terminal charges ($NH_3^+$ for the N-terminal and $COO^-$ for the C-terminal), the peptide portion of the glycotripeptide ligand was modeled with the N-terminal ACE [—C(=O)—CH$_3$] protecting group and the C-terminal NME [—C(=O)—NH—CH$_3$] protecting group as defined in xleap, a component of AMBER Tools 13.[10] Table 29 summarizes the models of the PNGase F clones complexed with a glycotripeptide ligand used for MD simulations, the calculated average RMSD, and the estimated relative binding energies.

normal $^4C_1$ chair conformation (FIGS. 50a & 51) with the Asn-Leu-Thr tripeptide portion relatively stable. The dynamic motion of the Leu and Thr residues is relatively unrestricted but stable, whereas the Asn residue is relatively constrained since the attached chitobiose is held in the binding pocket during the entire simulation. The N-acetyl group of the reducing GlcNAc was extended into a hydrophobic pocket consistent with 1PNF x-ray crystallography data.[1] However, between 71-74 ns, the peptide backbone of the Asn residue rotated towards the protein face aligning across a groove extending diagonally upwards from the chitobiose binding pocket (FIG. 50b). Simulated hydrogen bonds observed between D60-O-GlcNAc316 NAc and Y85-OH-N316-Oδ (chitobiose-linked asparagine) are lost during this conformational change (FIG. 51). Thus bringing the ligand backbone oxygen atom (N316-O) of chitobiose-linked asparagine into proximity of W207 in the extended groove. This orientation results in the formation of a simulated W207-Nε-N316-O hydrogen bond (FIG. 52). This conformation change strains the asparagine side-chain glycosidic bond to shift towards a more axial orientation, resulting in the previously observed $^4C_1$ chair conformation of the reducing GlcNAc to shift into a skew-boat conformation (FIGS. 50b and 52). The observed skew-boat conformation is similar to the Michaelis complex in glycosidic mechanisms.[11, 12] The simulated W207-Nε-N316-O hydrogen bond and the skew-boat conformation of the reducing GlcNAc persisted for the remainder of the simulation (26 ns).

The skew-boat conformation change of the reducing GlcNAc was only observed with the 1PNF (GLH206) complexed with the glycotripeptide ligand and none of the other 1PNF ligand complexes. Similarly, no similar conformational changes were observed in the D60A (GLH206), R911 Dyn, and R911 C60A Dyn trajectories with the glycotripeptide ligand, consistent with stable interaction ener-

TABLE 29

Structure models of wtPNGase F and clones used for MD simulations & MM-GBSA. Structural models with a glycotripeptide ligand in the binding pocket were constructed to conduct 100 ns MD simulations. Simulation stability was confirmed by analyzing RMSD over simulation time and the average RMSD values are listed. Estimated total theoretical binding energy for all 314 amino acids (Total $\Delta G_{BINDING}$) of each clone are listed (kcal/mol). Estimated theoretical binding interaction energy (Sub-total $\Delta\Delta G_{BINDING}$) comprised only of the 6 mutagenized residues of all clones relative to D60A are listed (kcal/mol). For comparison, experimental binding free energy ($\Delta\Delta G_{BIND-EXP}$) of all clones relative to D60A are also listed (kcal/mol).

| Structural Model | Ligand | RMSD (Å) | Total $\Delta G_{BINDING}$ | Sub-total $\Delta\Delta G_{BINDING}$ | $\Delta\Delta G_{BIND-EXP}$ |
|---|---|---|---|---|---|
| 1PNF (GLH206) | GlcNAcβ1-4GlcNAc-β-Asn-Leu-Thr | 1.2238 | −44.0 | 1.6 ± 1.2 | 0.5 |
| D60A (GLH206) | GlcNAcβ1-4GlcNAc-β-Asn-Leu-Thr | 1.1916 | −48.4 | — | — |
| R911 Dyn | GlcNAcβ1-4GlcNAc-β-Asn-Leu-Thr | 1.2705 | −54.4 | −1.4 ± 0.8 | −1.9 |
| R911 C60A Dyn | GlcNAcβ1-4GlcNAc-β-Asn-Leu-Thr | 1.2618 | −51.3 | −1.9 ± 0.8 | −0.7 |

Figure 49:
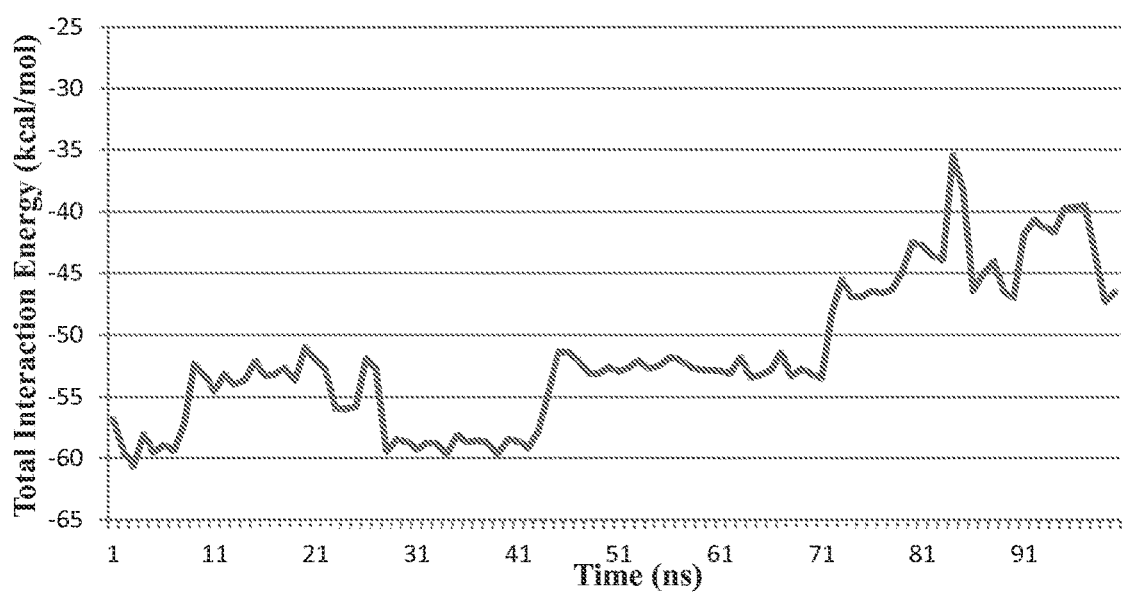
FIG. 49 shows interaction energy stability during 100 ns 1PNF (GLH206) MD simulation with the glycotripeptide ligand. The average interaction energy during 51-70 ns is approximately −52.7 kcal/mol and during 80-100 ns it is −44.0 kcal/mol.

The D60A (GLH206), R911 Dyn, and R911 C60A Dyn glycotripeptide complexed models all had stable interaction energies throughout the simulation. However, the 1PNF (GLH206) trajectory showed interaction energy fluctuations during the simulation (FIG. 49).

Visualization of the 1PNF (GLH206) glycotripeptide trajectory indicated a conformational change between 71-74 ns, consistent with interaction energy fluctuations. During the first 70 ns of the simulation the reducing GlcNAc had a gies. The observed skew-boat conformation indicates a unique interaction between the glycotripeptide and the wtPNGase F enzyme. For this reason, the final 20 ns of the 1PNF (GLH206) trajectory as well as the other three simulations were used for MM-GBSA analysis.

The interaction energies (of the 6 residues mutagenized in wtPNGase F) for all 4 models (1PNF (GLH206), D60A (GLH206), R911 Dyn, R911 C60A Dyn) complexed with the glycotripeptide are summarized in Tables 30-33.

TABLE 30

MM-GBSA of 1PNF (GLH206) complexed with glycotripeptide ligand. Estimated per residue contributions to the binding free energy (kcal/mol) for wtPNGase F complexed with the glycotripeptide (GlcNAcβ1-4GlcNAc-β-Asn-Leu-Thr) are shown. The interaction energy consists of only the 6 residues selected for mutagenesis via directed evolution for the R911 clones. Residues required for catalytic activity are indicated in bold.

| Key Contact Zone Residues | $\Delta E_{VDW}$ | $\Delta E_{ELE}$ | $\Delta E_{MM}$ | $\Delta G_{GB+SA}$ | $\Delta G_{BINDING}$ |
|---|---|---|---|---|---|
| D57 | −0.1 | 1.8 | 1.6 | −1.9 | −0.3 ± 0.7 |
| D60 (nucleophile) | −2.1 | −1.8 | −3.9 | 4.7 | 0.9 ± 1.5 |
| I156 | −0.8 | 0.2 | −0.6 | −0.4 | −0.9 ± 0.2 |
| G192 | −0.3 | 0.7 | 0.4 | −0.5 | −0.1 ± 0.3 |
| E206 | −1.6 | −1.2 | −2.7 | 2.0 | −0.7 ± 0.5 |
| R248 | −0.3 | −3.1 | −3.5 | 3.3 | −0.2 ± 1.2 |
| Sub-total Interaction Energy $\Delta G_{BINDING}$ | −5.2 | −3.3 | −8.6 | 7.2 | −1.4 ± 0.9 |

TABLE 31

MM-GBSA of D60A (GLH206) complexed with glycotripeptide ligand. Estimated per residue contributions to the binding free energy (kcal/mol) for D60A (GLH206) complexed with the glycotripeptide (GlcNAcβ1-4GlcNAc-β-Asn-Leu-Thr) are shown. The interaction energy consists of only the 6 residues selected for mutagenesis via directed evolution for the R911 clones.

| Key Contact Zone Residues | $\Delta E_{VDW}$ | $\Delta E_{ELE}$ | $\Delta E_{MM}$ | $\Delta G_{GB+SA}$ | $\Delta G_{BINDING}$ |
|---|---|---|---|---|---|
| D57 | −0.1 | 1.9 | 1.8 | −2.1 | −0.3 ± 0.5 |
| D60A | −1.0 | −2.8 | −3.8 | 2.3 | −1.5 ± 0.4 |
| I156 | −0.9 | 0.0 | −0.8 | −0.2 | −1.0 ± 0.2 |
| G192 | −0.2 | 0.3 | 0.1 | −0.2 | −0.1 ± 0.1 |
| E206 | −1.3 | 0.3 | −1.0 | 1.1 | 0.1 ± 1.1 |
| R248 | −0.6 | −5.9 | −6.5 | 6.3 | −0.2 ± 1.2 |
| Sub-total Interaction Energy $\Delta G_{BINDING}$ | −4.1 | −6.1 | −10.2 | 7.2 | −3.0 ± 0.8 |

TABLE 32

MM-GBSA of R911 Dyn complexed with a glycotripeptide ligand. Estimated per residue contributions to the binding free energy (kcal/mol) for R911 Dyn complexed with the glycotripeptide (GlcNAcβ1-4GlcNAc-β-Asn-Leu-Thr) are shown. The interaction energy consists of only the 6 residues selected for mutagenesis via directed evolution for the R911 clones.

| Key Contact Zone Residues | $\Delta E_{VDW}$ | $\Delta E_{ELE}$ | $\Delta E_{MM}$ | $\Delta G_{GB+SA}$ | $\Delta G_{BINDING}$ |
|---|---|---|---|---|---|
| D57L | −0.1 | 0.0 | −0.2 | 0.1 | −0.1 ± 0.1 |
| D60C | −1.6 | −2.2 | −3.8 | 2.0 | −1.8 ± 0.7 |
| I156L | −1.0 | −0.1 | −1.1 | 0.1 | −1.0 ± 0.2 |
| G192I | −0.7 | 0.0 | −0.6 | 0.0 | −0.7 ± 0.2 |
| E206S | −0.2 | −0.2 | −0.4 | 0.4 | 0.0 ± 0.1 |
| R248W | −1.1 | −0.1 | −1.2 | 0.4 | −0.8 ± 0.2 |
| Sub-total Interaction Energy $\Delta G_{BINDING}$ | −4.6 | −2.7 | −7.3 | 2.9 | −4.5 ± 0.4 |

TABLE 33

MM-GBSA of R911 C60A Dyn complexed with glycotripeptide ligand. Estimated per residue contributions to the binding free energy (kcal/mol) for R911 C60A Dyn complexed with the glycotripeptide (GlcNAcβ1-4GlcNAc-β-Asn-Leu-Thr) are shown. The interaction energy consists of only the 6 residues selected for mutagenesis via directed evolution for the R911 clones.

| Key Contact Zone Residues | $\Delta E_{VDW}$ | $\Delta E_{ELE}$ | $\Delta E_{MM}$ | $\Delta G_{GB+SA}$ | $\Delta G_{BINDING}$ |
|---|---|---|---|---|---|
| D57L | −0.1 | 0.0 | −0.1 | 0.0 | −0.1 ± 0.0 |
| D60A | −1.2 | −2.8 | −4.0 | 2.3 | −1.7 ± 0.3 |
| I156L | −1.0 | −0.1 | −1.1 | 0.0 | −1.1 ± 0.1 |
| G192I | −0.9 | 0.2 | −0.7 | −0.2 | −0.9 ± 0.1 |
| E206S | −0.4 | −0.3 | −0.7 | 0.6 | −0.1 ± 0.1 |
| R248W | −1.3 | −0.4 | −1.7 | 0.6 | −1.1 ± 0.2 |
| Sub-total Interaction Energy $\Delta G_{BINDING}$ | −4.9 | −3.4 | −8.3 | 3.4 | −4.9 ± 0.2 |

A comparison of the theoretical $\Delta G_{BINDING}$ interaction energy of all clones with the glycotripeptide ligand is provided in Table 34. Interaction energy analysis estimates of 1PNF (GLH206) and D60A (GLH206) indicate that the D60A mutation has favorable interaction energies relative to the wtPNGase F. This is primarily due to more favorable solvation energy ($\Delta G_{GB+SA}$) contributions for D60A relative to D60. These data are consistent with the computational alanine scanning results (Table 4). Relative to the wtPNGase F enzyme, the D60A single point mutant results in more favorable total interaction energy (of the 6 residues indicated) by −1.6 kcal/mol ($\Delta\Delta G_{BINDING}$) relative to 1PNF (GLH206). This is supported by several other data: 1) the stable interaction energy of D60A relative to 1PNF over the course of the simulation, 2) the lack of glycopeptide conformational change as observed with the 1PNF (GLH206) simulation data, and 3) the experimental binding energy of D60A is −0.5 kcal/mol more favorable than the wtPNGase F enzyme.

TABLE 34

Estimated MM-GBSA theoretical interaction energies of models complexed with a glycotripeptide ligand. Sub-total $\Delta G_{BINDING}$ (kcal/mol) of mutagenized residues were compared across 1PNF (GLH206), D60A (GLH206), R911 Dyn, and R911 C60A Dyn complexed with (GlcNAcβ1-4GlcNAc-β-Asn-Leu-Thr). Sub-total $\Delta\Delta G_{BINDING}$ (kcal/mol) energies relative to the D60A control clone are indicated. For comparison, experimentally determined binding interaction energy ($\Delta\Delta G_{BIND-EXP}$) of clones is also listed relative to D60A.

| Residue | 1PNF (GLH206) | D60A (GLH206) | R911 Dyn | R911 C60A Dyn |
|---|---|---|---|---|
| D57/—/L | −0.3 ± 0.7 | −0.3 ± 0.5 | −0.1 ± 0.1 | −0.1 ± 0.0 |
| D60/A/C/A | 0.9 ± 1.5 | −1.5 ± 0.4 | −1.8 ± 0.7 | −1.7 ± 0.3 |
| I156/—/L | −0.9 ± 0.2 | −1.0 ± 0.2 | −1.0 ± 0.2 | −1.1 ± 0.1 |
| G192/—/I | −0.1 ± 0.3 | −0.1 ± 0.1 | −0.7 ± 0.2 | −0.9 ± 0.2 |
| E206/—/S | −0.7 ± 0.5 | 0.1 ± 1.1 | 0.0 ± 0.1 | −0.1 ± 0.1 |
| R248/—/W | −0.2 ± 1.2 | −0.2 ± 1.2 | −0.8 ± 0.2 | −1.1 ± 0.2 |
| Sub-total $\Delta G_{BINDING}$ | −1.4 ± 0.9 | −3.0 ± 0.8 | −4.5 ± 0.4 | −4.9 ± 0.2 |
| Sub-total $\Delta\Delta G_{BINDING}$ | 1.6 ± 1.2 | — | −1.4 ± 0.8 | −1.9 ± 0.8 |
| $\Delta\Delta G_{BIND-EXP}$ | 0.5 | — | −1.9 | −0.7 |
| β-Chitobiose | −16.6 ± 1.2 | −14.4 ± 1.1 | −16.8 ± 1.5 | −16.5 ± 1.3 |
| Reducing GlcNAc | −10.6 ± 1.3 | −7.9 ± 1.1 | −11.7 ± 1.7 | −11.5 ± 1.3 |
| Terminal GlcNAc | −6.0 ± 1.1 | −6.5 ± 1.1 | −5.1 ± 1.2 | −5.1 ± 1.2 |
| Peptide | −4.9 ± 1.3 | −6.5 ± 1.6 | −4.3 ± 0.9 | −4.0 ± 0.9 |

The R911 Dyn data indicates that the D60C mutation is −0.3 kcal/mol more favorable than D60A (GLH206). However, the $\Delta\Delta G_{BINDING}$ relative to D60A (GLH206) indicates that R911 is −1.4 kcal/mol more favorable. The main favorable contributions are coming from G192I and R248W, increasing the hydrophobicity of the binding pocket. On the other hand D57L and E206S are estimated to make almost no favorable interaction energy contribution. This result might suggest that reverting these two residues back to wild-type may be more favorable. In the case of D57, this observation may be supported by simulation data that indicates that D57 is involved in stabilizing hydrogen bonds with R61, retaining R61 in a favorable orientation to make direct substrate recognizing hydrogen bonds with the 2$^{nd}$ GlcNAc (FIGS. 51 and 52). Similarly, E206 interaction data from the 1PNF x-ray crystal model, shows that it is involved in hydrogen bonds with conserved water molecules (Wat$^{346}$ and Wat$^{348}$) in the binding pocket and is not directly involved in substrate recognition (FIGS. 5 and 6).[1] Both Wat$^{346}$ and Wat$^{348}$ make direct hydrogen bonds with the reducing GlcNAc. Furthermore, the E206S mutation in R911 is a change from an acidic residue to a polar residue, which is favorable for protein-carbohydrate interactions. However, as these MD simulations were not conducted with conserved water molecules in the binding pocket, the estimated theoretical interaction energies for E206S are likely different than the estimates obtained in this simulation.

The $\Delta\Delta G_{BINDING}$ relative interaction energy estimation of R911 (−1.4 kcal/mol) was less favorable than R911 C60A (−1.9 kcal/mol), relative to the D60A (GLH206) model. This is in contrast to experimental data ($\Delta\Delta G_{BIND-EXP}$). However, these theoretical estimations are within calculated error, indicating the difference is not statistically significant. Given that the decomposition calculations approximate energetic contributions, it is not unusual to obtain MM-GBSA estimations with relatively high error, thus making qualitative assessment of data appropriate.

The energetic contribution of the β-Chitobiose and tripeptide moieties of the glycotripeptide ligand were also determined from MM-GBSA analysis (Table 34). The majority of the favorable interactions are between the protein and the carbohydrate portion (−14 kcal/mol--16 kcal/mol) of the glycotripeptide relative to the peptide (−4 kcal/mol--6 kcal/mol). Experimental data from 1PNF x-ray models shows a network of hydrogen bonds between the residues in the binding pocket and the chitobiose ligand (FIGS. 5 and 6).[1] Substrate specificity studies of PNGase F indicate that catalytic activity of PNGase F with a glycotripeptide substrate (Chitobiose-Asn-Ala-Thr) is 83%, and with a glycodipeptide substrate (Chitobiose-Asn-Ala) activity is 1.8%, where 100% activity is obtained with a pentapeptide substrate (Chitobiose Tyr-Ile-Asn-Ala-Ser) (SEQ ID NO:23).[7] Thus, substrate specificity studies indicate that the peptide portion is critical. As these simulations utilized a glycotripeptide ligand, based on the previously mentioned experimental data, it may be expected that more conclusive interaction energy results could be obtained with a glycopentapeptide ligand.

TABLE 35

Summary of R911 mutation theoretical and experimental characteristics. Characteristics of R911 mutations relative to wtPNGase F are listed. Estimated theoretical interaction energies (kcal/mol) relative to D60A (GLH206) complexed with a glycotripeptide (GlcNAcβ1-4GlcNAc-β-Asn-Leu-Thr) are included. For comparison, experimentally determined binding interaction energy ($\Delta\Delta G_{BIND-EXP}$) of clones is also listed relative to D60A.

| R911 mutations relative to wtPNGase F | Amino Acid Mutation Characteristics | $\Delta\Delta G_{BINDING}$ |
|---|---|---|
| D57L | Acidic to hydrophobic | −0.1 ± 0.1 |
| D60C | Acidic to polar | −1.8 ± 0.7 |
| I156L | Hydrophobicity preserved | −1.0 ± 0.2 |
| G192I | Non-polar to hydrophobic | −0.7 ± 0.2 |
| E206S | Acidic to polar | 0.0 ± 0.1 |
| R248W | Basic to hydrophobic | −0.8 ± 0.2 |
| Sub-total $\Delta\Delta G_{BINDING}$ | | −1.4 ± 0.8 |
| $\Delta\Delta G_{BIND-EXP}$ | | −1.9 |

A summary of the R911 mutations, characteristics, and relative binding interaction energies are provided in Table 35. MM-GBSA data indicates that 4 (D60C, I156L, G192I, & R248W) of the 6 mutagenized residues have favorable interaction energies relative to wtPNGase F ($\Delta\Delta G_{BINDING}$), with D57L making weak contributions.

Figure 5:
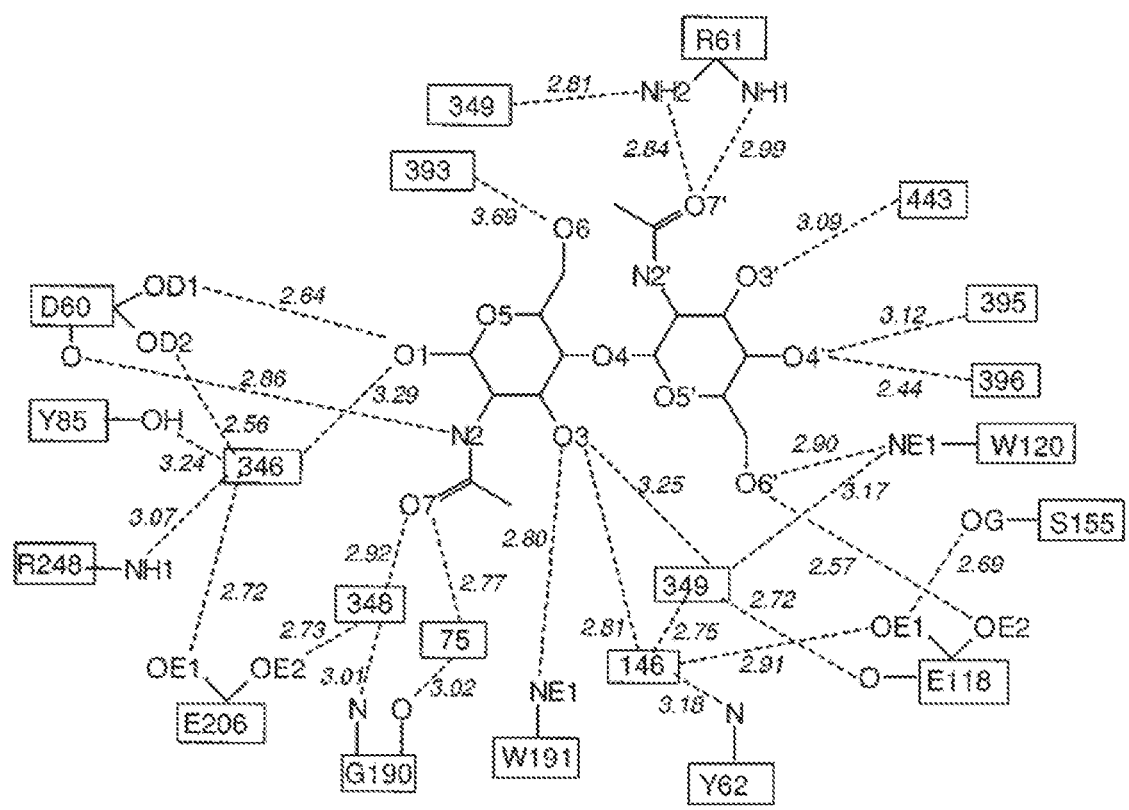
FIG. 5 shows a schematic diagram showing the intermolecular hydrogen bonding contacts between PNGase F, N,N'-diacetylchitobiose and water molecules. Protein residues are indicated with single-letter amino acid code and sequence number in rectangular boxes, water molecules are indicated by a number, corresponding to their number in the file deposited with the Protein Data Bank. The reducing end GlcNAc residue is on the left. Hydrogen bonding distances, in Å, are shown in italics. Note that Wat$^{349}$ (349) is present twice, once in contact with O3 and one in Arg-61. This research was originally published in the *Journal of Biological Chemistry*. Kuhn, P. et al. Active Site and Oligosaccharide Recognition Residues of Peptide-N$^4$-(N-acetyl-β-D-glucosaminyl)asparagine Amidase F. *Journal of Biological Chemistry*. 1995; 270: 29493-29497. © the American Society for Biochemistry and Molecular Biology.
Figure 6:
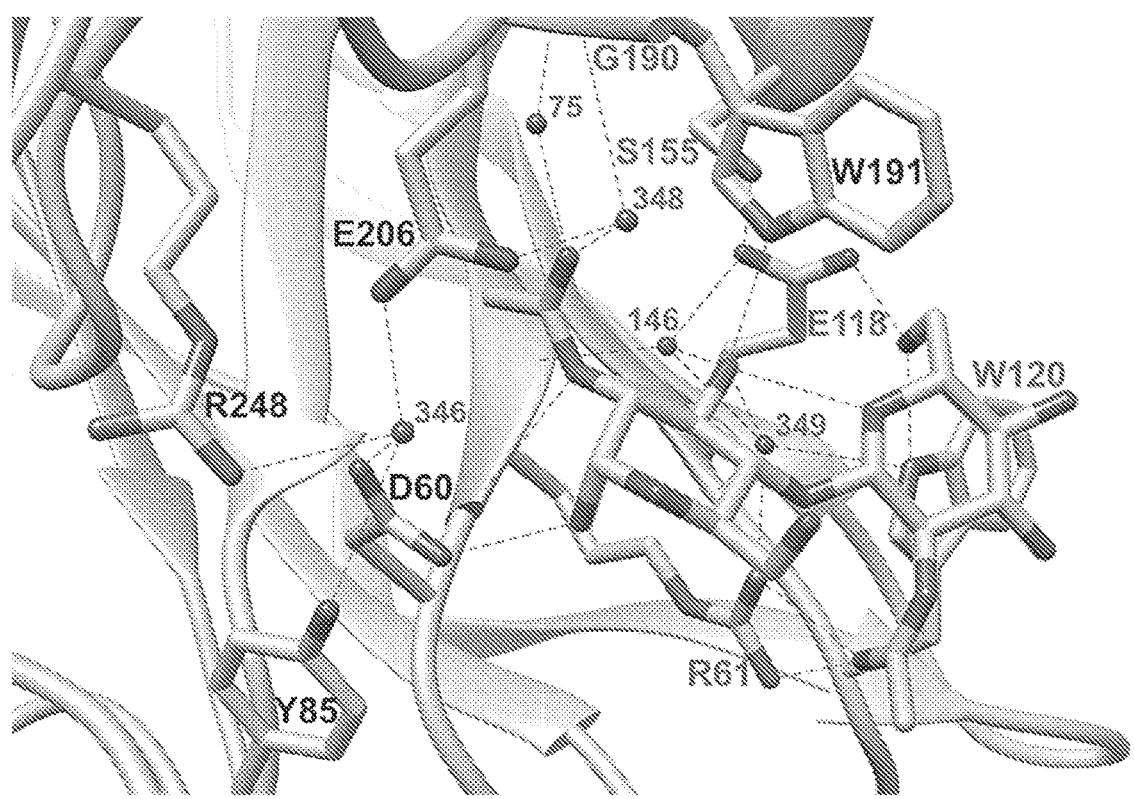
FIG. 6 shows an active site hydrogen bond network of the PNGase F:chitobiose complex. The hydrogen bond network in the binding cleft of PNGase F with the α-chitobiose ligand (outlined) is shown based on experimental x-ray data (PDB ID: 1PNF). Water molecules in the binding cleft between the protein the ligand are depicted as red spheres: Wat$^{75}$, Wat$^{146}$, Wat$^{346}$, Wat$^{348}$, Wat$^{349}$. Amino acids in the binding cleft involved in hydrogen bonds: D60, R61, Y85, E118, W120, S155, G190, W191, E206, R248.

The MD trajectory of 1PNF (GLH206) indicates that D57 is involved in hydrogen bonds with R61 throughout the duration of the simulation and visualized in FIGS. 51 and 52. This interaction was not originally reported[1] (FIG. 5) and re-analysis of 1PNF experimental data confirms D57 hydrogen bonding with R61. This hydrogen bond is critical for holding R61 in place underneath the chitobiose ligand as it is involved in hydrogen bonds with the solvent exposed side of the N-acetyl group of the $2^{nd}$ GlcNAc, keeping the $2^{nd}$ half of the chitobiose ligand in place (FIG. 6). R61 also hydrogen bonds with $Wat^9$, which facilitating part of the larger hydrogen bond network on the protein interface side of the chitobiose ligand (FIG. 6). These data indicate a previously unreported critical substrate-stabilizing role for D57 in wtPNGase F. Thus, mutation of this residue to D57L in R911 may be detrimental to substrate recognition. This is supported by MD trajectory data of R911 with the chitobiose ligand that shows the $2^{nd}$ GlcNAc swinging outward from the binding cleft and adopting a more solvent exposed position. R61, no longer being held in place by D57 hydrogen bonds due to the D57L mutation, moves back into the binding cleft and facilities hydrogen bonds with the protein facing side of the $2^{nd}$ GlcNAc. These observations are also supported by the MM-GBSA interaction energy estimation for the R911 D57L mutation making negligible favorable contributions towards the interaction energy (−0.1±0.1 kcal/mol). Thus reverting D57L back to wild-type can reasonably be expected to enhance substrate recognition and affinity.

In the case of R911 E206S, wild-type E206 experimental data indicates hydrogen-bonding interaction with conserver water molecules, which were not accounted for in the theoretical energy estimations. This may have contributed to the neutral interaction energy that was estimated (0.0±0.1 kcal/mol) for the E206S mutation. Over all, the theoretical sub-total $\Delta\Delta G_{BINDING}$ interaction energies for R911 (−1.4±0.8 kcal/mol) reproduced the experimentally determined value (−1.9 kcal/mol).

MD Simulations and Binding Free Energy Decomposition of PNGase F Clones with a Ser-O-GlcNAc Ligand The enrichment of O-GlcNAcylated glycoproteins by R911 Lectenz® affinity chromatography was unexpected given that R911 is derived from the N-glycan processing enzyme PNGase F, which has defined substrate specificity for the core N-glycopeptide.[1, 7, 13-15] Structural models of 1PNF, D60A, and R911 were constructed with the common O-GlcNAc motif (GlcNAc-β-Ser) in the binding pocket and utilized for 50 ns MD simulations and MM-GBSA analysis (Table 36). In order to neutralize terminal charges ($NH_3^+$ for the N-terminal and $COO^-$ for the C-terminal) the serine residue of the GlcNAc-β-Ser ligand was modeled with the N-terminal ACE [—C(=O)—$CH_3$] protecting group and the C-terminal NME [—C(=O)—NH—$CH_3$] protecting group as defined in xleap, a component of AMBER Tools 13.[10]

Figure 53:
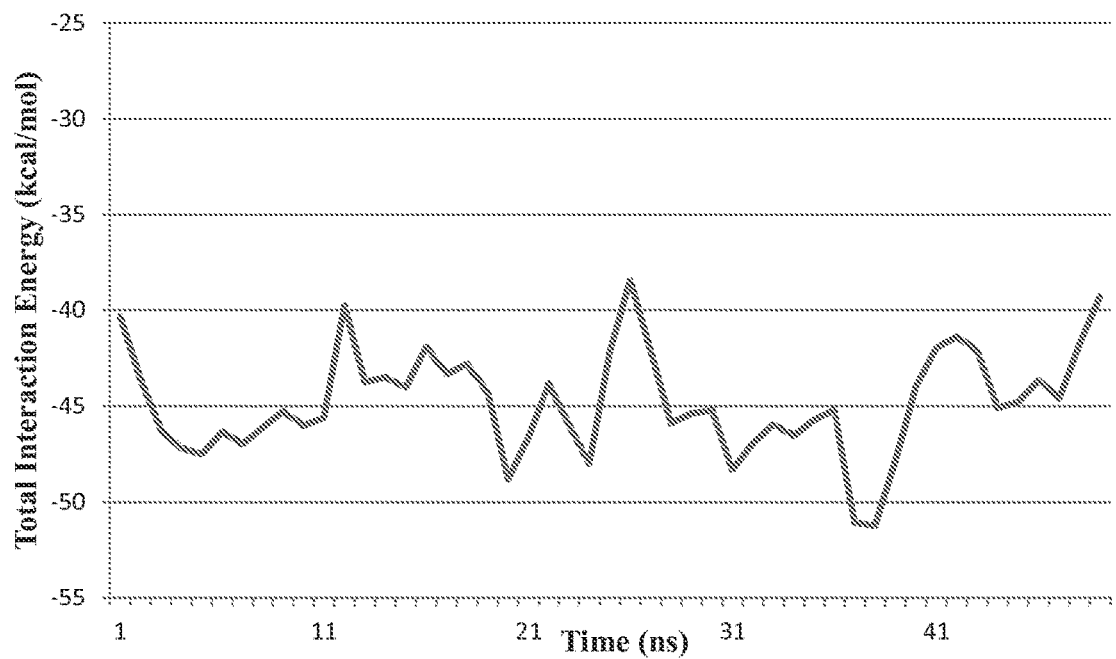
FIG. 53 shows interaction energy stability during 50 ns 1PNF (GLH206) MD simulation with an O-GlcNAc peptide ligand. The portion of the trajectory between 29 ns-39 ns was selected for MM-GBSA analysis.
Figure 54:
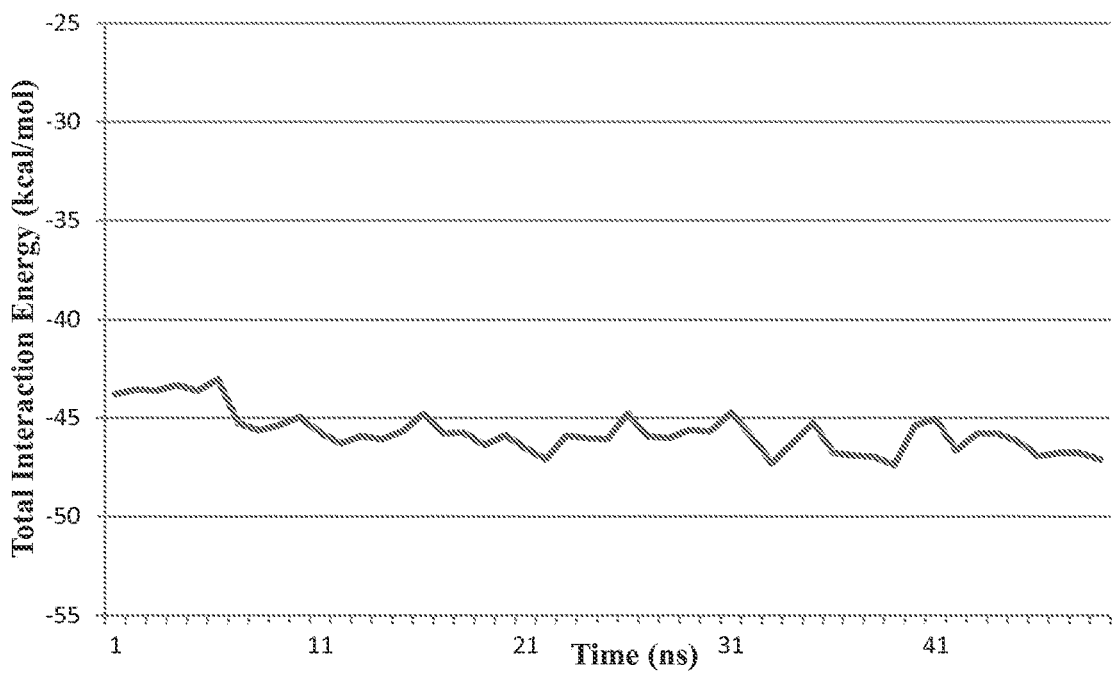
FIG. 54 shows interaction energy stability during 50 ns 1PNFD60A (GLH206) MD simulation with an O-GlcNAc peptide ligand. The last portion of the trajectory (39 ns-49 ns) was selected for MM-GBSA analysis.
Figure 55:
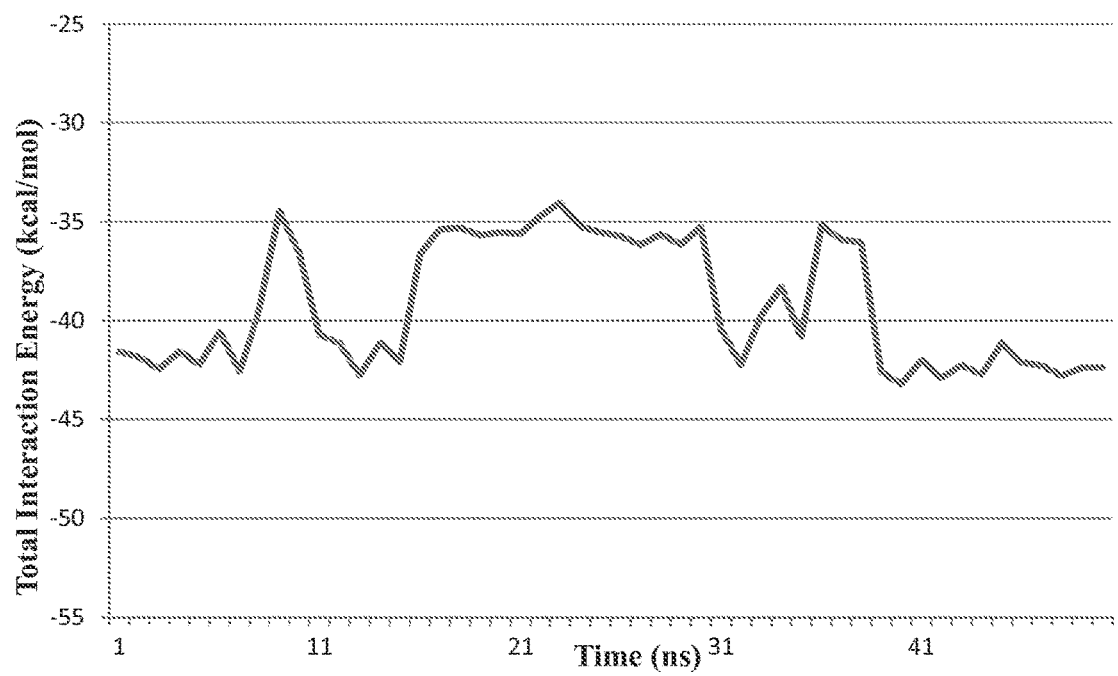
FIG. 55 shows interaction energy stability during 50 ns R911 Dyn MD simulation with an O-GlcNAc peptide ligand. The last portion of the trajectory (39 ns-49 ns) was selected for MM-GBSA analysis.

Structural equilibrium was confirmed by the low average RMSD computed during the course of the 50 ns MD simulation, consistent with previous models used in this study. Interaction energies were computed at 1 ns intervals over the duration of the 50 ns MD trajectory for each model (FIGS. 53-55). Unsurprisingly, the interaction energy for the 1PNF (GLH206) complex with the O-GlcNAc glycopeptide remained unstable during the entire 50 ns trajectory (FIG. 53). The observed instability is likely a confirmation of experimental data that indicate wtPNGase F specificity for N-glycopeptides. However, it is important to note that the ligand remains in the binding site during the trajectory facilitated by the extension of the N-acetyl group into the same hydrophobic pocket as observed in the wtPNGase F experimental structure, indicating that the common N-Acetyl group on both the wild-type chitobiose and the O-GlcNAc ligands are important for recognition. In addition, a majority of the instability appears to come from the ACE-Ser-NME peptide portion of the O-GlcNAc glycopeptide ligand based on the rapid conformation changes visually observed during the 50 ns trajectory, proximal to residue D60. Unlike the 1PNF (GLH206) model, the D60A (GLH206) model had stable interaction energy throughout the 50 ns MD trajectory (FIG. 54), indicating that the D60 residue is responsible for the interaction energy instability observed during the 1PNF (GLH206) MD simulation (FIG. 53) as mutation of this residue to D60A resulted in stabilized interaction energy.

Figure 56:
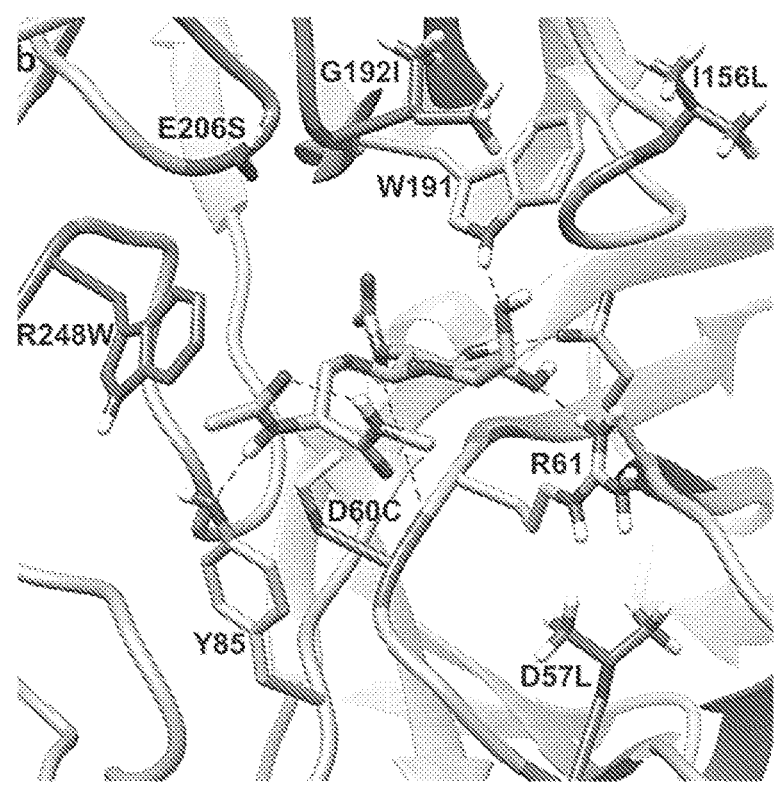
FIG. 56 shows R911 and GlcNAc-β-Ser MD simulation at 45 ns time point. The GlcNAc-β-Ser ligand is outlined. Surface hydrophobicity representation of the R91-GlcNAc-β-Ser complex depicting the ligand in the binding pocket with the N-Acetyl group extended into the deep hydrophobic groove. Theoretical hydrogen bonds are depicted as dashed lines. R911 mutagenized residues are shown.

The R911 Dyn model of the complex had regions of varied stable interaction energies most notable between 17 ns-30 ns and again between 39 ns-50 ns as shown in FIG. 55. A key difference between these two regions is the ligand conformation in the earlier time points that was altered due to the lack of hydrogen bond interaction between R61 and GlcNAc-O4. Once the R61 and GlcNAc-O4 hydrogen bond is formed starting at 39 ns, the complex adopts a more stabile conformation as evidence by the favourable interaction energy during the last 11 ns of MD simulation and by visual analysis of the trajectory (FIG. 56). A list of the theoretical hydrogen bonds between the R911 and O-GlcNAc ligand is provided in Table 37 and depicted in FIG. 56b. Due to these observations, the 10 ns trajectory between time points 39 ns-49 ns of the R911 Dyn and D60A (GLH206) trajectories were selected for MM-GBSA analysis. In the case of the 1PNF (GLH206) complex, the most stable region of the trajectory was selected for MM-GBSA analysis (29 ns-39 ns). However, even this region of the trajectory is relatively unstable and the MM-GBSA data should be considered less than optimal. A longer 100 ns MD simulation did not result in the 1PNF (GLH206)-O-GlcNAc complex adopting a more energetically stable conformation. Similarly, no significant changes in conformation were observed for D60A (GLH206) or R911 Dyn models complexed with O-GlcNAc when the MD simulation was extended to 100 ns.

TABLE 36

Structural models of wtPNGase F and clones used for MD simulations and MM-GBSA. Structural models with a Ser-O-GlcNAc ligand in the binding pocket were constructed to conduct 50 ns MD simulations. Simulation stability was confirmed by analyzing RMSD over simulation time and the average RMSD values are listed. Estimated total theoretical binding energy for all 314 amino acids (Total $\Delta G_{BINDING}$) of each clone are listed (kcal/mol).

| Structural Model | Ligand | RMSD (Å) | Total $\Delta G_{BINDING}$ |
|---|---|---|---|
| 1PNF (GLH206) | GlcNAc-β-Ser | 1.2584 | −47.2 |
| D60A (GLH206) | GlcNAc-β-Ser | 1.2090 | −46.0 |
| R911 Dyn | GlcNAc-β-Ser | 1.3029 | −42.6 |

TABLE 37

Theoretical hydrogen bond lengths between GlcNAc-β-Ser and R911.

| Hydrogen bonds | Average from R911 Ser-O-GlcNAc MD Simulation (Å) |
|---|---|
| D60-O - GlcNAc316-H2N | 3.09 ± 0.22 |
| R61-HH11 - GlcNAc318-O4 | 2.84 ± 0.11 |
| E118-Oε - GlcNAc318-H3O | 2.69 ± 0.12 |
| W191-NH - GlcNAc318-O6 | 3.02 ± 0.20 |
| Y85-OH - S316-H | 3.06 ± 0.16 |

The estimated binding free energies for the models with the GlcNAc-β-Ser complex are presented in Table 38. As observed with the interaction energy and trajectory visualization, the MM-GBSA data also indicates the relative unfavourable interaction energy of D60 in the 1PNF (GLH206) complex (−0.5±1.6 kcal/mol) relative to the D60A (GLH206) complex (−1.6±0.4 kcal/mol). This is also supported by the larger estimated error computed for the D60 residue in the 1PNF (GLH206) complex. The estimate interaction energy of the D60C mutation in the R911 Dyn complex is relatively favourable (−3.2±0.7). Unlike the D60C mutation, the E206S mutation is noticeably unfavorable; however, this may in part be due to an inaccurate under estimation as the conserved water molecule that is observed to interact with this site is not included in the MM-GBSA per residue estimation. Nonetheless, it is conceivable that reverting E206S to wild-type may also enhance ligand recognition specific for GlcNAc-β-Ser given the noticeably favorable interaction energy estimated in the D60A (GLH206) for E206 (−1.6±0.7 kcal/mol).

TABLE 38

Estimated MM-GBSA theoretical interaction energies of models complexed with an O-GlcNAc ligand. Sub-total $\Delta G_{BINDING}$ (kcal/mol) of mutagenized residues were compared across 1PNF (GLH206), D60A (GLH206), and R911 Dyn complexed with (GlcNAc-β-Ser). Sub-total $\Delta\Delta G_{BINDING}$ (kcal/mol) energies relative to the D60A control clone are indicated.

| Residue | 1PNF (GLH206) | D60A (GLH206) | R911 Dyn |
|---|---|---|---|
| D57/—/L | −0.3 ± 0.8 | −0.4 ± 0.5 | −0.1 ± 0.0 |
| D60/A/C | −0.5 ± 1.6 | −1.6 ± 0.4 | −3.2 ± 0.7 |
| I156/—/L | −0.1 ± 0.1 | −0.2 ± 0.1 | −0.1 ± 0.0 |
| G192/—/I | −0.1 ± 0.2 | −0.1 ± 0.1 | −0.4 ± 0.2 |
| E206/—/S | −1.7 ± 1.1 | −1.6 ± 0.7 | −0.1 ± 0.2 |
| R248/—/W | −0.1 ± 1.2 | −2.3 ± 0.8 | −0.9 ± 0.2 |
| Sub-total $\Delta G_{BINDING}$ | −3.0 ± 1.1 | −6.2 ± 0.6 | −4.9 ± 0.4 |
| Sub-total $\Delta\Delta G_{BINDING}$ | 3.2 ± 1.2 | — | 1.3 ± 0.7 |
| β-GlcNAc | −17.6 ± 1.8 | −14.7 ± 1.6 | −16.4 ± 1.5 |
| Serine | −4.9 ± 1.2 | −5.7 ± 0.8 | −2.9 ± 0.6 |

The I156 site is estimated to make minimal favorable interaction contributions. This is unsurprising as this site is more critical for interaction with the second GlcNAc of the wild-type chitobiose ligand, which is absent in GlcNAc-β-Ser ligand. However, the protein loop region of the I156 site may be important for modification via extension to improve specificity toward the GlcNAc-β-Ser ligand by blocking access of the $2^{nd}$ GlcNAc in chitobiose to the binding site. The D57L mutation is also making negligible favorable interactions and destabilizing R61 hydrogen bond interactions as observed previously in the R911 chitobiose complex. As discussed previously, experimental and modeling data indicate that R61 is important for substrate recognition mediated by hydrogen bonds with the N-Acetyl group of the $2^{nd}$ GlcNAc residue of the chitobiose. In the R911 Dyn complex with O-GlcNAc glycopeptide (GlcNAc-β-Ser), R61 hydrogen bonds with GlcNAc-O4 towards the last portion of the trajectory. These observations indicate that reverting D57L to wild-type would likely enhance substrate recognition as well as specificity.

Modeling data with the O-GlcNAc glycopeptide (Glc-NAc-β-Ser) provide a rationalization for the experimentally observed enrichment of O-GlcNAcylated glycoproteins. Furthermore, specificity towards O-GlcNAcylated glycoproteins may be enhanced by reverting E206S to wild-type and extending the loop region of I156L to block larger chitobiose ligands from the binding pocket. In addition, the modus of O-GlcNAc recognition by R911 appears to be driven by highly favorable interaction with the reducing GlcNAc (−16.4±1.5 kcal/mol) relative to the serine residue (−2.9±0.6 kcal/mol), consistent with observations of favorable interactions with the reducing GlcNAc in the wild-type chitobiose ligand interactions as reported in Table 34 and indicated in experimental data of the wtPNGase F complex.[1]

Methods

Building D60A and R911 Structures from 1PNF

The 1PNF x-ray structural model was used as the base model from which all other mutagenized PNGase F models were constructed using USCF Chimera v1.8.1.[1, 16] Dunbrack and Dynameomics rotamer libraries were utilized to select preferred rotamers for modeling and editing into the model using USCF Chimera's rotamer selection and torsion angle tools.[2, 3] Six models of PNGase F with the α-chitobiose ligand (GlcNAcβ1-4GlcNAc-αOH) were constructed as listed in Table 18. Four models of PNGase F with the β-chitobiose ligand (GlcNAcβ1-4GlcNAc-βOH) were constructed as listed in Table 23. Four models of PNGase F with the glycotripeptide ligand (GlcNAcβ1-4GlcNAc-β-Asn-Leu-Thr) were constructed as listed in Table 29. Three models with GlcNAc-β-Ser ligand were constructed as listed in Table 36. In order to neutralize terminal charges ($NH_3^+$ for the N-terminal and $COO^-$ for the C-terminal) the peptide portion of all glycopeptide ligands were modeled with the N-terminal ACE [—C(=O)—$CH_3$] protecting group and the C-terminal NME [—C(=O)—NH—$CH_3$] protecting group as defined in xleap, a component of AMBER Tools 13.[10]

MD Simulations

A 100 ns fully solvated MD simulation of the PNGase F—ligand complex was performed in water at room temperature and pressure (NPT) employing the AMBER-GLYCAM protein-carbohydrate force field. The system was minimized with implicit solvent (5000 steps) using a system restraint mask (protein Cα and ligand ring atoms) to permit all modeled rotamers into energy-minimized conformations. Using tleap the system was explicitly solvated with the TIP3P water model. The explicitly solvated system was then energy minimized (2000 steps, NVT) using a system restraint mask. A 30 ps heating step was performed (NVT) also with a system restrain mask, followed by a 1 ns equilibration (NPT) with a ligand restraint only (ligand ring atoms). The 100 ns production run was performed (50,000,000 steps, NPT) and data was saved at ever 0.002 ps, corresponding to 500 frames saved per ns of data. Trajectory analysis was performing using tleap, ptraj, and cpptraj as implemented in AMBER Tools13.[10, 17] Data was visualized using USCF Chimera 1.8.1.[16]

Binding Free Energy Decomposition

The per-residue contributions to the binding energy was computed for each of the 314 amino acids in PNGase F, employing the generalized Born (GB) continuum solvent model as implemented in AMBER as previously described in Example 2 over the energy converged portion of the trajectory.[18]

REFERENCES

1. Kuhn, P. et al. Active Site and Oligosaccharide Recognition Residues of Peptide-N4-(N-acetyl-β-D-glucosaminyl)asparagine Amidase F. Journal of Biological Chemistry 270, 29493-29497 (1995).

2. Dunbrack, R. L., Jr. Rotamer libraries in the 21st century. Current Opinion in Structural Biology 12, 431-440 (2002).
3. Scouras, A. D. & Daggett, V. The dynameomics rotamer library: Amino acid side chain conformations and dynamics from comprehensive molecular dynamics simulations in water. Protein Science 20, 341-352 (2011).
4. Woods, R. J. & Tessier, M. B. Computational glycoscience: characterizing the spatial and temporal properties of glycans and glycan-protein complexes. Current Opinion in Structural Biology 20, 575-583 (2010).
5. Genheden, S. & Ryde, U. Will molecular dynamics simulations of proteins ever reach equilibrium? Phys. Chem. Chem. Phys. 14, 8662-8677 (2012).
6. Hadden, J. A., Tessier, M. B., Fadda, E. & Woods, R. J. Calculating binding free energies for protein-carbohydrate complexes. (2012).
7. Fan, J. Q. Detailed Studies on Substrate Structure Requirements of Glycoamidases A and F. Journal of Biological Chemistry 272, 27058-27064 (1997).
8. Filitcheva, J. PNGases: A Diverse Family of Enzymes Related by Function Rather Than Catalytic Mechanism, Vol. Ph.D. (Massey University, Palmerston North; 2010).
9. Isom, D. G., Castaneda, C. A., Cannon, B. R., Velu, P. D. & Garcia-Moreno, E. B. Charges in the hydrophobic interior of proteins. Proc Natl Acad Sci USA 107, 16096-16100 (2010).
10. D. A. Case, T. A. D., T. E. Cheatham, III, C. L. Simmerling, J. Wang, R. E. Duke, R. Luo, R. C. Walker, W. Zhang, K. M. Merz, B. Roberts, S. Hayik, A. Roitberg, G. Seabra, J. Swails, A. W. Gotz, I. Kolossvary, K. F. Wong, F. Paesani, J. Vanicek, R. M. Wolf, J. Liu, X. Wu, S. R. Brozell, T. Steinbrecher, H. Gohlke, Q. Cai, X. Ye, J. Wang, M.-J. Hsieh, G. Cui, D. R. Roe, D. H. Mathews, M. G. Seetin, R. Salomon-Ferrer, C. Sagui, V. Babin, T. Luchko, S. Gusarov, A. Kovalenko, and P. A. Kollman (University of California, San Francisco, 2012).
11. Rye, C. S. & Withers, S. G. Glycosidase mechanisms. Curr Opin Chem Biol 4, 573-580 (2000).
12. Kozmon, S. & Tvaroška, I. Catalytic Mechanism of Glycosyltransferases: Hybrid Quantum Mechanical/Molecular Mechanical Study of the Inverting N-Acetylglucosaminyltransferase I. Journal of the American Chemical Society 128, 16921-16927 (2006).
13. Tretter, V., Altmann, F. & MÄRz, L. Peptide-N4-(N-acetyl-β-glucosaminyl)asparagine amidase F cannot release glycans with fucose attached α1→3 to the asparagine-linked N-acetylglucosamine residue. European Journal of Biochemistry 199, 647-652 (1991).
14. Mussar, K. J., Murray, G. J., Martin, B. M. & Viswanatha, T. Peptide: N-glycosidase F: studies on the glycoprotein aminoglycan amidase from *Flavobacterium meningosepticum*. Journal of biochemical and biophysical methods 20, 53-68 (1989).
15. Tarentino, A. L., Gomez, C. M. & Plummer, T. H., Jr. Deglycosylation of asparagine-linked glycans by peptide: N-glycosidase F. Biochemistry 24, 4665-4671 (1985).
16. Pettersen, E. F. et al. UCSF Chimera—a visualization system for exploratory research and analysis. Journal of Computational Chemistry 25, 1605-1612 (2004).
17. Roe, D. R. & Cheatham, T. E. PTRAJ and CPPTRAJ: Software for Processing and Analysis of Molecular Dynamics Trajectory Data. Journal of Chemical Theory and Computation 9, 3084-3095 (2013).
18. Tsui, V. & Case, D. A. Theory and applications of the generalized Born solvation model in macromolecular simulations. Biopolymers 56, 275-291 (2001).

Example 5

Generation and Screening of Biocombinatorial Libraries

For efficient generation and screening of biocombinatorial libraries, it is important to limit the library to approximately $10^9$ clones[1], which corresponds to 7 randomized positions ($20^7=1\times10^9$ clones). When it is not immediately known which residues should be changed, library design can be difficult. This is where input from computational simulations can aid in identifying the appropriate amino acids and thereby focusing the library design. The benefits of computational guidance, particularly in terms of the reduction in the number of potential clones, has been noted.[2] As observed in a recent review by Barakat and Love[3], computational algorithms blended with in vive screens are leading towards greater and more rapid success in the field of protein design.

Here the computationally-focused yeast displayed GeneArt library (Library 2) had a diversity of ~$1.36\times10^7$ clones, representing an estimated sequence coverage of ~22% of the theoretical diversity (Table 6). Selection via MACS prior to FACS served to ensure that the library was sufficiently enriched prior to using FACS as a stringent selection pressure for the practical sorting of functionally relevant clones (FIGS. 15 and 16a). The library was selected against a mixture of representative N-glycan targets on RNase B and Asialofetuin to enrich for clones that retained the cognate specificity of the PNGase F enzyme.

An examination of the R911 protein sequence indicated enrichment in residues that are commonly found in protein-glycan interactions. The hydrophobic face of carbohydrates frequently participates in stacking interactions with aromatic amino acids, which are estimated to contribute 1.5 kcal/mol.[4] It was notable then that selection led to the introduction of a Trp at position 248 that is estimated to favorable contribute −0.8±0.2 kcal/mol based on MM-GBSA analysis. In addition, several other mutations increased the overall hydrophobicity relative to the wt sequence (D57L, G192I, D60C and E206S) (Table 35).

The R248W mutation is of particular interest not only because of its known importance in facilitating carbohydrate-aromatic interactions, but also because of R248's proposed role in the catalytic mechanism of wtPNGase F (making the Asn-carbonyl atom more susceptible to nucleophilic attack) and interaction with Wat[346] (FIGS. 5 and 6) in the catalytic site.[5, 6] The R248A point mutant has 0.1% catalytic activity relative to the wtPNGase F enzyme.[5] R911's lack of catalytic activity (Table 10) may be attributed in part to the R248W mutation. Thus the R248W mutation may not only be enhancing affinity but also contributing to the catalytic inactivation of R911.

Wild-type E206 and D60 span the glycosidic linkage between asparagine and the reducing GlcNAc, are known to participate in hydrogen bonding interactions with conserved water molecules (Wat[346] and Wat[348]) in the x-ray crystal structure 1PNF (FIGS. 5 and 6), and contribute to catalytic activity.[6] Thus, it is important to note that the polar mutations of the catalytic residues (D60C and E206S) in R911 are likely also contributing to catalytic inactivity, but potentially preserving the hydrogen bond network that is critical for substrate recognition. MM-GBSA energy interaction analysis with conserved water molecules may provide additional insight into E206S and D60C roles in R911.

MD analysis of the wtPNGase F complexed with the glycotripeptide indicated that D57 is important for stabilizing R61 through hydrogen bond interactions, thereby facilitating substrate recognition between R61 and the $2^{nd}$ GlcNAc. This type of stabilizing interaction has been reported between S155 and E118 residues in the 1PNF x-ray crystal structure (FIGS. 5 and 6).[6] Like R61, E118 directly interacts with conserved water molecules in the binding cleft as well as the $2^{nd}$ GlcNAc. The orientation of E118 is stabilized via hydrogen bond interactions with S155. Reverting D57L to wild-type in R911 may improve substrate recognition via R61 and enhance affinity.

Free energy decomposition analysis offers a powerful tool to investigate the per residue interaction energy, for which there is no equivalent experimental method. The total interaction energy of −44.0 kcal/mol was computed for the 1PNF (GLH206) MD simulation with the glycotripeptide ligand (Table 29). This value overestimates the experimental binding free energy of −7.103 kcal/mol for wtPNgase F (Table 11), which is a typical feature of MM-GBSA calculations that omit entropic penalties associated with ligand binding.[7] Entropic effects, arising from changes in conformational flexibility can be estimated, but may require very long MD simulations in order to achieve convergence.[8] However, it may be anticipated that entropic effects arising from reduction in the flexibility of protein side chains will be most significant for those residues that interact strongly with the ligand, and least significant for the tepid or cold residues. For these reasons, the entropic contributions were not computed.

Unlike wtPNGase F and D60A, the expression and purification of R911 and R911 C60A clones resulted in a low yield (~150 μg/L). IMAC and SEC elution profiles of these clones differed from wtPNGase F and D60A. Furthermore, Western Blot analysis of multiple R911 SEC elution peaks suggests the presence of structural isoforms of R911 clones, some of which may be mis-folded R911 clones. Protein mutational tolerance, the risk of multiple mutations decreasing protein stability, is a common issue with protein library design, which can be compensated for by the use of appropriate selection parameters especially when selecting for enhanced enzyme thermostability or activity.[9] However, for affinity enhancement, these challenges persist and recent efforts to minimize destabilizing mutations has led to the development of protein folding algorithms to pre-screen sequence space for stabilizing effects.[9]

SPR kinetic data demonstrates that R911 has sub-micromolar affinity ($K_D$=0.26 μM) for the N-glycan bearing glycoprotein RNase B, a 10× affinity enhancement relative to the non-affinity optimized D60A control. R911 also has an 84× decreased off-rate ($k_{off}$=5.1×10$^{-3}$ s$^{-1}$). Where as R911 C60A exhibits relatively lower affinity and decreased off-rate, indicating that D60C R911 mutation makes a critical contribution to the binding interactions, which are further enhances by overall synergistic effects from other mutations. Importantly, the kinetic data satisfies the Lectenz® selection threshold for enhanced affinity and decreased off-rate relative as depicted in the design strategy (FIG. 5).

The application of the R911 Lectenz® in affinity chromatography demonstrated enrichment of the N-glycan bearing glycoprotein RNase B as well as of N-glycopeptides derived from RNase B. Furthermore, the lack of enrichment of deglycosylated RNase B and the competitive elution with chitobiose, demonstrates that R911 recognizes the common chitobiose glycopeptide core of N-glycan structures. This is consistent with the observed specificity of the wtPNGase F enzyme and the D60A glycan array screening results. Nonetheless, the glycan specificity of R911 will be further investigated by glycan array screening.

The application of R911 Lectenz® Affinity Chromatography (LAC) for the enrichment of native glycoproteins from MCF7 cell extract by competitive elution resulting in the 3.4× enrichment of both N-glycoproteins and O-GlcNAcylated O-glycoproteins that share a common reducing GlcNAc recognized by R911. This is significant as the R911 Lectenz® is the only known reagent that recognizes both the common chitobiose core of N-glycans and 0-glycoproteins containing the common core O-GlcNAcylation motif, making possible the enrichment of two major classes of glycoproteins using a single affinity reagent. Furthermore, in comparison to Multi-Lectin Affinity Chromatography (MLAC) with Jac, ConA, and WGA lectins, R911 LAC resulted in the enrichment of glycoproteins not enriched by MLAC.[10] The difference in the glycoprotein enrichment profiles is not surprising given the different specificities of the capture reagents employed as glycan detection is biased by the type of lectin employed in affinity chromatograph.[11] Not surprisingly, some non-glycoproteins were also identified in the eluted sample from R911 LAC. Another weakness of sample enrichment by affinity chromatography is false positives that results from proteins being captured by non-specific protein-protein interactions other than direct affinity selection of a targeting ligand.[12]

This first-of-its-kind application of biocombinatorial library design based on free energy decomposition for the engineering of a carbohydrate processing enzyme into a catalytically inactive, high affinity capture reagent generally confirms the Lectenz® design strategy and highlights the challenges associated with protein engineering. These studies indicate that the R911 Lectenz® can be further enhanced by selective mutagenesis to create two additional Lectenz® reagents, one specific for N-glycopeptides and N-glycoproteins, and a second Lectenz® reagent specific for O-GlcNAcylated glycoproteins and glycopeptides. An important next step would be to revert the D57L mutation to wild-type as this is likely the most effective way to enhance substrate specificity for N-glycoproteins. An O-GlcNAc specific Lectenz® could be engineering by reverting both E206S and D57L to wild-type and extending the loop region of I156L to block larger chitobiose ligands from the binding pocket.

The research presented here also lays the groundwork for the development of $2^{nd}$ generation biocombinatorial libraries for the exploration of alternative sequence spaces for Lectenz® generation. Based on literature reports and the data reported here, Table 39 lists the proposed roles of the critical residues identified in the binding cleft of wtPNGase F. This list represents an enhancement of understanding the substrate recognition by PNGase F to guide development of additional Lectenz® candidates. Another critical factor that would advance development would be generation of experimental structural data of a glycotripeptide or glycopentapeptide complexed with PNGase F. A complex with the D60A single point mutant developed in this study, which has significantly diminished catalytic activity, would be an equally useful structure to use for Lectenz® engineering. However, the lack of results in obtaining such data over the past 20 years is an indication of the challenges of obtaining experimental structural data.

TABLE 39

Proposed functions of PNGase F active site residues. Residues that impact catalytic activity based on point mutant studies and are proposed as part of the catalytic mechanism are indicated in bold.

| 1PNF Residue | Proposed Function | Interactions | Contact w/AA or Ligand |
|---|---|---|---|
| D57 | Stabilizing | H-bond w/R61 (MD) | R61 |
| W59 | Impacts catalytic activity[5] | Hydrophobic environment | D60 |
| D60 | Catalytic mechanisms[5, 6] | H-bond w/Wat$^{346}$ & ligand | $1^{st}$ GlcNAc |
| R61 | Substrate binding/ recognition[5, 6] | H-bond w/ligand | $2^{nd}$ GlcNAc |
| Y62 | Stabilizing[6, 13] | H-bond w/Wat$^{146}$ w/N152 | N152 |
| I82 | Impacts catalytic activity[5] | Hydrophobic environment | D60 |
| Y85 | Stabilizing[6] | H-bond w/Wat$^{346}$ | $1^{st}$ GlcNAc |
| E118 | Substrate binding/ recognition[6] | H-bond w/Wat$^{349}$ & ligand | $2^{nd}$ GlcNAc |
| W120 | Substrate binding/ recognition[5] | H-bond w/Wat$^{349}$ & ligand, and potential hydrophobic interaction predicted w/$1^{st}$ mannose | $2^{nd}$ GlcNAc & $1^{st}$ mannose? |
| S155 | Stabilizing[6] | H-bond w/E118 | E118 |
| I156 | Stabilizing | Potential hydrophobic interaction predicted w/$1^{st}$ mannose (MD) | $1^{st}$ mannose? |
| W191 | Substrate binding/ recognition[6] | H-bond w/ligand | $1^{st}$ GlcNAc |
| G190 | Stabilizing[6] | H-bond w/Wat$^{75}$ & Wat$^{348}$ | $1^{st}$ GlcNAc |
| H193 | Substrate binding/ recognition[5] | — | — |
| E206 | Catalytic mechanism[5, 6] | H-bond w/Wat$^{346}$ & Wat$^{348}$ | $1^{st}$ GlcNAc |
| W207 | Impacts catalytic activity[5] | Hydrophobic environment and H-bond with Asn-O (MD) | E206 & Asn-O |
| R248 | Potentially involved in catalytic mechanism[5] | Electrostatic and H-bond w/Wat$^{346}$ | $1^{st}$ GlcNAc |
| W251 | Impacts catalytic activity[5] | Hydrophobic environment | E206 |

The R911 Lectenz® has been selected using the computationally-guided design of a yeast-surfaced displayed PNGase F biocombinatorial library. The R911 Lectenz® is a novel pan-specific reagent for detecting the core glycopeptide component common to all N-linked glycans and core O-GlcNAcylated glycoproteins. This application of the Lectenz® design strategy presents opportunities to engineer additional Lectenz® reagents from carbohydrate-processing enzymes with glycan specificity and enhanced affinity. Lectenz® reagents will thus complement the use of existing carbohydrate-recognizing lectins and antibodies and can be employed in sample enrichment applications like affinity chromatography. The utility of Lectenz® reagents in other applications like glycan detection arrays, FACS and Multiplexed Suspension Arrays, immunohistochemistry, and bioprocess monitoring will be investigated further.

REFERENCES

1. Bonsor, D. A. & Sundberg, E. J. Dissecting protein-protein interactions using directed evolution. Biochemistry 50, 2394-2402 (2011).
2. Voigt, C. A., Mayo, S. L., Arnold, F. H. & Wang, Z. G. Computationally focusing the directed evolution of proteins. J Cell Biochem Suppl Suppl 37, 58-63 (2001).
3. Barakat, N. & Love, J. Molecular Diversity in Engineered Protein Libraries. Curr Opin Chem Biol 11, 335-341 (2007).
4. Asensio, J. L., Ardá, A., Cañada, F. J. & Jiménez-Barbero, J. Carbohydrate-Aromatic Interactions. Accounts of Chemical Research 46, 946-954 (2012).
5. Filitcheva, J. PNGases: A Diverse Family of Enzymes Related by Function Rather Than Catalytic Mechanism, Vol. Ph.D. (Massey University, Palmerston North; 2010).
6. Kuhn, P. et al. Active Site and Oligosaccharide Recognition Residues of Peptide-N4-(N-acetyl-β-D-glucosaminyl)asparagine Amidase F. Journal of Biological Chemistry 270, 29493-29497 (1995).
7. Woods, R. J. & Tessier, M. B. Computational glycoscience: characterizing the spatial and temporal properties of glycans and glycan-protein complexes. Current Opinion in Structural Biology 20, 575-583 (2010).
8. Genheden, S. & Ryde, U. Will molecular dynamics simulations of proteins ever reach equilibrium? Phys. Chem. Chem. Phys. 14, 8662-8677 (2012).
9. Socha, R. D. & Tokuriki, N. Modulating protein stability—directed evolution strategies for improved protein function. Febs J 280, 5582-5595 (2013).
10. Lee, L. Y. et al. An optimized approach for enrichment of glycoproteins from cell culture lysates using native multi-lectin affinity chromatography. J Sep Sci 35, 2445-2452 (2012).
11. Krishnamoorthy, L. & Mahal, L. K. Glycomic analysis: an array of technologies. ACS chemical biology 4, 715-732 (2009).
12. Jung, K. & Cho, W. Serial affinity chromatography as a selection tool in glycoproteomics. Anal Chem 85, 7125-7132 (2013).
13. Kuhn, P., Tarentino, A. L., Plummer, T. H., Jr. & Van Roey, P. Crystal structure of peptide-N4-(N-acetyl-beta-D-glucosaminyl)asparagine amidase F at 2.2-A resolution. Biochemistry 33, 11699-11706 (1994).

Example 6

An Engineered LECTENZ Biosensor for Enrichment of O-GlcNAcylated Glycoproteins and Glycopeptides Characterization of the engineered R911 Lectenz indicated specificity for both N-glycosylated and O-GlcNAcylated glycoproteins and glycopeptides. This dual specificity is based on the recognition of the reduced GlcNAc structural motif common to both N-glycosylation and O-GlcNAcylation (Example 4). The work presented here continues the investigation and development of variant R911 Lectenz: one with further enhanced specificity towards N-glycopeptides and N-glycoproteins, and a second Lectenz variant specific for 0-GlcNAcylated glycopeptides and N-glycoproteins (Example 5). Furthermore, a third Lectenz variant specific for O-GalNAcylation is investigated. The basis of O-GalNAc specificity is based on the observation that GalNAc is a C4 epimer of GlcNAc (the key structural motif recognized by wt PNGase F and the engineered R911 Lectenz).

Point Mutagenesis Studies of R911

Eight mutants have been made of R911 (Table 40). Seven of these mutants revert R911 amino acids back to the wt PNGaseF sequences. An eighth mutant was created that converts glutamic acid 118, which is also in PNGase F and its D60A mutant, to glutamine (E118Q). Each of these mutations addresses key issues that could tailor unique interactions with specific glycosylation sites.

TABLE 40

| R911 mutation | Rationale |
|---|---|
| 1. L57D | Restore Chitobiose 2nd GlcNAc recognition via R61, and drive specificity towards N-glycan structures |
| 2. C60D | Enhance glycosidic linkage recognition |
| 3. L156I | Enhance protein stability |
| 4. I192G | Enhance protein stability |
| 5. S206E | Enhance glycosidic linkage recognition |
| 6. W248R | Stabilize N-glycan linkage recognition |
| 7. L156I/S206E | Stabilize and enhance O-GlcNAc recognition |
| 8. E118Q | Destabilize 2nd GlcNAc recognition, and drive specificity towards O-GlcNAc structures. |
| 9. T119 | Destabilize 2nd GlcNAc recognition via D57, and drive specificity towards O-GlcNAc structures. |
| 10. K123 | Destabilize 2nd GlcNAc recognition via D57, and drive specificity towards O-GlcNAc structures. |
| 11. R125 | Destabilize 2nd GlcNAc recognition via R61, and drive specificity towards O-GlcNAc structures. |

R911 interacts with both N-glycan and O-GlcNAc, based on previous in vitro data. Molecular dynamics and binding free energy estimation of R911 with various glycans and glycopeptides indicate that the reversion mutations listed above would tailor R911 affinity towards interactions with specific glycosylations. For instance, molecular dynamics data of R911 predicts the D57L mutation destabilizes H-bond interactions with the adjacent R61 residue that is critical for terminal GlcNAc recognition on the chitobiose core (FIGS. 51 and 56b). Thus, the L57D reversion mutation is anticipated to enhance N-glycan recognition and affinity. Similarly, the L156I/S206E reversions may enhance O-GlcNAc recognition, due to minimal or unfavorable estimated binding free energies for these introduced mutations (Table 38). E118, present in R911, PNGase F, and D60A is expected to stabilize interactions with the second GlcNAc of the chitobiose core. The E118Q mutation is reported to abolish catalytic activity as this mutation destabilizes substrate binding and recognition and would therefore shift specificity toward O-GlcNAcylated glycoproteins (Table 39). T119 stabilizes D57 via H-bond interactions, thus a mutation at this site that disrupts this H-bond interaction would destabilize D57 and its H-bond interaction with R61, thereby driving specificity away from N-glycan structures and towards O-GlcNAc recognition. K123 stabilizes backbone interactions with T55, C56, and D57. A disruption of these interactions would destabilize D57, and thus R61 resulting in a similar shift in specificity towards O-GlcNAc. Similarly, R125 stabilizes R61 via H-bond interactions, thus a mutation at this site that disrupts this H-bond interaction would destabilize R61's interactions with the terminal GlcNAc, resulting in a similar shift in specificity towards O-GlcNAc.

Figure 57:
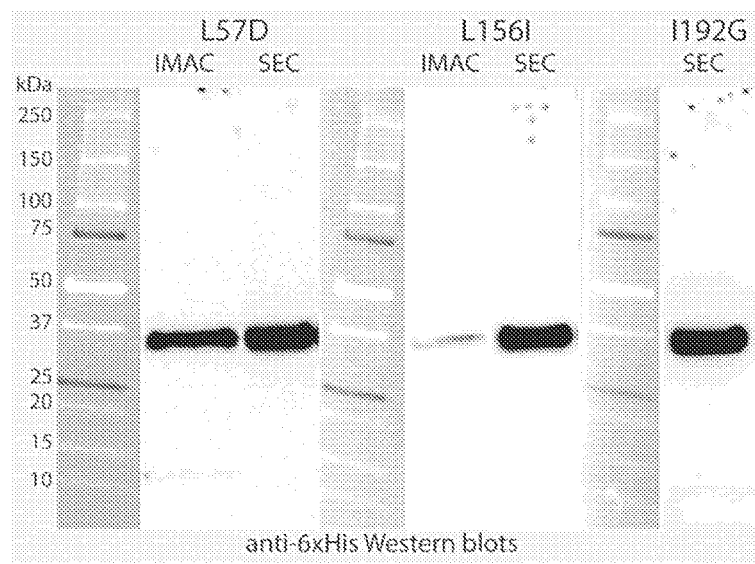
FIG. 57 shows SDS-PAGE purification of L57D, L156I, and I192G of R911 mutants.
Figure 58:
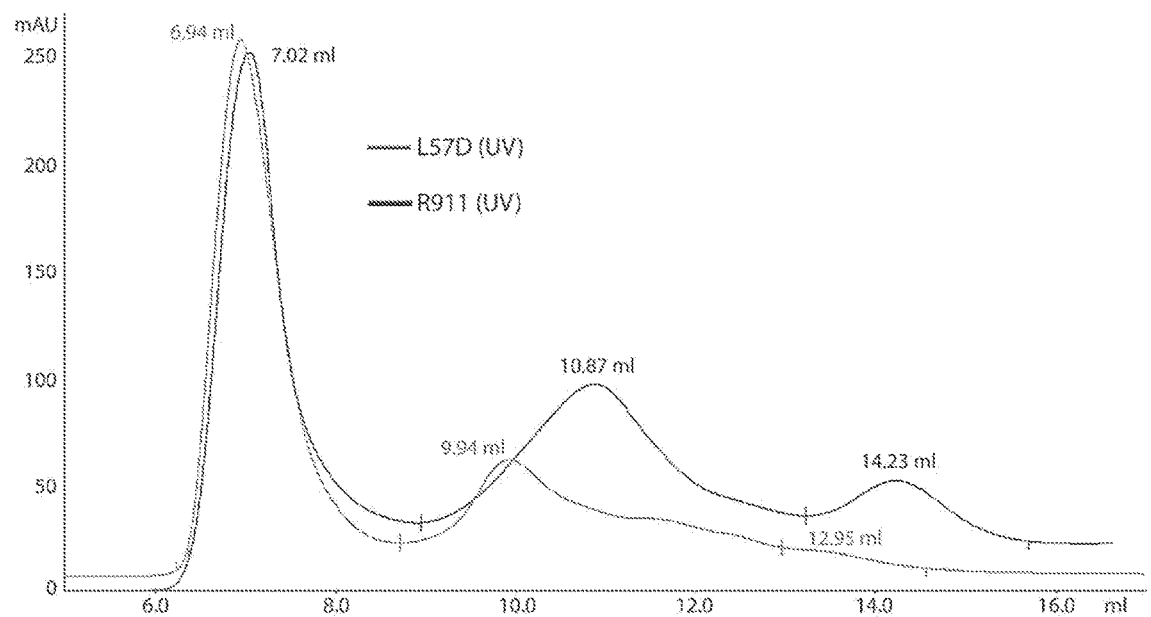
FIG. 58 shows a L57D purification profile. L57D has two elution peaks from IMAC resolution.
Figure 59:
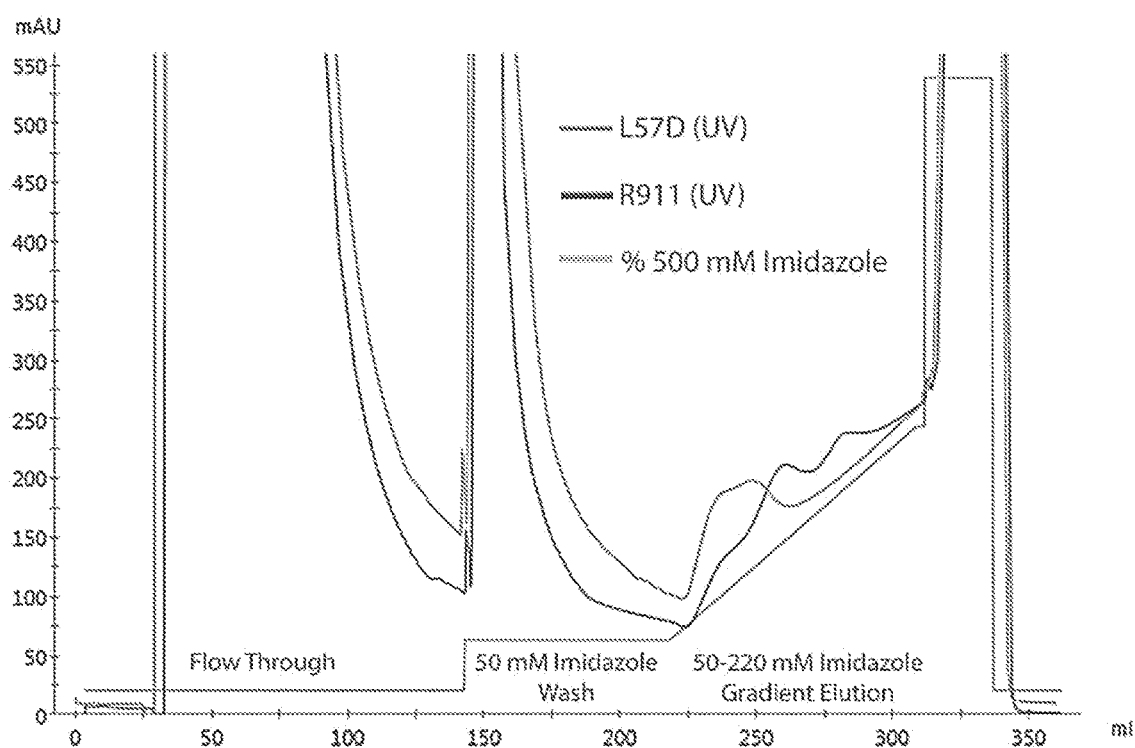
FIG. 59 shows an L57D mutant exhibiting an SEC elution pattern that is unlike R911.

Successful protein expression was achieved for all seven R911 revertant mutants listed above. The E118Q mutant was created, with expression data soon to come. Western blots demonstrate detection of 6×His-tagged L57D and L156I purified from immobilized metal ion affinity chromatography (IMAC) and size exclusion chromatography (SEC), along with I192G purified from SEC (FIG. 57). L57D has a purification profile that is qualitatively unique from R911: L57D has two elution peaks from IMAC resolution, whereas R911 exhibits three elution peaks (see UV traces in FIG. 58). Additionally, each mutant exhibits an SEC elution pattern that is unlike R911, as shown in the UV trace overlay (FIG. 59). These differences in elution patterns would suggest that these mutants have properties distinct from R911, such as protein conformation. However, L57D does behave similarly to R911 in amount of protein purified and SDS-PAGE migration at 36 kDa (see FIG. 57). Further functional analysis for each of these mutants is ongoing, including specificity comparison of L57D and R911 binding profiles using glycan array screening (FIG. 38). A matrix list of PNGase F mutants is illustrated in Table 1.

Investigating PNGase F and ogOGA Activity Against pNP-β-GlcNAc, pNP-Chitobioside, pNP-α-GalNAc, and pNP-β-GalNAc Substrates To unambiguously rule out the possibility that the O-Glycan affinity of R911 is a "carry-over" from wild-type PNGase F, we performed enzyme activity assays on four O-glycan substrates that are similar in size but different in structure and/or conformation. They are: p-Nitrophenyl N-acetyl-β-D-glucosaminide (β-GlcNAc), a known substrate of an O-glycanase, β-N-acetylglucosaminidase from Oceanicola granulosus (ogOGA), p-Nitrophenyl N,N'-diacetyl-β-D-chitobioside (Chitobiose), p-Nitrophenyl 2-Acetamido-2-deoxy-α-D-galactopyranoside (α-GalNAc), and p-Nitrophenyl 2-Acetamido-2-deoxy-β-D-galactopyranoside (β-GalNAc).

Figure 60:
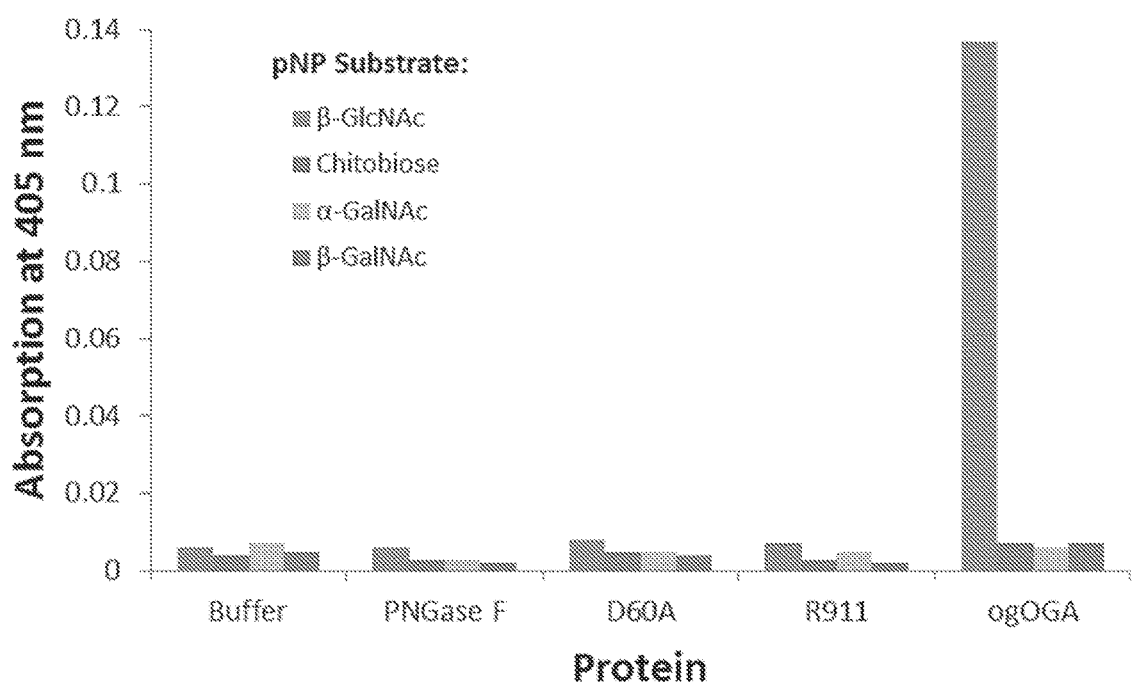
FIG. 60 shows O-glycanase activity assay. pNP-O-glycan substrates (250 µg/mL) were incubated with 10 pmoles of a test protein in 25 µL of 25 mM Tris-Cl buffer, pH 7.5, and 100 µg/mL BSA at 37° C. for 60 min. Reactions were stopped by addition of 200 µL of 0.2M $Na_2CO_3$ solution. Absorption at 405 nm was measured as indication of enzyme activity. Substrate abbreviations: GlcNAc: p-Nitrophenyl N-acetyl-β-D-glucosaminide; Chitobiose: p-Nitrophenyl N,N'-diacetyl-β-D-chitobioside; α-GalNAc: p-Nitrophenyl 2-Acetamido-2-deoxy-α-D-galactopyranoside; β-GalNAc: p-Nitrophenyl 2-Acetamido-2-deoxy-β-D-galactopyranoside.

The results confirm the activity of ogOGA on β-GlcNAc (positive control), but not on any of Chitobiose, α-GalNAc or β-GalNAc substrates (FIG. 60). More importantly, this experiment rules out any residual O-glycanase activity of PNGase F and its derivatives, D60A and R911.

Figure 61:
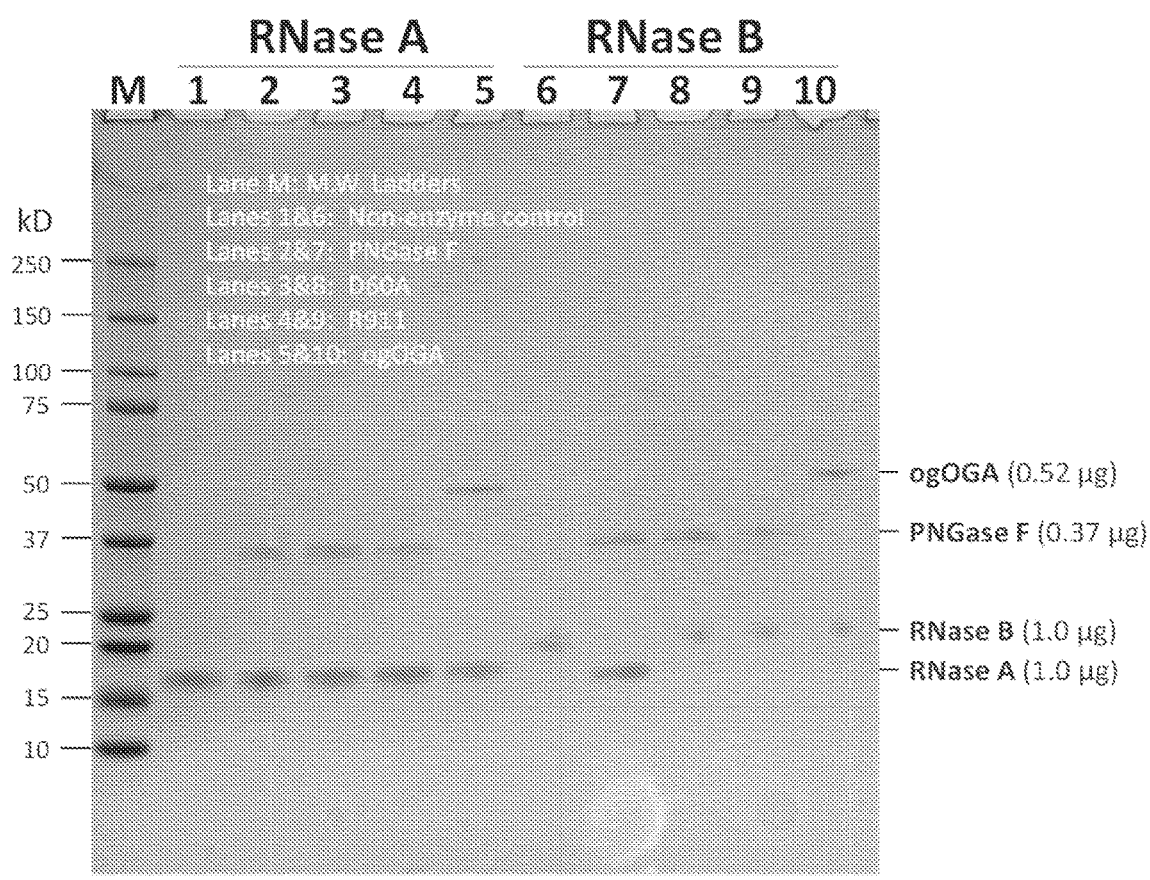
FIG. 61 shows N-glycanase activity assay. N-glycosylated substrate (1 µg of denatured RNase B) was incubated with 10 pmoles of a test protein in 15 µL of 50 mM EPPS buffer, pH 8.0, at 37° C. for 60 min. As a negative control and M. W. marker, denatured RNase A was incubated with the test proteins in parallel. The reactions were stopped by addition of concentrated SDS-Sample Buffer and heating at 100° C. for 5 min. The final products were analyzed by denaturing polyacrylamide gel electrophoresis.

In addition, positive N-glycanase activity of PNGase F was re-confirmed by a standard gel-shift assay (Table 10). FIG. 61 shows that PNGase F completely de-glycosylates 1 μg of RNase B under the assay conditions described, resulting in RNase B migrating to a position similar to the size of RNase A, which is not glycosylated. In contrast, R911 and D60A are inactive against the glycosylated RNase B as a band indicating deglycosylated RNase B (equivalent to RNase A) was not observed. As a negative control, ogOGA was included in the experiment.

In conclusion, the activity assays unambiguously demonstrate that the O-Glycan affinity of R911 is an acquired new property as a result of the engineering of wt PNGase F into a Lectenz®. In addition, these data also demonstrate that wt PNGase F also does not have catalytic activity on α-GalNAc or β-GalNAc indicating that engineering of PNGase F into a GalNAc recognizing Lectenz® would also be an acquired new property.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. An isolated catalytically inactive carbohydrate-binding PNGase F protein with binding specificity and affinity to an O-linked glycan, said protein having a plurality of amino acid mutations compared to a corresponding wild-type PNGase F protein, said plurality of mutations comprising
   (a) at least one first mutation that reduces or eliminates the catalytic activity of the PNGase F protein; and
   (b) at least one second mutation that provides binding specificity and affinity to an O-linked glycan;
      wherein the at least one second mutation comprises an amino acid substitution at position D57 of SEQ ID NO: 1, or a corresponding position in a homologous PNGase F sequence, with leucine, alanine, methionine, arginine, lysine, cysteine, or tryptophan.

2. The catalytically inactive carbohydrate-binding PNGase F protein of claim 1 wherein the O-linked glycan comprises an O-linked GlcNAc.

3. The catalytically inactive carbohydrate-binding PNGase F protein of claim 1 wherein the corresponding wild-type protein comprises a protein selected from the group consisting of PNGase F from *Elizabethkingia meningosepticum* (SEQ ID NO:1), PNGase F-II from *Elizabethkingia meningosepticum* (SEQ ID NO:3), PNGase F from *Bacteroides fragilis* (SEQ ID NO:4), and PNGase F from *Elizabethkingia miricola* (SEQ ID NO:5).

4. The catalytically inactive carbohydrate-binding PNGase F protein of claim 1 comprising mutations at amino acid positions 60, 156, 192, 206, and/or 248 in *E. meningosepticum* PNGase F (SEQ ID NO: 1), or a corresponding position in a homologous PNGase F sequence.

5. The catalytically inactive carbohydrate-binding PNGase F protein of claim 4 further comprising a mutation at amino acid position 61, 85, 118, 119, 123, 125, 190, and/or 191 in *E. meningosepticum* PNGase F (SEQ ID NO:1), or a corresponding position in a homologous PNGase F sequence.

6. The catalytically inactive carbohydrate-binding PNGase F protein of claim 5, wherein the amino acid substitution at position 118 of SEQ ID NO:1, or a corresponding position in a homologous PNGase F sequence, comprises alanine, glutamine, threonine, or cysteine.

7. The catalytically inactive carbohydrate-binding PNGase F protein of claim 4, wherein:
  the amino acid substitution at position 60 of SEQ ID NO: 1, or a corresponding position in a homologous PNGase F sequence, comprises alanine, cysteine, valine, serine, glycine, or tryptophan;
  the amino acid substitution at position 156 of SEQ ID NO: 1, or a corresponding position in a homologous PNGase F sequence, comprises leucine, threonine, methionine, glycine, tryptophan, or histidine;
  the amino acid substitution at position 192 of SEQ ID NO: 1, or a corresponding position in a homologous PNGase F sequence, comprises isoleucine, tryptophan, alanine, histidine, threonine, cysteine, or serine;
  the amino acid substitution at position 206 of SEQ ID NO: 1, or a corresponding position in a homologous PNGase F sequence, comprises serine, tryptophan, histidine, cysteine, or arginine; and/or
  the amino acid substitution at position 248 of SEQ ID NO: 1, or a corresponding position in a homologous PNGase F sequence, comprises tryptophan, serine, proline, valine, aspartate, tyrosine, phenylalanine, or lysine.

8. The catalytically inactive carbohydrate-binding PNGase F protein of claim 7, wherein the a homologous PNGase F sequence comprises SEQ ID NO: 3, SEQ ID NO: 4 or SEQ ID NO:5.

9. The catalytically inactive carbohydrate-binding PNGase F protein of claim 1, comprising SEQ ID NO:1 with a D57L amino acid substitution at position 57, a D60C amino acid substitution at position 60, an I156L amino acid substitution at position 156, a G192I amino acid substitution at position 192, an E206S amino acid substitution at position 206, and/or a R248W amino acid substitution at position 248.

10. The catalytically inactive carbohydrate-binding PNGase F protein of claim 9, further comprising an E118Q amino acid substitution at position 118.

11. The catalytically inactive carbohydrate-binding PNGase F protein of claim 1, which binds to an O-linked glycan, O-linked glycoconjugate, O-linked glycopeptide, O-linked glycoprotein, or free O-glycan.

12. A conjugate comprising a first component comprising a catalytically inactive carbohydrate-binding PNGase F protein of claim 1 covalently linked to a second component.

13. A diagnostic or therapeutic composition comprising a catalytically inactive carbohydrate-binding PNGase F protein of claim 1.

14. An isolated polynucleotide encoding a catalytically inactive carbohydrate-binding PNGase F protein of claim 1.

15. A method for detecting a glycan comprising:
  contacting a biological or laboratory sample with a catalytically inactive carbohydrate-binding PNGase F protein of claim 1 under conditions to allow binding of PNGase F protein to a glycan; and
  detecting the glycan;
wherein the glycan is selected from the group consisting of an O-linked glycan, and a free O-glycan.

16. A method for enriching, isolating or purifying an O-linked glycan or free O-glycan, the method comprising:
  contacting a biological or laboratory sample with a catalytically inactive carbohydrate-binding PNGase F protein of claim 1 under conditions to allow binding of PNGase F protein to an O-glycan so as to yield an enriched, isolated or purified O-linked glycan or free O-glycan.

17. The method of claim 16 further comprising identifying a constituent saccharide, determining saccharide composition, determining linkage positions, or determining stereochemistry of the enriched, isolated or purified O-linked glycan or free O-glycan.

* * * * *

UNITED STATES PATENT AND TRADEMARK OFFICE
CERTIFICATE OF CORRECTION

PATENT NO. : 10,358,637 B2
APPLICATION NO. : 15/304725
DATED : July 23, 2019
INVENTOR(S) : Kausar N. Samli et al.

Page 1 of 1

It is certified that error appears in the above-identified patent and that said Letters Patent is hereby corrected as shown below:

In the Specification

In Column 1, Line 7, before the SEQUENCE LISTING paragraph, please insert the following:
--GOVERNMENT SUPPORT CLAUSE
This invention was made with government support under Agreement Nos. R41 GM086991 and R43 GM123856 awarded by the NIH. The Government has certain rights in the invention." (37 CFR 401.14 f (4))--

Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 20

<210> SEQ ID NO 1
<211> LENGTH: 314
<212> TYPE: PRT
<213> ORGANISM: Flavobacterium meningosepticum
<220> FEATURE:
<221> NAME/KEY: VARIANT
<222> LOCATION: (39)..(39)
<223> OTHER INFORMATION: X at position 39 may be alanine (A, Ala) or
      threonine (T, Thr)
<220> FEATURE:
<221> NAME/KEY: VARIANT
<222> LOCATION: (149)..(149)
<223> OTHER INFORMATION: X at position 149 may be valine (V, Val) or
      isoleucine (I, Ile)
<220> FEATURE:
<221> NAME/KEY: VARIANT
<222> LOCATION: (168)..(168)
<223> OTHER INFORMATION: X at position 168 may be alanine (A, Ala) or
      glycine (G, Gly)
<220> FEATURE:
<221> NAME/KEY: VARIANT
<222> LOCATION: (219)..(219)
<223> OTHER INFORMATION: X at position 219 may be serine (S, Ser) or
      alanine (A, Ala)
<220> FEATURE:
<221> NAME/KEY: VARIANT
<222> LOCATION: (243)..(243)
<223> OTHER INFORMATION: X at position 243 may be asparagine (N, Asn
      ) or isoleucine (I, Ile)
<220> FEATURE:
<221> NAME/KEY: VARIANT
<222> LOCATION: (245)..(245)
<223> OTHER INFORMATION: X at position 245 may be threonine (T, Thr) or
      alanine (A, Ala)
<220> FEATURE:
<221> NAME/KEY: VARIANT
<222> LOCATION: (269)..(269)
<223> OTHER INFORMATION: X at position 269 may be isoleucine (I, Ile)
      or threonine (T, Thr)
<220> FEATURE:
<221> NAME/KEY: VARIANT
<222> LOCATION: (281)..(281)
<223> OTHER INFORMATION: X at position 281 may be Asparagine (N, Asn)
      or serine (S, Ser)

<400> SEQUENCE: 1

Ala Pro Ala Asp Asn Thr Val Asn Ile Lys Thr Phe Asp Lys Val Lys
1               5                   10                  15

Asn Ala Phe Gly Asp Gly Leu Ser Gln Ser Ala Glu Gly Thr Phe Thr
            20                  25                  30

Phe Pro Ala Asp Val Thr Xaa Val Lys Thr Ile Lys Met Phe Ile Lys
        35                  40                  45

Asn Glu Cys Pro Asn Lys Thr Cys Asp Glu Trp Asp Arg Tyr Ala Asn
    50                  55                  60
```

```
Val Tyr Val Lys Asn Lys Thr Thr Gly Glu Trp Tyr Glu Ile Gly Arg
65                  70                  75                  80

Phe Ile Thr Pro Tyr Trp Val Gly Thr Glu Lys Leu Pro Arg Gly Leu
                85                  90                  95

Glu Ile Asp Val Thr Asp Phe Lys Ser Leu Leu Ser Gly Asn Thr Glu
            100                 105                 110

Leu Lys Ile Tyr Thr Glu Thr Trp Leu Ala Lys Gly Arg Glu Tyr Ser
        115                 120                 125

Val Asp Phe Asp Ile Val Tyr Gly Thr Pro Asp Tyr Lys Tyr Ser Ala
    130                 135                 140

Val Val Pro Val Xaa Gln Tyr Asn Lys Ser Ser Ile Asp Gly Val Pro
145                 150                 155                 160

Tyr Gly Lys Ala His Thr Leu Xaa Leu Lys Lys Asn Ile Gln Leu Pro
                165                 170                 175

Thr Asn Thr Glu Lys Ala Tyr Leu Arg Thr Thr Ile Ser Gly Trp Gly
            180                 185                 190

His Ala Lys Pro Tyr Asp Ala Gly Ser Arg Gly Cys Ala Glu Trp Cys
        195                 200                 205

Phe Arg Thr His Thr Ile Ala Ile Asn Asn Xaa Asn Thr Phe Gln His
    210                 215                 220

Gln Leu Gly Ala Leu Gly Cys Ser Ala Asn Pro Ile Asn Asn Gln Ser
225                 230                 235                 240

Pro Gly Xaa Trp Xaa Pro Asp Arg Ala Gly Trp Cys Pro Gly Met Ala
                245                 250                 255

Val Pro Thr Arg Ile Asp Val Leu Asn Asn Ser Leu Xaa Gly Ser Thr
            260                 265                 270

Phe Ser Tyr Glu Tyr Lys Phe Gln Xaa Trp Thr Asn Asn Gly Thr Asn
        275                 280                 285

Gly Asp Ala Phe Tyr Ala Ile Ser Ser Phe Val Ile Ala Lys Ser Asn
    290                 295                 300

Thr Pro Ile Ser Ala Pro Val Val Thr Asn
305                 310
```

<210> SEQ ID NO 2
<211> LENGTH: 945
<212> TYPE: DNA
<213> ORGANISM: Flavobacterium meningosepticum

<400> SEQUENCE: 2

```
gctccggcag ataatacggt aaatattaaa acattcgaca aagtaaaaaa tgcctttggt      60
gacggattgt cccaaagtgc ggaaggaacc tttacatttc cggccgatgt aacagccgta     120
aaaacgatta agatgttcat taaaaatgaa tgtcctaata aaacttgtga tgaatgggat     180
cgttatgcca atgtttatgt aaaaaataaa acaacaggtg agtggtacga aataggacgc     240
tttattactc catattgggt gggaacggaa aaattacctc gtggactgga aattgatgtt     300
acagatttca aatctttact atccggaaat acagaactta aaatttatac ggagacatgg     360
ctggccaaag gaagagaata cagtgtagat ttcgatattg tatacgggac accggattat     420
aaatattcgg ctgtagtacc tgtagttcag tataacaaat catctattga cggagtccct     480
tatggtaaag cacatacatt ggctttgaaa aagaatatcc agttaccaac aaacacagaa     540
aaagcttatc ttagaactac tatttccgga tggggacatg ctaagccata tgatgcggga     600
agcagaggtt gtgcagaatg gtgcttcaga acacacacta tagcaataaa taattcgaat     660
actttccagc atcagctggg tgctttagga tgttcagcaa accctatcaa taatcagagt     720
```

```
ccgggaaatt ggactcccga cagagccggt tggtgcccgg gaatggcagt tccaacacgt    780
atagatgtac tgaataattc tttaataggc agtacttttta gttatgaata taaattccag    840
aactggacaa ataacggaac caatggagat gctttttatg caatttccag ttttgtgatt    900
gcaaaaagta atacacctat tagtgctccg gtagttacaa actaa                     945
```

<210> SEQ ID NO 3
<211> LENGTH: 567
<212> TYPE: PRT
<213> ORGANISM: Flavobacterium meningosepticum

<400> SEQUENCE: 3

```
Met Leu Phe Phe Leu Pro Leu Leu Lys Thr Asn Leu Met Gln Lys Ile
1               5                   10                  15

Leu Leu Cys Ser Leu Ile Thr Gly Ala Gln Met Ile Phe Ala Gln Thr
            20                  25                  30

Tyr Glu Ile Thr Tyr Gln Asn Ser Phe Glu Gly Lys Ile Asn Pro Asn
        35                  40                  45

Gln Asn His Ile Ile Ser Ile Thr Asn Ser Asp Lys Thr Leu Leu Phe
    50                  55                  60

Asn Glu Lys Ile Lys Asn Lys Lys Ala Asp Phe Pro Phe Glu Val Asn
65                  70                  75                  80

Glu Ile Asn Arg Lys Asn Asn Glu Val Ser Gln Phe Ala Phe Leu Asn
                85                  90                  95

Asn Asn Glu Ile Val Lys Thr Ser Asp Asn Thr Ile Leu Ala Lys Gln
            100                 105                 110

Glu Phe Lys Pro Thr Ser Glu Thr Gly Lys Ile Leu Gly Tyr Asn Val
        115                 120                 125

Lys Lys Ala Val Thr Ser Val Asn Ser Asn Thr Ile Glu Val Trp Tyr
    130                 135                 140

Thr Asn Asp Leu Lys Val Lys Gly Gly Pro Ser Ile Leu Gly Gln Asp
145                 150                 155                 160

Leu Gly Leu Val Leu Lys Thr Val Arg Asn Gly Ser Ser Val Val Glu
                165                 170                 175

Ala Thr Ser Val Lys Lys Ile Lys Ala Leu Asp Asp Gln Ser Leu Phe
            180                 185                 190

Asn Gly Lys Asn Ile Thr Glu Lys Asp Ala Leu Thr Tyr Lys Asp Met
        195                 200                 205

Ile Trp Lys Ser Arg Phe Ile Thr Ile Pro Val Phe Glu Asn Glu Thr
    210                 215                 220

Ile Asn Phe Ser Asp Ala Ser Lys Ser Asp Gln Val Ile Gln Arg Phe
225                 230                 235                 240

Gly Asn Gly Thr Ile Ile Leu Lys Lys Val Lys Ile Pro Glu Ile Lys
                245                 250                 255

Gln Gly Asn Thr Ile Phe Val Glu Leu Lys Gln Lys Ser Asn Gly Asp
            260                 265                 270

Ala Tyr Asp Arg Thr Gly Asp Val Phe Ile Ile Pro Gln Glu Arg Ala
        275                 280                 285

Ile Ser Tyr Tyr Thr Gly Leu Thr Gln Gly Val Lys Ser Leu Pro Val
    290                 295                 300

Tyr Gln Asn Gly Asn Gly Lys Ser Tyr Gln Gly Val Ala Leu Thr Pro
305                 310                 315                 320

Asp Tyr Leu Pro Phe Ile Glu Leu Met Arg Phe Phe Thr Pro Phe Gly
                325                 330                 335
```

```
Ile Gly His Phe Asn Glu Lys Ile Gln Leu Lys Gly Lys Asn Trp His
            340                 345                 350

Asn Asn Thr Pro Tyr Arg Gln Asp Ile Thr Glu Leu Arg Pro Gln Leu
            355                 360                 365

Ser Gly Lys Glu Ile Leu Ile Gly Ala Phe Ile Gly Asn Tyr Asp Lys
370                 375                 380

Gly Gly His Gln Ile Ser Leu Glu Leu Ser Ile His Pro Asp Gln Gln
385                 390                 395                 400

Lys Ile Val Asn Asn Phe Val Leu Pro Val Phe Asn Thr Thr Asn
            405                 410                 415

Val Met Glu Met Ala Gly Gln Asp Tyr Pro Thr Met Phe Asn Ser Asp
            420                 425                 430

Lys Gly Val Glu Val Glu Phe Ile Leu Thr Lys Asp Leu Lys Asn Ala
            435                 440                 445

Gln Leu Arg Tyr Ile Thr Thr Gly His Gly Gly Trp Gly Ala Gly Asp
            450                 455                 460

Glu Phe Val Pro Lys Glu Asn Ser Ile Tyr Leu Asp Gly Lys Leu Ala
465                 470                 475                 480

His Ala Phe Thr Pro Trp Arg Thr Asp Cys Gly Ser Tyr Arg Leu Phe
            485                 490                 495

Asn Pro Ala Ser Gly Asn Phe Glu Asp Gly Leu Ser Ser Ser Asp Leu
            500                 505                 510

Ser Arg Ser Asn Trp Cys Pro Gly Thr Ile Thr Asn Pro Val Tyr Ile
            515                 520                 525

Asn Leu Gly Asn Leu Asn Ala Gly Lys His Thr Ile Gln Val Lys Ile
            530                 535                 540

Pro Gln Gly Ala Pro Glu Gly Ser Ser Gln Ser Phe Trp Asn Val Ser
545                 550                 555                 560

Gly Val Leu Leu Gly Gln Glu
            565

<210> SEQ ID NO 4
<211> LENGTH: 415
<212> TYPE: PRT
<213> ORGANISM: Bacteroides fragilis

<400> SEQUENCE: 4

Met Asn Ile Arg Leu Thr Ser Leu Phe Val Ser Leu Phe Leu Ser Val
1               5                   10                  15

Pro Val Trp Ala Gly Gly His Lys Asn Leu Pro Ala Lys Gly Asp Leu
            20                  25                  30

His Ile Pro Val Phe Glu Asn Val Asn Val Arg Phe Ser Pro Asp Thr
            35                  40                  45

Tyr Pro Asp Asn Tyr Asn Glu Ala Asp Gly Thr Gly Val Tyr His Leu
50                  55                  60

Val Asn Gly Arg Ile Ile Leu Lys Lys Ile Thr Leu Pro Glu Tyr Lys
65                  70                  75                  80

Arg Asn Val Ser Val Ser Leu Lys Val Thr Leu Ala Ser Asn Gly Asp
            85                  90                  95

Arg Trp Asp Lys Ser Gly Ser Cys Phe Val Leu Pro Lys Ser Ser Ala
            100                 105                 110

Ile Asn Leu Leu Thr Ile Ala Arg Asp Gly Met Lys Phe Pro Ser Val
            115                 120                 125

Asp Ser Leu Lys Leu Glu Lys Met Val Gly Ile Val Pro Gly Lys Asp
```

```
                130                 135                 140
Tyr Leu Pro Thr Val Glu Leu Met Arg Phe Met Thr Pro Phe Gly Ile
145                 150                 155                 160

Gly His Tyr Ser Asn Asn Asp Ser Leu Ser Ser Lys Arg Arg Pro
                165                 170                 175

Val Tyr Ile Pro Lys Trp Glu Ser Asn Val Thr Trp Gln Gln Asp Ile
                180                 185                 190

Thr Asp Leu Tyr Pro Leu Leu Glu Gly Glu Ala Tyr Val Gly Ile Tyr
            195                 200                 205

Ile Asp Thr Trp Thr Ser Glu Gly Tyr Leu Val Asn Ala Asp Ile Asp
        210                 215                 220

Val Lys Glu Ser Arg Leu Ala Cys Asp Val Leu Pro Lys Arg His Val
225                 230                 235                 240

Glu Pro Leu Met Asn Thr Val Tyr Tyr Met Gly Gln Ser Tyr Pro Asp
                245                 250                 255

Ile Phe Ala Arg Arg Asp Val Ser Thr Asp Phe Thr Val Pro Lys Gly
                260                 265                 270

Ala Lys Asn Ile Arg Leu Lys Tyr Ile Val Thr Gly His Gly Gly His
                275                 280                 285

Ser Gly Gly Asp Glu Phe Val Gln Lys Arg Asn Ile Ile Ser Val Asp
        290                 295                 300

Gly Lys Glu Val Leu Asn Phe Ile Pro Trp Arg Asp Asp Cys Ala Ser
305                 310                 315                 320

Phe Arg Arg Phe Asn Pro Ala Thr Gly Val Trp Leu Ile Lys Arg Leu
                325                 330                 335

Ala Ser Tyr Ile Gly Glu Lys Gly Tyr Thr Glu Lys Glu Val Glu Glu
                340                 345                 350

Pro Leu Ala Ser Ser Asp Leu Ser Arg Ser Asn Trp Cys Pro Gly Ser
                355                 360                 365

Asp Val Val Pro Glu Glu Ala Val Ile Gly Thr Leu Ala Pro Gly Lys
            370                 375                 380

His Thr Phe Thr Val Ser Ile Pro Glu Ala Gln Ala Val Asp Gly Asn
385                 390                 395                 400

Lys Leu Asn His Trp Leu Val Ser Ala Tyr Leu Val Trp Glu Glu
                405                 410                 415

<210> SEQ ID NO 5
<211> LENGTH: 354
<212> TYPE: PRT
<213> ORGANISM: Flavobacterium miricola

<400> SEQUENCE: 5

Met Arg Lys Leu Leu Ile Phe Ser Ile Ser Ala Tyr Leu Met Ala Gly
1               5                   10                  15

Ile Val Ser Cys Lys Gly Val Asp Ser Ala Thr Pro Val Thr Glu Asp
                20                  25                  30

Arg Leu Ala Leu Asn Ala Val Asn Ala Pro Ala Asp Asn Thr Val Asn
            35                  40                  45

Ile Lys Thr Phe Asp Lys Val Lys Asn Ala Phe Gly Asp Gly Leu Ser
        50                  55                  60

Gln Ser Ala Glu Gly Thr Phe Thr Phe Pro Ala Asp Val Thr Thr Val
65                  70                  75                  80

Lys Thr Ile Lys Met Phe Ile Lys Asn Glu Cys Pro Asn Lys Thr Cys
                85                  90                  95
```

```
Asp Glu Trp Asp Arg Tyr Ala Asn Val Tyr Val Lys Asn Lys Thr Thr
                100                 105                 110

Gly Glu Trp Tyr Glu Ile Gly Arg Phe Ile Thr Pro Tyr Trp Val Gly
            115                 120                 125

Thr Glu Lys Leu Pro Arg Gly Leu Glu Ile Asp Val Thr Asp Phe Lys
        130                 135                 140

Ser Leu Leu Ser Gly Asn Thr Glu Leu Lys Ile Tyr Thr Glu Thr Trp
145                 150                 155                 160

Leu Ala Lys Gly Arg Glu Tyr Ser Val Asp Phe Asp Ile Val Tyr Gly
                165                 170                 175

Thr Pro Asp Tyr Lys Tyr Ser Ala Val Val Pro Val Ile Gln Tyr Asn
            180                 185                 190

Lys Ser Ser Ile Asp Gly Val Pro Tyr Gly Lys Ala His Thr Leu Gly
        195                 200                 205

Leu Lys Lys Asn Ile Gln Leu Pro Thr Asn Thr Glu Lys Ala Tyr Leu
210                 215                 220

Arg Thr Thr Ile Ser Gly Trp Gly His Ala Lys Pro Tyr Asp Ala Gly
225                 230                 235                 240

Ser Arg Gly Cys Ala Glu Trp Cys Phe Arg Thr His Thr Ile Ala Ile
                245                 250                 255

Asn Asn Ala Asn Thr Phe Gln His Gln Leu Gly Ala Leu Gly Cys Ser
            260                 265                 270

Ala Asn Pro Ile Asn Asn Gln Ser Pro Gly Asn Trp Ala Pro Asp Arg
        275                 280                 285

Ala Gly Trp Cys Pro Gly Met Ala Val Pro Thr Arg Ile Asp Val Leu
        290                 295                 300

Asn Asn Ser Leu Thr Gly Ser Thr Phe Ser Tyr Glu Tyr Lys Phe Gln
305                 310                 315                 320

Ser Trp Thr Asn Asn Gly Thr Asn Gly Asp Ala Phe Tyr Ala Ile Ser
                325                 330                 335

Ser Phe Val Ile Ala Lys Ser Asn Thr Pro Ile Ser Ala Pro Val Val
            340                 345                 350

Thr Asn

<210> SEQ ID NO 6
<211> LENGTH: 326
<212> TYPE: PRT
<213> ORGANISM: artificial
<220> FEATURE:
<223> OTHER INFORMATION: Synthetic PNGase F polypeptide
      including a N-terminal secretion tag and a C-terminal hexa-His tag

<400> SEQUENCE: 6

Gly Ile Pro Ala Pro Ala Asp Asn Thr Val Asn Ile Lys Thr Phe Asp
1               5                   10                  15

Lys Val Lys Asn Ala Phe Gly Asp Gly Leu Ser Gln Ser Ala Glu Gly
            20                  25                  30

Thr Phe Thr Phe Pro Ala Asp Val Thr Ala Lys Thr Ile Lys Met
        35                  40                  45

Phe Ile Lys Asn Glu Cys Pro Asn Lys Thr Cys Asp Glu Trp Asp Arg
50                  55                  60

Tyr Ala Asn Val Tyr Val Lys Asn Lys Thr Thr Gly Glu Trp Tyr Glu
65                  70                  75                  80

Ile Gly Arg Phe Ile Thr Pro Tyr Trp Val Gly Thr Glu Lys Leu Pro
                85                  90                  95
```

Arg Gly Leu Glu Ile Asp Val Thr Asp Phe Lys Ser Leu Leu Ser Gly
            100                 105                 110

Asn Thr Glu Leu Lys Ile Tyr Thr Glu Thr Trp Leu Ala Lys Gly Arg
        115                 120                 125

Glu Tyr Ser Val Asp Phe Asp Ile Val Tyr Gly Thr Pro Asp Tyr Lys
    130                 135                 140

Tyr Ser Ala Val Val Pro Val Gln Tyr Asn Lys Ser Ser Ile Asp
145                 150                 155                 160

Gly Val Pro Tyr Gly Lys Ala His Thr Leu Ala Leu Lys Lys Asn Ile
                165                 170                 175

Gln Leu Pro Thr Asn Thr Glu Lys Ala Tyr Leu Arg Thr Thr Ile Ser
            180                 185                 190

Gly Trp Gly His Ala Lys Pro Tyr Asp Ala Gly Ser Arg Gly Cys Ala
        195                 200                 205

Glu Trp Cys Phe Arg Thr His Thr Ile Ala Ile Asn Asn Ser Asn Thr
    210                 215                 220

Phe Gln His Gln Leu Gly Ala Leu Gly Cys Ser Ala Asn Pro Ile Asn
225                 230                 235                 240

Asn Gln Ser Pro Gly Asn Trp Thr Pro Asp Arg Ala Gly Trp Cys Pro
                245                 250                 255

Gly Met Ala Val Pro Thr Arg Ile Asp Val Leu Asn Asn Ser Leu Ile
            260                 265                 270

Gly Ser Thr Phe Ser Tyr Glu Tyr Lys Phe Gln Asn Trp Thr Asn Asn
        275                 280                 285

Gly Thr Asn Gly Asp Ala Phe Tyr Ala Ile Ser Ser Phe Val Ile Ala
    290                 295                 300

Lys Ser Asn Thr Pro Ile Ser Ala Pro Val Val Thr Asn Leu Asp Pro
305                 310                 315                 320

His His His His His His
            325

<210> SEQ ID NO 7
<211> LENGTH: 981
<212> TYPE: DNA
<213> ORGANISM: artificial
<220> FEATURE:
<223> OTHER INFORMATION: Synthetic PNGase F pOPH6 coding
      sequence including a N-terminal secretion tag and a C-terminal
      hexa-His tag

<400> SEQUENCE: 7
ggaattccag ctccggcaga taatacggta aatattaaaa cattcgacaa agtaaaaaat    60
gcctttggtg acggattgtc ccaaagtgcg gaaggaacct ttacatttcc ggccgatgta   120
acagccgtaa aaacgattaa gatgttcatt aaaaatgaat gtcctaataa aacttgtgat   180
gaatgggatc gttatgccaa tgtttatgta aaaaataaaa caacaggtga gtggtacgaa   240
ataggacgct ttattactcc atattgggtg gaacgaaaa attacctcg tggactggaa    300 attgatgtta cagatttcaa atctttacta tccggaaata cagaacttaa aatttatacg   360
gagacatggc tggccaaagg aagagaatac agtgtagatt tcgatattgt atacgggaca   420
ccggattata atattcggc tgtagtacct gtagttcagt ataacaaatc atctattgac   480
ggagtccctt atggtaaagc acatacattg gctttgaaaa agaatatcca gttaccaaca   540
aacacagaaa aagcttatct tagaactact atttccggat ggggacatgc taagccatat   600
gatgcgggaa gcagaggttg tgcagaatgg tgcttcagaa cacacactat agcaataaat   660

```
aattcgaata ctttccagca tcagctgggt gctttaggat gttcagcaaa ccctatcaat    720
aatcagagtc cgggaaattg gactcccgac agagccggtt ggtgcccggg aatggcagtt    780
ccaacacgta tagatgtact gaataattct ttaataggca gtacttttag ttatgaatat    840
aaattccaga actggacaaa taacggaacc aatggagatg cttttatgc aatttccagt     900 tttgtgattg caaaaagtaa tacacctatt agtgctccgg tagttacaaa cttggatccg    960
catcaccatc accaccattg a                                              981
```

```
<210> SEQ ID NO 8
<211> LENGTH: 1151
<212> TYPE: DNA
<213> ORGANISM: artificial
<220> FEATURE:
<223> OTHER INFORMATION: Sequence of non-amplified GenScript Library 1
<220> FEATURE:
<221> NAME/KEY: misc_feature
<222> LOCATION: (280)..(281)
<223> OTHER INFORMATION: n is a, c, g, or t
<220> FEATURE:
<221> NAME/KEY: misc_feature
<222> LOCATION: (295)..(296)
<223> OTHER INFORMATION: n is a, c, g, or t
<220> FEATURE:
<221> NAME/KEY: misc_feature
<222> LOCATION: (463)..(464)
<223> OTHER INFORMATION: n is a, c, g, or t
<220> FEATURE:
<221> NAME/KEY: misc_feature
<222> LOCATION: (574)..(575)
<223> OTHER INFORMATION: n is a, c, g, or t
<220> FEATURE:
<221> NAME/KEY: misc_feature
<222> LOCATION: (577)..(578)
<223> OTHER INFORMATION: n is a, c, g, or t
<220> FEATURE:
<221> NAME/KEY: misc_feature
<222> LOCATION: (685)..(686)
<223> OTHER INFORMATION: n is a, c, g, or t
<220> FEATURE:
<221> NAME/KEY: misc_feature
<222> LOCATION: (727)..(728)
<223> OTHER INFORMATION: n is a, c, g, or t
```

```
<400> SEQUENCE: 8
aggaaacagc tatgaccatg ttaatgcagc tggcacgaca ggtttcccga ctggaaagcg    60
ggcagtgagc ggaaggccca tgaggccagt taattaagag gtaccgctag cgctccggca   120
gataatacgg taaatattaa acattcgac aaagtaaaaa atgcctttgg tgacggattg    180
tcccaaagtg cggaaggaac ctttacattt ccggccgatg taacagccgt aaaaacgatt   240
aagatgttca ttaaaaatga atgtcctaat aaaacttgtn nkgaatgggc tcgtnnkgcc   300
aatgtttatg taaaaataa aacaacaggt gagtggtacg aaataggacg ctttattact    360
ccatattggg tgggaacgga aaaattacct cgtggactgg aaattgatgt tacagatttc    420
aaatctttac tatccggaaa tacagaactt aaaatttata cgnnkacatg gctggccaaa   480
ggaagagaat acagtgtaga tttcgatatt gtatacggga caccggatta taaatattcg    540
gctgtagtac ctgtagttca gtataacaaa tcannknnkg acggagtccc ttatggtaaa    600
gcacatacat tggctttgaa aaagaatatc cagttaccaa caaacacaga aaagcttat    660 cttagaacta ctatttccgg atggnnkcat gctaagccat atgatgcggg aagcagaggt    720
tgtgcannkt ggtgcttcag aacacacact atagcaataa ataattcgaa tactttccag    780
catcagctgg gtgctttagg atgttcagca aaccctatca ataatcagag tccgggaaat   840
tggactcccg acagagccgg ttggtgcccg ggaatggcag ttccaacacg tatagatgta   900
```
ctgaataatt ctttaatagg cagtactttt agttatgaat ataaattcca gaactggaca    960
aataacggaa ccaatggaga tgctttttat gcaatttcca gttttgtgat tgcaaaaagt   1020
aatacaccta ttagtgctcc ggtagttaca aacggatccg agctcatggc gcgcctaggc   1080
cttgacggcc ttccgccaat tcgccctata gtgagtcgta ttacgtcgcg ctcactggcc   1140
gtcgttttac a                                                        1151

<210> SEQ ID NO 9
<211> LENGTH: 18
<212> TYPE: DNA
<213> ORGANISM: artificial
<220> FEATURE:
<223> OTHER INFORMATION: Synthetic oligonucleotide primer

<400> SEQUENCE: 9
tgtaaaacga cggccagt                                                   18

<210> SEQ ID NO 10
<211> LENGTH: 16
<212> TYPE: DNA
<213> ORGANISM: artificial
<220> FEATURE:
<223> OTHER INFORMATION: Synthetic oligonucleotide primer

<400> SEQUENCE: 10
aggaaacagc tatgac                                                     16

<210> SEQ ID NO 11
<211> LENGTH: 1151
<212> TYPE: DNA
<213> ORGANISM: artificial
<220> FEATURE:
<223> OTHER INFORMATION: Sequence of non-amplified GenArt Library 2
<220> FEATURE:
<221> NAME/KEY: misc_feature
<222> LOCATION: (280)..(282)
<223> OTHER INFORMATION: n is a, c, g, or t
<220> FEATURE:
<221> NAME/KEY: misc_feature
<222> LOCATION: (289)..(291)
<223> OTHER INFORMATION: n is a, c, g, or t
<220> FEATURE:
<221> NAME/KEY: misc_feature
<222> LOCATION: (577)..(579)
<223> OTHER INFORMATION: n is a, c, g, or t
<220> FEATURE:
<221> NAME/KEY: misc_feature
<222> LOCATION: (685)..(687)
<223> OTHER INFORMATION: n is a, c, g, or t
<220> FEATURE:
<221> NAME/KEY: misc_feature
<222> LOCATION: (727)..(729)
<223> OTHER INFORMATION: n is a, c, g, or t
<220> FEATURE:
<221> NAME/KEY: misc_feature
<222> LOCATION: (853)..(855)
<223> OTHER INFORMATION: n is a, c, g, or t

<400> SEQUENCE: 11
aggaaacagc tatgaccatg ttaatgcagc tggcacgaca ggtttcccga ctggaaagcg     60
ggcagtgagc ggaaggccca tgaggccagt taattaagag gtaccgctag cgctccggca   120
gataatacgg taaatattaa acattcgac aaagtaaaaa atgcctttgg tgacggattg    180
tcccaaagtg cggaaggaac ctttacattt ccggccgatg taacagccgt aaaaacgatt   240
aagatgttca ttaaaaatga atgtcctaat aaaacttgtn nngaatggnn ncgttatgcc   300

```
aatgtttatg taaaaaataa acaacaggt gagtggtacg aaataggacg ctttattact    360
ccatattggg tgggaacgga aaaattacct cgtggactgg aaattgatgt tacagatttc    420
aaatctttac tatccggaaa tacagaactt aaaatttata cggagacatg gctggccaaa    480
ggaagagaat acagtgtaga tttcgatatt gtatacggga caccggatta taaatattcg    540
gctgtagtac ctgtagttca gtataacaaa tcatctnnng acggagtccc ttatggtaaa    600
gcacatacat tggctttgaa aaagaatatc cagttaccaa caaacacaga aaaagcttat    660
cttagaacta ctatttccgg atggnnncat gctaagccat atgatgcggg aagcagaggt    720
tgtgcannnt ggtgcttcag aacacacact atagcaataa ataattcgaa tactttccag    780
catcagctgg gtgctttagg atgttcagca aaccctatca ataatcagag tccgggaaat    840
tggactcccg acnnngccgg ttggtgcccg ggaatggcag ttccaacacg tatagatgta    900
ctgaataatt ctttaatagg cagtactttt agttatgaat ataaattcca gaactggaca    960
aataacggaa ccaatggaga tgcttttat gcaatttcca gttttgtgat tgcaaaaagt   1020
aatacaccta ttagtgctcc ggtagttaca aacggatccg agctcatggc gcgcctaggc   1080
cttgacggcc ttccgccaat tcgccctata gtgagtcgta ttacgtcgcg ctcactggcc   1140
gtcgttttac a                                                       1151
```

<210> SEQ ID NO 12
<211> LENGTH: 18
<212> TYPE: DNA
<213> ORGANISM: artificial
<220> FEATURE:
<223> OTHER INFORMATION: Synthetic oligonucleotide primer

<400> SEQUENCE: 12
tgtaaaacga cggccagt                                                 18

<210> SEQ ID NO 13
<211> LENGTH: 16
<212> TYPE: DNA
<213> ORGANISM: artificial
<220> FEATURE:
<223> OTHER INFORMATION: Synthetic oligonucleotide primer

<400> SEQUENCE: 13
aggaaacagc tatgac                                                   16

<210> SEQ ID NO 14
<211> LENGTH: 21
<212> TYPE: DNA
<213> ORGANISM: artificial
<220> FEATURE:
<223> OTHER INFORMATION: Synthetic oligonucleotide primer

<400> SEQUENCE: 14
gtacgagcta aaagtacagt g                                             21

<210> SEQ ID NO 15
<211> LENGTH: 20
<212> TYPE: DNA
<213> ORGANISM: artificial
<220> FEATURE:
<223> OTHER INFORMATION: Synthetic oligonucleotide primer

<400> SEQUENCE: 15
tagataccca tacgacgttc                                               20

```
<210> SEQ ID NO 16
<211> LENGTH: 20
<212> TYPE: DNA
<213> ORGANISM: artificial
<220> FEATURE:
<223> OTHER INFORMATION: Synthetic oligonucleotide primer

<400> SEQUENCE: 16
tctgcaggct agtggtggtg                                                    20

<210> SEQ ID NO 17
<211> LENGTH: 35
<212> TYPE: DNA
<213> ORGANISM: artificial
<220> FEATURE:
<223> OTHER INFORMATION: Synthetic oligonucleotide primer

<400> SEQUENCE: 17
cgcaggccgg aattccagct ccggcagata atacc                                   35

<210> SEQ ID NO 18
<211> LENGTH: 37
<212> TYPE: DNA
<213> ORGANISM: artificial
<220> FEATURE:
<223> OTHER INFORMATION: Synthetic oligonucleotide primer

<400> SEQUENCE: 18
tggtgatgcg gatccaagtt tgtaactacc ggagcac                                  37

<210> SEQ ID NO 19
<211> LENGTH: 20
<212> TYPE: DNA
<213> ORGANISM: artificial
<220> FEATURE:
<223> OTHER INFORMATION: Synthetic oligonucleotide primer

<400> SEQUENCE: 19
taatacgact cactataggg                                                    20

<210> SEQ ID NO 20
<211> LENGTH: 27
<212> TYPE: DNA
<213> ORGANISM: artificial
<220> FEATURE:
<223> OTHER INFORMATION: Synthetic oligonucleotide primer

<400> SEQUENCE: 20
ctcgagtcaa tggtggtgat ggtgatg                                            27
```